US012806260B2

(12) United States Patent
Ozay et al.

(10) Patent No.: US 12,806,260 B2
(45) Date of Patent: Nov. 24, 2026

(54) METHODS TO STIMULATE HLA-AGNOSTIC IMMUNE RESPONSES TO PROTEINS USING NUCLEATED CELLS

(71) Applicant: STEMCELL TECHNOLOGIES CANADA INC., Vancouver (CA)

(72) Inventors: Emrah Ilker Ozay, Watertown, MA (US); Michael Maloney, Watertown, MA (US); Scott Loughhead, Watertown, MA (US); Howard Bernstein, Watertown, MA (US); Katherine Seidl, Watertown, MA (US); Melissa Myint, Watertown, MA (US); Armon R. Sharei, Watertown, MA (US)

(73) Assignee: STEMCELL TECHNOLOGIES CANADA INC., Vancouver (CA)

( * ) Notice: Subject to any disclaimer, the term of this patent is extended or adjusted under 35 U.S.C. 154(b) by 839 days.

(21) Appl. No.: 18/043,613

(22) PCT Filed: Sep. 1, 2021

(86) PCT No.: PCT/US2021/048771

§ 371 (c)(1),
(2) Date: Mar. 1, 2023

(87) PCT Pub. No.: WO2022/051437

PCT Pub. Date: Mar. 10, 2022

(65) Prior Publication Data

US 2023/0263879 A1 Aug. 24, 2023

Related U.S. Application Data

(60) Provisional application No. 63/147,473, filed on Feb. 9, 2021, provisional application No. 63/073,910, filed on Sep. 2, 2020.

(51) Int. Cl.

| | |
|---|---|
| ***A61K 39/12*** | (2006.01) |
| ***A61K 9/00*** | (2006.01) |
| ***A61K 39/39*** | (2006.01) |
| ***A61K 40/10*** | (2025.01) |
| ***A61K 40/11*** | (2025.01) |
| ***A61K 40/32*** | (2025.01) |
| ***A61K 40/46*** | (2025.01) |
| ***C12N 5/0783*** | (2010.01) |

(52) U.S. Cl.

CPC ............ *A61K 39/12* (2013.01); *A61K 9/0019* (2013.01); *A61K 39/39* (2013.01); *A61K 40/10* (2025.01); *A61K 40/11* (2025.01); *A61K 40/32* (2025.01); *A61K 40/46* (2025.01); *C12N 5/0636* (2013.01); *C12N 5/0646* (2013.01); *A61K 2239/31* (2023.05); *A61K 2239/38* (2023.05); *C12N 2710/20034* (2013.01)

(58) Field of Classification Search

None

See application file for complete search history.

(56) References Cited

FOREIGN PATENT DOCUMENTS

| | | | | |
|---|---|---|---|---|
| WO | 2016070136 A1 | | 5/2016 | |
| WO | WO2026/070136 | * | 5/2016 | ............ C12N 5/078 |
| WO | 2019178005 A2 | | 9/2019 | |
| WO | 2020176789 A1 | | 9/2020 | |

OTHER PUBLICATIONS

Liang et al. (bioRxiv, 2019, p. 1-47).*

V. F. Van Tendeloo et al, "Induction of complete and molecular remissions in acute myeloid leukemia by Wilms' tumor 1 antigen-targeted dendritic cell vaccination", Proceedings of the National Academy of Sciences, vol. 0 107, No. 0 31, Aug. 3, 2010 (Aug. 3, 2010), p. 13824-13829.

Margarita Salcedo et al, "Vaccination of melanoma patients using dendritic cells loaded with an allogeneic tumor cell lysate", Cancer Immunology, Immunotherapy, Springer, Berlin, DE,vol. 0 55, No. 0 7, Jul. 1, 2006 (Jul. 1, 2006), p. 819-829.

Tanja D De Gruijl et al, "Whole-cell cancer vaccination: from autologous to allogeneic tumor and dendritic cell-based vaccines", Cancer Immunology, Immunotherapy, Springer, Berlin, De,vol. 0 57, No. 0 10, Jun. 4, 2008 (Jun. 4, 2008), p. 1569-1577.

Cecele J. Denman et al, "Membrane-Bound IL-21 Promotes Sustained Ex Vivo Proliferation of Human Natural Killer Cells", PLOS ONE,vol. 0 7, No. 0 1, Jan. 18, 2012 (Jan. 18, 2012, p. 1-13.

Realini C et al, "KEKE motifs", Jul. 11, 1994 (Jul. 11, 1994), vol. 0 348, No. 0 2, p. 109-113.

* cited by examiner

*Primary Examiner* — Agnieszka Boesen

(74) *Attorney, Agent, or Firm* — Smart & Biggar LP; Micheline Gravelle

(57) ABSTRACT

The present application provides nucleated cells comprising a protein or fragment thereof, methods of manufacturing such nucleated cells comprising the protein or fragment thereof, and methods of using such modified nucleated cells (e.g., immune cells) for stimulating an immune response in a HLA agnostic manner.

15 Claims, 80 Drawing Sheets

Specification includes a Sequence Listing.

| mRNA Construct | Empty SQZ Mean Fluorescent Intensity (a.u.) | SQZ-loaded Mean Fluorescent Intensity (a.u.) |
|---|---|---|
| TFRC-$(G_4S)_3$-IL-12 | 176 | 2,596 |
| TFRC-$(G_4S)_3$-IFN-α2a | 176 | 2,466 |

5M pp65 mRNA only vs 5M eAPC-CMV 1M pp65 mRNA only vs 1M eAPC-CMV

SEQUENCE LISTING

<160> NUMBER OF SEQ ID NOS: 93

<210> SEQ ID NO 1
<211> LENGTH: 10
<212> TYPE: PRT
<213> ORGANISM: Homo sapiens

<400> SEQUENCE: 1

```
Thr Ile His Asp Ile Ile Leu Glu Cys Val
1               5                   10
```

<210> SEQ ID NO 2
<211> LENGTH: 10
<212> TYPE: PRT
<213> ORGANISM: Mus musculus

<400> SEQUENCE: 2

```
Glu Val Tyr Asp Phe Ala Phe Arg Asp Leu
1               5                   10
```

<210> SEQ ID NO 3

<211> LENGTH: 10
<212> TYPE: PRT
<213> ORGANISM: Homo sapiens

<400> SEQUENCE: 3

Tyr Met Leu Asp Leu Gln Pro Glu Thr Thr
1 5 10

<210> SEQ ID NO 4
<211> LENGTH: 9
<212> TYPE: PRT
<213> ORGANISM: Mus musculus

<400> SEQUENCE: 4

Arg Ala His Tyr Asn Ile Val Thr Phe
1 5

<210> SEQ ID NO 5
<211> LENGTH: 10
<212> TYPE: PRT
<213> ORGANISM: Homo sapiens

<400> SEQUENCE: 5

Leu Pro Gln Leu Ser Thr Glu Leu Gln Thr
1 5 10

<210> SEQ ID NO 6
<211> LENGTH: 8
<212> TYPE: PRT
<213> ORGANISM: Homo sapiens

<400> SEQUENCE: 6

Gln Leu Cys Thr Glu Leu Gln Thr
1 5

<210> SEQ ID NO 7
<211> LENGTH: 7
<212> TYPE: PRT
<213> ORGANISM: Mus musculus

<400> SEQUENCE: 7

Lys Gln Gln Leu Leu Arg Arg
1 5

<210> SEQ ID NO 8
<211> LENGTH: 10
<212> TYPE: PRT
<213> ORGANISM: Mus musculus

<400> SEQUENCE: 8

Val Tyr Ser Lys Gln Gln Leu Leu Arg Arg
1 5 10

<210> SEQ ID NO 9
<211> LENGTH: 10
<212> TYPE: PRT
<213> ORGANISM: Homo sapiens

<400> SEQUENCE: 9

Met His Gly Asp Thr Pro Thr Leu His Glu
1 5 10

<210> SEQ ID NO 10
<211> LENGTH: 6
<212> TYPE: PRT

<213> ORGANISM: Mus musculus

<400> SEQUENCE: 10

Gly Gln Ala Glu Pro Asp
1 5

<210> SEQ ID NO 11
<211> LENGTH: 16
<212> TYPE: PRT
<213> ORGANISM: Homo sapiens

<400> SEQUENCE: 11

Tyr Ser Lys Gln Gln Leu Leu Arg Arg Glu Val Tyr Asp Phe Ala Phe
1 5 10 15

<210> SEQ ID NO 12
<211> LENGTH: 7
<212> TYPE: PRT
<213> ORGANISM: Homo sapiens

<400> SEQUENCE: 12

Tyr Cys Lys Gln Gln Leu Leu
1 5

<210> SEQ ID NO 13
<211> LENGTH: 8
<212> TYPE: PRT
<213> ORGANISM: Mus musculus

<400> SEQUENCE: 13

Cys Ile Val Tyr Arg Asp Gly Asn
1 5

<210> SEQ ID NO 14
<211> LENGTH: 15
<212> TYPE: PRT
<213> ORGANISM: Mus musculus

<400> SEQUENCE: 14

Ser Ile Val Tyr Arg Asp Gly Asn Pro Tyr Ala Val Ser Asp Lys
1 5 10 15

<210> SEQ ID NO 15
<211> LENGTH: 15
<212> TYPE: PRT
<213> ORGANISM: Homo sapiens

<400> SEQUENCE: 15

Asp Leu Tyr Cys Tyr Glu Gln Leu Asn Asp Ser Ser Glu Glu Glu
1 5 10 15

<210> SEQ ID NO 16
<211> LENGTH: 20
<212> TYPE: PRT
<213> ORGANISM: Mus musculus

<400> SEQUENCE: 16

Cys Cys Lys Cys Asp Ser Thr Leu Arg Leu Cys Val Gln Ser Thr His
1 5 10 15

Val Asp Ile Arg
20

<210> SEQ ID NO 17
<211> LENGTH: 20

<212> TYPE: PRT
<213> ORGANISM: Mus musculus

<400> SEQUENCE: 17

Ser Ser Lys Ser Asp Ser Thr Leu Arg Leu Ser Val Gln Ser Thr His
1               5                   10                  15

Val Asp Ile Arg
            20

<210> SEQ ID NO 18
<211> LENGTH: 36
<212> TYPE: PRT
<213> ORGANISM: Homo sapiens

<400> SEQUENCE: 18

Leu Pro Gln Leu Ser Thr Glu Leu Gln Thr Thr Ile His Asp Ile Ile
1               5                   10                  15

Leu Glu Cys Val Tyr Ser Lys Gln Gln Leu Leu Arg Arg Glu Val Tyr
            20                  25                  30

Asp Phe Ala Phe
        35

<210> SEQ ID NO 19
<211> LENGTH: 25
<212> TYPE: PRT
<213> ORGANISM: Homo sapiens

<400> SEQUENCE: 19

Gln Leu Cys Thr Glu Leu Gln Thr Thr Ile His Asp Ile Ile Leu Glu
1               5                   10                  15

Cys Val Tyr Cys Lys Gln Gln Leu Leu
            20                  25

<210> SEQ ID NO 20
<211> LENGTH: 25
<212> TYPE: PRT
<213> ORGANISM: Mus musculus

<400> SEQUENCE: 20

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 21
<211> LENGTH: 35
<212> TYPE: PRT
<213> ORGANISM: Mus musculus

<400> SEQUENCE: 21

Val Tyr Ser Lys Gln Gln Leu Leu Arg Arg Glu Val Tyr Asp Phe Ala
1               5                   10                  15

Phe Arg Asp Leu Ser Ile Val Tyr Arg Asp Gly Asn Pro Tyr Ala Val
            20                  25                  30

Ser Asp Lys
        35

<210> SEQ ID NO 22
<211> LENGTH: 35
<212> TYPE: PRT
<213> ORGANISM: Homo sapiens

<400> SEQUENCE: 22

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
        35

<210> SEQ ID NO 23
<211> LENGTH: 25
<212> TYPE: PRT
<213> ORGANISM: Homo sapiens

<400> SEQUENCE: 23

Gln Leu Cys Thr Glu Leu Gln Thr Tyr Met Leu Asp Leu Gln Pro Glu
1               5                   10                  15

Thr Thr Tyr Cys Lys Gln Gln Leu Leu
            20                  25

<210> SEQ ID NO 24
<211> LENGTH: 35
<212> TYPE: PRT
<213> ORGANISM: Mus musculus

<400> SEQUENCE: 24

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 25
<211> LENGTH: 35
<212> TYPE: PRT
<213> ORGANISM: Mus musculus

<400> SEQUENCE: 25

Gly Gln Ala Glu Pro Asp Arg Ala His Tyr Asn Ile Val Thr Phe Ser
1               5                   10                  15

Ser Lys Ser Asp Ser Thr Leu Arg Leu Ser Val Gln Ser Thr His Val
            20                  25                  30

Asp Ile Arg
        35

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
ggggtcaacg ttgagggggg                                                20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
gggggacgat cgtcgggggg 20

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
ggggacgacg tcgtgggggg g 21

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
tccatgacgt tcctgatgct 20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
tccatgacgt tcctgacgtt 20

<210> SEQ ID NO 31
<211> LENGTH: 24
<212> TYPE: DNA
<213> ORGANISM: Artificial Sequence
<220> FEATURE:
<223> OTHER INFORMATION: Synthetic Construct

<400> SEQUENCE: 31
tcgtcgtttt gtcgttttgt cgtt 24

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
tcgtcgttgt cgttttgtcg tt 22

<210> SEQ ID NO 33
<211> LENGTH: 23
<212> TYPE: DNA
<213> ORGANISM: Artificial Sequence
<220> FEATURE:
<223> OTHER INFORMATION: Synthetic Construct

<400> SEQUENCE: 33
tcgacgttcg tcgttcgtcg ttc 23

<210> SEQ ID NO 34
<211> LENGTH: 26

<212> TYPE: DNA
<213> ORGANISM: Artificial Sequence
<220> FEATURE:
<223> OTHER INFORMATION: Synthetic Construct

<400> SEQUENCE: 34
tcgcgacgtt cgcccgacgt tcggta 26

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct

<400> SEQUENCE: 35
tcgtcgtttt cggcgcgcgc cg 22

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
tcgtcgtcgt tcgaacgacg ttgat 25

<210> SEQ ID NO 37
<211> LENGTH: 29
<212> TYPE: DNA
<213> ORGANISM: Artificial Sequence
<220> FEATURE:
<223> OTHER INFORMATION: Synthetic Construct

<400> SEQUENCE: 37
tcgcgaacgt tcgccgcgtt cgaacgcgg 29

<210> SEQ ID NO 38
<211> LENGTH: 35
<212> TYPE: PRT
<213> ORGANISM: Artificial Sequence
<220> FEATURE:
<223> OTHER INFORMATION: Synthetic Construct

<400> SEQUENCE: 38

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
        35
```

<210> SEQ ID NO 39
<211> LENGTH: 35
<212> TYPE: PRT
<213> ORGANISM: Artificial Sequence
<220> FEATURE:
<223> OTHER INFORMATION: Synthetic Construct

<400> SEQUENCE: 39

```
Leu Tyr Cys Tyr Glu Gln Leu Asn Asp Ser Ser Glu Glu Glu Asp Glu
1               5                   10                  15

Ile Asp Gly Pro Ala Gly Gln Ala Glu Pro Asp Arg Ala His Tyr Asn
            20                  25                  30
```

Ile Val Thr
35

<210> SEQ ID NO 40
<211> LENGTH: 35
<212> TYPE: PRT
<213> ORGANISM: Artificial Sequence
<220> FEATURE:
<223> OTHER INFORMATION: Synthetic Construct

<400> SEQUENCE: 40

Gly Gln Ala Glu Pro Asp Arg Ala His Tyr Asn Ile Val Thr Phe Cys
1 5 10 15

Cys Lys Cys Asp Ser Thr Leu Arg Leu Cys Val Gln Ser Thr His Val
20 25 30

Asp Ile Arg
35

<210> SEQ ID NO 41
<211> LENGTH: 35
<212> TYPE: PRT
<213> ORGANISM: Artificial Sequence
<220> FEATURE:
<223> OTHER INFORMATION: Synthetic Construct

<400> SEQUENCE: 41

Thr Leu Arg Leu Cys Val Gln Ser Thr His Val Asp Ile Arg Thr Leu
1 5 10 15

Glu Asp Leu Leu Met Gly Thr Leu Gly Ile Val Cys Pro Ile Cys Ser
20 25 30

Gln Lys Pro
35

<210> SEQ ID NO 42
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

Met His Gln Lys Arg Thr Ala Met Phe Gln Asp Pro Gln Glu Arg Pro
1 5 10 15

Arg Lys Leu Pro Gln Leu Cys Thr Glu Leu Gln Thr Thr Ile His Asp
20 25 30

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct

<400> SEQUENCE: 43

Leu Pro Gln Leu Cys Thr Glu Leu Gln Thr Thr Ile His Asp Ile Ile
1 5 10 15

Leu Glu Cys Val Tyr Cys Lys Gln Gln Leu Leu Arg Arg Glu Val Tyr
20 25 30

<210> SEQ ID NO 44
<211> LENGTH: 25
<212> TYPE: PRT
<213> ORGANISM: Artificial Sequence
<220> FEATURE:
<223> OTHER INFORMATION: Synthetic Construct

<400> SEQUENCE: 44

Lys Gln Gln Leu Leu Arg Arg Glu Val Tyr Asp Phe Ala Phe Arg Asp
1 5 10 15

Leu Cys Ile Val Tyr Arg Asp Gly Asn
20 25

<210> SEQ ID NO 45
<211> LENGTH: 26
<212> TYPE: PRT
<213> ORGANISM: Artificial Sequence
<220> FEATURE:
<223> OTHER INFORMATION: Synthetic Construct

<400> SEQUENCE: 45

Arg Asp Leu Cys Ile Val Tyr Arg Asp Gly Asn Pro Tyr Ala Val Cys
1 5 10 15

Asp Lys Cys Leu Lys Phe Tyr Ser Lys Ile
20 25

<210> SEQ ID NO 46
<211> LENGTH: 25
<212> TYPE: PRT
<213> ORGANISM: Artificial Sequence
<220> FEATURE:
<223> OTHER INFORMATION: Synthetic Construct

<400> SEQUENCE: 46

Asp Lys Cys Leu Lys Phe Tyr Ser Lys Ile Ser Glu Tyr Arg His Tyr
1 5 10 15

Cys Tyr Ser Leu Tyr Gly Thr Thr Leu
20 25

<210> SEQ ID NO 47
<211> LENGTH: 25
<212> TYPE: PRT
<213> ORGANISM: Artificial Sequence
<220> FEATURE:
<223> OTHER INFORMATION: Synthetic Construct

<400> SEQUENCE: 47

His Tyr Cys Tyr Ser Leu Tyr Gly Thr Thr Leu Glu Gln Gln Tyr Asn
1 5 10 15

Lys Pro Leu Cys Asp Leu Leu Ile Arg
20 25

<210> SEQ ID NO 48
<211> LENGTH: 32
<212> TYPE: PRT
<213> ORGANISM: Artificial Sequence
<220> FEATURE:
<223> OTHER INFORMATION: Synthetic Construct

<400> SEQUENCE: 48

Tyr Gly Thr Thr Leu Glu Gln Gln Tyr Asn Lys Pro Leu Cys Asp Leu
1 5 10 15

Leu Ile Arg Cys Ile Asn Cys Gln Lys Pro Leu Cys Pro Glu Glu Lys
20 25 30

<210> SEQ ID NO 49
<211> LENGTH: 32
<212> TYPE: PRT

<213> ORGANISM: Artificial Sequence
<220> FEATURE:
<223> OTHER INFORMATION: Synthetic Construct

<400> SEQUENCE: 49

```
Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30
```

<210> SEQ ID NO 50
<211> LENGTH: 32
<212> TYPE: PRT
<213> ORGANISM: Artificial Sequence
<220> FEATURE:
<223> OTHER INFORMATION: Synthetic Construct

<400> SEQUENCE: 50

```
Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30
```

<210> SEQ ID NO 51
<211> LENGTH: 158
<212> TYPE: PRT
<213> ORGANISM: Artificial Sequence
<220> FEATURE:
<223> OTHER INFORMATION: Synthetic Construct

<400> SEQUENCE: 51

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155
```

<210> SEQ ID NO 52
<211> LENGTH: 98
<212> TYPE: PRT
<213> ORGANISM: Artificial Sequence
<220> FEATURE:
<223> OTHER INFORMATION: Synthetic Construct

<400> SEQUENCE: 52

```
Met His Gly Asp Thr Pro Thr Leu His Glu Tyr Met Leu Asp Leu Gln
```

1 5 10 15

Pro Glu Thr Thr Asp Leu Tyr Cys Tyr Glu Gln Leu Asn Asp Ser Ser
20 25 30

Glu Glu Glu Asp Glu Ile Asp Gly Pro Ala Gly Gln Ala Glu Pro Asp
35 40 45

Arg Ala His Tyr Asn Ile Val Thr Phe Cys Cys Lys Cys Asp Ser Thr
50 55 60

Leu Arg Leu Cys Val Gln Ser Thr His Val Asp Ile Arg Thr Leu Glu
65 70 75 80

Asp Leu Leu Met Gly Thr Leu Gly Ile Val Cys Pro Ile Cys Ser Gln
85 90 95

Lys Pro

<210> SEQ ID NO 53
<211> LENGTH: 108
<212> TYPE: PRT
<213> ORGANISM: Artificial Sequence
<220> FEATURE:
<223> OTHER INFORMATION: Synthetic Construct

<400> SEQUENCE: 53

Met Arg Thr Ala Leu Gly Asp Ile Gly Asn Met His Gly Asp Thr Pro
1 5 10 15

Thr Leu His Glu Tyr Met Leu Asp Leu Gln Pro Glu Thr Thr Asp Leu
20 25 30

Tyr Cys Tyr Glu Gln Leu Asn Asp Ser Ser Glu Glu Glu Asp Glu Ile
35 40 45

Asp Gly Pro Ala Gly Gln Ala Glu Pro Asp Arg Ala His Tyr Asn Ile
50 55 60

Val Thr Phe Cys Cys Lys Cys Asp Ser Thr Leu Arg Leu Cys Val Gln
65 70 75 80

Ser Thr His Val Asp Ile Arg Thr Leu Glu Asp Leu Leu Met Gly Thr
85 90 95

Leu Gly Ile Val Cys Pro Ile Cys Ser Gln Lys Pro
100 105

<210> SEQ ID NO 54
<211> LENGTH: 179
<212> TYPE: PRT
<213> ORGANISM: Artificial Sequence
<220> FEATURE:
<223> OTHER INFORMATION: Synthetic Construct

<400> SEQUENCE: 54

Met Arg Val Thr Ala Pro Arg Thr Leu Ile Leu Leu Leu Ser Gly Ala
1 5 10 15

Leu Ala Leu Thr Glu Thr Trp Ala Gly Ser Met His Gly Asp Thr Pro
20 25 30

Thr Leu His Glu Tyr Met Leu Asp Leu Gln Pro Glu Thr Thr Asp Leu
35 40 45

Tyr Cys Tyr Glu Gln Leu Asn Asp Ser Ser Glu Glu Glu Asp Glu Ile
50 55 60

Asp Gly Pro Ala Gly Gln Ala Glu Pro Asp Arg Ala His Tyr Asn Ile
65 70 75 80

Val Thr Phe Cys Cys Lys Cys Asp Ser Thr Leu Arg Leu Cys Val Gln
85 90 95

Ser Thr His Val Asp Ile Arg Thr Leu Glu Asp Leu Leu Met Gly Thr

```
            100                 105                 110

Leu Gly Ile Val Cys Pro Ile Cys Ser Gln Lys Pro Ile Val Gly Ile
        115                 120                 125

Val Ala Gly Leu Ala Val Leu Ala Val Val Val Ile Gly Ala Val Val
    130                 135                 140

Ala Thr Val Met Cys Arg Arg Lys Ser Ser Gly Gly Lys Gly Gly Ser
145                 150                 155                 160

Tyr Ser Gln Ala Ala Ser Ser Asp Ser Ala Gln Gly Ser Asp Val Ser
                165                 170                 175

Leu Thr Ala


<210> SEQ ID NO 55
<211> LENGTH: 98
<212> TYPE: PRT
<213> ORGANISM: Artificial Sequence
<220> FEATURE:
<223> OTHER INFORMATION: Synthetic Construct

<400> SEQUENCE: 55

Met His Gly Asp Ala Pro Ala Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro


<210> SEQ ID NO 56
<211> LENGTH: 127
<212> TYPE: PRT
<213> ORGANISM: Artificial Sequence
<220> FEATURE:
<223> OTHER INFORMATION: Synthetic Construct

<400> SEQUENCE: 56

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Lys Glu Lys Glu Lys Asn Lys Leu Lys Arg Lys Lys Leu Glu
            100                 105                 110

Asn Lys Asp Lys Lys Asp Glu Glu Arg Asn Lys Ile Arg Glu Glu
        115                 120                 125
```

<210> SEQ ID NO 57
<211> LENGTH: 26
<212> TYPE: PRT
<213> ORGANISM: Artificial Sequence
<220> FEATURE:
<223> OTHER INFORMATION: Synthetic Construct

<400> SEQUENCE: 57

```
Met Gln Leu Cys Thr Glu Leu Gln Thr Tyr Met Leu Asp Leu Gln Pro
1               5                   10                  15

Glu Thr Thr Tyr Cys Lys Gln Gln Leu Leu
            20                  25
```

<210> SEQ ID NO 58
<211> LENGTH: 176
<212> TYPE: PRT
<213> ORGANISM: Artificial Sequence
<220> FEATURE:
<223> OTHER INFORMATION: Synthetic Construct

<400> SEQUENCE: 58

```
Met Gln Leu Cys Thr Glu Leu Gln Thr Tyr Met Leu Asp Leu Gln Pro
1               5                   10                  15

Glu Thr Thr Tyr Cys Lys Gln Gln Leu Leu Gly Gly Gly Gly Ser Gln
            20                  25                  30

Leu Cys Thr Glu Leu Gln Thr Tyr Met Leu Asp Leu Gln Pro Glu Thr
        35                  40                  45

Thr Tyr Cys Lys Gln Gln Leu Leu Gly Gly Gly Gly Ser Gln Leu Cys
    50                  55                  60

Thr Glu Leu Gln Thr Tyr Met Leu Asp Leu Gln Pro Glu Thr Thr Tyr
65                  70                  75                  80

Cys Lys Gln Gln Leu Leu Gly Gly Gly Gly Ser Gln Leu Cys Thr Glu
                85                  90                  95

Leu Gln Thr Tyr Met Leu Asp Leu Gln Pro Glu Thr Thr Tyr Cys Lys
            100                 105                 110

Gln Gln Leu Leu Gly Gly Gly Gly Ser Gln Leu Cys Thr Glu Leu Gln
        115                 120                 125

Thr Tyr Met Leu Asp Leu Gln Pro Glu Thr Thr Tyr Cys Lys Gln Gln
    130                 135                 140

Leu Leu Gly Gly Gly Gly Ser Gln Leu Cys Thr Glu Leu Gln Thr Tyr
145                 150                 155                 160

Met Leu Asp Leu Gln Pro Glu Thr Thr Tyr Cys Lys Gln Gln Leu Leu
                165                 170                 175
```

<210> SEQ ID NO 59
<211> LENGTH: 477
<212> TYPE: DNA
<213> ORGANISM: Artificial Sequence
<220> FEATURE:
<223> OTHER INFORMATION: Synthetic Construct

<400> SEQUENCE: 59

```
atgcaccaaa agagaactgc aatgtttcag gacccacagg agcgacccag aaagttacca      60

cagttatgca cagagctgca aacaactata catgatataa tattagaatg tgtgtactgc     120

aagcaacagt tactgcgacg tgaggtatat gactttgctt ttcgggattt atgcatagta     180

tatagagatg ggaatccata tgctgtatgt gataaatgtt taaagtttta ttctaaaatt     240

agtgagtata gacattattg ttatagtttg tatggaacaa cattagaaca gcaatacaac     300
```

aaaccgttgt gtgatttgtt aattaggtgt attaactgtc aaaagccact gtgtcctgaa 360
gaaaagcaaa gacatctgga caaaaagcaa agattccata atataagggg tcggtggacc 420
ggtcgatgta tgtcttgttg cagatcatca agaacacgta gagaaaccca gctgtaa 477

<210> SEQ ID NO 60
<211> LENGTH: 477
<212> TYPE: DNA
<213> ORGANISM: Artificial Sequence
<220> FEATURE:
<223> OTHER INFORMATION: Synthetic Construct

<400> SEQUENCE: 60
atgcaccaga aacggaccgc catgttccag gatcctcaag agaggcccag aaagctgcct 60
cagctgtgta ccgagctgca gaccaccatc cacgacatca tcctggaatg cgtgtactgc 120
aagcagcagc tcctgcggag agaggtgtac gatttcgcct tccgggacct gtgcatcgtg 180
tacagagatg gcaaccccta cgccgtgtgc gacaagtgcc tgaagttcta cagcaagatc 240
agcgagtacc ggcactactg ctacagcctg tacggcacca cactggaaca gcagtacaac 300
aagcccctgt gcgacctgct gatccggtgc atcaactgcc agaaacctct gtgccccgag 360
gaaaagcagc ggcacctgga caagaagcag cggttccaca acatcagagg ccggtggacc 420
ggcagatgca tgagctgttg tcggagcagc agaaccagac gggaaaccca gctgtga 477

<210> SEQ ID NO 61
<211> LENGTH: 297
<212> TYPE: DNA
<213> ORGANISM: Artificial Sequence
<220> FEATURE:
<223> OTHER INFORMATION: Synthetic Construct

<400> SEQUENCE: 61
atgcatggag atacacctac attgcatgaa tatatgttag atttgcaacc agagacaact 60
gatctctact gttatgagca attaaatgac agctcagagg aggaggatga aatagatggt 120
ccagctggac aagcagaacc ggacagagcc cattacaata ttgtaacctt ttgttgcaag 180
tgtgactcta cgcttcggtt gtgcgtacaa agcacacacg tagacattcg tactttggaa 240
gacctgttaa tgggcacact aggaattgtg tgccccatct gttctcagaa accataa 297

<210> SEQ ID NO 62
<211> LENGTH: 324
<212> TYPE: DNA
<213> ORGANISM: Artificial Sequence
<220> FEATURE:
<223> OTHER INFORMATION: Synthetic Construct

<400> SEQUENCE: 62
atgagaacag ctcttgggga cattggtaac catggagata cacctacatt gcatgaatat 60
atgttagatt tgcaaccaga gacaactgat ctctactgtt atgagcaatt aaatgacagc 120
tcagaggagg aggatgaaat agatggtcca gctggacaag cagaaccgga cagagcccat 180
tacaatattg taaccttttg ttgcaagtgt gactctacgc ttcggttgtg cgtacaaagc 240
acacacgtag acattcgtac tttggaagac ctgttaatgg gcacactagg aattgtgtgc 300
cccatctgtt ctcagaaacc ataa 324

<210> SEQ ID NO 63
<211> LENGTH: 296
<212> TYPE: DNA

<213> ORGANISM: Artificial Sequence
<220> FEATURE:
<223> OTHER INFORMATION: Synthetic Construct

<400> SEQUENCE: 63
atgcacggcg acacccctac cctgcacgag tacatgctgg acctgcagcc tgagacaacc 60
gacctgtact gctacgagca gctgaacgac agcagcgagg aagaggacga gatcgacggc 120
cctgccggcc aggccgagcc tgatagagcc cactacaaca tcgtgacctt ctgctgcaag 180
tgcgacagca ccctgagact gtgcgtgcag agcacacacg tggacatcag aaccctggaa 240
gatctgctga tgggcacctt gggcatcgtg tgccccatct gcagccagaa gccttg 296

<210> SEQ ID NO 64
<211> LENGTH: 297
<212> TYPE: DNA
<213> ORGANISM: Artificial Sequence
<220> FEATURE:
<223> OTHER INFORMATION: Synthetic Construct

<400> SEQUENCE: 64
atgcacggcg atacccctac actgcacgag tacatgctgg acctgcagcc tgagacaacc 60
gacctgtact gctacgagca gctgaacgac agcagcgagg aagaggacga gattgacgga 120
cctgccggac aggccgaacc tgatagagcc cactacaata tcgtgacctt ctgctgcaag 180
tgcgacagca ccctgagact gtgtgtgcag agcacccacg tggacatcag aaccctggaa 240
gatctgctga tgggcaccct gggcatcgtg tgccctatct gtagccagaa gccttga 297

<210> SEQ ID NO 65
<211> LENGTH: 540
<212> TYPE: DNA
<213> ORGANISM: Artificial Sequence
<220> FEATURE:
<223> OTHER INFORMATION: Synthetic Construct

<400> SEQUENCE: 65
atgagagtga cagcccctcg gacactgatc ctgctgcttt ctggtgccct ggctctgaca 60
gaaacatggg ccggatctat gcacggcgat acccctacac tgcacgagta catgctggac 120
ctgcagcctg agacaaccga cctgtactgc tacgagcagc tgaacgacag cagcgaggaa 180
gaggacgaga ttgacggacc tgccggacag gccgaacctg atagagccca ctacaatatc 240
gtgaccttct gctgcaagtg cgacagcacc ctgagactgt gtgtgcagag cacccacgtg 300
gacatcagaa ccctggaaga tctgctgatg ggcaccctgg gcatcgtgtg ccctatctgt 360
agccagaagc ctatcgtggg aatcgtggcc ggactggctg tgctggcagt ggtggttatt 420
ggagccgtgg tggccacagt gatgtgcaga agaaagagca gcggcggcaa aggcggcagc 480
tattctcagg ccgcctctag cgattctgcc cagggaagtg atgtgtccct gacagcttga 540

<210> SEQ ID NO 66
<211> LENGTH: 327
<212> TYPE: DNA
<213> ORGANISM: Artificial Sequence
<220> FEATURE:
<223> OTHER INFORMATION: Synthetic Construct

<400> SEQUENCE: 66
atgagaacag ctctcggcga catcggcaac atgcacggcg atacccctac actgcacgag 60
tacatgctgg acctgcagcc tgagacaacc gacctgtact gctacgagca gctgaacgac 120
agcagcgagg aagaggacga gattgacgga cctgccggac aggccgaacc tgatagagcc 180

```
cactacaata tcgtgacctt ctgctgcaag tgcgacagca ccctgagact gtgtgtgcag    240

agcacccacg tggacatcag aaccctggaa gatctgctga tgggcaccct gggcatcgtg    300

tgccctatct gtagccagaa gccttga                                        327


<210> SEQ ID NO 67
<211> LENGTH: 384
<212> TYPE: DNA
<213> ORGANISM: Artificial Sequence
<220> FEATURE:
<223> OTHER INFORMATION: Synthetic Construct

<400> SEQUENCE: 67

atgcacggcg ataccccctac actgcacgag tacatgctgg acctgcagcc tgagacaacc     60

gacctgtact gctacgagca gctgaacgac agcagcgagg aagaggacga gattgacgga    120

cctgccggac aggccgaacc tgatagagcc cactacaata tcgtgacctt ctgctgcaag    180

tgcgacagca ccctgagact gtgtgtgcag agcacccacg tggacatcag aaccctggaa    240

gatctgctga tgggcaccct gggcatcgtg tgccctatct gtagccagaa gcctaaagag    300

aaagagaaga acaagctgaa gcggaagaag ctcgagaaca aggacaagaa ggacgaggaa    360

cggaacaaga tccgggaaga gtga                                           384


<210> SEQ ID NO 68
<211> LENGTH: 81
<212> TYPE: DNA
<213> ORGANISM: Artificial Sequence
<220> FEATURE:
<223> OTHER INFORMATION: Synthetic Construct

<400> SEQUENCE: 68

atgcagctgt gtaccgagct gcagacctac atgctggacc tgcagcctga gacaacctac     60

tgcaagcagc aactgctttg a                                               81


<210> SEQ ID NO 69
<211> LENGTH: 531
<212> TYPE: DNA
<213> ORGANISM: Artificial Sequence
<220> FEATURE:
<223> OTHER INFORMATION: Synthetic Construct

<400> SEQUENCE: 69

atgcagctgt gtaccgagct gcagacctac atgctggacc tgcagcctga gacaacctac     60

tgcaagcagc aactgcttgg cggcggaggc tctcagctct gtactgaact ccagacatat    120

atgctcgatc tccagccaga aaccacgtac tgtaaacagc agctcctcgg aggcggcgga    180

tctcaactgt gcaccgaact gcaaacttat atgttggatc tgcaacccga aaccacatat    240

tgcaagcaac agttgctcgg tggcggtggc agtcagttgt gcacagaact tcagacttac    300

atgcttgatc ttcagcccga aacgacctat tgcaaacagc agcttcttgg cggaggcggc    360

agccagttgt gtactgagct tcaaacttat atgcttgacc tccaaccaga gactacttac    420

tgcaaacaac aactcctcgg cggtggtgga agccagctct gcacggaatt gcagacctat    480

atgctcgact tgcaaccgga aacgacgtac tgcaaacaac agctgctgtg a             531


<210> SEQ ID NO 70
<211> LENGTH: 297
<212> TYPE: DNA
<213> ORGANISM: Artificial Sequence
<220> FEATURE:
```

<223> OTHER INFORMATION: Synthetic Construct

<400> SEQUENCE: 70
atgcacggcg atgcccctgc cctgcacgag tacatgctgg acctgcagcc tgagacaacc 60
gacctgtact gctacgagca gctgaacgac agcagcgagg aagaggacga gattgacgga 120
cctgccggac aggccgaacc tgatagagcc cactacaata tcgtgacctt ctgctgcaag 180
tgcgacagca ccctgagact gtgtgtgcag agcacccacg tggacatcag aaccctggaa 240
gatctgctga tgggcaccct gggcatcgtg tgccctatct gtagccagaa gccttga 297

<210> SEQ ID NO 71
<211> LENGTH: 762
<212> TYPE: DNA
<213> ORGANISM: Artificial Sequence
<220> FEATURE:
<223> OTHER INFORMATION: Synthetic Construct

<400> SEQUENCE: 71
atgatggtgg acggcgacaa cagccacgtg gaaatgaagc tggccgtgga cgaggaagag 60
aacgccgaca acaacaccaa ggccaacgtg accaagccta agagatgcag cggcagcatc 120
tgctacggca caatcgccgt gatcgtgttc ttcctgatcg gctttatgat cggctacctg 180
ggctactgca agagcagtga tggacctggc gaaacaggcg gaggcggagg atctggtggc 240
ggaggaagcg gtggcggcgg atcttgtgat ctgcctcaga cacacagcct gggcagcaga 300
cgaacactga tgctgctggc ccagatgcgg aagatcagcc tgttcagctg cctgaaggac 360
cggcacgatt tcggcttccc tcaagaggaa ttcggcaacc agttccagaa ggccgagaca 420
atccctgtgc tgcacgagat gatccagcag atcttcaacc tgttctccac caaggacagc 480
agcgccgcct gggatgagac actgctggac aagttctaca ccgagctgta ccagcagctg 540
aatgacctgg aagcctgcgt gatccaaggc gtgggagtga cagagacacc cctgatgaag 600
gaagatagca tcctggccgt gcgcaagtac ttccagcgga tcaccctgta cctgaaagag 660
aagaagtaca gcccctgcgc ctgggaagtc gtgcgggccg aaatcatgag aagcttcagc 720
ctgagcacca acctgcaaga gagcctgcgg agcaaagagt ga 762

<210> SEQ ID NO 72
<211> LENGTH: 1836
<212> TYPE: DNA
<213> ORGANISM: Artificial Sequence
<220> FEATURE:
<223> OTHER INFORMATION: Synthetic Construct

<400> SEQUENCE: 72
atgatggtgg acggcgacaa cagccacgtg gaaatgaagc tggccgtgga cgaggaagag 60
aacgccgaca acaacaccaa ggccaacgtg accaagccta agagatgcag cggcagcatc 120
tgctacggca caatcgccgt gatcgtgttc ttcctgatcg gctttatgat cggctacctg 180
ggctactgca agagcagtga tggacctggc gaaacaggcg gaggcggagg atctggtggc 240
ggaggaagtg gcggcggagg ttctatttgg gagctgaaga aagacgtgta cgtggtggaa 300
ctggactggt atcccgatgc tcctggcgag atggtggtgc tgacctgcga tacccctgaa 360
gaggacggca tcacctggac actggatcag tctagcgagg tgctcggcag cggcaagacc 420
ctgaccatcc aagtgaaaga gtttggcgac gccggccagt acacctgtca caaaggcgga 480
gaagtgctga gccacagcct gctgctgctc cacaagaaag aggatggcat ttggagcacc 540
gacatcctga aggaccagaa agagcccaag aacaagacct tcctgagatg cgaggccaag 600
aactacagcg gccggttcac atgttggtgg ctgaccacca tcagcaccga cctgaccttc 660
agcgtgaagt ccagcagagg cagcagtgat cctcagggcg ttacatgtgg cgccgctaca 720
ctgtctgccg aaagagtgcg gggcgataac aaagaatacg agtacagcgt ggaatgccaa 780
gaggacagcg cctgtccagc cgccgaagag tctctgccta tcgaagtgat ggtcgacgcc 840
gtgcacaagc tgaagtacga gaactacacc agcagctttt tcatccggga catcatcaag 900
cccgatcctc caaagaacct gcagctgaag cctctgaaga acagcagaca ggtggaagtg 960
tcctgggagt accccgacac ctggtctaca ccccacagct acttcagcct gaccttttgc 1020
gtgcaagtgc agggcaagtc caagcgcgag aaaaaggacc gggtgttcac cgacaagacc 1080
agcgccaccg tgatctgcag aaagaacgcc agcatcagcg tcagagccca ggaccggtac 1140
tacagcagct cttggagcga atgggccagc gtgccatgta gcggaggtgg tggtagcgga 1200
ggcggcggaa gcggcggtgg tggatcaggt ggtggtggct ctagaaacct gccagtggct 1260
acccctgatc ctggcatgtt cccttgtctg caccacagcc agaacctgct gagagccgtg 1320
tccaacatgc tgcagaaggc cagacagacc ctggaattct acccctgcac cagcgaggaa 1380
atcgaccacg aggacatcac caaggataag accagcaccg tggaagcctg cctgcctctg 1440
gaactgacca agaacgagag ctgcctgaac agccgggaaa cctccttcat caccaacggc 1500
tcttgcctgg ccagcagaaa gacaagcttc atgatggccc tgtgcctgag cagcatctac 1560
gaggacctga agatgtacca ggtggaattc aagaccatga acgccaagct gctgatggac 1620
cccaagcggc agatcttcct ggaccagaac atgctggctg tgatcgacga gctgatgcag 1680
gccctgaact tcaacagcga gacagtgccc cagaagtcta gcctggaaga acccgacttc 1740
tacaagacca agatcaagct gtgcatcctg ctgcacgcct tccggatcag agccgtgacc 1800
atcgacagag tgatgagcta cctgaacgcc tcctga 1836

<210> SEQ ID NO 73
<211> LENGTH: 15
<212> TYPE: PRT
<213> ORGANISM: Artificial Sequence
<220> FEATURE:
<223> OTHER INFORMATION: Synthetic Construct

<400> SEQUENCE: 73

Gly Gly Gly Gly Ser Gly Gly Gly Gly Ser Gly Gly Gly Gly Ser
1 5 10 15

<210> SEQ ID NO 74
<211> LENGTH: 15
<212> TYPE: PRT
<213> ORGANISM: Artificial Sequence
<220> FEATURE:
<223> OTHER INFORMATION: Synthetic Construct

<400> SEQUENCE: 74

Glu Ala Ala Ala Lys Glu Ala Ala Ala Lys Glu Ala Ala Ala Lys
1 5 10 15

<210> SEQ ID NO 75
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5

<223> OTHER INFORMATION: Can be present in repeats of any number

<400> SEQUENCE: 75

Gly Gly Gly Gly Ser
1 5

<210> SEQ ID NO 76
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5
<223> OTHER INFORMATION: Can be present in repeats of any number

<400> SEQUENCE: 76

Glu Ala Ala Ala Lys
1 5

<210> SEQ ID NO 77
<211> LENGTH: 220
<212> TYPE: PRT
<213> ORGANISM: Artificial Sequence
<220> FEATURE:
<223> OTHER INFORMATION: Synthetic Construct

<400> SEQUENCE: 77

Met Met Val Asp Gly Asp Asn Ser His Val Glu Met Lys Leu Ala Val
1 5 10 15

Asp Glu Glu Glu Asn Ala Asp Asn Asn Thr Lys Ala Asn Val Thr Lys
20 25 30

Pro Lys Arg Cys Ser Gly Ser Ile Cys Tyr Gly Thr Ile Ala Val Ile
35 40 45

Val Phe Phe Leu Ile Gly Phe Met Ile Gly Tyr Leu Gly Tyr Cys Lys
50 55 60

Ser Ser Asp Gly Pro Gly Glu Thr Gly Gly Gly Gly Gly Ser Gly Gly
65 70 75 80

Gly Gly Ser Gly Gly Gly Gly Ser Ala Pro Thr Ser Ser Ser Thr Lys
85 90 95

Lys Thr Gln Leu Gln Leu Glu His Leu Leu Leu Asp Leu Gln Met Ile
100 105 110

Leu Asn Gly Ile Asn Asn Tyr Lys Asn Pro Lys Leu Thr Arg Met Leu
115 120 125

Thr Phe Lys Phe Tyr Met Pro Lys Lys Ala Thr Glu Leu Lys His Leu
130 135 140

Gln Cys Leu Glu Glu Glu Leu Lys Pro Leu Glu Glu Val Leu Asn Leu
145 150 155 160

Ala Gln Ser Lys Asn Phe His Leu Arg Pro Arg Asp Leu Ile Ser Asn
165 170 175

Ile Asn Val Ile Val Leu Glu Leu Lys Gly Ser Glu Thr Thr Phe Met
180 185 190

Cys Glu Tyr Ala Asp Glu Thr Ala Thr Ile Val Glu Phe Leu Asn Arg
195 200 205

Trp Ile Thr Phe Cys Gln Ser Ile Ile Ser Thr Leu
210 215 220

<210> SEQ ID NO 78
<211> LENGTH: 191

<212> TYPE: PRT
<213> ORGANISM: Artificial Sequence
<220> FEATURE:
<223> OTHER INFORMATION: Synthetic Construct

<400> SEQUENCE: 78

Met Leu Lys Lys Arg Gly Asn His Ser Thr Gly Leu Cys Leu Leu Val
1 5 10 15

Met Phe Phe Met Val Leu Val Ala Leu Val Gly Leu Gly Leu Gly Met
20 25 30

Phe Gln Leu Phe His Leu Gln Lys Glu Thr Gly Gly Gly Gly Gly Ser
35 40 45

Gly Gly Gly Gly Ser Gly Gly Gly Gly Ser Ala Pro Thr Ser Ser Ser
50 55 60

Thr Lys Lys Thr Gln Leu Gln Leu Glu His Leu Leu Leu Asp Leu Gln
65 70 75 80

Met Ile Leu Asn Gly Ile Asn Asn Tyr Lys Asn Pro Lys Leu Thr Arg
85 90 95

Met Leu Thr Phe Lys Phe Tyr Met Pro Lys Lys Ala Thr Glu Leu Lys
100 105 110

His Leu Gln Cys Leu Glu Glu Glu Leu Lys Pro Leu Glu Glu Val Leu
115 120 125

Asn Leu Ala Gln Ser Lys Asn Phe His Leu Arg Pro Arg Asp Leu Ile
130 135 140

Ser Asn Ile Asn Val Ile Val Leu Glu Leu Lys Gly Ser Glu Thr Thr
145 150 155 160

Phe Met Cys Glu Tyr Ala Asp Glu Thr Ala Thr Ile Val Glu Phe Leu
165 170 175

Asn Arg Trp Ile Thr Phe Cys Gln Ser Ile Ile Ser Thr Leu Thr
180 185 190

<210> SEQ ID NO 79
<211> LENGTH: 611
<212> TYPE: PRT
<213> ORGANISM: Artificial Sequence
<220> FEATURE:
<223> OTHER INFORMATION: Synthetic Construct

<400> SEQUENCE: 79

Met Met Val Asp Gly Asp Asn Ser His Val Glu Met Lys Leu Ala Val
1 5 10 15

Asp Glu Glu Glu Asn Ala Asp Asn Asn Thr Lys Ala Asn Val Thr Lys
20 25 30

Pro Lys Arg Cys Ser Gly Ser Ile Cys Tyr Gly Thr Ile Ala Val Ile
35 40 45

Val Phe Phe Leu Ile Gly Phe Met Ile Gly Tyr Leu Gly Tyr Cys Lys
50 55 60

Ser Ser Asp Gly Pro Gly Glu Thr Gly Gly Gly Gly Gly Ser Gly Gly
65 70 75 80

Gly Gly Ser Gly Gly Gly Gly Ser Ile Trp Glu Leu Lys Lys Asp Val
85 90 95

Tyr Val Val Glu Leu Asp Trp Tyr Pro Asp Ala Pro Gly Glu Met Val
100 105 110

Val Leu Thr Cys Asp Thr Pro Glu Glu Asp Gly Ile Thr Trp Thr Leu
115 120 125

Asp Gln Ser Ser Glu Val Leu Gly Ser Gly Lys Thr Leu Thr Ile Gln
130 135 140

```
Val Lys Glu Phe Gly Asp Ala Gly Gln Tyr Thr Cys His Lys Gly Gly
145                 150                 155                 160

Glu Val Leu Ser His Ser Leu Leu Leu Leu His Lys Lys Glu Asp Gly
                165                 170                 175

Ile Trp Ser Thr Asp Ile Leu Lys Asp Gln Lys Glu Pro Lys Asn Lys
            180                 185                 190

Thr Phe Leu Arg Cys Glu Ala Lys Asn Tyr Ser Gly Arg Phe Thr Cys
        195                 200                 205

Trp Trp Leu Thr Thr Ile Ser Thr Asp Leu Thr Phe Ser Val Lys Ser
    210                 215                 220

Ser Arg Gly Ser Ser Asp Pro Gln Gly Val Thr Cys Gly Ala Ala Thr
225                 230                 235                 240

Leu Ser Ala Glu Arg Val Arg Gly Asp Asn Lys Glu Tyr Glu Tyr Ser
                245                 250                 255

Val Glu Cys Gln Glu Asp Ser Ala Cys Pro Ala Ala Glu Glu Ser Leu
            260                 265                 270

Pro Ile Glu Val Met Val Asp Ala Val His Lys Leu Lys Tyr Glu Asn
        275                 280                 285

Tyr Thr Ser Ser Phe Phe Ile Arg Asp Ile Ile Lys Pro Asp Pro Pro
    290                 295                 300

Lys Asn Leu Gln Leu Lys Pro Leu Lys Asn Ser Arg Gln Val Glu Val
305                 310                 315                 320

Ser Trp Glu Tyr Pro Asp Thr Trp Ser Thr Pro His Ser Tyr Phe Ser
                325                 330                 335

Leu Thr Phe Cys Val Gln Val Gln Gly Lys Ser Lys Arg Glu Lys Lys
            340                 345                 350

Asp Arg Val Phe Thr Asp Lys Thr Ser Ala Thr Val Ile Cys Arg Lys
        355                 360                 365

Asn Ala Ser Ile Ser Val Arg Ala Gln Asp Arg Tyr Tyr Ser Ser Ser
    370                 375                 380

Trp Ser Glu Trp Ala Ser Val Pro Cys Ser Gly Gly Gly Gly Ser Gly
385                 390                 395                 400

Gly Gly Gly Ser Gly Gly Gly Gly Ser Gly Gly Gly Gly Ser Arg Asn
                405                 410                 415

Leu Pro Val Ala Thr Pro Asp Pro Gly Met Phe Pro Cys Leu His His
            420                 425                 430

Ser Gln Asn Leu Leu Arg Ala Val Ser Asn Met Leu Gln Lys Ala Arg
        435                 440                 445

Gln Thr Leu Glu Phe Tyr Pro Cys Thr Ser Glu Glu Ile Asp His Glu
    450                 455                 460

Asp Ile Thr Lys Asp Lys Thr Ser Thr Val Glu Ala Cys Leu Pro Leu
465                 470                 475                 480

Glu Leu Thr Lys Asn Glu Ser Cys Leu Asn Ser Arg Glu Thr Ser Phe
                485                 490                 495

Ile Thr Asn Gly Ser Cys Leu Ala Ser Arg Lys Thr Ser Phe Met Met
            500                 505                 510

Ala Leu Cys Leu Ser Ser Ile Tyr Glu Asp Leu Lys Met Tyr Gln Val
        515                 520                 525

Glu Phe Lys Thr Met Asn Ala Lys Leu Leu Met Asp Pro Lys Arg Gln
    530                 535                 540

Ile Phe Leu Asp Gln Asn Met Leu Ala Val Ile Asp Glu Leu Met Gln
545                 550                 555                 560
```

```
Ala Leu Asn Phe Asn Ser Glu Thr Val Pro Gln Lys Ser Ser Leu Glu
                565                 570                 575

Glu Pro Asp Phe Tyr Lys Thr Lys Ile Lys Leu Cys Ile Leu Leu His
            580                 585                 590

Ala Phe Arg Ile Arg Ala Val Thr Ile Asp Arg Val Met Ser Tyr Leu
        595                 600                 605

Asn Ala Ser
    610


<210> SEQ ID NO 80
<211> LENGTH: 253
<212> TYPE: PRT
<213> ORGANISM: Artificial Sequence
<220> FEATURE:
<223> OTHER INFORMATION: Synthetic Construct

<400> SEQUENCE: 80

Met Met Val Asp Gly Asp Asn Ser His Val Glu Met Lys Leu Ala Val
1               5                   10                  15

Asp Glu Glu Glu Asn Ala Asp Asn Asn Thr Lys Ala Asn Val Thr Lys
            20                  25                  30

Pro Lys Arg Cys Ser Gly Ser Ile Cys Tyr Gly Thr Ile Ala Val Ile
        35                  40                  45

Val Phe Phe Leu Ile Gly Phe Met Ile Gly Tyr Leu Gly Tyr Cys Lys
    50                  55                  60

Ser Ser Asp Gly Pro Gly Glu Thr Gly Gly Gly Gly Gly Ser Gly Gly
65                  70                  75                  80

Gly Gly Ser Gly Gly Gly Gly Ser Cys Asp Leu Pro Gln Thr His Ser
                85                  90                  95

Leu Gly Ser Arg Arg Thr Leu Met Leu Leu Ala Gln Met Arg Lys Ile
            100                 105                 110

Ser Leu Phe Ser Cys Leu Lys Asp Arg His Asp Phe Gly Phe Pro Gln
        115                 120                 125

Glu Glu Phe Gly Asn Gln Phe Gln Lys Ala Glu Thr Ile Pro Val Leu
    130                 135                 140

His Glu Met Ile Gln Gln Ile Phe Asn Leu Phe Ser Thr Lys Asp Ser
145                 150                 155                 160

Ser Ala Ala Trp Asp Glu Thr Leu Leu Asp Lys Phe Tyr Thr Glu Leu
                165                 170                 175

Tyr Gln Gln Leu Asn Asp Leu Glu Ala Cys Val Ile Gln Gly Val Gly
            180                 185                 190

Val Thr Glu Thr Pro Leu Met Lys Glu Asp Ser Ile Leu Ala Val Arg
        195                 200                 205

Lys Tyr Phe Gln Arg Ile Thr Leu Tyr Leu Lys Glu Lys Lys Tyr Ser
    210                 215                 220

Pro Cys Ala Trp Glu Val Val Arg Ala Glu Ile Met Arg Ser Phe Ser
225                 230                 235                 240

Leu Ser Thr Asn Leu Gln Glu Ser Leu Arg Ser Lys Glu
                245                 250


<210> SEQ ID NO 81
<211> LENGTH: 73
<212> TYPE: PRT
<213> ORGANISM: Artificial Sequence
<220> FEATURE:
<223> OTHER INFORMATION: Synthetic Construct

<400> SEQUENCE: 81
```

Met Met Val Asp Gly Asp Asn Ser His Val Glu Met Lys Leu Ala Val
1 5 10 15

Asp Glu Glu Glu Asn Ala Asp Asn Asn Thr Lys Ala Asn Val Thr Lys
20 25 30

Pro Lys Arg Cys Ser Gly Ser Ile Cys Tyr Gly Thr Ile Ala Val Ile
35 40 45

Val Phe Phe Leu Ile Gly Phe Met Ile Gly Tyr Leu Gly Tyr Cys Lys
50 55 60

Ser Ser Asp Gly Pro Gly Glu Thr Gly
65 70

<210> SEQ ID NO 82
<211> LENGTH: 43
<212> TYPE: PRT
<213> ORGANISM: Artificial Sequence
<220> FEATURE:
<223> OTHER INFORMATION: Synthetic Construct

<400> SEQUENCE: 82

Met Leu Lys Lys Arg Gly Asn His Ser Thr Gly Leu Cys Leu Leu Val
1 5 10 15

Met Phe Phe Met Val Leu Val Ala Leu Val Gly Leu Gly Leu Gly Met
20 25 30

Phe Gln Leu Phe His Leu Gln Lys Glu Thr Gly
35 40

<210> SEQ ID NO 83
<211> LENGTH: 756
<212> TYPE: DNA
<213> ORGANISM: Artificial Sequence
<220> FEATURE:
<223> OTHER INFORMATION: Synthetic Construct

<400> SEQUENCE: 83
atgagcctgc tgaccgaagt ggaaacctat gtgctgagca ttgtgccgag cggcccgctg 60
aaagcggaaa ttgcgcagcg cctggaagat gtgtttgcgg gcaaaaacac cgatctggaa 120
gtgctgatgg aatggctgaa aacccgcccg attctgagcc cgctgaccaa aggcattctg 180
ggctttgtgt ttaccctgac cgtgccgagc gaacgcggcc tgcagcgccg ccgctttgtg 240
cagaacgcgc tgaacggcaa cggcgatccg aacaacatgg ataaagcggt gaaactgtat 300
cgcaaactga aacgcgaaat tacctttcat ggcgcgaaag aaattgcgct gagctatagc 360
gcgggcgcgc tggcgagctg catgggcctg atttataacc gcatgggcgc ggtgaccacc 420
gaagtggcgt ttggcctggt gtgcgcgacc tgcgaacaga ttgcggatag ccagcatcgc 480
agccatcgcc agatggtgac caccaccaac ccgctgattc gccatgaaaa ccgcatggtg 540
ctggcgagca ccaccgcgaa agcgatggaa cagatggcgg gcagcagcga acaggcggcg 600
gaagcgatgg atattgcgag ccaggcgcgc cagatggtgc aggcgatgcg caccattggc 660
acccatccga gcagcagcgc gggcctgaaa gatgatctgc tggaaaacct gcaggcgtat 720
cagaaacgca tgggcgtgca gatgcagcgc tttaaa 756

<210> SEQ ID NO 84
<211> LENGTH: 759
<212> TYPE: DNA
<213> ORGANISM: Artificial Sequence
<220> FEATURE:
<223> OTHER INFORMATION: Synthetic Construct

<400> SEQUENCE: 84

```
atgtctctgc tgaccgaggt cgagacatac gtgctgagca tcgtgcctag cggccctctg     60
aaggccgaga tcgcccagag actggaagat gtgttcgccg gcaagaacac cgacctggaa    120
gtgctgatgg aatggctgaa aaccagacct atcctgagcc ccctgacaaa gggcatcctg    180
ggcttcgtgt tcaccctgac cgtgccaagc gagagaggcc tgcagcgcag aaggttcgtg    240
cagaacgccc tcaacggcaa tggcgacccc aacaacatgg ataaggctgt gaagctgtat    300
agaaagctga aaagagagat cacatttcac ggcgctaaag agattgccct ctcctacagc    360
gccggagccc tggcttcttg tatgggactg atctacaaca gaatgggagc cgtgaccacc    420
gaggtggcct tcggcctggt gtgcgccaca tgcgagcaaa tcgcagatag ccagcacaga    480
agccatcggc agatggtcac cacaacaaac cctctgatcc ggcacgagaa ccggatggtg    540
ctggccagca ccaccgccaa ggccatggaa cagatggccg gcagctctga gcaggccgct    600
gaagccatgg acatcgccag ccaggctaga cagatggttc aggccatgag aaccatcggc    660
acccaccctt ctagctccgc cggactgaag gacgacctgc tggaaaatct gcaagcctac    720
cagaagcgga tgggcgtgca gatgcagcgg tttaagtag                           759
```

<210> SEQ ID NO 85
<211> LENGTH: 1686
<212> TYPE: DNA
<213> ORGANISM: Artificial Sequence
<220> FEATURE:
<223> OTHER INFORMATION: Synthetic Construct

<400> SEQUENCE: 85

```
atggaaagca gaggcagacg gtgccccgag atgatctctg tgctgggccc tatctctggc     60
cacgtgctga aggccgtgtt cagcagaggc gatacacctg tgctgcccca cgagacaaga    120
ctgctgcaga caggcatcca tgtgcgggtg tcacagccta gcctgatcct ggtgtctcag    180
tacacccctg acagcacccc ttgtcacaga ggcgacaatc agctgcaggt ccagcacacc    240
tacttcaccg gcagcgaggt ggaaaacgtg tccgtgaacg tgcacaatcc caccggcaga    300
tccatctgtc ccagccaaga gcctatgagc atctacgtgt acgccctgcc tctgaagatg    360
ctgaacatcc ccagcatcaa tgtgcatcac taccccctctg ccgccgagcg gaaacacaga    420
catctgcctg tggccgatgc cgtgattcac gcctctggca aacagatgtg gcaggccaga    480
ctgacagtgt ccggactggc ttggaccaga cagcagaacc agtggaaaga acccgacgtg    540
tactacacca gcgccttcgt gttccccacc aaggatgtgg ccctgagaca cgttgtgtgc    600
gcccacgaac tcgtgtgcag catggaaaac acccgggcca ccaagatgca agtgatcggc    660
gaccagtacg tgaaggtgta cctggaaagc ttctgcgagg atgtgcccag cggcaagctg    720
ttcatgcacg tgacactggg ctccgacgtg gaagaggacc tgaccatgac cagaaatccc    780
cagcctttca tgcggcctca cgagagaaat ggcttcaccg tgctgtgccc caagaacatg    840
atcatcaagc ccggcaagat cagccacatc atgctggacg tggccttcac cagccacgag    900
cactttggac tgctgtgtcc taagagcatc cccggcctga gcatcagcgg caacctgctg    960
atgaatggcc agcagatctt cctggaagtg caggccatcc gggaaaccgt ggaactgaga   1020
cagtacgacc ctgtggctgc cctgttcttc ttcgacatcg acctgctgct ccagagaggc   1080
cctcagtact ctgagcaccc cacctttacc agccagtacc ggatccaggg aaagctggaa   1140
taccggcaca cctgggatag acacgatgaa ggtgctgccc agggcgacga tgatgtgtgg   1200
acaagcggca gcgatagcga cgaggaactg gtcaccaccg agagaaagac ccctagagtt   1260
```

```
acaggcggag gcgctatggc tggcgcctct acatctgccg gacggaagag aaagagcgcc   1320

tcttctgcca ccgcctgtac aagcggcgtg atgacaagag gcaggctgaa agccgagagc   1380

acagtggccc ctgaagagga cacagacgag gacagcgaca acgagattca caaccccgcc   1440

gtgtttacct ggcctccttg gcaggctgga atcctggcca gaaacctggt gcctatggtg   1500

gccacagtgc agggccagaa cctgaagtac caagagttct tctgggacgc caacgacatc   1560

taccggatct tcgccgaact ggaaggcgtg tggcaaccag ccgctcagcc taagagaaga   1620

aggcacagac aagacgctct gcccggacct tgtatcgcca gcactcccaa gaagcacaga   1680

ggctga                                                              1686
```

```
<210> SEQ ID NO 86
<211> LENGTH: 5
<212> TYPE: PRT
<213> ORGANISM: Artificial Sequence
<220> FEATURE:
<223> OTHER INFORMATION: Synthetic Construct

<400> SEQUENCE: 86

Gly Gly Gly Gly Ser
1               5


<210> SEQ ID NO 87
<211> LENGTH: 5
<212> TYPE: PRT
<213> ORGANISM: Artificial Sequence
<220> FEATURE:
<223> OTHER INFORMATION: Synthetic Construct

<400> SEQUENCE: 87

Glu Ala Ala Ala Lys
1               5


<210> SEQ ID NO 88
<211> LENGTH: 9
<212> TYPE: PRT
<213> ORGANISM: Artificial Sequence
<220> FEATURE:
<223> OTHER INFORMATION: Synthetic Construct

<400> SEQUENCE: 88

Asn Leu Val Pro Met Val Ala Thr Val
1               5


<210> SEQ ID NO 89
<211> LENGTH: 11
<212> TYPE: PRT
<213> ORGANISM: Artificial Sequence
<220> FEATURE:
<223> OTHER INFORMATION: Synthetic Construct

<400> SEQUENCE: 89

Arg Pro His Glu Arg Asn Gly Phe Thr Val Leu
1               5                   10


<210> SEQ ID NO 90
<211> LENGTH: 10
<212> TYPE: PRT
<213> ORGANISM: Artificial Sequence
<220> FEATURE:
<223> OTHER INFORMATION: Synthetic Construct

<400> SEQUENCE: 90
```

-continued

```
Thr Pro Arg Val Thr Gly Gly Gly Ala Met
1               5                   10


<210> SEQ ID NO 91
<211> LENGTH: 11
<212> TYPE: PRT
<213> ORGANISM: Artificial Sequence
<220> FEATURE:
<223> OTHER INFORMATION: Synthetic Construct

<400> SEQUENCE: 91

Tyr Ser Glu His Pro Thr Phe Thr Ser Gln Tyr
1               5                   10


<210> SEQ ID NO 92
<211> LENGTH: 9
<212> TYPE: PRT
<213> ORGANISM: Artificial Sequence
<220> FEATURE:
<223> OTHER INFORMATION: Synthetic Construct

<400> SEQUENCE: 92

Gly Ile Leu Gly Phe Val Phe Thr Leu
1               5


<210> SEQ ID NO 93
<211> LENGTH: 13
<212> TYPE: PRT
<213> ORGANISM: Artificial Sequence
<220> FEATURE:
<223> OTHER INFORMATION: Synthetic Construct

<400> SEQUENCE: 93

Thr Pro Pro Ala Tyr Arg Pro Pro Asn Ala Pro Ile Leu
1               5                   10
```

METHODS TO STIMULATE HLA-AGNOSTIC IMMUNE RESPONSES TO PROTEINS USING NUCLEATED CELLS

CROSS REFERENCE TO RELATED APPLICATIONS

This application claims the benefit of U.S. Provisional Application No. 63/073,910, filed on Sep. 2, 2020 and U.S. Provisional Application No. 63/147,473, filed on Feb. 9, 2021, the entire contents of each of which are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750322002940SEQLIST.TXT, date recorded: Sep. 1, 2021, size: 50,203 bytes).

FIELD OF THE INVENTION

The present disclosure relates generally to nucleated cells comprising a protein or fragment thereof, methods of manufacturing such modified nucleated cells, and methods of using such modified nucleated cells to stimulate an immune response.

BACKGROUND OF THE INVENTION

There are various challenges associated with the development of epitope vaccines. The research for these vaccines have been a focus in the field for decades, and though research and development of HLA-restricted epitope vaccines to treat cancer and to prevent infectious diseases have made substantial progress, only one peptide-based renal cell cancer vaccine (IMA901,9,10 which was developed by Immatics biotechnologies GmbH) is known to have entered a Phase III clinical trial (world wide web.immatics.com) See also, Zhao, L et al., *Hum Vaccin Immunother.* 2013 Dec. 1; 9(12): 2566-2577.

While effective, the limitations of HLA-restricted epitope vaccines are that they limit patient population coverage due to the rules of MHC restriction. In most cases, for example, a single peptide epitope vaccine restricted to HLA-A*02 will only be useful for treating patients expressing the HLA-A*02 (~40% of human population). Generating a vaccine that does not have these HLA restrictions and is therefore HLA agnostic would allow for the treatment of all patients regardless of HLA expression. HLA agnostic vaccines can be achieved by including full length protein of target antigens as part of the vaccine. Full length protein can be achieved by delivery of the protein itself, mRNA encoding the full-length protein and/or the use of overlapping synthetic long peptides (SLPs).

Current methods for inducing endogenous $CD8^+$ T cell responses in an HLA agnostic manner have relied on targeting antigen to dendritic cells for cross-presentation. Targeting antigen to dendritic cells and subsequent cross-presentation have compounding inefficiencies that have generally elicited CD4 T cell responses while sparing CD8 T cell responses. Therefore, there is a need for advancements in the field of epitope vaccines. $CD8^+$ cytotoxic T lymphocytes (CTL) and $CD4^+$ helper T (Th) cells stimulated by disease-associated antigens have the potential to target and destroy diseased cells.

All references cited herein, including patent applications and publications, are incorporated by reference in their entirety. The patent publications WO 2016070136, US 20180142198, WO 2017008063, US 20180201889, WO 2019178005, and WO 2019178006 and PCT/US2020/020194 are hereby expressly incorporated by reference in their entirety.

BRIEF SUMMARY OF THE INVENTION

In some aspects, the invention provides methods for stimulating an immune response in an individual, the method comprising administering an effective amount of a composition comprising nucleated cells to an individual, wherein the nucleated cells comprises a protein or fragment thereof; wherein the protein or fragment thereof stimulates an immune response regardless of the HLA haplotype of the individual. In some aspects, the invention provides methods for vaccinating an individual in need thereof, the method comprising administering an effective amount of a composition comprising nucleated cells to an individual, wherein the nucleated cells comprises a protein or fragment thereof; wherein the protein or fragment thereof stimulates an immune response regardless of the HLA haplotype of the individual.

In some aspects, the invention provides methods for stimulating an immune response in an individual, the method comprising administering an effective amount of a composition comprising nucleated cells to an individual, wherein the nucleated cells comprise a mRNA encoding a protein or fragment thereof; wherein the protein or fragment thereof stimulates an immune response regardless of the HILA haplotype of the individual. In some aspects, the invention provide methods for vaccinating an individual in need thereof, the method comprising administering an effective amount of a composition comprising nucleated cells to an individual, wherein the nucleated cells comprise a mRNA encoding a protein or fragment thereof; wherein the protein or fragment thereof stimulates an immune response regardless of the HLA haplotype of the individual. In some embodiments, the nucleotide sequence of the mRNA is codon optimized for expression in the nucleated cell. In some embodiments, one or more residues of the mRNA is modified. In some embodiments, one or more residues of the mRNA is a phosphorothioate residue, a pseudouridine residue, an N1-methyladenosine residue, a 5-methylcytidine residue, or a morpholino residue.

In some embodiments, the protein or fragment thereof is a fusion protein comprising the protein or fragment thereof and one or more immunoproteasome-targeting motifs. In some embodiments, the mRNA comprises one or more nucleic acid sequences encoding a immunoproteasome-targeting motif, wherein translation of the mRNA generates a fusion protein of the protein and the one or more immunoproteasome-targeting motifs. In some embodiments, the one or more immunoproteasome-targeting motifs enhance degradation of the protein in the cell and/or presentation of peptides derived from the protein on the surface of the cell compared to degradation of the protein in the cell and/or presentation of peptides derived from the protein on the surface of the cell in the absence of a immunoproteasome-targeting motif. In some embodiments, the one or more immunoproteasome-targeting motifs is at the N-terminus and/or the C-terminus of the fusion protein. In some embodiments, the one or more immunoproteasome-targeting motifs is a destruction box (D-box) domain, a KEKE domain, and/or a sec/MITD domain.

In some aspects, the invention provides methods for stimulating an immune response in an individual, the method comprising administering an effective amount of a composition comprising nucleated cells to an individual, wherein the nucleated cells comprises two or more antigens derived from a protein; wherein the two or more antigens stimulates an immune response regardless of the HLA haplotype of the individual. In some embodiments, the invention provides methods for vaccinating an individual in need thereof, the method comprising administering an effective amount of a composition comprising nucleated cells to an individual, wherein the nucleated cells comprises two or more antigens derived from a protein; wherein the two or more antigens stimulates an immune response regardless of the HLA haplotype of the individual. In some embodiments, the cells comprise three, four, five, six, seven, eight, nine, ten or more than ten antigens derived from the protein. In some embodiments, at least two of the antigens comprise partially overlapping amino acid sequences. In some embodiments, the combined amino acid sequences of all the antigens overlaps the amino acid sequence of the protein by about 90% or more. In some embodiments, the antigen is a polypeptide comprising two or more epitopes of the protein. In some embodiments, the antigen is a polypeptide comprising one or more epitopes of the protein and one or more heterologous peptide sequences. In some embodiments, one or more epitopes is flanked on the N-terminus and/or the C-terminus by one or more heterologous peptide sequences. In some embodiments, the N-terminal and/or C-terminal flanking polypeptides are derived from an immunogenic synthetic long peptide (SLP). In some embodiments, the N-terminal and/or C-terminal flanking polypeptides are derived from a disease-associated immunogenic SLP. In some embodiments, the one or more antigens is a series of overlapping SLPs that correspond to greater than about 90% of the amino acid sequence protein or about 100% of the amino acid sequence of the protein.

In some embodiments of the invention, wherein the protein is a mutated protein associated with cancer, a product of an oncogene, a neoantigen, a viral protein, a bacterial protein or a fungal protein. In some embodiments, stimulating an immune response in an individual is used for the treatment of a cancer, an infectious disease, or a viral-associated disease. In some embodiments, the viral-associated disease is a disease associated with human papillomavirus (HPV), hepatitis A virus (HAV), hepatitis B virus (HBV), hepatitis C virus (HCV), herpes simplex virus 1 (HSV-1), herpes simplex virus (HSV-2), varicella-zoster virus (VZV), human herpesvirus 6 (HHV-6), human herpesvirus 7 (HHV-7), human herpesvirus 8 (HHV-8), cytomegalovirus (CMV), human immunodeficiency virus (HIV), Epstein Barr virus (EBV) or influenza. In some embodiments, the protein is a human papillomavirus (HPV) protein. In some embodiments, the HPV is HPV-16 or HPV-18. In some embodiments, the protein is an HPV E6 or HPV E7 protein. In some embodiments, the protein is a hepatitis B virus (HBV) protein. In some embodiments, the HBV protein is a core protein, a small surface antigen, a medium surface antigen, a large surface antigen, an e antigen, an X antigen, or a polymerase protein.

In some embodiments of the invention, the composition further comprises an adjuvant. In some embodiments, the composition is administered in conjunction with an adjuvant. In some embodiments, the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR 9 agonist.

In some embodiments of the invention, the nucleated cells comprising the protein or fragment thereof are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the protein or fragment thereof to pass through to form a perturbed input nucleated cells; and b) incubating the perturbed input nucleated cells with the protein or fragment thereof to allow the protein or fragment thereof to enter the perturbed input nucleated cells; thereby generating nucleated cells comprising the protein or fragment thereof. In some embodiments, the nucleated cells comprising the mRNA encoding the protein or fragment thereof are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass though to form a perturbed input nucleated cells; and b) incubating the perturbed input nucleated cells with the mRNA encoding the protein or fragment thereof to allow the mRNA encoding the protein or fragment thereof to enter the perturbed input nucleated cells; thereby generating nucleated cells comprising the mRNA encoding the protein or fragment thereof. In some embodiments, the nucleated cells comprising two or more antigens are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the two or more antigens to pass through to form a perturbed input nucleated cells; and b) incubating the perturbed input nucleated cells with the two or more antigens to allow the two or more antigens to enter the perturbed input nucleated cells; thereby generating nucleated cells comprising two or more antigens. In some embodiments, the width of the constriction is about 10% to about 99% of the mean diameter of the input nucleated cells. In some embodiments, the width of the constriction is about 3.0 μm to about 4.2 μm or about 3.0 μm to about 4.8 μm or about 3.0 μm to about 6 μm or about 4.2 μm to about 4.8 pnm or about 4.2 μm to about 6 μm. In some embodiments, the width of the constriction is about 3.5 μm. In some embodiments, the width of the constriction is about 4.5 μm or about 4.0 μm. In some embodiments, the cell suspension comprising the plurality of input nucleated cells are passed through multiple constrictions wherein the multiple constrictions are arranged in series and/or in parallel.

In some embodiments of the invention, the nucleated cells are autologous or allogeneic to the individual. In some embodiments, the nucleated cells are immune cells. In some embodiments, the nucleated cells are a plurality of peripheral blood mononuclear cells (PBMCs). In some embodiments, the plurality of PBMCs comprise two or more of T cell, B cell, NK cell, monocytes, dendritic cells or NK-T cells. In some embodiments, the nucleated cells are one or more of T cells, B cells, NK cells, monocytes, dendritic cells and/or NK-T cells. In some embodiments, the nucleated cells are conditioned with an adjuvant to form conditioned cells. In some embodiments, the nucleated cells are incubated with the adjuvant for about 1 hour to about 24 hours, about 2 hours to about 10 hours, about 3 hours to about 6 hours, or about 4 hours for the cells to condition. In some embodiments, the nucleated cells are conditioned before or after introducing the protein or fragment thereof or the mRNA encoding the protein or fragment thereof into the nucleated cells. In some embodiments, the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR 9 agonist. In some embodiments, the adjuvant is a CpG oligodeoxynucleotide (ODN). In some embodiments, the adjuvant is CpG 7909.

In some embodiments of the invention, the conditioned cells are a conditioned plurality of PBMCs. In some embodiments, the plurality of PBMCs are modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of PBMCs are modified to increase expression of one or more cytokines. In some embodiments, the plurality of PBMCs are modified to comprise a chimeric membrane-bound cytokine. In some embodiments, the chimeric membrane-bound cytokine is a fusion protein comprising the cytokine and a transmembrane domain. In some embodiments, the cytokine is joined to the transmembrane domain by a peptide linker. In some embodiments, the peptide linker is $(G_4S)_3$ (SEQ ID NO:73) or $(EAAAK)_3$ (SEQ ID NO:74). In some embodiments, the cytokine is a Type I cytokine. In some embodiments, the cytokine is IL-15, IL-12, IL-2, IFN α, IFN β, or IL-21 or functional variant thereof. In some embodiments, the chimeric membrane-bound cytokine comprises the amino acid sequence of SEQ ID NOs:77-80.

In some embodiments, one or more co-stimulatory molecules is upregulated in the B cells of the conditioned plurality of PBMCs compared to the B cells in the plurality of nonconditioned PBMCs, wherein the co-stimulatory molecule is CD80 and/or CD86. In some embodiments, the plurality of PBMCs have increased expression of one or more of IFN-γ, IL-6, MCP-1, MIP-1β, IP-10, or TNF-α compared to a plurality of unconditioned PBMCs. In some embodiments, the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to the plurality of unconditioned PBMCs.

In some embodiments of the invention, the composition comprising nucleated cells is administered a plurality of times. In some embodiments, the composition is administered intravenously. In some embodiments, the individual is a human. In some embodiments, the composition is administered prior to, concurrently with, or following administration of another therapy. In some embodiments, another therapy is a chemotherapy, a radiation therapy, an antibody, a cytokine, an immune checkpoint inhibitor, or a bispecific polypeptide used in immune-oncology therapy.

In some aspects, the invention provides compositions comprising nucleated cells, wherein the nucleated cells comprises a protein or fragment thereof; wherein the protein or fragment thereof stimulates an immune response in an individual in an HLA agnostic manner. In some aspects, the invention provides a composition comprising nucleated cells, wherein the nucleated cells comprises a mRNA encoding a protein or fragment thereof; wherein the protein or fragment thereof stimulates an immune response in an individual in an HLA agnostic manner. In some embodiments, the nucleotide sequence of the mRNA is codon optimized for expression in the nucleated cell. In some embodiments, one or more residues of the mRNA is modified. In some embodiments, one or more residues of the mRNA is a phosphorothioate residue, a pseudouridine residue, an N1-methyladenosine residue, a 5-methylcytidine residue, or a morpholino residue.

In some embodiments, the protein or fragment thereof is a fusion protein comprising the protein or fragment thereof and one or more immunoproteasome-targeting motifs. In some embodiments, the mRNA comprises one or more nucleic acid sequences encoding a immunoproteasome-targeting motif, wherein translation of the mRNA generates a fusion protein of the protein and the one or more immunoproteasome-targeting motifs. In some embodiments, the one or more immunoproteasome-targeting motifs enhance degradation of the protein in the cell and/or presentation of peptides derived from the protein on the surface of the cell compared to degradation of the protein in the cell and/or presentation of peptides derived from the protein on the surface of the cell in the absence of a immunoproteasome-targeting motif. In some embodiments, the one or more immunoproteasome-targeting motifs is at the N-terminus and/or the C-terminus of the fusion protein. In some embodiments, the one or more immunoproteasome-targeting motifs is a destruction box (D-box) domain, a KEKE domain, and/or a sec/MITD domain.

In some embodiments the invention provides compositions comprising nucleated cells, wherein the nucleated cells comprises two or more antigens derived from a protein; wherein the protein or fragment thereof stimulates an immune response in an individual in an HLA agnostic manner. In some embodiments, the cells comprise three, four, five, six, seven, eight, nine, ten or more than ten antigens derived from the protein. In some embodiments, at least two of the antigens comprise partially overlapping amino acid sequences. In some embodiments, the combined amino acid sequences of all the antigens overlaps the amino acid sequence of the protein by about 90% or more. In some embodiments, the antigen is a polypeptide comprising two or more epitopes of the protein. In some embodiments, the antigen is a polypeptide comprising one or more epitopes of the protein and one or more heterologous peptide sequences. In some embodiments, one or more epitopes is flanked on the N-terminus and/or the C-terminus by one or more heterologous peptide sequences. In some embodiments, the N-terminal and/or C-terminal flanking polypeptides are derived from an immunogenic synthetic long peptide (SLP). In some embodiments, the N-terminal and/or C-terminal flanking polypeptides are derived from a disease-associated immunogenic SLP. In some embodiments, the one or more antigens is a series of overlapping SLPs that correspond to greater than about 90% of the amino acid sequence protein or about 100% of the amino acid sequence of the protein.

In some embodiments of the invention, wherein the protein is a mutated protein associated with cancer, a product of an oncogene, a neoantigen, a viral protein, a bacterial protein or a fungal protein. In some embodiments, stimulating an immune response in an individual is used for the treatment of a cancer, an infectious disease, or a viral-associated disease. In some embodiments, the viral-associated disease is a disease associated with human papillomavirus (HPV), hepatitis A virus (HAV), hepatitis B virus (HBV), hepatitis C virus (HCV), herpes simplex virus 1 (HSV-1), herpes simplex virus (HSV-2), varicella-zoster virus (VZV), human herpesvirus 6 (HHV-6), human herpesvirus 7 (HHV-7), human herpesvirus 8 (HHV-8), cytomegalovirus (CMV), human immunodeficiency virus (HIV), Epstein Barr virus (EBV) or influenza. In some embodiments, the protein is a human papillomavirus (HPV) protein. In some embodiments, the HPV is HPV-16 or HPV-18. In some embodiments, the protein is an HPV E6 or HPV E7 protein. In some embodiments, the protein is a hepatitis B virus (HBV) protein. In some embodiments, the HBV protein is a core protein, a small surface antigen, a medium surface antigen, a large surface antigen, an e antigen, an X antigen, or a polymerase protein. In some embodiments, the protein is a CMV protein. In some embodiments, the protein is CMV structural protein. In some embodiments, the protein is CMV pp65 protein. In some embodiments, the protein is an influenza protein. In some embodiments, the protein is an influenza matrix protein. In some embodiments, the protein is an influenza protein. In some embodiments, the protein is an influenza matrix protein. In some embodiments, the protein is influenza M1 protein. In some embodiments stimulating an immune response in an individual is used for the treatment of melanoma. In some embodiments, the protein is melanoma-associated antigen recognized by T cells (MART-1).

In some embodiments of the invention, the composition further comprises an adjuvant. In some embodiments, the composition is administered in conjunction with an adjuvant. In some embodiments, the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR 9 agonist.

In some embodiments of the invention, the nucleated cells comprising the protein or fragment thereof are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the protein or fragment thereof to pass through to form a perturbed input nucleated cells; and b) incubating the perturbed input nucleated cells with the protein or fragment thereof to allow the protein or fragment thereof to enter the perturbed input nucleated cells; thereby generating nucleated cells comprising the protein or fragment thereof. In some embodiments, the nucleated cells comprising the mRNA encoding the protein or fragment thereof are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; thereby generating nucleated cells comprising the mRNA encoding the protein or fragment thereof. In some embodiments, the nucleated cells comprising two or more antigens are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the two or more antigens to pass through to form a perturbed input nucleated cells; and b) incubating the perturbed input nucleated cells with the two or more antigens to allow the two or more antigens to enter the perturbed input nucleated cells; thereby generating nucleated cells comprising two or more antigens. In some embodiments, the width of the constriction is about 10% to about 99% of the mean diameter of the input nucleated cells. In some embodiments, the width of the constriction is about 3.0 μm to about 4.2 μm or about 3.0 μm to about 4.8 μm or about 3.0 μm to about 6 μm or about 4.2 μm to about 4.8 μm or about 4.2 μm to about 6 μm. In some embodiments, the width of the constriction is about 3.5 μm. In some embodiments, the width of the constriction is about 4.5 μm or about 4.0 μm. In some embodiments, the cell suspension comprising the plurality of input nucleated cells are passed through multiple constrictions wherein the multiple constrictions are arranged in series and/or in parallel.

In some embodiments of the invention, the nucleated cells are autologous or allogeneic to the individual. In some embodiments, the nucleated cells are immune cells. In some embodiments, the nucleated cells are a plurality of peripheral blood mononuclear cells (PBMCs). In some embodiments, the plurality of PBMCs comprise two or more of T cell, B cell, NK cell, monocytes, dendritic cells or NK-T cells. In some embodiments, the nucleated cells are one or more of T cells, B cells, NK cells, monocytes, dendritic cells and/or NK-T cells. In some embodiments, the nucleated cells are conditioned with an adjuvant to form conditioned cells. In some embodiments, the nucleated cells are incubated with the adjuvant for about 1 hour to about 24 hours, about 2 hours to about 10 hours, about 3 hours to about 6 hours, or about 4 hours for the cells to condition. In some embodiments, the nucleated cells are conditioned before or after introducing the protein or fragment thereof or the mRNA encoding the protein or fragment thereof into the nucleated cells. In some embodiments, the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR 9 agonist. In some embodiments, the adjuvant is a CpG oligodeoxynucleotide (ODN). In some embodiments, the adjuvant is CpG 7909.

In some embodiments of the invention, the conditioned cells are a conditioned plurality of PBMCs. In some embodiments, the plurality of PBMCs are modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1 BBL, OX40L, TL1A, GITRL, CD30L, TIM4, SLAM, CD48, CD58, CD155, or CD112. In some embodiments, the plurality of PBMCs are modified to increase expression of one or more cytokines. In some embodiments, the plurality of PBMCs are modified to comprise a chimeric membrane-bound cytokine. In some embodiments, the chimeric membrane-bound cytokine is a fusion protein comprising the cytokine and a transmembrane domain. In some embodiments, the cytokine is joined to the transmembrane domain by a peptide linker. In some embodiments, the peptide linker is $(G_4S)_3$ (SEQ ID NO:73) or $(EAAAK)_3$ (SEQ ID NO:74). In some embodiments, the cytokine is a Type I cytokine. In some embodiments, the cytokine is IL-15, IL-12, IL-2, IFN α, IFN β, or IL-21 or functional variant thereof. In some embodiments, the chimeric membrane-bound cytokine comprises the amino acid sequence of SEQ ID NOs:77-80.

In some embodiments, one or more co-stimulatory molecules is upregulated in the B cells of the conditioned plurality of PBMCs compared to the B cells in the plurality of nonconditioned PBMC, wherein the co-stimulatory molecule is CD80 and/or CD86. In some embodiments, the plurality of PBMCs have increased expression of one or more of IFN-γ, IL-6, MCP-1, MIP-1β, IP-10, or TNF-α compared to a plurality of unconditioned PBMCs. In some embodiments, the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to the plurality of unconditioned PBMCs.

In some aspects, the invention provides compositions for stimulating an immune response in an individual, wherein the composition comprises an effective amount of composition as described herein, wherein the composition stimulates an immune response in an individual in an HLA agnostic manner. In some aspects, the invention provides compositions for use as a medicine, wherein the composition comprises an effective amount of composition as described herein, wherein the composition stimulates an immune response in an individual in an HLA agnostic manner. In some aspects, the invention provides compositions for treating a cancer, an infectious disease, or a viral-associated disease in an individual, wherein the composition comprises an effective amount of composition as described herein, wherein the composition stimulates an immune response in an individual in an HLA agnostic manner. In some embodiments, the composition further comprises an adjuvant. In some embodiments, the composition is administered in conjunction with an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, a TLR3 agonist, a TLR4 agonist, a TLR7 agonist, a TLR8 agonist, or a TLR9 agonist. In some embodiments, the composition comprising nucleated cells is administered a plurality of times. In some embodiments, the composition is administered intravenously. In some embodiments, the individual is a human. In some embodiments, the composition is administered prior to, concurrently with, or following administration of another therapy. In some embodiments, another therapy is a chemotherapy, a radiation therapy, an antibody, a cytokine, an immune checkpoint inhibitor, or a bispecific polypeptide used in immune-oncology therapy.

In some aspects, the invention provides the use of a composition for in the manufacture of a medicament for stimulating an immune response in an individual, wherein the composition comprises an effective amount of composition as described herein, wherein the composition stimulates an immune response in an individual in an HILA agnostic manner. In some aspects, the invention provides the use of a composition in the manufacture of a medicament for treating a cancer, an infectious disease, or a viral-associated disease in an individual, wherein the composition comprises an effective amount of composition as described herein, wherein the composition stimulates an immune response in an individual in an HLA agnostic manner. In some embodiments, the composition further comprises an adjuvant. In some embodiments, the composition is formulated for administration in conjunction with an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, a TLR3 agonist, a TLR4 agonist, a TLR7 agonist, a TLR8 agonist, or a TLR9 agonist. In some embodiments, the composition comprising nucleated cells is administered a plurality of times. In some embodiments, the composition is administered intravenously. In some embodiments, the individual is a human. In some embodiments, the composition is administered prior to, concurrently with, or following administration of another therapy. In some embodiments, another therapy is a chemotherapy, a radiation therapy, an antibody, a cytokine, an immune checkpoint inhibitor, or a bispecific polypeptide used in immune-oncology therapy.

In some embodiments, the invention provides a kit for use in any one of the methods described herein. In some embodiments, the invention provides a kit comprising any of the compositions described herein. In some embodiments, the kit further comprises one or more of buffers, diluents, filters, needles, syringes, or package inserts with instructions for administering the composition to an individual to stimulate an immune response in an HLA agnostic manner.

In some aspects, the invention provides methods for producing nucleated cells comprising a protein or fragment thereof; the method comprising introducing the protein or fragment thereof into the nucleated cells, wherein the protein or fragment thereof stimulates an immune response in an individual in an HLA agnostic manner. In some aspects, the invention provides methods for producing nucleated cells comprising a protein or fragment thereof; the method comprising introducing mRNA encoding the protein or fragment thereof into the nucleated cells, wherein the mRNA is expressed to produce the protein or fragment thereof; wherein the protein or fragment thereof stimulates an immune response in an individual in an HLA agnostic manner. In some aspects, the invention provides methods for producing nucleated cells comprising a two or more antigens from a protein; the method comprising introducing the two or more antigens into the nucleated cells; wherein the protein or fragment thereof stimulates an immune response in an individual in an HLA agnostic manner. In some embodiments, introducing the protein or fragment thereof to the nucleate cell intracellularly comprises a) passing a cell suspension comprising input nucleated cells through a cell-deforming constriction, wherein a diameter of the constriction is a function of a diameter of the input nucleated cells in the suspension, thereby causing perturbations of the input nucleate cells large enough for the protein or fragment thereof to pass through to form a perturbed input nucleated cells; and b) incubating the perturbed input nucleated cells with the protein or fragment thereof to allow the protein or fragment thereof to enter the perturbed input nucleated cells; thereby generating nucleated cells comprising the protein or fragment thereof. In some embodiments of the inventions, the nucleated cells comprising the mRNA encoding the protein or fragment thereof are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; thereby generating nucleated cells comprising the mRNA encoding the protein or fragment thereof. In some embodiments, the nucleated cells comprising two or more antigens are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the two or more antigens to pass through to form a perturbed input nucleated cells; and b) incubating the perturbed input nucleated cells with the two or more antigens to allow the two or more antigens to enter the perturbed input nucleated cells; thereby generating nucleated cells comprising two or more antigens. In some embodiments, the width of the constriction is about 10% to about 99% of the mean diameter of the input nucleated cells. In some embodiments, the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm. In some embodiments, the width of the constriction is about 3.5 μm. In some embodiments, the width of the constriction is about 4.5 μm. In some embodiments, the cell suspension comprising the plurality of input nucleated cells are passed through multiple constrictions wherein the multiple constrictions are arranged in series and/or in parallel. In some embodiments, the method further comprising conditioning the nucleated cells with an adjuvant to form conditioned cells. In some embodiments, the nucleated cells are incubated with the adjuvant for about 1 hour to about 24 hours, about 2 hours to about 10 hours, about 3 hours to about 6 hours, or about 4 hours for the cells to condition. In some embodiments, the nucleated cells are conditioned before or after introducing the protein or fragment thereof, the mRNA encoding the protein or fragment thereof, or the two or more antigens from a protein into the nucleated cells.

In some aspects, the invention provides methods for enhancing the activity of an immune cell, the methods comprising expressing a nucleic acid encoding a chimeric membrane-bound cytokine in the immune cell. In some embodiments, the chimeric membrane-bound cytokine is a fusion protein comprising a transmembrane domain and a cytokine. In some embodiments, the transmembrane domain is a transferrin receptor protein 1 (TFRC) or a tumor necrosis factor transmembrane domain. In some embodiments, the cytokine is a Type I cytokine. In some embodiments, the cytokine is IL-15, IL-12, IL-2, IFN α, IFN β, or IL-21 or functional variant thereof. In some embodiments, the cytokine is joined to the transmembrane domain by a peptide linker. In some embodiments, the peptide linker is $(G_4S)_3$ (SEQ ID NO:73) or $(EAAAK)_3$ (SEQ ID NO:74). In some embodiments, the chimeric membrane-bound cytokine comprises the amino acid sequence of SEQ ID NOs:77-80.

In some embodiments, the immune cell further comprises an antigen. In some embodiments, the immune cell further comprises a mRNA encoding an antigen. In some embodiments, the antigen is a protein or fragment thereof, wherein the protein or fragment thereof stimulates an immune response regardless of the HLA haplotype of the individual. In some embodiments, the immune cell further comprises two or more antigens derived from a protein. In some embodiments, the two or more antigens stimulates an immune response regardless of the HLA haplotype of the individual. In some embodiments, the protein is a mutated protein associated with cancer, a product of an oncogene, a neoantigen, a viral protein, a bacterial protein or a fungal protein. In some embodiments, the protein is a human papillomavirus (HPV) protein. In some embodiments, the HPV is HPV-16 or HPV-18. In some embodiments, the protein is an HPV E6 or HPV E7 protein. In some embodiments, the protein is a hepatitis B virus (HBV) protein. In some embodiments, the HBV protein is a core protein, a small surface antigen, a medium surface antigen, a large surface antigen, an e antigen, an X antigen, or a polymerase protein.

In some embodiments of the invention, the immune cells are a plurality of peripheral blood mononuclear cells (PBMCs). In some embodiments, the plurality of PBMCs comprise two or more of T cell, B cell, NK cell, monocytes, dendritic cells or NK-T cells. In some embodiments, the immune cells are one or more of r cells, B cells, NK cells, monocytes, dendritic cells and/or NK-T cells. In some embodiments, the nucleated cells are conditioned with an adjuvant to form conditioned cells. In some embodiments, the nucleated cells are incubated with the adjuvant for about 1 hour to about 24 hours, about 2 hours to about 10 hours, about 3 hours to about 6 hours, or about 4 hours for the cells to condition. In some embodiments, the nucleated cells are conditioned before or after introducing the protein or fragment thereof or the mRNA encoding the protein or fragment thereof into the nucleated cells. In some embodiments, the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR9 agonist. In some embodiments, the adjuvant is a CpG oligodeoxynucleotide (ODN).

In some embodiments of the invention, the immune cells comprising the chimeric membrane-bound cytokine are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine to pass through to form a perturbed input immune cells; and b) incubating the perturbed input immune cells with the nucleic acid encoding the chimeric membrane-bound cytokine to allow the nucleic acid to enter the perturbed input immune cells where the nucleic acid encoding the chimeric membrane-bound cytokine is expressed; thereby generating immune cells comprising a chimeric membrane-bound cytokine. In some embodiments, the nucleic acid encoding the chimeric membrane-bound cytokine is a mRNA encoding the chimeric membrane-bound cytokine. In some embodiments, the immune cells comprising the chimeric membrane-bound cytokine and an antigen are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the antigen to pass through to form a perturbed input immune cells; and b) incubating the perturbed input immune cells with the nucleic acid encoding the chimeric membrane-bound cytokine and the antigen to allow the nucleic acid and the antigen to enter the perturbed input immune cells where the nucleic acid encoding the chimeric membrane-bound cytokine is expressed; thereby generating immune cells comprising a chimeric membrane-bound cytokine and an antigen. In some embodiments, the immune cells comprising the chimeric membrane-bound cytokine and an mRNA encoding a protein or fragment thereof are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and a nucleic acid encoding the antigen to pass through to form a perturbed input immune cells; and b) incubating the perturbed input immune cells with the nucleic acid encoding the chimeric membrane-bound cytokine and the nucleic acid encoding the antigen to allow the nucleic acid to enter the perturbed input immune cells where the nucleic acid encoding the chimeric membrane-bound cytokine and the nucleic acid encoding the antigen is expressed; thereby generating immune cells comprising a chimeric membrane-bound cytokine and an antigen. In some embodiments, the nucleic acid encoding the chimeric membrane-bound cytokine and/or the nucleic acid encoding the antigen is a mRNA. In some embodiments, the immune cells comprising the chimeric membrane-bound cytokine and the two or more antigens derived from a protein are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the two or more antigens derived from a protein to pass through to form a perturbed input immune cells; and b) incubating the perturbed input immune cells with the nucleic acid encoding the chimeric membrane-bound cytokine and the two or more antigens derived from a protein to allow the nucleic acid to enter the perturbed input immune cells where the nucleic acid encoding the chimeric membrane-bound cytokine is expressed; thereby generating immune cells comprising a chimeric membrane-bound cytokine and an antigen. In some embodiments, the width of the constriction is about 10% to about 99% of the mean diameter of the input nucleated cells. In some embodiments, the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm. In some embodiments, the width of the constriction is about 3.5 μm. In some embodiments, the width of the constriction is about 4.5 μm. In some embodiments, the cell suspension comprising the plurality of input nucleated cells are passed through multiple constrictions wherein the multiple constrictions are arranged in series and/or in parallel.

In some aspects, the invention provides compositions for enhancing the activity of an immune cell, the composition comprising a chimeric membrane-bound cytokine in the immune cell. In some embodiments, the chimeric membrane-bound cytokine is a fusion protein comprising a transmembrane domain and a cytokine. In some embodiments, the transmembrane domain is a transferrin receptor protein 1 (TFRC) or a tumor necrosis factor transmembrane domain. In some embodiments, the cytokine is a Type I cytokine. In some embodiments, the cytokine is IL-15, IL-12, IL-2, IFN α, IFN β, or IL-21 or functional variant thereof. In some embodiments, the cytokine is joined to the transmembrane domain by a peptide linker. In some embodiments, the peptide linker is $(G_4S)_3$ (SEQ ID NO:73) or $(EAAAK)_3$ (SEQ ID NO:74). In some embodiments, the chimeric membrane-bound cytokine comprises the amino acid sequence of SEQ ID NOs:77-80.

In some embodiments, the immune cell further comprises an antigen. In some embodiments, the immune cell further comprises a mRNA encoding an antigen. In some embodiments, the antigen is a protein or fragment thereof, wherein the protein or fragment thereof stimulates an immune response regardless of the HLA haplotype of the individual. In some embodiments, the immune cell further comprises two or more antigens derived from a protein. In some embodiments, the two or more antigens stimulates an immune response regardless of the HLA haplotype of the individual. In some embodiments, the protein is a mutated protein associated with cancer, a product of an oncogene, a neoantigen, a viral protein, a bacterial protein or a fungal protein. In some embodiments, the protein is a human papillomavirus (HPV) protein. In some embodiments, the HPV is HPV-16 or HPV-18. In some embodiments, the protein is an HPV E6 or HPV E7 protein. In some embodiments, the protein is a hepatitis B virus (HBV) protein. In some embodiments, the HBV protein is a core protein, a small surface antigen, a medium surface antigen, a large surface antigen, an e antigen, an X antigen, or a polymerase protein.

In some embodiments of the invention, the immune cells are a plurality of peripheral blood mononuclear cells (PBMCs). In some embodiments, the plurality of PBMCs comprise two or more of T cell, B cell, NK cell, monocytes, dendritic cells or NK-T cells. In some embodiments, the immune cells are one or more of T cells, B cells, NK cells, monocytes, dendritic cells and/or NK-T cells. In some embodiments, the nucleated cells are conditioned with an adjuvant to form conditioned cells. In some embodiments, the nucleated cells are incubated with the adjuvant for about 1 hour to about 24 hours, about 2 hours to about 10 hours, about 3 hours to about 6 hours, or about 4 hours for the cells to condition. In some embodiments, the nucleated cells are conditioned before or after introducing the protein or fragment thereof or the mRNA encoding the protein or fragment thereof into the nucleated cells. In some embodiments, the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR9 agonist. In some embodiments, the adjuvant is a CpG oligodeoxynucleotide (ODN).

In some embodiments of the invention, the immune cells comprising the chimeric membrane-bound cytokine are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine to pass through to form a perturbed input immune cells; and b) incubating the perturbed input immune cells with the nucleic acid encoding the chimeric membrane-bound cytokine to allow the nucleic acid to enter the perturbed input immune cells where the nucleic acid encoding the chimeric membrane-bound cytokine is expressed; thereby generating immune cells comprising a chimeric membrane-bound cytokine. In some embodiments, the nucleic acid encoding the chimeric membrane-bound cytokine is a mRNA encoding the chimeric membrane-bound cytokine. In some embodiments, the immune cells comprising the chimeric membrane-bound cytokine and an antigen are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the antigen to pass through to form a perturbed input immune cells; and b) incubating the perturbed input immune cells with the nucleic acid encoding the chimeric membrane-bound cytokine and the antigen to allow the nucleic acid and the antigen to enter the perturbed input immune cells where the nucleic acid encoding the chimeric membrane-bound cytokine is expressed; thereby generating immune cells comprising a chimeric membrane-bound cytokine and an antigen. In some embodiments, the immune cells comprising the chimeric membrane-bound cytokine and an mRNA encoding a protein or fragment thereof are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and a nucleic acid encoding the antigen to pass through to form a perturbed input immune cells; and b) incubating the perturbed input immune cells with the nucleic acid encoding the chimeric membrane-bound cytokine and the nucleic acid encoding the antigen to allow the nucleic acid to enter the perturbed input immune cells where the nucleic acid encoding the chimeric membrane-bound cytokine and the nucleic acid encoding the antigen is expressed; thereby generating immune cells comprising a chimeric membrane-bound cytokine and an antigen. In some embodiments, the nucleic acid encoding the chimeric membrane-bound cytokine and/or the nucleic acid encoding the antigen is a mRNA. In some embodiments, the immune cells comprising the chimeric membrane-bound cytokine and the two or more antigens derived from a protein are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the two or more antigens derived from a protein to pass through to form a perturbed input immune cells; and b) incubating the perturbed input immune cells with the nucleic acid encoding the chimeric membrane-bound cytokine and the two or more antigens derived from a protein to allow the nucleic acid to enter the perturbed input immune cells where the nucleic acid encoding the chimeric membrane-bound cytokine is expressed; thereby generating immune cells comprising a chimeric membrane-bound cytokine and an antigen. In some embodiments, the width of the constriction is about 10% to about 99% of the mean diameter of the input nucleated cells. In some embodiments, the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm. In some embodiments, the width of the constriction is about 3.5 μm. In some embodiments, the width of the constriction is about 4.5 μm. In some embodiments, the cell suspension comprising the plurality of input nucleated cells are passed through multiple constrictions wherein the multiple constrictions are arranged in series and/or in parallel.

In some aspects, the invention provides compositions for use as a medicine, wherein the composition comprises an effective amount of composition comprising cells comprising a chimeric membrane-bound cytokine as described herein. In some aspects, the invention provides compositions for treating a cancer, an infectious disease, or a viral-associated disease in an individual, wherein the composition comprises an effective amount of composition comprising cells comprising a chimeric membrane-bound cytokine as described herein.

In some aspects, the invention provides methods for producing immune cells comprising a chimeric membrane-bound cytokine, the method comprising introducing a nucleic acid encoding the chimeric membrane-bound cytokine to the immune cells. In some embodiments, the immune cells comprising the chimeric membrane-bound cytokine are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine to pass through to form a perturbed input immune cells; and b) incubating the perturbed input immune cells with the nucleic acid encoding the chimeric membrane-bound cytokine to allow the nucleic acid to enter the perturbed input immune cells where the nucleic acid encoding the chimeric membrane-bound cytokine is expressed; thereby generating immune cells comprising a chimeric membrane-bound cytokine. In some embodiments, the nucleic acid encoding the chimeric membrane-bound cytokine is a mRNA encoding the chimeric membrane-bound cytokine. In some embodiments, the width of the constriction is about 10% to about 99% of the mean diameter of the input nucleated cells. In some embodiments, the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm. In some embodiments, the width of the constriction is about 3.5 μm. In some embodiments, the width of the constriction is about 4.5 μm. In some embodiments, the cell suspension comprising the plurality of input nucleated cells are passed through multiple constrictions wherein the multiple constrictions are arranged in series and/or in parallel.

Figure 29B:
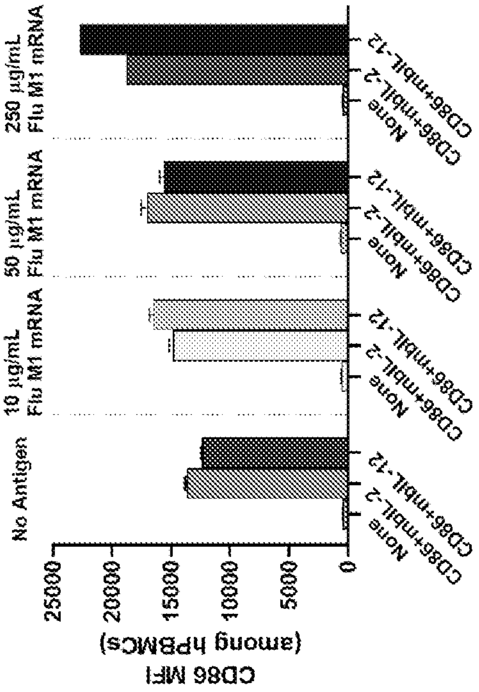
FIGS. 29A, B are graphs showing the percentage of CD86-expressing cells and the amount of CD86 expression, respectively, in PBMCs that are squeeze-loaded with the indicated amount of mRNAs encoding for Influenza M1 antigen, CD86, membrane-bound IL-2 (mbIL-2) and/or membrane-bound IL-12 (mbIL-12).
Figure 29A:
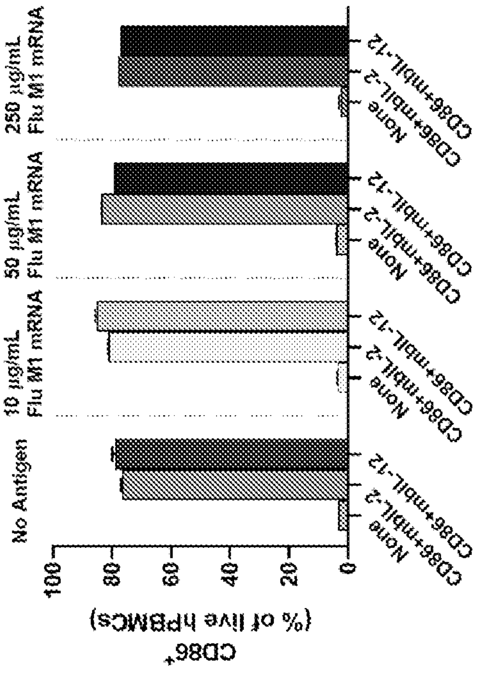
Figure 29C:
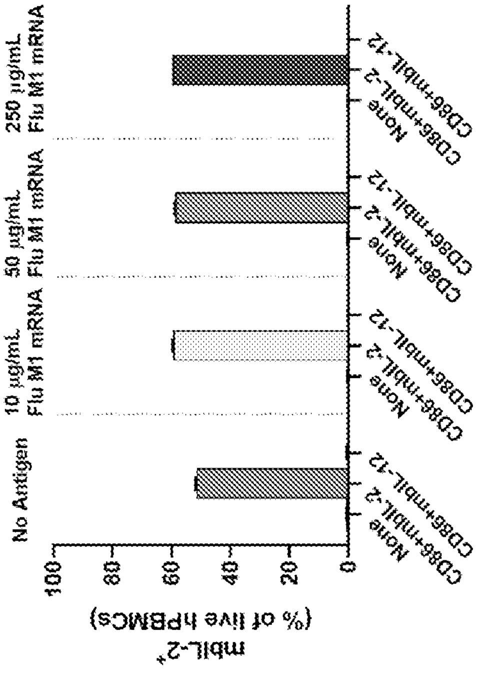
Figure 29D:
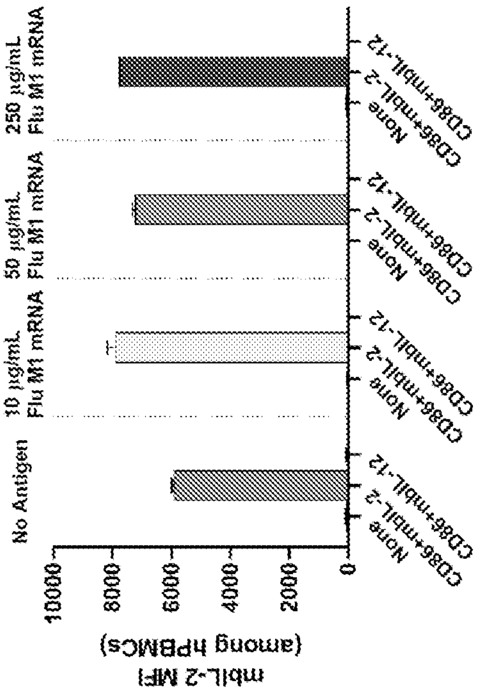

FIGS. 29C, D are graphs showing the percentage of membrane-bound IL-2 (mbIL-2) expressing cells and the amount of mbIL-2 expression, respectively, in PBMCs that are squeeze-loaded with the indicated amount of mRNAs encoding for Influenza M1 antigen, CD86, membrane-bound IL-2 (mbIL-2) and/or membrane-bound IL-12 (mbIL-12).

Figure 29E:
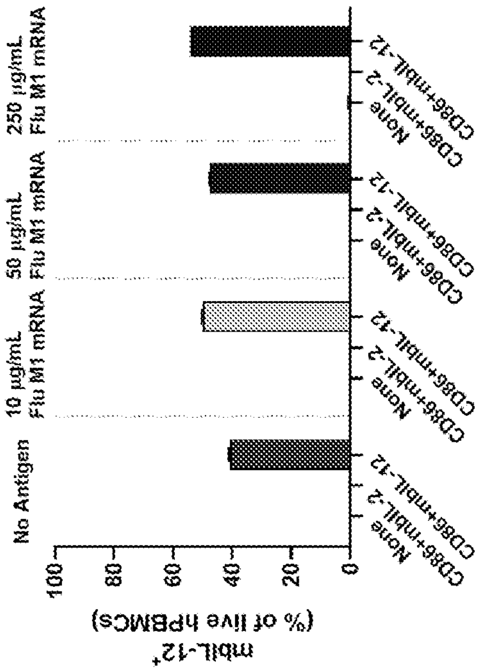
Figure 29F:
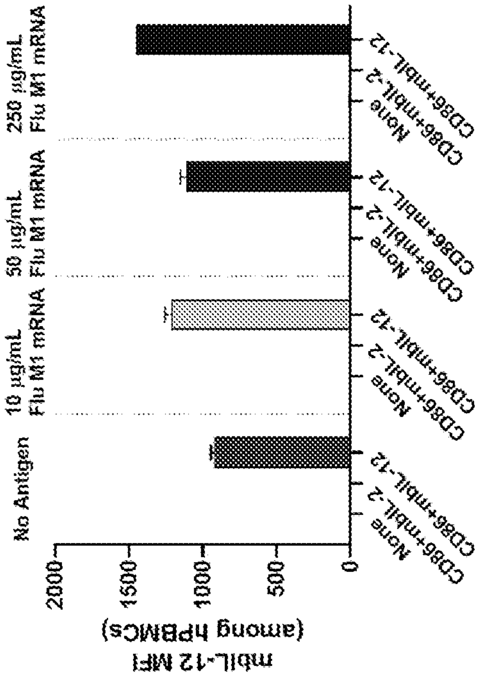

FIGS. 29E, Fare graphs showing the percentage of membrane-bound IL-12 (mbIL-12) expressing cells and the amount of mbIL-12 expression, respectively, in PBMCs that are squeeze-loaded with the indicated amount of mRNAs encoding for Influenza M1 antigen, CD86, membrane-bound IL-2 (mbIL-2) and/or membrane-bound IL-12 (mbIL-12).

Figure 30:
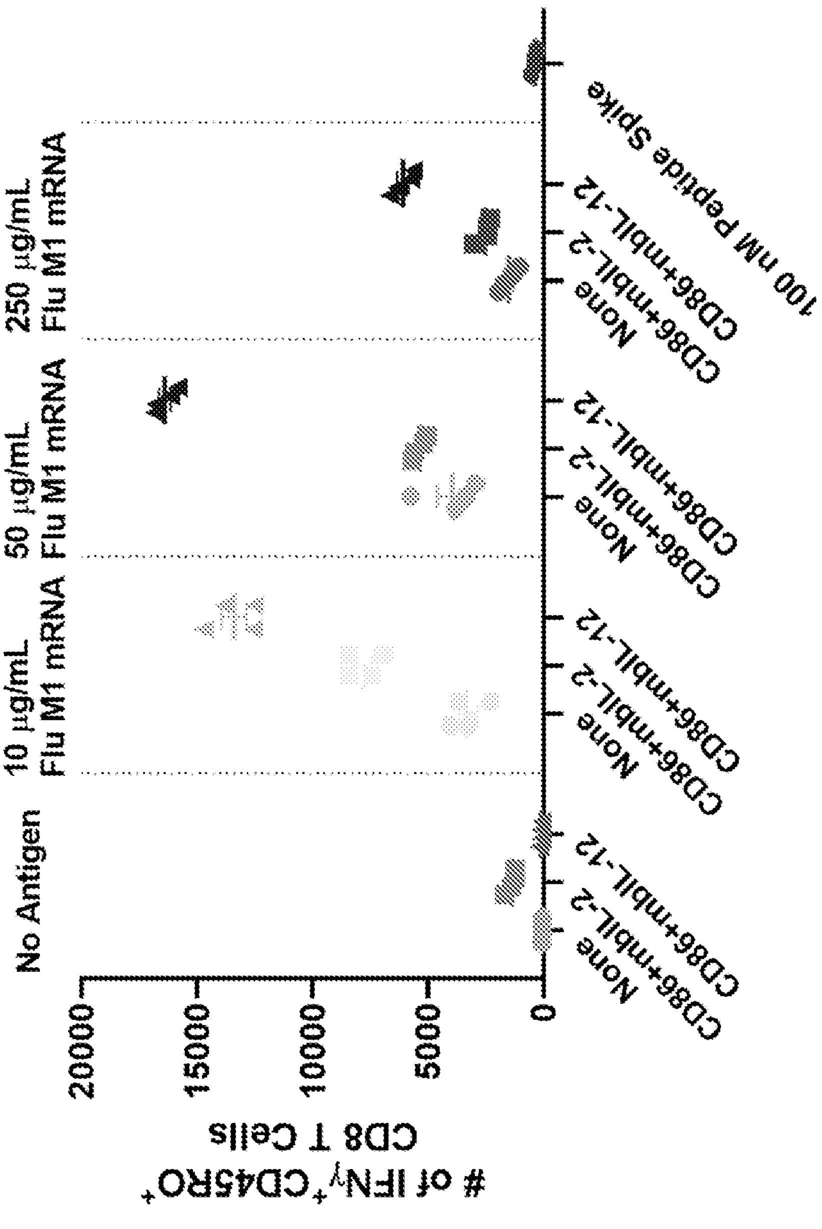

FIG. 30 is a graph showing the amount of IFN-γ+ CD45RO+ CD8 T cells when PBMCs are squeeze-loaded with the indicated amount of mRNAs encoding for Influenza M1 antigen, CD86, mbIL-2 and/or mbIL-12, with further re-stimulation with 1 μM of M1 antigen peptide.

Figure 31:
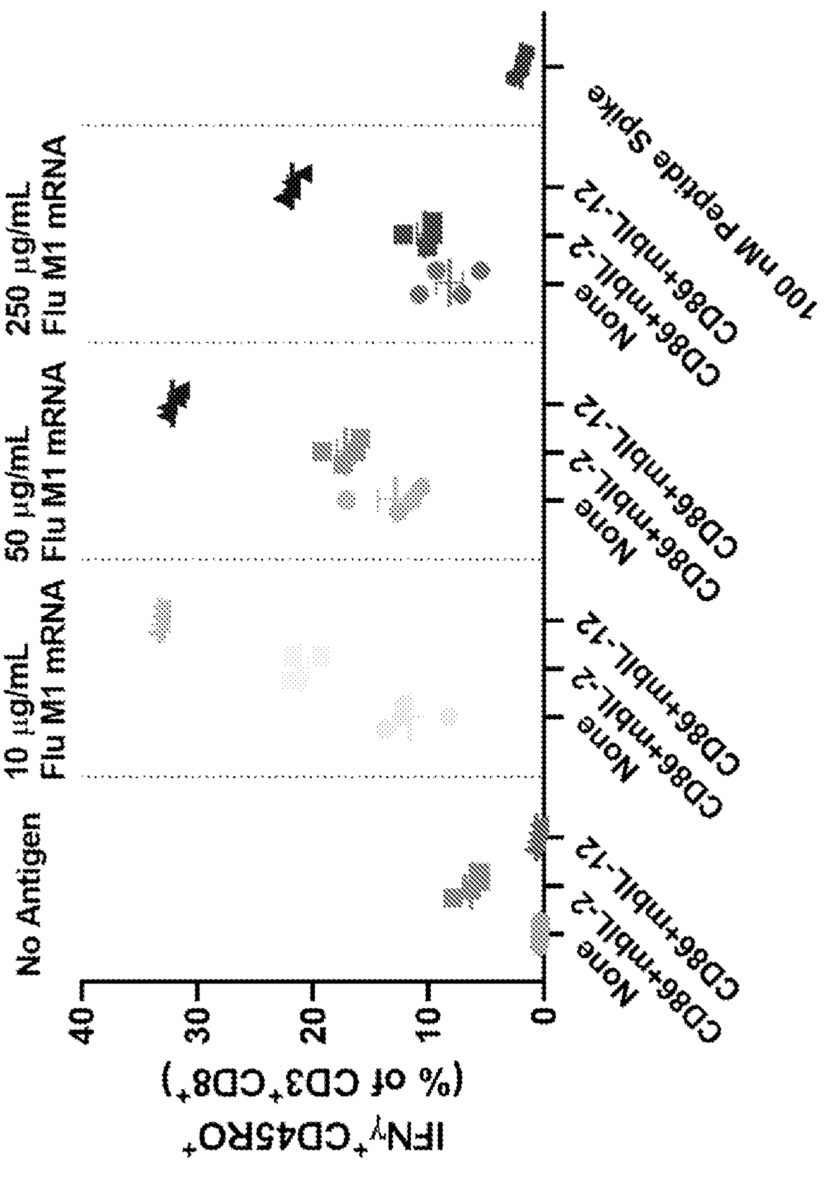

FIG. 31 is a graph showing the amount of IFN-γ+ CD45RO+ population within CD3+CD8+ responder T cells when PBMCs are squeeze-loaded with the indicated amount of mRNAs encoding for Influenza M1 antigen, CD86, mbIL-2 and/or mbIL-12, with further re-stimulation with 1 μM of M1 antigen peptide.

Figure 32:
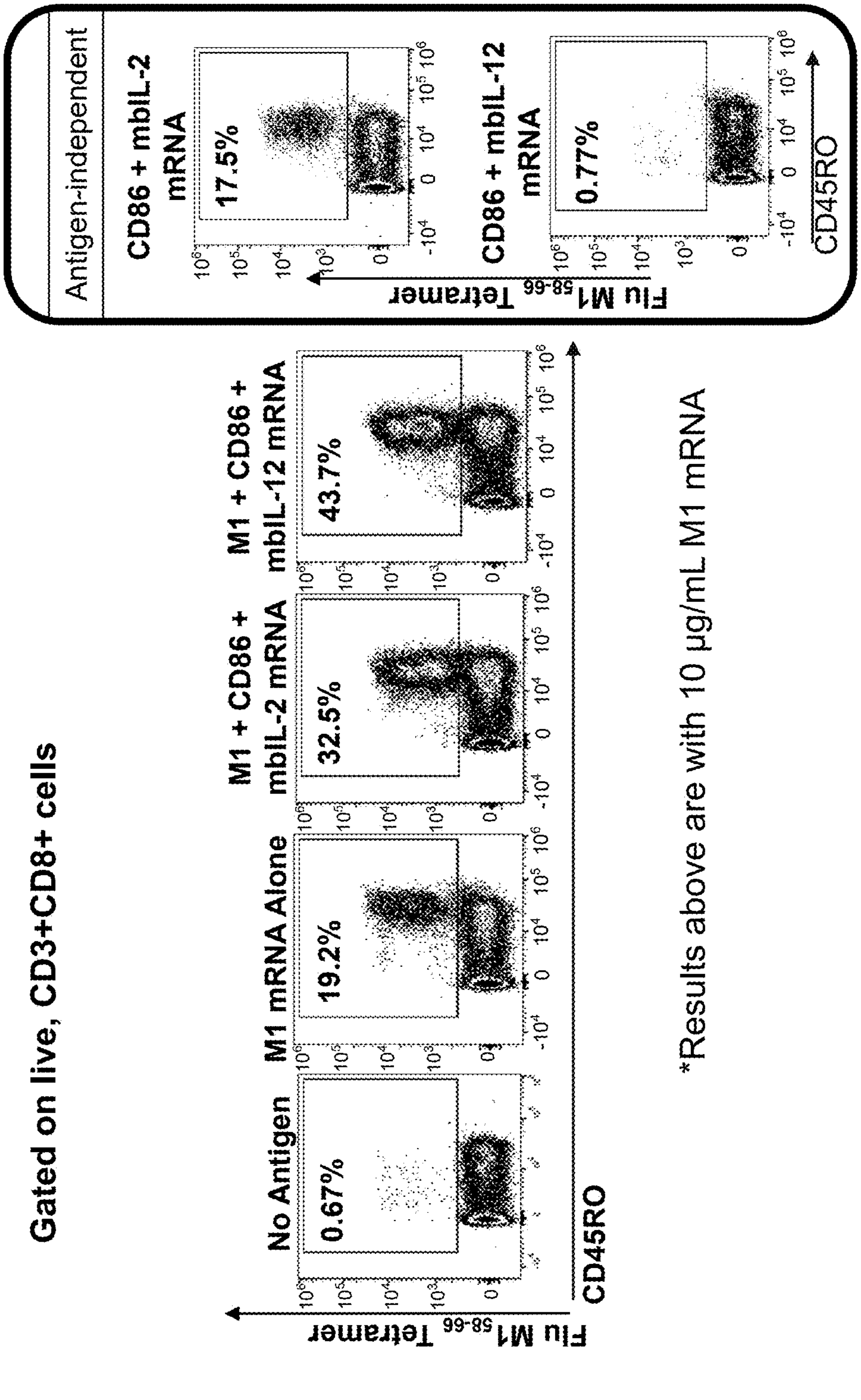

FIG. 32 contains graphs showing the amount of Influenza M1 tetramer-positive T cell population within CD3+CD8+ responder T cells when PBMCs are squeeze-loaded with the indicated amount of mRNAs encoding for M1 antigen, CD86, mbIL-2 and/or mbIL-12, that are treated with or without re-stimulation by 1 μM of pp65 antigen, and further cultured with or without conditioning by CpG adjuvant.

Figure 33:
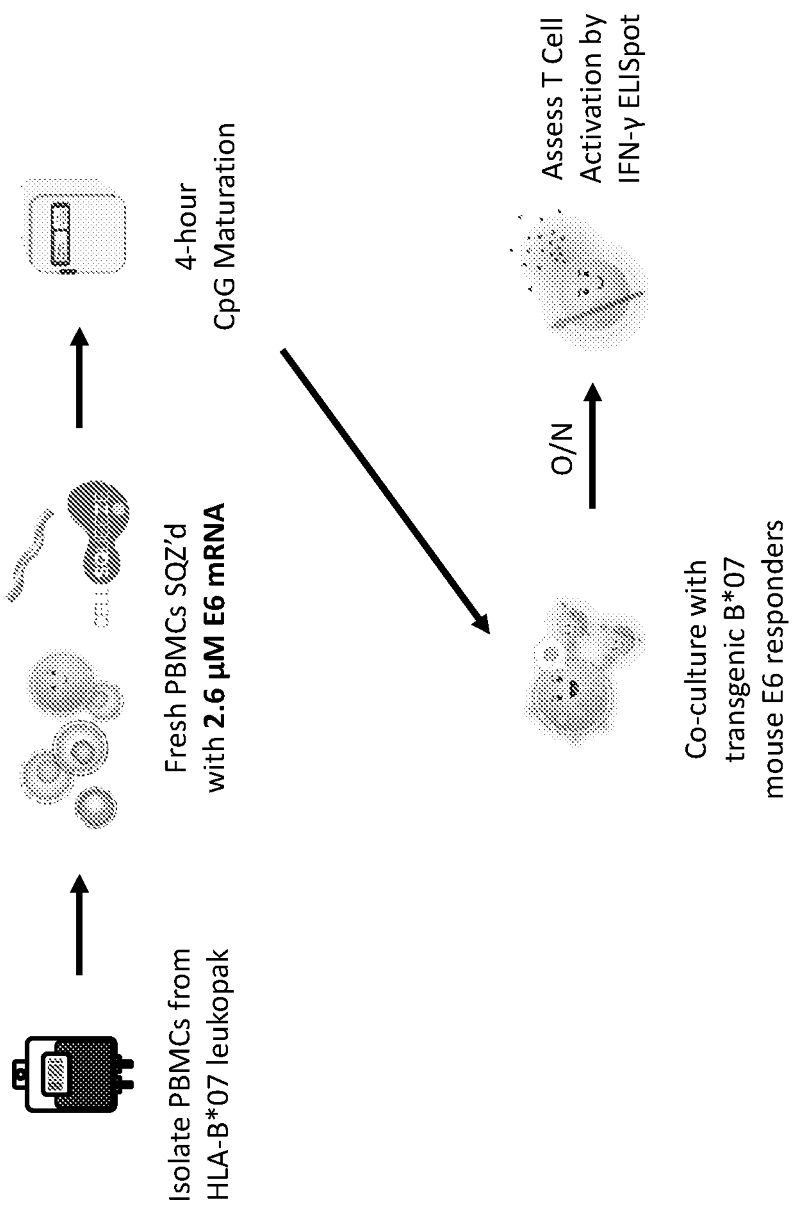

FIG. 33 is a schematic diagram showing an experiment to determine if PBMCs of a specific HLA haplotype squeeze-loaded with mRNA encoding for HPV16 E6 can induce an antigen-specific T cell response.

Figure 34:
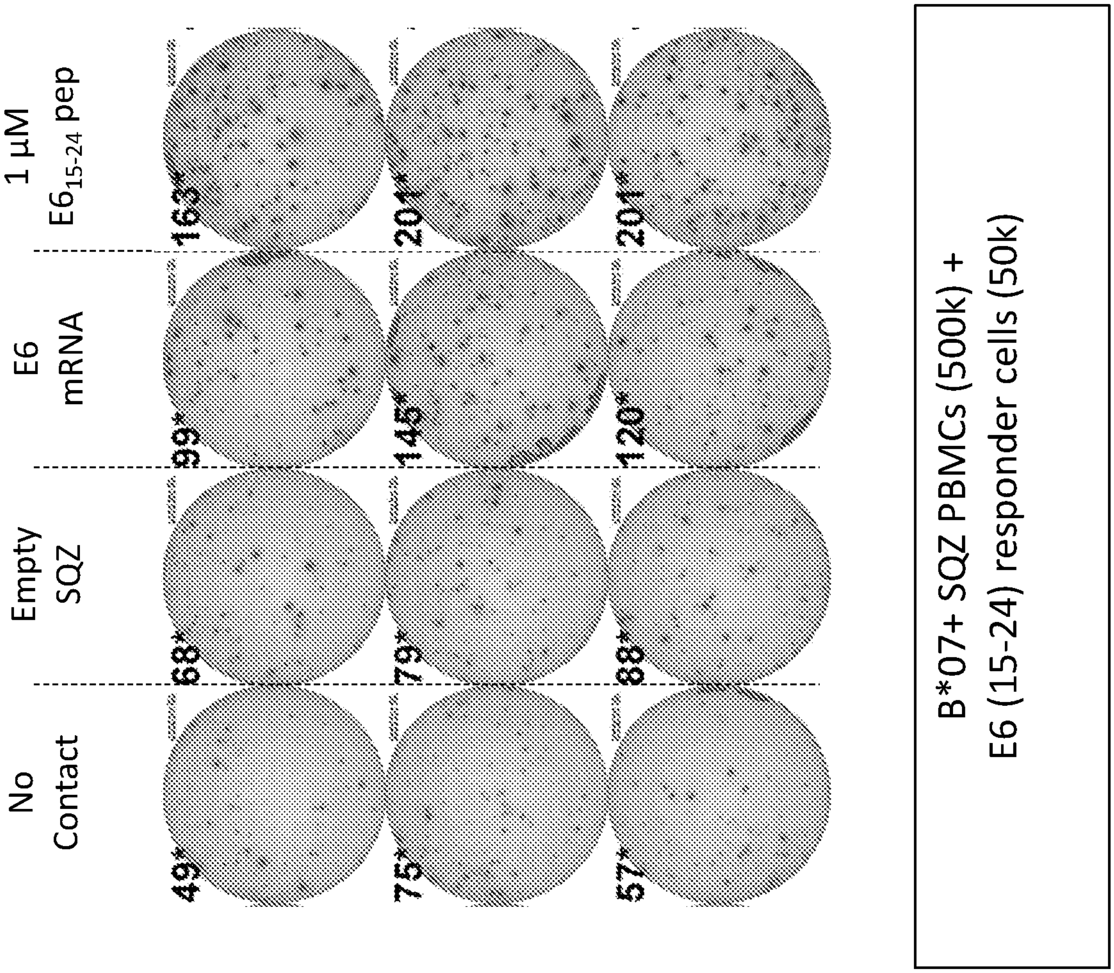

FIG. 34 is the image of ELISPOT plates of $E6_{15-24}$ responder T cells co-cultured with either E6 mRNA squeeze-loaded PBMCs (E6 mRNA), untreated PBMCs (No Contact), mock-squeeze-loaded PBMCs (Empty squeeze), or No Contact PBMCs spiked with 1 mM $E6_{15-24}$ peptide (positive control), and developed according to manufacturer's protocol.

Figure 35:
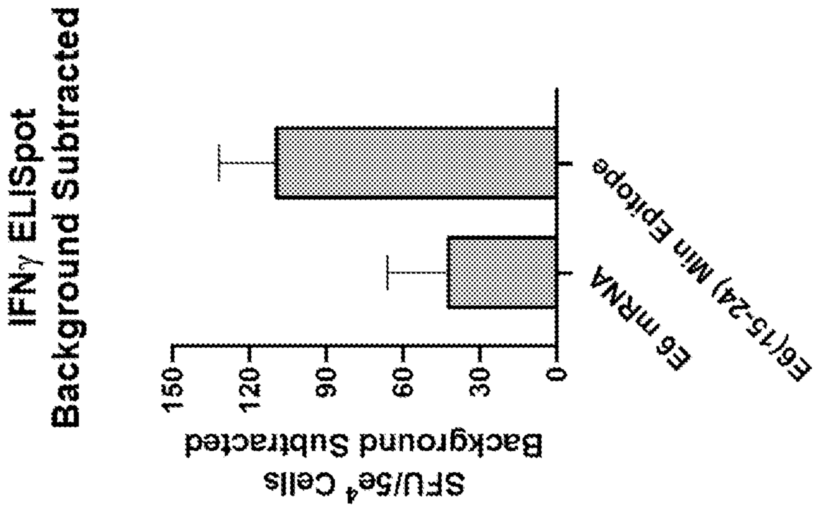
Figure 36:
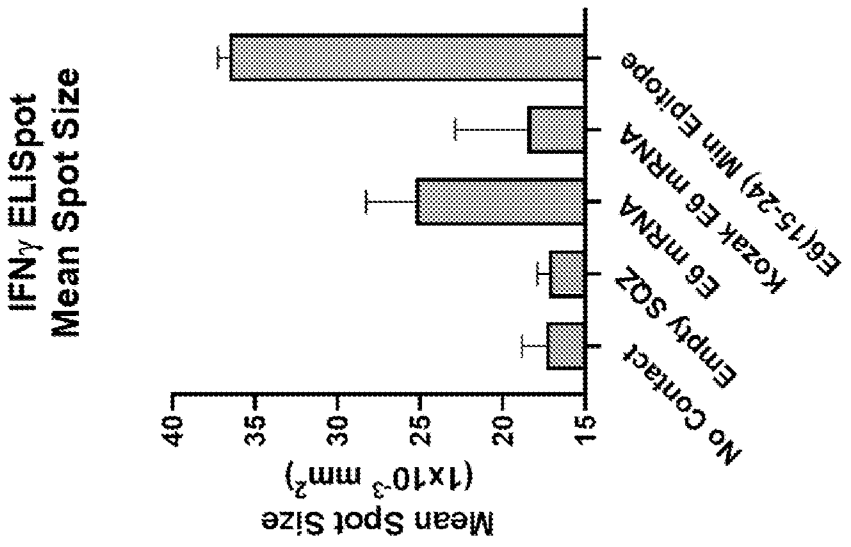

FIG. 35 shows the average amount of spot formation units (SFU) per cells in IFN-γ ELISPOT assay on $E6_{15-24}$ responder T cells that were co-cultured with either E6 mRNA squeeze-loaded PBMCs (E6 mRNA), untreated PBMCs spiked with 1 mM $E6_{15-24}$ peptide (positive control), and developed according to manufacturer's protocol FIG. 36 shows the mean spot size in IFN-γ ELISPOT assay on $E6_{15-24}$ responder T cells were co-cultured with either E6 mRNA squeeze-loaded PBMCs (E6 mRNA), untreated PBMCs (Empty squeeze), mock-squeeze-loaded PBMCs (Empty squeeze), or untreated PBMCs spiked with 1 mM $E6_{15-24}$ peptide (positive control), and developed according to manufacturer's protocol.

Figure 37:
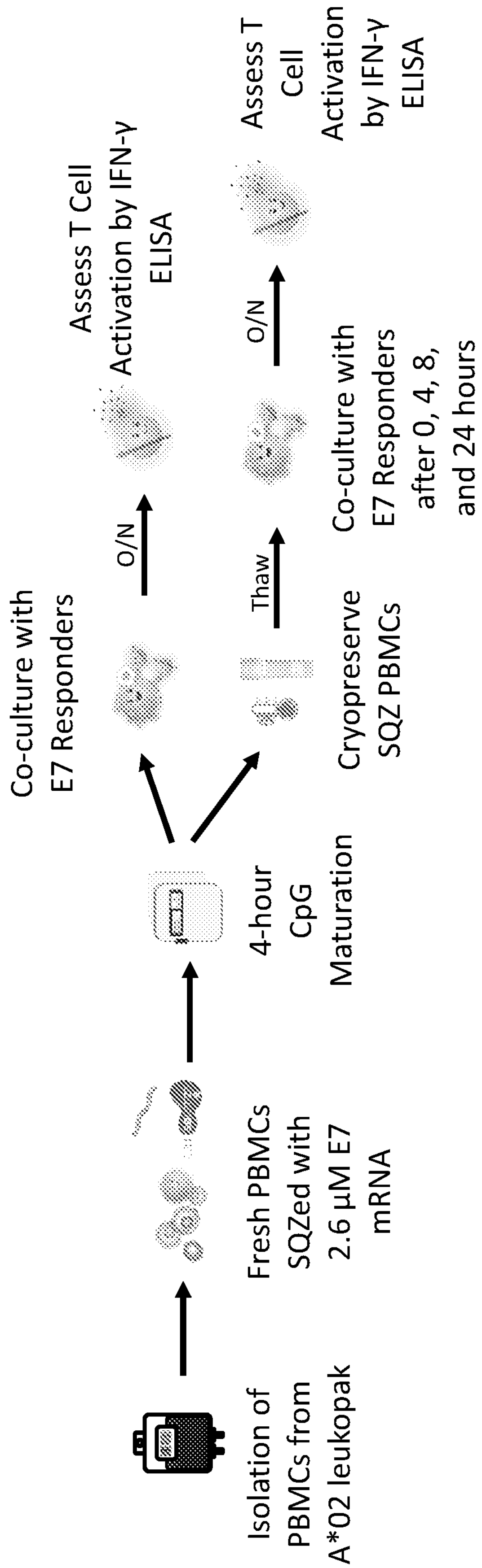

FIG. 37 is a schematic diagram showing the length of time that PBMCs of a specific HLA haplotype squeeze-loaded with E7 mRNA can elicit an antigen-specific T cell response.

Figure 38A:
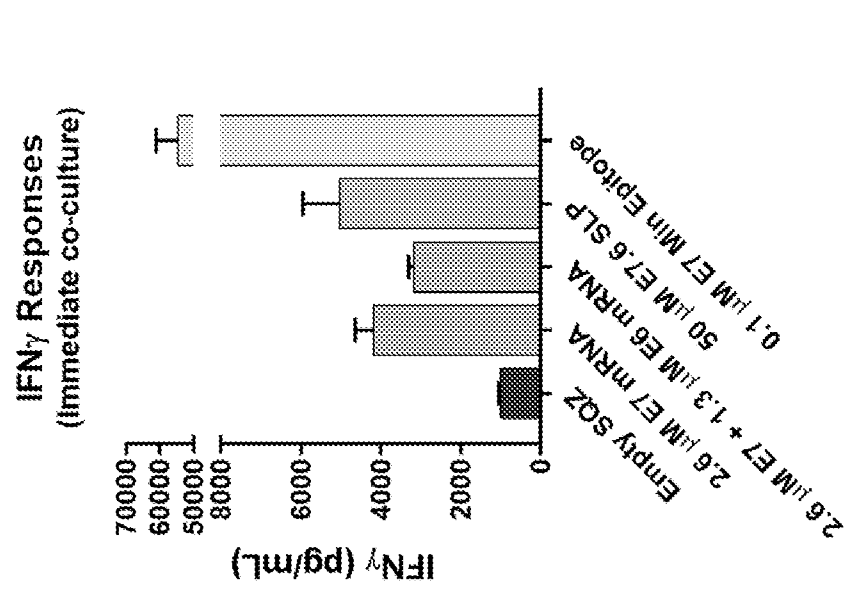

FIG. 38A is a graph showing the results of IFN-γ ELISA on $E7_{11-20}$ responder T cells that were co-cultured with PBMCs that were squeeze-loaded with (i) E7 mRNA, (ii) E7 mRNA and E6 mRNA, (iv) E7.6 synthetic long peptide (SLP) or (v) with no cargo (Empty squeeze), or with untreated PBMCs in the presence of $E7_{11-20}$ peptide (E7 Min Epitope).

Figure 38B:
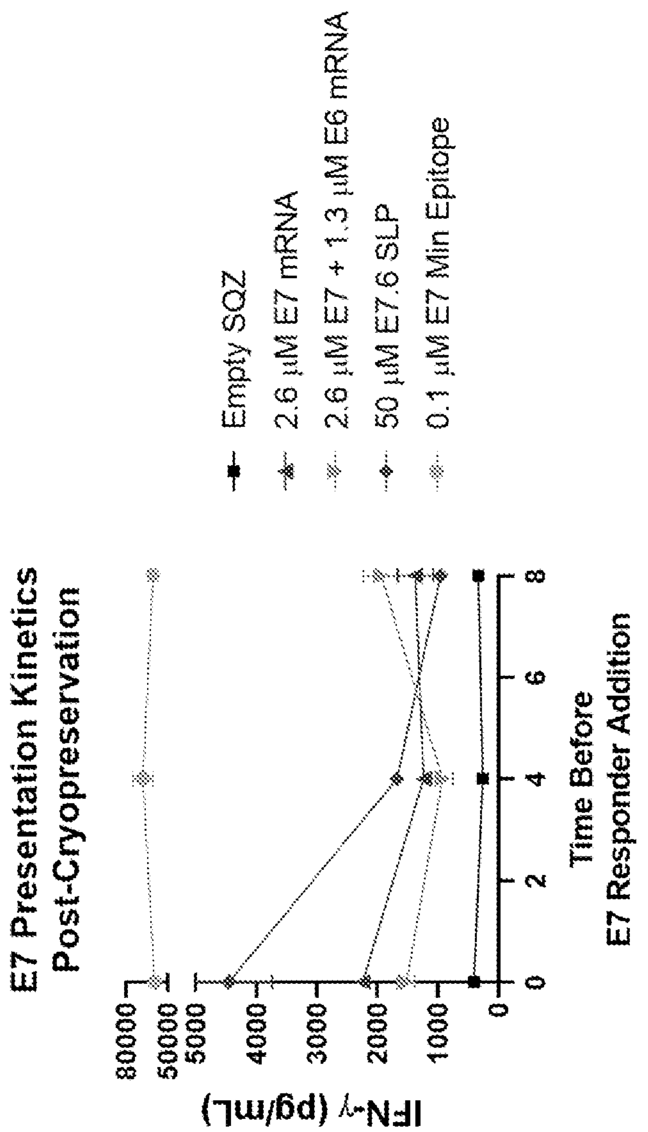

FIG. 38B is a graph showing the results of IFN-γ ELISA on $E7_{11-20}$ responder T cells that were co-cultured with PBMCs that were squeeze-loaded with (i) E7 mRNA, (ii) E7 mRNA and E6 mRNA, (iv) E7.6 synthetic long peptide (SLP) or (v) with no cargo (Empty squeeze), or with untreated PBMCs in the presence of $E7_{11-20}$ a peptide (E7 Min Epitope) wherein the PBMCs were cultured for the indicated time periods before co-culturing.

Figure 39B:
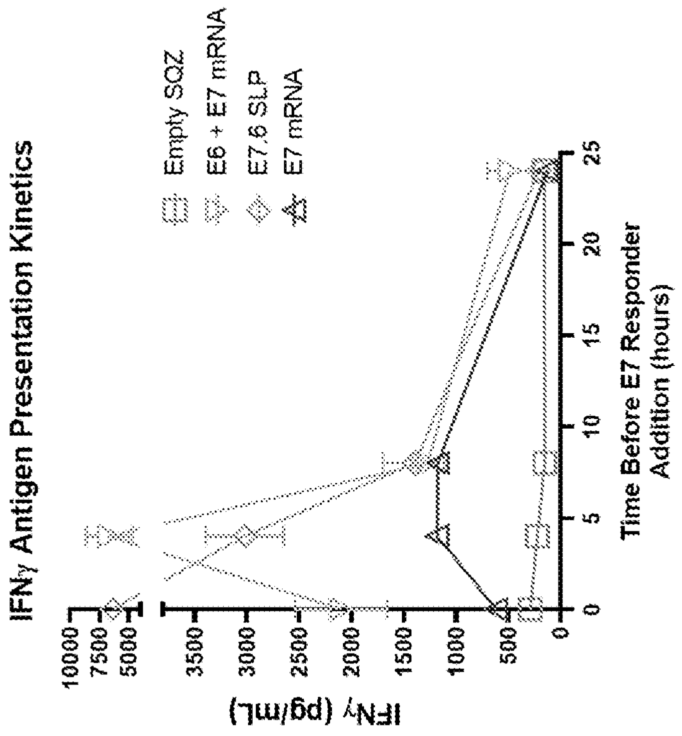
Figure 39A:
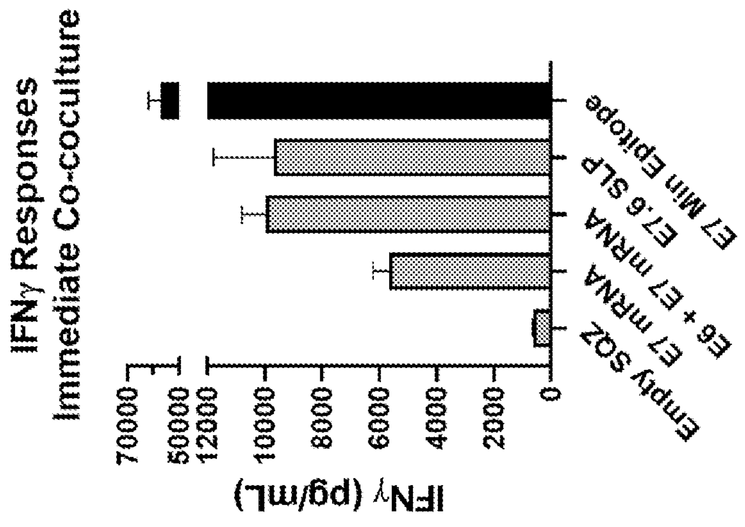

FIG. 39A is a graph showing the results of IFN-γ ELISA on $E7_{11-20}$ responder T cells co-cultured with PBMCs that were squeeze-loaded with (i) E7 mRNA, (ii) E7 mRNA and E6 mRNA, (iv) E7.6 synthetic long peptide (SLP) or iv) with no cargo (Empty squeeze), or with untreated PBMCs in the presence of $E7_{11-20}$ peptide (E7 Min Epitope).

FIG. 39B is a graph showing the results of IFN-γ ELISA on $E7_{11-20}$ responder T cells co-cultured with PBMCs that were squeeze-loaded with (i) E7 mRNA, (ii) E7 mRNA and E6 mRNA, (iv) E7.6 synthetic long peptide (SLP) or (v) with no cargo (Empty squeeze), or with untreated PBMCs in the presence of $E7_{11-20}$ peptide (E7 Min Epitope) wherein the PBMCs were cultured for the indicated time periods before co-culturing.

Figure 40:
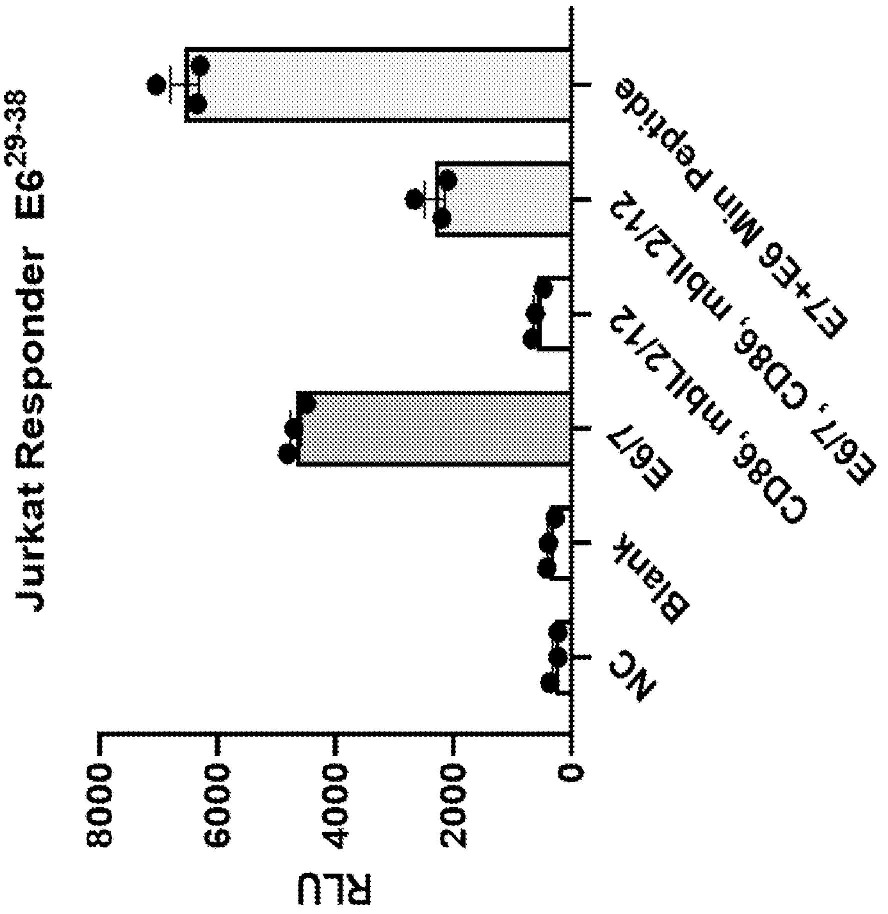

FIG. 40 is a graph showing the luminescence in QUANTI-Luc GOLD luciferase assay on $E6_{29-38}$ TCR Jurkat-Lucia NFAT cells that were co-cultured with PBMCs that were squeeze-loaded with (i) 500 μg/ml E6 mRNA and 500 μg/ml E7 mRNA, (ii) mRNAs encoding for CD86, membrane-bound IL-2 (mbIL-2) and membrane-bound IL-12 (mbIL-12), (iii) E6 and E7 mRNA, and mRNAs encoding for CD86, mbIL-2 and mbIL-12, (iv) E6 and E7. synthetic long peptides (SLP) or (v) with no cargo (Empty squeeze), or with untreated PBMCs in the presence of $E6_{29-38}$ peptide (E6 min Epitope) and/or E7 minimal peptide (E7 Min Epitope).

Figure 41B:
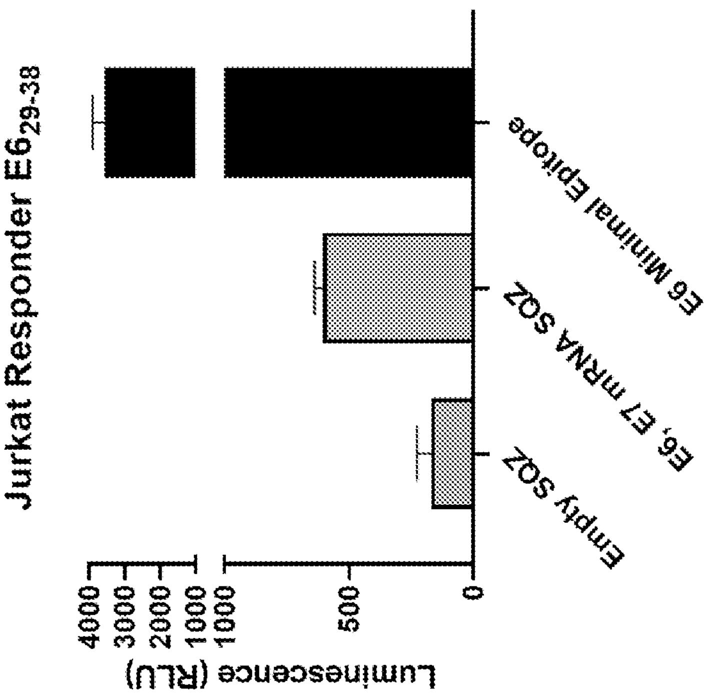
Figure 41A:
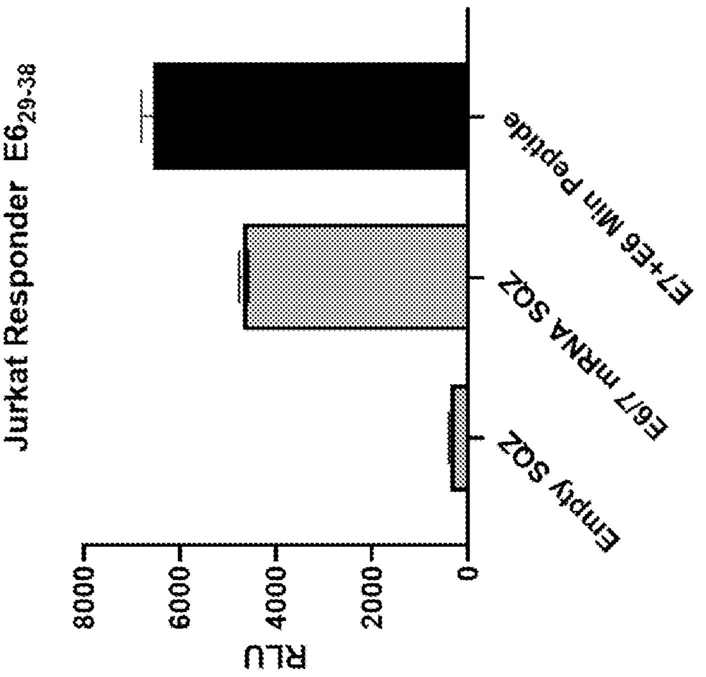

FIGS. 41A, B are graphs showing the luminescence in QUANTI-Luc GOLD luciferase assay on $E6_{29-38}$ TCR Jurkat-Lucia NFAT cells co-cultured with PBMCs that were squeeze-loaded with (i) E6 mRNA and E7 mRNA, (ii) E7.6 and E6 synthetic long peptide (SLPs) or (iii) with no cargo (Empty squeeze), or with untreated PBMCs in the presence of $E6_{29-38}$ peptide (E6 min Epitope) and/or E7 minimal peptide (E7 Min Epitope).

Figure 42A:
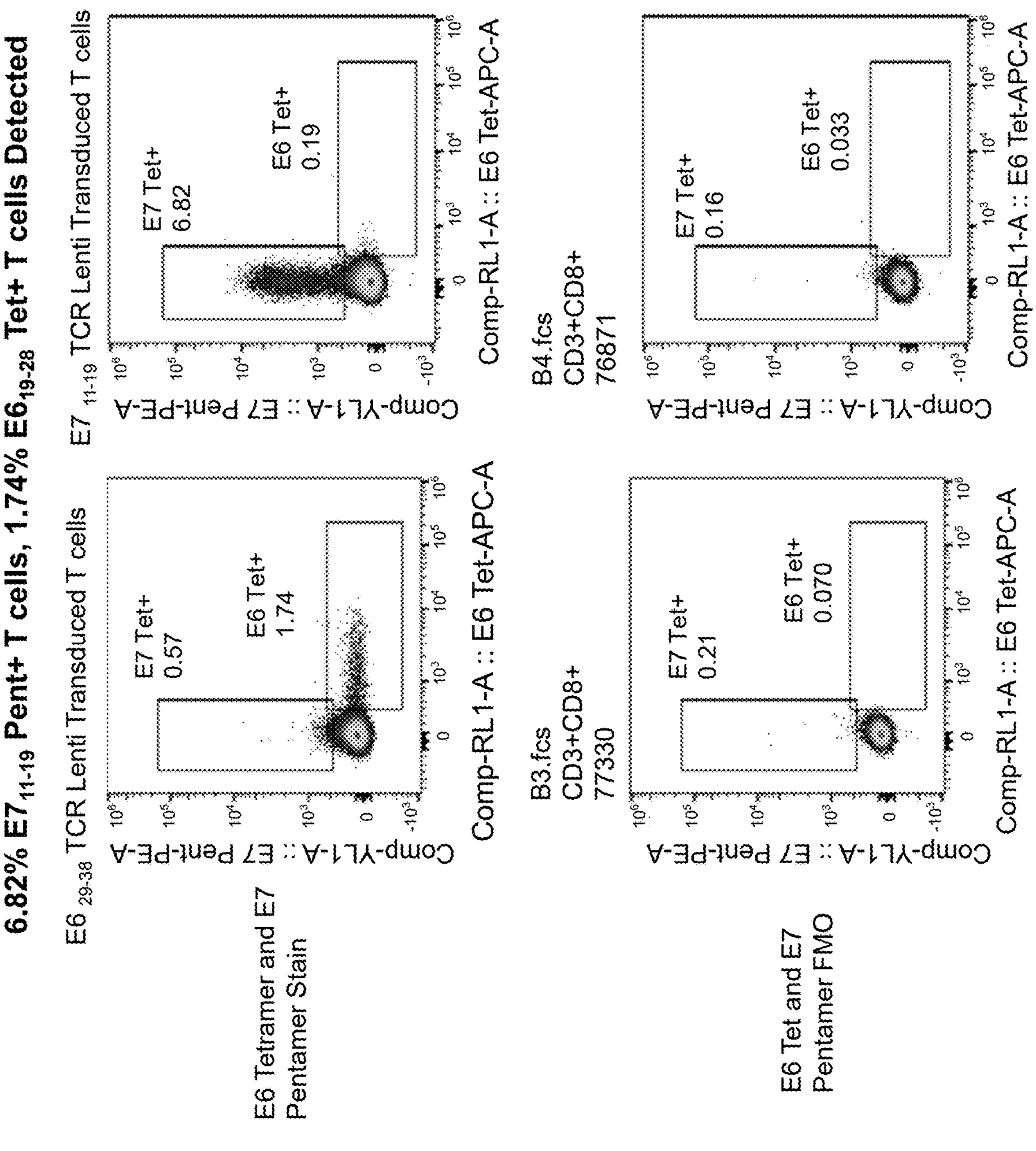
Figure 42C:
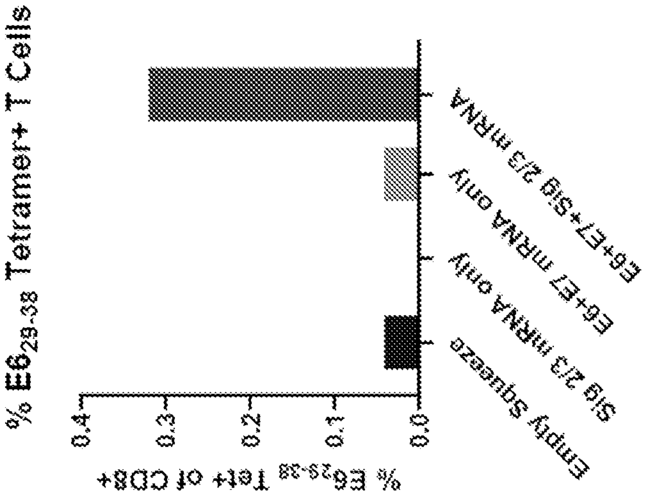
Figure 42B:
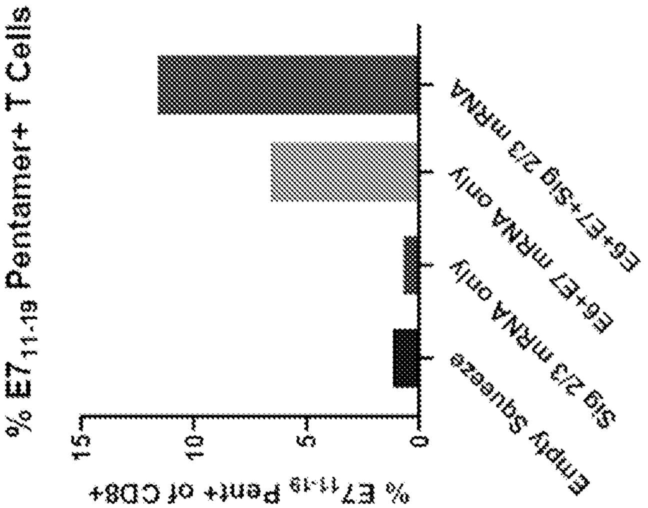
Figure 42D:
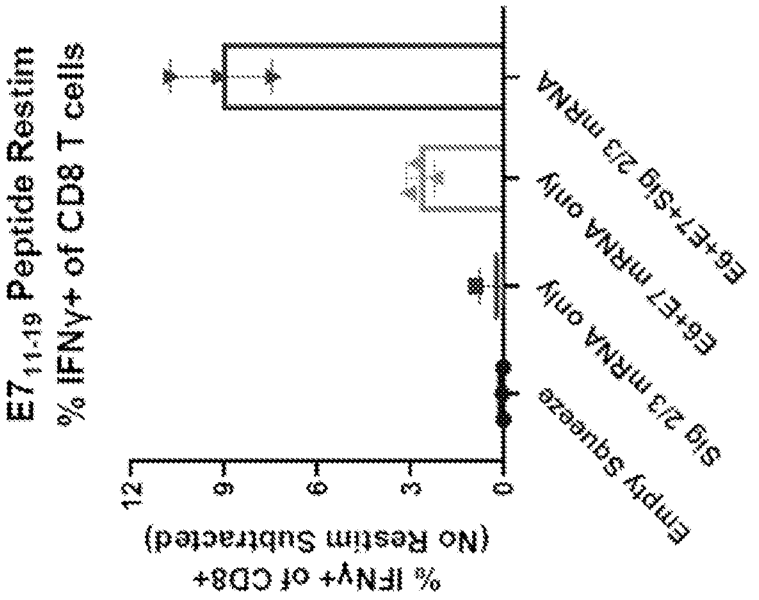
Figure 42E:
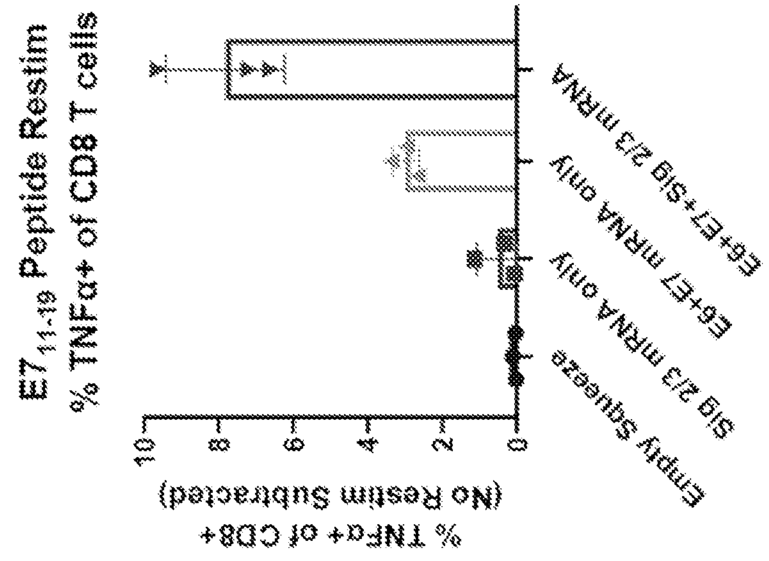
Figure 42F:
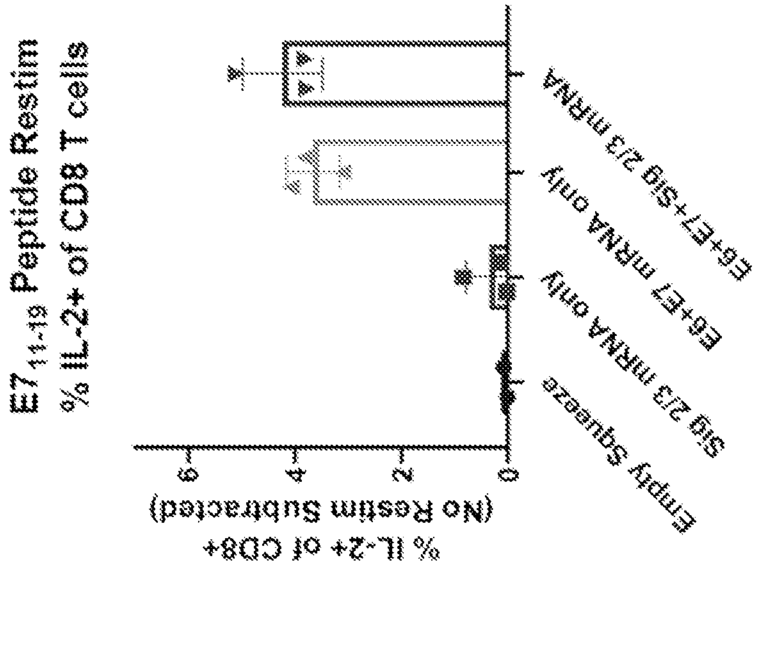
Figure 42G:
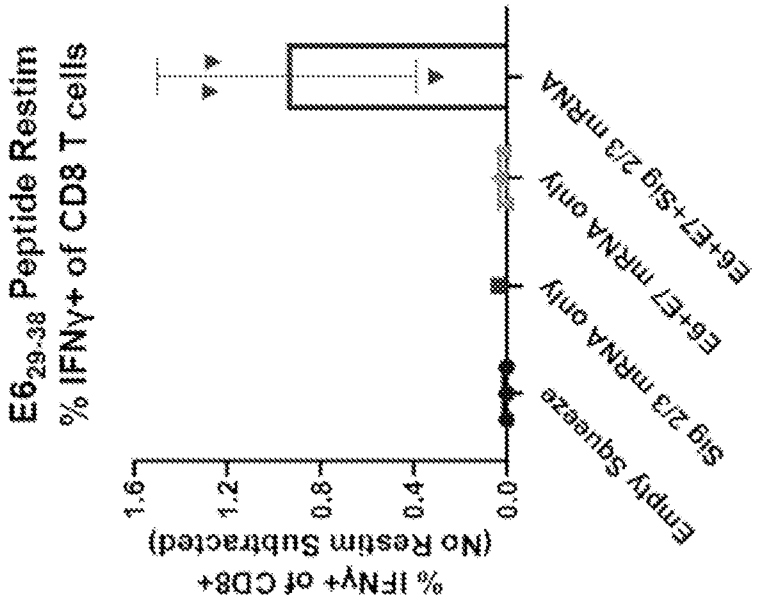
Figure 42H:
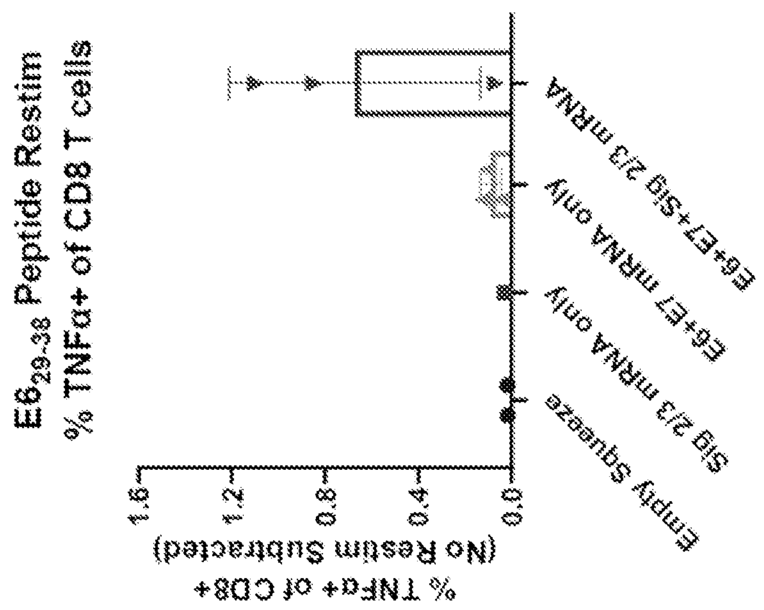
Figure 42I:
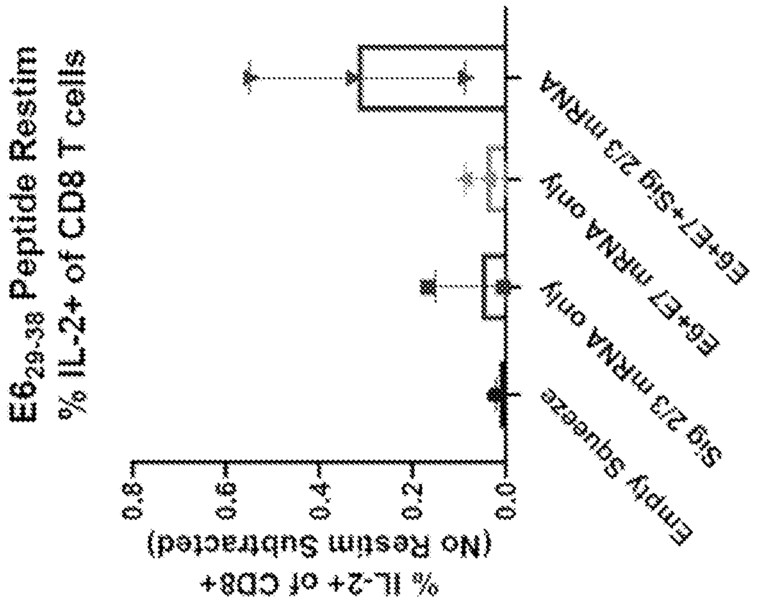

FIG. 42A is a graph showing the FACs analysis of E6- or E7-specific T cells subsequent to transduction of $E6_{19-28}$ TCR or $E7_{11-19}$ TCR. FIGS. 42B, C are graphs showing the increase in the E6- or E7-specific T cells upon coculture with: E6+E7+sig 2/3 mRNA cells (PBMCs squeeze-loaded with mRNAs encoding E6, E7 and signal 2/3 mediators), E6+E7 mRNA only cells (PBMCs squeeze-loaded with mRNAs encoding E6, E7), sig 2/3 mRNA (PBMCs squeeze-loaded with mRNAs encoding signal 2/3 mediators) or control PBMCs (Empty Squeeze). FIGS. 42D, E, F, G, H, I are graphs showing the stimulation of IFNγ-producing T cells, or TNF-α-producing T cells, in E6- or E7-TCR transduced T cells upon co-culture with: E6+E7+sig 2/3 mRNA cells (PBMCs squeeze-loaded with mRNAs encoding E6, E7 and signal 2/3 mediators), E6+E7 mRNA only cells (PBMCs squeeze-loaded with mRNAs encoding E6, E7), sig 2/3 mRNA (PBMCs squeeze-loaded with mRNAs encoding signal 2/3 mediators) or control PBMCs (Empty Squeeze), and upon re-stimulation with E6 or E7 minimal eptiope.

Figure 43B:
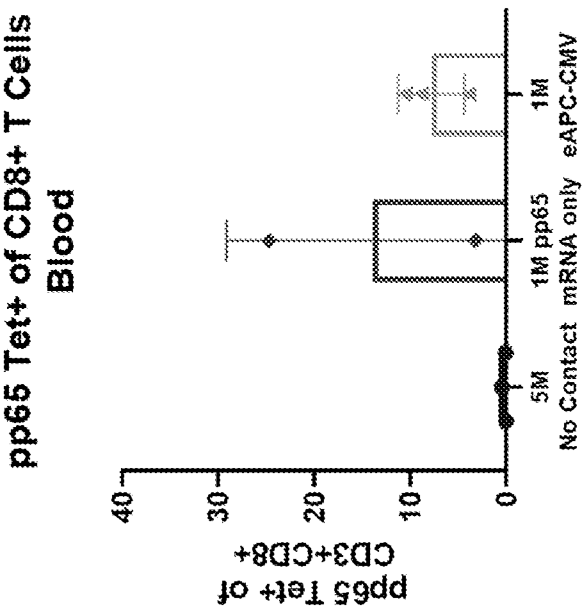
Figure 43A:
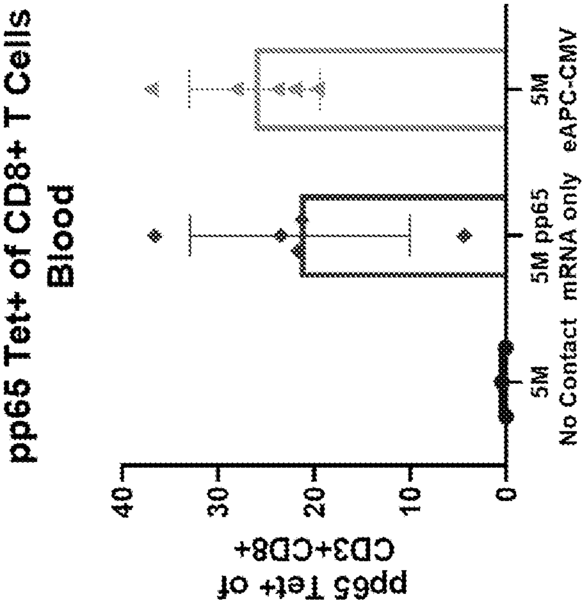
Figure 43D:
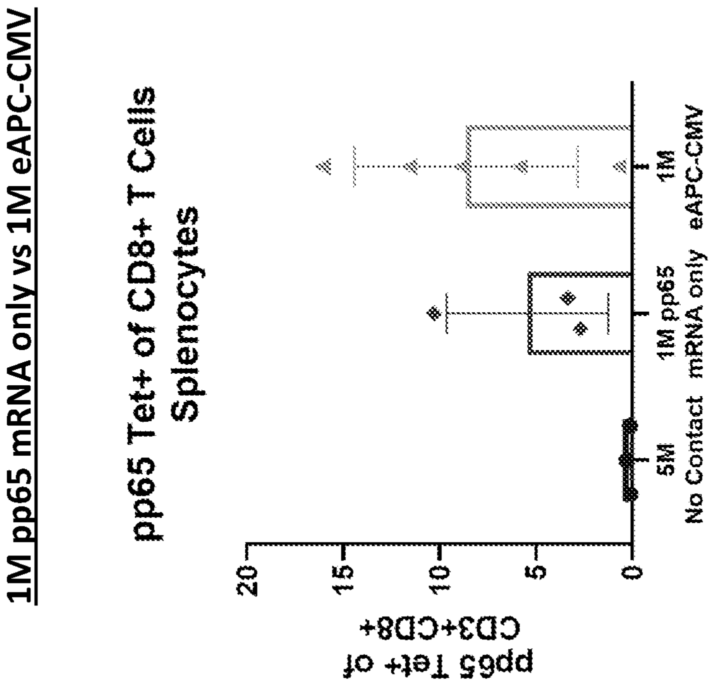
Figure 43C:
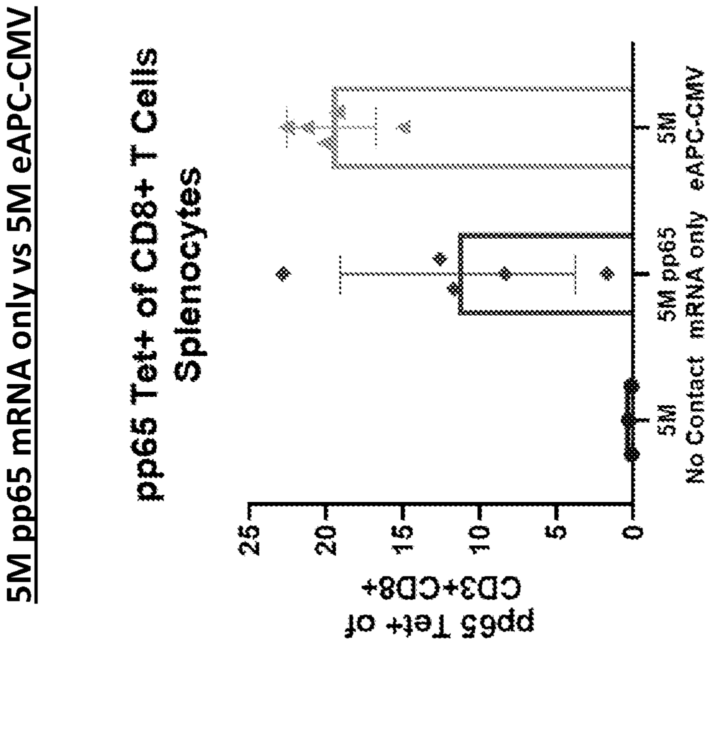

FIGS. 43A, B, C, D and E are graphs showing the increase in the pp65 antigen-specific T cells in mice immunized with:

eAPC-CMV cells (PBMCs squeeze-loaded with mRNAs encoding pp65 and sig2/sig3 mediators), pp65 only cells (PBMCs squeeze-loaded with mRNA encoding pp65), or unprocessed PBMCs (no contact). FIGS. 43F, G, H and FIGS. 43 I, J, K are graphs showing the stimulation of IFNγ-producing T cells, TNF-α-producing T cells, or IL-2-producing T cells in mice immunized with: eAPC-CMV cells (PBMCs squeeze-loaded with mRNAs encoding pp65 and sig2/sig3 mediators), pp65 only cells (PBMCs squeeze-loaded with mRNA encoding pp65), or unprocessed PBMCs (no contact).

DETAILED DESCRIPTION OF THE INVENTION

In some aspects, the present invention provides methods for simulating an immune response in an individual, and/or vaccinating an individual in need thereof, comprising administering to the individual a composition comprising nucleated cells (e.g. PBMCs) comprising a protein or fragment thereof, wherein the protein or fragment thereof stimulates an immune response regardless of the HLA haplotype of the individual. In some aspects, the present invention provides methods for simulating an immune response in an individual, and/or vaccinating an individual in need thereof, the method comprising administering to the individual an effective amount of a composition comprising nucleated cells comprising a protein or fragment thereof delivered intracellularly; wherein the nucleated cells are prepared by first passing a cell suspension comprising an input cell through a cell-deforming constriction, wherein a diameter of the constriction is a function of a diameter of the input nucleated cells in the suspension, thereby causing perturbations of the input nucleated cells large enough for the protein or fragment thereof to pass through to form perturbed input nucleated cells; and then incubating the perturbed input nucleated cells with the protein or fragment thereof for a sufficient time to allow the protein or fragment thereof to enter the perturbed input cell; thereby generating the modified nucleated cells comprising the protein or fragment thereof, wherein the protein or fragment thereof stimulates an immune response regardless of the HLA haplotype of the individual. In some aspects, the present invention provides methods for simulating an immune response in an individual, and/or vaccinating an individual in need thereof, the method comprising administering to the individual an effective amount of a composition comprising nucleated cells comprising a protein or fragment thereof delivered intracellularly; wherein the nucleated cells are prepared by first passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells and incubating the perturbed input nucleated cells with the mRNA encoding the protein or fragment thereof to allow the mRNA encoding the protein or fragment thereof to enter the perturbed input nucleated cells; wherein the mRNA encoding the protein or fragment thereof is expressed in the nucleated cells, thereby generating the modified nucleated cells comprising the protein or fragment thereof, wherein the protein or fragment thereof stimulates an immune response regardless of the HLA haplotype of the individual. Certain aspects of the present disclosure relate to methods for generating a composition comprising nucleated cells comprising a protein or fragment thereof delivered intracellularly, wherein a nucleated cell is passed through a constriction, wherein the constriction deforms the cell thereby causing a perturbation of the cell such that a protein or fragment thereof enters the immune cell to be modified. In some embodiments, the nucleated cells are a plurality of PBMCs. In some embodiments, the nucleated cells are conditioned by incubating with one or more adjuvants. In some embodiments, the protein or fragment introduced intracellularly comprises the entirety or a substantial majority of the native protein sequence. In some embodiments, the protein or fragment encoded by mRNA introduced intracellularly comprises the entirety or a substantial majority of the native protein sequence.

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4th ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6th ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011).

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

The term "about" as used herein refers to the usual error range for the respective value readily known to the skilled person in this technical field. Reference to "about" a value or parameter herein includes (and describes) embodiments that are directed to that value or parameter per se.

As used herein, "treatment" is an approach for obtaining beneficial or desired clinical results. "Treatment" as used herein, covers any administration or application of a therapeutic for disease in a mammal, including a human. For purposes of this invention, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods of the invention contemplate any one or more of these aspects of treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms. In some embodiments, an individual may be treated if they have a precancerous lesion.

As used herein, by "combination therapy" is meant that a first agent be administered in conjunction with another agent. "In conjunction with" refers to administration of one treatment modality in addition to another treatment modality, such as administration of a composition of nucleated cells as described herein in addition to administration of an immunoconjugate as described herein to the same individual. As such, "in conjunction with" refers to administration of one treatment modality before, during, or after delivery of the other treatment modality to the individual.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

In the context of cancer, the term "treating" includes any or all of killing cancer cells, inhibiting growth of cancer cells, inhibiting replication of cancer cells, lessening of overall tumor burden and ameliorating one or more symptoms associated with the disease.

The term "pore" as used herein refers to an opening, including without limitation, a hole, tear, cavity, aperture, break, gap, or perforation within a material. In some examples, (where indicated) the term refers to a pore within a surface of the present disclosure. In other examples, (where indicated) a pore can refer to a pore in a cell membrane.

The term "membrane" as used herein refers to a selective barrier or sheet containing pores. The term includes a pliable sheet-like structure that acts as a boundary or lining. In some examples, the term refers to a surface or filter containing pores. This term is distinct from the term "cell membrane".

The term "filter" as used herein refers to a porous article that allows selective passage through the pores. In some examples the term refers to a surface or membrane containing pores.

The term "exogenous" when used in reference to an agent, such as an antigen or an adjuvant, with relation to a cell refers to an agent outside of the cell or an agent delivered into the cell from outside the cell. The cell may or may not have the agent already present, and may or may not produce the agent after the exogenous agent has been delivered.

The term "heterogeneous" as used herein refers to something which is mixed or not uniform in structure or composition. In some examples the term refers to pores having varied sizes, shapes or distributions within a given surface.

The term "homogeneous" as used herein refers to something which is consistent or uniform in structure or composition throughout. In some examples, the term refers to pores having consistent sizes, shapes, or distribution within a given surface.

The term "homologous" as used herein refers to a molecule which is derived from the same organism. In some examples, the term refers to a nucleic acid or protein which is normally found or expressed within the given organism.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The term "heterologous" as it relates to amino acid sequences such as peptide sequences and polypeptide sequences, denotes sequences that are not normally joined together, and/or are not normally associated with a particular cell. Thus, a "heterologous" region of a peptide sequence is a segment of amino acids within or attached to another amino acid molecule that is not found in association with the other molecule in nature. For example, a heterologous region of a peptide construct could include the amino acid sequence of the peptide flanked by sequences not found in association with the amino acid sequence of the peptide in nature. Another example of a heterologous peptide sequence is a construct where the peptide sequence itself is not found in nature (e.g., synthetic sequences having amino acids different as coded from the native gene). Similarly, a cell transformed with a vector that expresses an amino acid construct which is not normally present in the cell would be considered heterologous for purposes of this invention. Allelic variation or naturally occurring mutational events do not give rise to heterologous peptides, as used herein.

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting an immune response may refer to any act leading to a blockade, reduction, elimination, or any other antagonism of an immune response. In other examples, inhibition of the expression of a nucleic acid may include, but not limited to reduction in the transcription of a nucleic acid, reduction of mRNA abundance (e.g., silencing mRNA transcription), degradation of mRNA, inhibition of mRNA translation, and so forth. In another example, inhibit may refer to the act of slowing or stopping growth; for example, retarding or preventing the growth of a tumor cell.

As used herein, the term "suppress" may refer to the act of decreasing, reducing, prohibiting, limiting, lessening, or otherwise diminishing the presence, or an activity of, a particular target. Suppression may refer to partial suppression or complete suppression. For example, suppressing an immune response may refer to any act leading to decreasing, reducing, prohibiting, limiting, lessening, or otherwise diminishing an immune response. In other examples, suppression of the expression of a nucleic acid may include, but not limited to reduction in the transcription of a nucleic acid, reduction of mRNA abundance (e.g., silencing mRNA transcription), degradation of mRNA, inhibition of mRNA translation, and so forth.

As used herein, the term "enhance" may refer to the act of improving, boosting, heightening, or otherwise increasing the presence, or an activity of, a particular target. For example, enhancing an immune response may refer to any act leading to improving, boosting, heightening, or otherwise increasing an immune response. In one exemplary example, enhancing an immune response may refer to employing an antigen and/or adjuvant to improve, boost, heighten, or otherwise increase an immune response. In other examples, enhancing the expression of a nucleic acid may include, but not limited to increase in the transcription of a nucleic acid, increase in mRNA abundance (e.g., increasing mRNA transcription), decrease in degradation of mRNA, increase in mRNA translation, and so forth.

As used herein, the term "modulate" may refer to the act of changing, altering, varying, or otherwise modifying the presence, or an activity of, a particular target. For example, modulating an immune response may refer to any act leading to changing, altering, varying, or otherwise modifying an immune response. In some examples, "modulate" refers to enhancing the presence or activity of a particular target. In some examples, "modulate" refers to suppressing the presence or activity of a particular target. In other examples, modulating the expression of a nucleic acid may include, but not limited to a change in the transcription of a nucleic acid, a change in mRNA abundance (e.g., increasing mRNA transcription), a corresponding change in degradation of mRNA, a change in mRNA translation, and so forth.

As used herein, the term "induce" may refer to the act of initiating, prompting, stimulating, establishing, or otherwise producing a result. For example, inducing an immune response may refer to any act leading to initiating, prompting, stimulating, establishing, or otherwise producing a desired immune response. In other examples, inducing the expression of a nucleic acid may include, but not limited to initiation of the transcription of a nucleic acid, initiation of mRNA translation, and so forth.

As used herein, a "peripheral blood mononuclear cells" or "PBMCs" refers to a heterogeneous population of blood cells having a round nucleus. Examples of cells that may be found in a population of PBMCs include lymphocytes such as T cells, B cells, NK cells (including natural killer T cells (NKT cells) and cytokine-induced killer cells (CIK cells)) and monocytes such as macrophages and dendritic cells. A "plurality of PBMCs" as used herein refers to a preparation of PBMCs comprising cells of at least two types of blood cells. In some embodiments, a plurality of PBMCs comprises two or more of T cells, B cells, NK cells, macrophages or dendritic cells. In some embodiments, a plurality of PBMCs comprises three or more of T cells, B cells, NK cells, macrophages or dendritic cells. In some embodiments, a plurality of PBMCs comprises four or more of T cells, B cells, NK cells, macrophages or dendritic cells. In some embodiments, a plurality of PBMCs comprises T cells, B cells, NK cells, macrophages and dendritic cells.

PBMCs can be isolated by means known in the art. For example, PBMCs can be derived from peripheral blood of an individual based on density of PBMCs compared to other blood cells. In some embodiments, PBMCs are derived from peripheral blood of an individual using Ficoll (e.g., a ficoll gradient). In some embodiments, PBMCs are derived from peripheral blood of an individual using ELUTRA® cell separation system. PBMCs can be obtained form an individual undergoing apheresis.

In some embodiments, a population of PBMCs is isolated from an individual. In some embodiments, a plurality of PBMCs is an autologous population of PBMCs where the population is derived from a particular individual, manipulated by any of the methods described herein, and returned to the particular individual. In some embodiments, a plurality of PBMCs is an allogeneic population of PBMCs where the population is derived from one individual, manipulated by any of the methods described herein, and administered to a second individual.

In some embodiments, a plurality of PBMCs is a reconstituted preparation of PBMCs. In some embodiments, the plurality of PBMCs may be generated by mixing cells typically found in a population of PBMCs; for example, by mixing populations of two or more of T cells, B cells, NK cells, or monocytes.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and phosphorothioates, and thus can be an oligodeoxynucleoside phosphoramidate (P-NH2), a mixed phosphorothioate-phosphodiester oligomer, or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, the term "adjuvant" refers to a substance which modulates and/or engenders an immune response. Generally, the adjuvant is administered in conjunction with an antigen to effect enhancement of an immune response to the antigen as compared to antigen alone. Various adjuvants are described herein.

The terms "CpG oligodeoxynucleotide" and "CpG ODN" herein refer to DNA molecules of 10 to 30 nucleotides in length containing a dinucleotide of cytosine and guanine separated by a phosphate (also referred to herein as a "CpG" dinucleotide, or "CpG"). The CpG ODNs of the present disclosure contain at least one unmethylated CpG dinucleotide. That is, the cytosine in the CpG dinucleotide is not methylated (i.e., is not 5-methylcytosine). CpG ODNs may have a partial or complete phosphorothioate (PS) backbone.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

For any of the structural and functional characteristics described herein, methods of determining these characteristics are known in the art.

Methods of Stimulating Immune Response Regardless of Host HLA Haplotype

In some aspects, provided are methods for stimulating an immune response in an individual, the method comprising administering an effective amount of a composition comprising nucleated cells (e.g., PBMC) to an individual, wherein the nucleated cells comprises a protein or fragment thereof; wherein the protein or fragment thereof stimulates an immune response regardless of the HLA haplotype of the individual. In some embodiments, the method comprises administering an effective amount of any of the compositions described herein. In some embodiments, the individual has cancer.

In some aspects, provided are methods for vaccinating an individual in need thereof, the method comprising administering an effective amount of a composition comprising nucleated cells to an individual, wherein the nucleated cells comprises a protein or fragment thereof; wherein the protein or fragment thereof stimulates an immune response regardless of the HLA haplotype of the individual.

In some aspects, provided are methods for stimulating an immune response in an individual, the method comprising administering an effective amount of a composition comprising nucleated cells to an individual, wherein the nucleated cells comprise an mRNA (e.g., exogenous mRNA) encoding a protein or fragment thereof; wherein the protein or fragment thereof stimulates an immune response regardless of the HLA haplotype of the individual.

In some aspects, provided are methods for vaccinating an individual in need thereof, the method comprising administering an effective amount of a composition comprising nucleated cells to an individual, wherein the nucleated cells comprise an mRNA (e.g., exogenous mRNA) encoding a protein or fragment thereof; wherein the protein or fragment thereof stimulates an immune response regardless of the HLA haplotype of the individual.

In some embodiments, provided are methods for stimulating an immune response in an individual, the method comprising administering an effective amount of a composition comprising nucleated cells to an individual, wherein the nucleated cells comprises two or more antigens derived from a protein; wherein the two or more antigens stimulates an immune response regardless of the HLA haplotype of the individual. In some embodiments, provided are methods for stimulating an immune response in an individual, the method comprising administering an effective amount of a composition comprising nucleated cells to an individual, wherein the nucleated cells comprises two or more antigens derived from a protein; wherein the two or more antigens stimulates an immune response regardless of the HLA haplotype of the individual.

In some embodiments, the cell comprises two or more antigens derived from the protein. In some embodiments, the cell comprises about any one of: 2, 3, 4, 5, 6, 7, 8, 9, 10, 11, 12, 13, 14, 15, 16, 17, 18, 19, 20, 22, 24, 26, 28, 30, 35, 40, 45, 50, 55, 60, 70, 75, 80, 90, 100 or more antigens derived from the protein. In some embodiments, at least two of the antigens comprise partially overlapping amino acid sequences. In some embodiments, the combined amino acid sequences of all the antigens overlaps the amino acid sequence of the protein by about 90% or more. In some embodiments, the combined amino acid sequences of all the antigens overlaps with about any one of: 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the amino acid sequence of the protein. In some embodiments, each amino acid of about 80% of the amino acid sequence of the protein overlaps with at least two antigens derived from the protein. In some embodiments, each amino acid of about 80% of the amino acid sequence of the protein overlaps with at least three antigens derived from the protein. In some embodiments, each amino acid of about 90% of the amino acid sequence of the protein overlaps with at least two antigens derived from the protein. In some embodiments, each amino acid of about 90% of the amino acid sequence of the protein overlaps with at least three antigens derived from the protein. In some embodiments, each amino acid of about 95% of the amino acid sequence of the protein overlaps with at least two antigens derived from the protein. In some embodiments, each amino acid of about 95% of the amino acid sequence of the protein overlaps with at least three antigens derived from the protein.

In some embodiments, the antigen is a polypeptide comprising two or more epitopes of the protein. In some embodiments, embodiments, the immunogenic peptide epitope is fused to an N-terminal flanking polypeptide and/or a C-terminal flanking polypeptide. In some embodiments, the antigen is a one or more epitopes of the protein and one or more heterologous peptide sequences. In some embodiments, the one or more epitopes is flanked on the N-terminus and/or the C-terminus by heterologous peptide sequences. In some embodiments, the flanking heterologous peptide sequences are derived from disease-associated immunogenic peptides. In some embodiments, the flanking heterologous peptide sequences are non-naturally occurring sequence. In some embodiments, the flanking heterologous peptide sequences are derived from an immunogenic synthetic long peptide (SLP). In some embodiments, the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17. In some embodiments, the antigen is capable of being processed into an MHC class I-restricted peptide and/or an MHC class II-restricted peptide.

In some embodiments, the protein is a mutated protein associated with cancer (for example, but not limited to neoantigen), a viral protein, a bacterial protein or a fungal protein. In some embodiments, the protein is a human papillomavirus (HPV) protein. In some embodiments, the HPV is HPV-16 or HPV-18. In some embodiments, the protein is an HPV E6 or HPV E7 protein. In some embodiments, the protein is a hepatitis B virus (HBV) protein.

In some embodiments, the nucleated cells comprising the protein or fragment thereof are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the protein or fragment thereof to pass through to form a perturbed input nucleated cells; and b) incubating the perturbed input nucleated cells with the protein or fragment thereof to allow the protein or fragment thereof to enter the perturbed input nucleated cells; thereby generating nucleated cells comprising the protein or fragment thereof. In some embodiments, the nucleated cells comprising the mRNA encoding the protein or fragment thereof are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; thereby generating nucleated cells comprising the mRNA encoding the protein or fragment thereof.

In some embodiments, the input cell suspension may comprise the input nucleated cells and an antigen. In some embodiments, the input cell suspension comprises the input nucleated cells and the protein or fragment thereof. In some embodiments, the input cell suspension comprises the input nucleated cells and the mRNA encoding the protein or fragment thereof. In some embodiments, the method comprises incubating the nucleated cells with the protein or fragment thereof, or with the mRNA encoding the protein or fragment thereof before, during and/or after passing the cell suspension through the cell-deforming constriction. In some embodiments, the method comprises incubating the nucleated cells with the protein or fragment thereof, or with the mRNA encoding the protein or fragment thereof before passing the cell suspension through the cell-deforming constriction.

In some embodiments, provided are methods for stimulating an immune response in an individual, comprising: a) passing a cell suspension comprising input nucleated cells (e.g., PBMCs) through a cell-deforming constriction, wherein a diameter of the constriction is a function of a diameter of the input nucleated cells in the suspension, thereby causing perturbations of the input nucleated cells large enough for the protein or fragment thereof to pass through to form a perturbed input nucleated cells; b) incubating the perturbed input nucleated cells with the protein or fragment thereof to allow the protein or fragment thereof to enter the perturbed input nucleated cells; thereby generating nucleated cells comprising the protein or fragment thereof; and (c) administering the nucleated cells comprising the protein or fragment thereof to the individual. In some embodiments, provided are methods for stimulating an immune response in an individual, comprising: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; wherein the mRNA is expressed thereby generating the nucleated cells comprising the protein or fragment thereof; and (c) administering the nucleated cells comprising the protein or fragment thereof to the individual. In some embodiments, the protein or fragment thereof stimulates an immune response in an individual in an HLA agnostic manner.

In some embodiments, provided are methods for vaccinating an individual in need thereof, comprising: a) passing a cell suspension comprising input nucleated cells (e.g., PBMCs) through a cell-deforming constriction, wherein a diameter of the constriction is a function of a diameter of the input nucleated cells in the suspension, thereby causing perturbations of the input nucleated cells large enough for the protein or fragment thereof to pass through to form a perturbed input nucleated cells; b) incubating the perturbed input nucleated cells with the protein or fragment thereof to allow the protein or fragment thereof to enter the perturbed input nucleated cells; thereby generating nucleated cells comprising the protein or fragment thereof; and (c) administering the nucleated cells comprising the protein or fragment thereof to the individual. In some embodiments, provided are methods for vaccinating an individual in need thereof, comprising: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; wherein the mRNA is expressed thereby generating the nucleated cells comprising the protein or fragment thereof; and (c) administering the nucleated cells comprising the protein or fragment thereof to the individual. In some embodiments, the protein or fragment thereof stimulates an immune response in an individual in an HLA agnostic manner.

In some embodiments, the width of the constriction is about 10% to about 99% of the mean diameter of the input nucleated cells. In some embodiments, the width of the constriction is about 10% to about 99% of the mean diameter of the input nucleated cells having the smallest diameter within the population of nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells having the smallest diameter within the population of nucleated cells. In some embodiments, the width of the constriction is about 2 μm to about 5 μm, about 3 μm to about 5 μm, about 2 μm to about 2.2 μm, about 2.2 μm to about 2.5 μm, about 2.5 μm to about 3 μm, about 3 μm to about 3.5 μm, about 3.5 μm to about 4 μm, about 4 μm to about 4.5 μm, about 3.2 μm to about 3.8 μm, about 3.8 μm to about 4.3 μm, about 4.2 μm to about 6 μm, or about 4.2 μm to about 4.8 μm. In some embodiments, the width of the constriction is about 4.5 μm. In some embodiments, the width of the constriction is about or less than any one of 2 μm, 2.2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the cell suspension comprising the input nucleated cells are passed through multiple constrictions wherein the multiple constrictions are arranged in series and/or in parallel.

In some embodiments according to any one of the methods, uses or compositions described herein, the nucleated cells (e.g., PBMCs) are incubated with the adjuvant for a sufficient time for the nucleated cells to condition. In some embodiments, the nucleated cells are incubated with the adjuvant for about 1 to about 24 hours for the nucleated cells to condition. In some embodiments, the nucleated cells are incubated with the adjuvant for about 2 to about 10 hours for the nucleated cells to condition. In some embodiments, the nucleated cells are incubated with the adjuvant for about 3 to about 6 hours for the nucleated cells to condition. In some embodiments, the nucleated cells are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the nucleated cells to condition. In some embodiments, the nucleated cells are incubated with the adjuvant for about 4 hours for the nucleated cells to condition. In some embodiments, the nucleated cells are conditioned before introducing the protein or fragment thereof or the nucleic acid encoding protein or fragment thereof into the nucleated cells. In some embodiments, the nucleated cells are conditioned after introducing the protein or fragment thereof or the nucleic acid encoding the protein or fragment thereof into the nucleated cells. In some embodiments, the adjuvant used for conditioning is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), a TLR3 agonist, a TLR4 agonist, a TLR7 agonist, a TLR8 agonist, or a TLR9 agonist. Exemplary adjuvants include, without limitation, CpG ODN, interferon-α (IFN-α), polyinosinic: polycytidylic acid (polyI:C), imiquimod (R837), resiquimod (R848), or lipopolysaccharide (LPS). In some embodiments, the adjuvant is a CpG oligodeoxynucleotide (ODN). In some embodiments, the adjuvant is CpG 7909 (also known as CpG ODN 2006).

In some embodiments, wherein the nucleated cells comprise B cells, one or more co-stimulatory molecules is upregulated in the B cells of the conditioned nucleated cells compared to the B cells of the unconditioned nucleated cells. In some embodiments, the nucleated cells are a plurality of peripheral blood mononuclear cells (PBMCs). In some embodiments, wherein the nucleated cells are a plurality of PBMCs, one or more co-stimulatory molecules is upregulated in the B cells of the conditioned plurality of PBMCs compared to the B cells of the unconditioned plurality of PBMCs. In some embodiments, the co-stimulatory molecule is CD80 and/or CD86. In some embodiments, the conditioned plurality of PBMCs has increased expression of one or more of IFN-γ, IL-6, MCP-1, MIP-1β, IP-10, or TNF-α compared to an unconditioned plurality of PBMCs. In some embodiments, the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to an unconditioned plurality of PBMCs In some embodiments according to any one of the methods, uses or compositions described herein, the nucleated cells are immune cells. In some embodiments, the nucleated cells are human cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the nucleated cells are a plurality of PBMCS. In some embodiments, the conditioned nucleated cells are a conditioned plurality of modified PBMCs. In some embodiments, the plurality of PBMCs comprises two or more of T cell, B cell, NK cell, monocytes, dendritic cells or NK-T cells. In some embodiments, the nucleated cells are one or more of T cells, B cells, NK cells, monocytes, dendritic cells and/or NK-T cells.

In some embodiments, the plurality of PBMCs are further modified to increase expression of one or more of co-stimulatory molecules. In some embodiments, the co-stimulatory molecule is B7-H2 (ICOSL), B7-1 (CD80), B7-2 CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of PBMCs are further modified to increase expression of one or more cytokines. In some embodiments, the cytokine is IL-10, IL-15, IL-12, IL-2, IFN-α, IFN-γ, IL-21, or a functional variant thereof. In some embodiments, the cytokine is IFN-α2 or a functional variant thereof. In some embodiments, the cytokine is a variant cytokine (such as a modified cytokine). In some embodiments, the plurality of PBMCs are further modified to increase expression of one or more chimeric membrane-bound cytokines. In some embodiments, the cytokine is modified, and the modified cytokine is a fusion protein comprising the cytokine and a transmembrane domain. In some embodiments, the cytokine is joined to the transmembrane domain by a peptide linker. In some embodiments, the plurality of PBMCs are further modified to increase expression of one or more chimeric membrane-bound cytokines. In some embodiments, the cytokine is modified, and the modified cytokine is a fusion protein comprising the cytokine and a transmembrane domain. In some embodiments, the cytokine is joined to the transmembrane domain by a peptide linker. In some embodiments, the transmembrane domain is a transferrin receptor protein 1 (TFRC) or a tumor necrosis factor (e.g., FasL) transmembrane domain. In some embodiments, the transmembrane domain comprises the amino acid sequence of SEQ ID NO: 81 or SEQ ID NO: 82. In some embodiments, the peptide linker is a $G_4S$ linker or an EAAAK linker. In embodiments, the $G_4S$ linker comprises any one of 2, 3, 4, 5, 6, 7, 8, 9, or 10 repeats of $G_4S$ sequence. In some embodiments, the EAAAK linker comprises any one of 2, 3, 4, 5, 6, 7, 8, 9, or 10 repeats of EAAAK sequence. In some embodiments, the peptide linker is $(G_4S)_3$ (SEQ ID NO: 73) or $(EAAAK)_3$ (SEQ ID NO: 74). In some embodiments, the chimeric membrane-bound cytokine comprises the amino acid sequence of any one of SEQ ID NOs: 77-80. In some embodiments, the plurality of modified PBMCs comprises a nucleic acid that results in increased expression and/or secretion of the one or more cytokines. In some embodiments, the nucleic acid encoding the chimeric membrane-bound cytokine comprises the nucleotide sequence of SEQ ID NO: 71 or 72. In some embodiments, the cytokine is a Signal 3 effector in stimulating T cell activation. In some embodiments, the cytokine induces activation of CD4+ T cells and/or CD8+ T cells. In some embodiments, the cytokine induces activation of antigen-specific CD4+ T cells and/or CD8+ T cells. In some embodiments, the chimeric membrane-bound cytokine enhances the half-life of the cytokine in an individual compared to a non-membrane-bound cytokine. In some embodiments, the half-life of the chimeric membrane-bound cytokine is increased by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a non-membrane-bound cytokine. In some embodiments, the membrane-bound cytokine prolongs the spatial association of the cytokine with the antigens presented by the nucleated cell introduced with the protein or fragment thereof, by about any one of: 1, 2, 3, 4, 6, 8, 12, 16, 20, 24, 28, 32, 36, 48, 72, 96 or more hours, compared to a corresponding nucleated cell comprising a non-membrane-bound cytokine. In some embodiments, a nucleated cell comprising the protein or fragment thereof and further comprising a membrane-bound cytokine exhibits a local cytokine concentration that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine. In some embodiments, a nucleated cell comprising the protein or fragment thereof and further comprising a membrane-bound cytokine can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine.

In some embodiments, the membrane-tethered cytokine is a membrane-tethered chemokine.

In some embodiments, the method comprises multiple administrations of the nucleated cells comprising the protein or fragment thereof. In some embodiments, the method comprises about 3 to about 9 administrations of the nucleated cells comprising the protein or fragment thereof. In some embodiments, the method comprises about any one of 1, 2, 3, 4, 5, 6, 7, 8, 9, 10, 11, 12, 13, 14 or 15 administrations of the nucleated cells comprising the protein or fragment thereof. In some embodiments, the method comprises continuous administrations of the nucleated cells as needed. In some embodiments, the time interval between two successive administrations of the nucleated cells comprising the protein or fragment thereof is between about 1 day and about 30 days. In some embodiments, the time interval between two successive administrations of nucleated cells comprising the protein or fragment thereof is about 21 days. In some embodiments, the time the time interval between two successive administrations of the nucleated cells comprising the protein or fragment thereof is about any one of 1, 2, 3, 4, 5, 6, 7, 8, 10, 12, 14, 16, 20, 25, 30, 35, 40, 45, 50, 55, 60, 65, 70, 75, 80, 85, 90, 95, 100, or 150 days. In some embodiments, the time interval between the first two successive administrations of the nucleated cells comprising the protein or fragment thereof is 1 day or 2 days. In some embodiments, the time interval between the first two successive administrations of the nucleated cells comprising the protein or fragment thereof is 1 day or 2 days, wherein the method comprises more than 2 administration of the nucleated cells comprising the protein or fragment thereof (such as but not limited to 3, 4, 5, 6, 7, 8, 9, 10, 11, 12, 13, 14, 15 or more administrations). In some embodiments, the nucleated cells comprising the protein or fragment thereof are administered intravenously, intratumorally and/or subcutaneously. In some embodiments, the nucleated cells comprising the protein or fragment thereof are administered intravenously.

In some embodiments, the composition further comprises an adjuvant. In some embodiments, the adjuvant is a CpG oligodeoxynucleotide (ODN), LPS, IFN-α, IFNγ, STING agonists, cyclic dinucleotides (CDN), alpha-Galactosyl Ceramide, RIG-I agonists, polyinosinic-polycytidylic acid, a TLR3 agonist, a TLR4 agonist, a TLR7 agonist, a TLR8 agonist, or a TLR9 agonist. Exemplary adjuvants include, without limitation, CpG ODN, interferon-α (IFN-α), polyinosinic:polycytidylic acid (polyI:C), imiquimod (R837), resiquimod (R848), or lipopolysaccharide (LPS). In some embodiments, the adjuvant is a CpG oligodeoxynucleotide. In some embodiments, the adjuvant is CpG 7909.

In some embodiments, the composition comprising the nucleated cells comprising the protein or fragment thereof and the adjuvant are administered simultaneously. In some embodiments, the composition comprising nucleated cells comprising the protein or fragment thereof and the adjuvant are administered sequentially. In some embodiments, the adjuvant and/or the nucleated cells comprising the protein or fragment thereof are administered intravenously, intratumorally and/or subcutaneously. In some embodiments, the adjuvant and/or the nucleated cells comprising the protein or fragment thereof are administered intravenously.

In some embodiments, the composition comprising nucleated cells comprising the protein or fragment thereof is administered prior to administering the adjuvant. For example, the composition comprising the nucleated cells comprising the protein or fragment thereof is administered from about 1 hour to about 1 week prior to administration of the adjuvant. For example, in some embodiments, the composition comprising the nucleated cells comprising the protein or fragment thereof is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the adjuvant. In some embodiments, the composition comprising the nucleated cells comprising the protein or fragment thereof is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the adjuvant.

In some embodiments, the composition comprising the nucleated cells comprising the protein or fragment thereof is administered following administration of the adjuvant. For example, the composition comprising the nucleated cells comprising the protein or fragment thereof is administered from about 1 hour to about 1 week following administration of the adjuvant. For example, in some embodiments, the composition comprising the nucleated cells comprising the protein or fragment thereof is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the adjuvant. In some embodiments, the composition comprising the nucleated cells comprising the protein or fragment thereof is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the adjuvant.

In some embodiments, the individual is positive for expression of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the individual is positive for expression of HLA-A*02, HLA-A*11 and/or HLA-B*07. In some embodiments, at least one cell in the nucleated cells comprising the protein or fragment thereof is positive for expression of HLA-A*02, HLA-A*11 and/or HLA-B*07. In some embodiments, at least about any one of 10%, 20%, 30%, 40%, 50%, 60%, 70%, 80%, 90%, or 99% of the nucleated cells comprising the protein or fragment thereof is positive for expression of HLA-A*02, HLA-A*11 and/or HLA-B*07. In some embodiments, wherein the nucleated cells are a plurality of PBMCs, at least about any one of 10%, 20%, 30%, 40%, 50%, 60%, 70%, 80%, 90%, or 99% of T cells within the modified PBMCs comprising the protein or fragment thereof are positive for expression of HLA-A*02, HLA-A*11 and/or HLA-B*07. In some embodiments, at least about any one of 10%, 20%, 30%, 40%, 50%, 60%, 70%, 80%, 90%, or 99% of B cells within the modified PBMCs comprising the protein or fragment thereof are positive for expression of HLA-A*02, HLA-A*11 and/or HLA-B*07. In some embodiments, at least about any one of 10%, 20%, 30%, 40%, 50%, 60%, 70%, 80%, 90%, or 99% of NK cells within the modified PBMCs comprising the protein or fragment thereof are positive for expression of HLA-A*02, HLA-A*11 and/or HLA-B*07. In some embodiments, at least about any one of 10%, 20%, 30%, 40%, 50%, 60%, 70%, 80%, 90%, or 99% of monocytes within the modified PBMCs comprising the protein or fragment thereof are positive for expression of HLA-A*02, HLA-A*11 and/or HLA-B*07.

In some embodiments according to any one of the methods, uses or compositions described herein, the nucleated cells comprising the protein or fragment thereof are administered prior to, concurrently with, or following administration of a therapeutic agent. In some embodiments, the therapeutic agent comprises one or more of an immune checkpoint inhibitor, a chemotherapy, or a radiotherapy. In some embodiments, the therapeutic agent comprises one or more cytokines. In some embodiments, the therapeutic agent comprises one or more antibodies. In some embodiments, the therapeutic agent comprises one or more bispecific polypeptides used in immuno-oncology (e.g., an immunoconjugate).

Immune checkpoints are regulators of the immune system and keep immune responses in check. Immune checkpoint inhibitors can be employed to facilitate the enhancement of immune response. In some embodiments, the composition comprising the nucleated cells comprising the protein or fragment thereof is administered in combination with administration of an immune checkpoint inhibitor. In some embodiments, the composition comprising the nucleated cells comprising the protein or fragment thereof and the immune checkpoint inhibitor are administered simultaneously. In some embodiments, the composition comprising the nucleated cells comprising the protein or fragment thereof and the immune checkpoint inhibitor are administered sequentially. In some embodiments, the immune checkpoint inhibitor and/or the nucleated cells comprising the protein or fragment thereof are administered intravenously, intratumorally and/or subcutaneously. In some embodiments, the immune checkpoint inhibitor and/or the nucleated cells comprising the protein or fragment thereof are administered intravenously.

In some embodiments, the composition comprising the nucleated cells comprising the protein or fragment thereof is administered prior to administration of the immune checkpoint inhibitor. In some embodiments, the composition comprising the nucleated cells comprising the protein or fragment thereof is administered following administration of the immune checkpoint inhibitor. For example, the composition comprising the nucleated cells comprising the protein or fragment thereof is administered from about 1 hour to about 1 week prior to administration of the immune checkpoint inhibitor. For example, in some embodiments, the composition comprising the nucleated cells comprising the protein or fragment thereof is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the immune checkpoint inhibitor. In some embodiments, the composition comprising the nucleated cells comprising the protein or fragment thereof is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the immune checkpoint inhibitor.

In some embodiments, the composition comprising the nucleated cells comprising the protein or fragment thereof is administered about 7 days, about 10 days, about 14 days, about 18 days, about 21 days, about 24 days, about 28 days, about 30 days, about 35 days, about 40 days, about 45 days, or about 50 days prior to administration of the immune checkpoint inhibitor. In some embodiments, the composition comprising the nucleated cells comprising the protein or fragment thereof is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days prior to administration of the immune checkpoint inhibitor.

In some embodiments, the composition comprising the nucleated cells comprising the protein or fragment thereof is administered following administration of the immune checkpoint inhibitor. For example, the composition comprising the nucleated cells comprising the protein or fragment thereof is administered from about 1 hour to about 1 week following administration of the immune checkpoint inhibitor. For example, in some embodiments, the composition comprising the nucleated cells comprising the protein or fragment thereof is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the immune checkpoint inhibitor. In some embodiments, the composition comprising the nucleated cells comprising the protein or fragment thereof is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the immune checkpoint inhibitor.

In some embodiments, the composition comprising the nucleated cells comprising the protein or fragment thereof is administered about 7 days, about 10 days, about 14 days, about 18 days, about 21 days, about 24 days, about 28 days, about 30 days, about 35 days, about 40 days, about 45 days, or about 50 days following administration of the immune checkpoint inhibitor. In some embodiments, the composition comprising the nucleated cells comprising the protein or fragment thereof is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the immune checkpoint inhibitor.

In some embodiments, the method comprises multiple administration of the composition comprising the nucleated cells comprising the protein or fragment thereof and/or multiple administration of the immune checkpoint inhibitor.

For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the nucleated cells comprising the protein or fragment thereof and/or the immune checkpoint inhibitor. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the nucleated cells comprising the protein or fragment thereof and/or the immune checkpoint inhibitor.

Exemplary immune checkpoint inhibitor is targeted to, without limitation, PD-1, PD-L1, CTLA-4, LAG3, TIM-3, TIGIT, VISTA, TIM1, B7-H4 (VTCN1) or BTLA. In some embodiments, the immune checkpoint inhibitor is targeted to one or more of PD-1, PD-L1, CTLA-4, LAG3, TIM-3, TIGIT, VISTA, TIM1, B7-14 (VTCN1) or BTLA. In some embodiments, the immune checkpoint inhibitor is one or more of: an antibody that binds to PD-1, an antibody that binds PD-L1, an antibody that binds CTLA-4, an antibody that binds LAG3, or an antibody that binds TIM-3, an antibody that binds TIGIT, an antibody that binds VISTA, an antibody that binds TIM-1, an antibody that binds B7-H4, or an antibody that binds BTLA. In further embodiments, the antibody can be a full-length antibody or any variants, for example but not limited to, an antibody fragment, a single chain variable fragment (ScFv), or a fragment antigen-binding (Fab). In further embodiments, the antibody can be bispecific, trispecific or multispecific. In some embodiments, the immune checkpoint inhibitor is one or more chemical compounds that binds to and/or inhibits one or more of PD-1, PD-L1, CTLA-4, LAG3, TIM-3, TIGIT, VISTA, TIM1, B7-H4 (VTCN1) or BTLA. In some embodiments, the immune checkpoint inhibitor is one or more peptides that binds to and/or inhibits one or more of PD-1, PD-L1, CTLA-4, LAG3, TIM-3, TIGIT, VISTA, TIM1, B7-H4 (VTCN1) or BTLA. In some embodiments, the immune checkpoint inhibitor is targeted to PD-1. In some embodiments, the immune checkpoint inhibitor is targeted to PD-L1.

Cytokines can be used in combination with any one of the pluralities of modified PBMCs described herein to achieve additive or synergistic effects against cancers, for example, cancer associated with a mutated protein. In some embodiments, the composition comprising the nucleated cells comprising the protein or fragment thereof is administered in combination with administration of one or more cytokines. In some embodiments, the composition comprising the nucleated cells comprising the protein or fragment thereof and the cytokine are administered simultaneously. In some embodiments, the composition comprising the nucleated cells comprising the protein or fragment thereof and the cytokine are administered sequentially.

In some embodiments, the composition comprising the nucleated cells comprising the protein or fragment thereof is administered prior to administration of the cytokine In some embodiments, the composition comprising the nucleated cells comprising the protein or fragment thereof is administered following administration of the cytokine. For example, the composition comprising the nucleated cells comprising the protein or fragment thereof is administered from about 1 hour to about 1 week prior to administration of the cytokine. For example, in some embodiments, the composition comprising the nucleated cells comprising the protein or fragment thereof is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the cytokine. In some embodiments, the composition comprising the nucleated cells comprising the protein or fragment thereof is administered from between about 1 hour and about 2 hours, from between about 2 hours and about 3 hours, from between about 3 hours and about 4 hours, from between about 4 hour, and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the cytokine.

In some embodiments, the composition comprising the nucleated cells comprising the protein or fragment thereof is administered about 7 days, about 10 days, about 14 days, about 18 days, about 21 days, about 24 days, about 28 days, about 30 days, about 35 days, about 40 days, about 45 days, or about 50 days prior to administration of the cytokine. In some embodiments, the composition comprising the nucleated cells comprising the protein or fragment thereof is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days prior to administration of the cytokine.

In some embodiments, the composition comprising the nucleated cells comprising the protein or fragment thereof is administered following administration of the cytokine. For example, the composition comprising the nucleated cells comprising the protein or fragment thereof is administered from about 1 hour to about 1 week following administration of the cytokine. For example, in some embodiments, the composition comprising the nucleated cells comprising the protein or fragment thereof is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the cytokine. In some embodiments, the composition comprising the nucleated cells comprising the protein or fragment thereof is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the cytokine.

Exemplary cytokines include but are not limited to chemokines, interferons, interleukins, lymphokines, and tumor necrosis factors, or functional derivatives thereof. In some embodiments, the cytokine enhances cellular immune responses. In some embodiments, the cytokine enhances antibody responses. In some embodiments, the cytokine is a type I cytokine. In some embodiments, the cytokine is a type 2 cytokine. In some embodiments, the cytokine comprises one or more of: IL-2, IL-15, IL-10, IL-12, IFN-α, or IL-21. In some embodiments, the cytokine comprises IL-15.

In some embodiments, the composition comprising the nucleated cells comprising the protein or fragment thereof is administered prior to administration of a bispecific polypeptide comprising a cytokine moiety. In some embodiments, the composition comprising the nucleated cells comprising the protein or fragment thereof is administered prior to administration of a bispecific polypeptide comprising a cytokine moiety and an immune checkpoint inhibitor moiety. In some embodiments, the bispecific polypeptide comprises a CD3 targeting moiety and a tumor antigen targeting moiety. In some embodiments, the bispecific polypeptide comprises moieties that target two immune checkpoints. In some embodiments, the bispecific polypeptide comprises a moiety that targets antigens found in stroma or expressed on cancer-associated fibroblasts. In some embodiments, the bispecific polypeptide comprises a moiety that targets antigens found in stroma or expressed on cancer-associated fibroblasts and a cytokine moiety.

Chemotherapy can be used in combination with any one of the pluralities of modified PBMCs described herein to achieve additive or synergistic effects against cancers, for example, cancer associated with a mutated protein. In some embodiments, the composition comprising the nucleated cells comprising the protein or fragment thereof is administered in combination with administration of a chemotherapy. In some embodiments, the composition comprising the nucleated cells comprising the protein or fragment thereof and the chemotherapy are administered simultaneously. In some embodiments, the composition comprising the nucleated cells comprising the protein or fragment thereof and the chemotherapy are administered sequentially.

In some embodiments, the composition comprising the nucleated cells comprising the protein or fragment thereof is administered prior to administration of the chemotherapy. In some embodiments, the composition comprising the nucleated cells comprising the protein or fragment thereof is administered following administration of the chemotherapy. For example, the composition comprising the nucleated cells comprising the protein or fragment thereof is administered from about 1 hour to about 1 week prior to administration of the chemotherapy. For example, in some embodiments, the composition comprising the nucleated cells comprising the protein or fragment thereof is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 6) hours, about 3 days, about 4 days, about 5 days, about 6 days, or about 7 days prior to administration of the chemotherapy. In some embodiments, the composition comprising the nucleated cells comprising the protein or fragment thereof is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the chemotherapy.

In some embodiments, the composition comprising the nucleated cells comprising the protein or fragment thereof is administered following administration of the chemotherapy. For example, the composition comprising the nucleated cells comprising the protein or fragment thereof is administered from about 1 hour to about 1 week following administration of the chemotherapy. For example, in some embodiments, the composition comprising the nucleated cells comprising the protein or fragment thereof is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the chemotherapy. In some embodiments, the composition comprising the nucleated cells comprising the protein or fragment thereof is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the chemotherapy.

In some embodiments, the composition comprising the nucleated cells comprising the protein or fragment thereof is administered about 7 days, about 10 days, about 14 days, about 18 days, about 21 days, about 24 days, about 28 days, about 30 days, about 35 days, about 40 days, about 45 days, or about 50 days following administration of the chemotherapy. In some embodiments, the composition comprising the nucleated cells comprising the protein or fragment thereof is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the chemotherapy.

In some embodiments, the method comprises multiple administration of the composition comprising the nucleated cells comprising the protein or fragment thereof and/or multiple administration of the chemotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the nucleated cells comprising the protein or fragment thereof and/or the chemotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the nucleated cells comprising the protein or fragment thereof and/or the chemotherapy.

Exemplary chemotherapy can be cell cycle dependent or cell cycle independent. In some embodiments, the chemotherapy comprises one or more chemotherapeutic agents. In some embodiments, a chemotherapeutic agent can target one or more of cell division, DNA, or metabolism in cancer. In some embodiments, the chemotherapeutic agent is a platinum-based agent, such as but not limited to cisplatin, oxaliplatin or carboplatin. In some embodiments, the chemotherapeutic agent is a taxane (such as docetaxel or paclitaxel). In some embodiments, the chemotherapeutic agent is 5-fluorouracil, doxorubicin, or irinotecan. In some embodiments, the chemotherapeutic agent is one or more of: an alkylating agent, an antimetabolite, an antitumor antibiotic, a topoisomerase inhibitor or a mitotic inhibitor. In some embodiments, the chemotherapy comprises cisplatin.

Radiotherapy can be used in combination with any one of the pluralities of modified PBMCs described herein to achieve additive or synergistic effects against cancers, for example, a cancer associated with a mutated protein or fragment thereof. In some embodiments, the composition comprising the nucleated cells comprising the protein or fragment thereof is administered in combination with administration of a radiotherapy. In some embodiments, the composition comprising the nucleated cells comprising the protein or fragment thereof and the radiotherapy are administered simultaneously. In some embodiments, the composition comprising the nucleated cells comprising the protein or fragment thereof and the radiotherapy are administered sequentially. In some embodiments, the composition comprising the nucleated cells comprising the protein or fragment thereof is administered in combination with administration of a radiotherapy, in combination with a chemotherapy, and/or in combination with an immune checkpoint inhibitor.

In some embodiments, the composition comprising the nucleated cells comprising the protein or fragment thereof is administered prior to administration of the radiotherapy. In some embodiments, the composition comprising the nucleated cells comprising the protein or fragment thereof is administered following administration of the radiotherapy. For example, the composition comprising the nucleated cells comprising the protein or fragment thereof is administered from about 1 hour to about 1 week prior to administration of the radiotherapy. For example, in some embodiments, the composition comprising the nucleated cells comprising the protein or fragment thereof is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the radiotherapy. In some embodiments, the composition comprising the nucleated cells comprising the protein or fragment thereof is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the radiotherapy.

In some embodiments, the composition comprising the nucleated cells comprising the protein or fragment thereof is administered following administration of the radiotherapy. For example, the composition comprising the nucleated cells comprising the protein or fragment thereof is administered from about 1 hour to about 1 week following administration of the radiotherapy. For example, in some embodiments, the composition comprising the nucleated cells comprising the protein or fragment thereof is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the radiotherapy. In some embodiments, the composition comprising the nucleated cells comprising the protein or fragment thereof is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the radiotherapy.

In some embodiments, the composition comprising the nucleated cells comprising the protein or fragment thereof is administered about 7 days, about 10 days, about 14 days, about 18 days, about 21 days, about 24 days, about 28 days, about 30 days, about 35 days, about 40 days, about 45 days, or about 50 days following administration of the radiotherapy. In some embodiments, the composition comprising the nucleated cells comprising the protein or fragment thereof is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the radiotherapy.

In some embodiments, the method comprises multiple administration of the composition comprising the nucleated cells comprising the protein or fragment thereof and/or multiple administration of the radiotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the nucleated cells comprising the protein or fragment thereof and/or the radiotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the nucleated cells comprising the protein or fragment thereof and/or the radiotherapy.

In some embodiments, there is provided a plurality of nucleated cells (e.g. PBMCs) comprising a protein or fragment thereof for use in a method of stimulating an immune response in an individual according to any one of the methods described herein.

In some embodiments, there is provided a composition for stimulating an immune response to a protein or fragment thereof in an individual, wherein the composition comprises an effective amount of any one of the compositions comprising nucleated cells comprising the protein of fragment described herein. In some embodiments, there is provided a composition for reducing tumor growth, wherein the composition comprises an effective amount of any one of the compositions comprising nucleated cells comprising the protein or fragment described herein. In some embodiments, the individual has cancer and/or an infection. In some embodiments, there is provided a composition for treating cancer and/or an infection in an individual, wherein the composition comprises an effective amount of any one of the compositions comprising nucleated cells comprising a protein or fragment described herein. In some embodiments, the cancer is an HPV-associated cancer or an HBV-associated cancer. In some embodiments, the individual is infected with HPV and/or HBV.

mRNA Encoding a Protein or Fragment Thereof

In some embodiments, provided are methods for simulating an immune response in an individual, and/or vaccinating an individual in need thereof, the method comprising administering to the individual an effective amount of a composition comprising nucleated cells comprising a protein or fragment thereof delivered intracellularly; wherein the nucleated cells are prepared by first passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells and incubating the perturbed input nucleated cells with the mRNA encoding the protein or fragment thereof to allow the mRNA encoding the protein or fragment thereof to enter the perturbed input nucleated cells; wherein the mRNA encoding the protein or fragment thereof is expressed in the nucleated cells, thereby generating the modified nucleated cells comprising the protein or fragment thereof, wherein the protein or fragment thereof stimulates an immune response regardless of the HLA haplotype of the individual.

In some embodiments, the nucleotide sequence of the mRNA is codon optimized for expression in the nucleated cell. In some embodiments, the nucleotide sequence of the mRNA is codon optimized for expression in PBMCs. In some embodiments, the codon optimization of mRNA does not affect or does not significantly affect conformation and function of the expressed protein. In some embodiments, the codon optimization of mRNA does not affect or does not significantly affect conformation and function of the antigen processed from the expressed protein. In some embodiments, the mRNA is a non-self mRNA. In some embodiments, the mRNA is an exogenous mRNA. In some embodiments, the mRNA is an in vitro transcribed (IVT) mRNA. In some embodiments, the exogenous mRNA is an in vitro transcribed (IVT) mRNA. In some embodiments, the mRNA encodes for a recombinant protein.

In some embodiments, the mRNA comprises one or more modifications to enhance the antigen processing and presentation of the protein expressed.

As used herein, an immunoproteasome-targeting motif is a portion of a protein that is important in regulation of protein degradation rates. In some embodiments, an immunoproteasome-targeting motif enhances the degradation of a protein in an antigen processing pathway. In some embodiments, an immunoproteasome-targeting motif facilitates the localization of a protein to an antigen processing pathway. In some embodiments, an immunoproteasome-targeting motif enhances the processing of the protein in an immunoproteasome complex. An example of an immunoproteasome-targeting motif is a degron. Degrons known to be targeted by anaphase-promoting complex or cyclosome (APC/C) include the destruction box (D box), the KEN box, and the ABBA motif. Proteins containing these motifs interact with APC/C, resulting in protein ubiquitination and destruction by proteasome. Other exemplary immunoproteasome-targeting motifs that includes KEKE motif, In some embodiments, the mRNA further comprises one or more nucleic acid sequences encoding an immunoproteasome-targeting motif, wherein translation of the mRNA generates a fusion protein of the protein and the one or more immunoproteasome-targeting motifs. In some embodiments, the one or more immunoproteasome-targeting motifs enhance degradation of the protein in the cell and/or presentation of peptides derived from the protein on the surface of the cell compared to degradation of the protein in the cell and/or presentation of peptides derived from the protein on the surface of the cell in the absence of an immunoproteasome-targeting motif.

In some embodiments, the amount of degradation of the protein encoded by an mRNA comprising the one or more nucleic acid sequences encoding an immunoproteasome-targeting motif is increased by about any one of 10%, 20%, 30%, 40%, 50%, 75%, 100%, 2-fold, 3-fold, 4-fold, 5-fold, 10-fold, 25-fold, 50-fold, 100-fold, 200-fold, or 500-fold or more compared to a protein encoded by an mRNA that does not comprise nucleic acid encoding an immunoproteasome-targeting motif. In some embodiments, the rate of degradation of the protein encoded by an mRNA comprising the one or more nucleic acid sequences encoding an immunoproteasome-targeting motif is increased by about any one of: 10%, 20%, 30%, 40%, 50%, 75%, 100%, 2-fold, 3-fold, 4-fold, 5-fold, 10-fold, 25-fold, 50-fold, 100-fold, 200-fold, or 500-fold or more compared to a protein encoded by an mRNA that does not comprise nucleic acid encoding an immunoproteasome-targeting motif.

In some embodiments, the amount of cell-surface presentation of peptides derived from the protein encoded by an mRNA comprising the one or more nucleic acid sequences encoding an immunoproteasome-targeting motif is increased by about any one of: 10%, 20%, 30%, 40%, 50%, 75%, 100%, 2-fold, 3-fold, 4-fold, 5-fold, 10-fold, 25-fold, 50-fold, 100-fold, 200-fold, or 500-fold or more compared to a protein encoded by an mRNA that does not comprise nucleic acid encoding an immunoproteasome-targeting motif. In some embodiments, the rate of cell-surface presentation of peptides derived from the protein encoded by an mRNA comprising the one or more nucleic acid sequences encoding an immunoproteasome-targeting motif is increased by about any one of 10%, 20%, 30%, 40%, 50%, 75%, 100%, 2-fold, 3-fold, 4-fold, 5-fold, 10-fold, 25-fold, 50-fold, 100-fold, 200-fold, or 500-fold or more compared to the protein encoded by an mRNA that does not comprise nucleic acid encoding an immunoproteasome-targeting motif.

In some embodiments, the one or more immunoproteasome-targeting motifs is at the N-terminus of the fusion protein. In some embodiments, the one or more immunoproteasome-targeting motifs is at the C-terminus of the fusion protein. In some embodiments, the one or more immunoproteasome-targeting motifs is at the N-terminus and/or the C-terminus of the fusion protein.

In some embodiments, the one or more immunoproteasome-targeting motifs comprises one or more of: a D-box domain, a sec/MITD domain, a KEKE motif.

In some embodiments, the mRNA encodes the native HPV E6 protein. In some embodiments, the mRNA encodes the native HPV E6 protein, and comprises the sequence of SEQ ID NO: 59. In some embodiments, the mRNA is a codon-optimized mRNA encoding the native HPV E6 protein. In some embodiments, the mRNA is a codon-optimized mRNA encoding the native HPV E6 protein, wherein the codon-optimized mRNA comprises the sequence of SEQ ID NO: 60. In some embodiments, the mRNA encodes the native HPV E7 protein. In some embodiments, the mRNA encodes the native HPV E7 protein, and comprises the sequence of SEQ ID NO: 61. In some embodiments, the mRNA is a codon-optimized mRNA encoding the native HPV E7 protein. In some embodiments, the mRNA is a codon-optimized mRNA encoding the native HPV E7 protein, wherein the codon-optimized mRNA comprises the sequence of SEQ ID NO: 63 or 64. In some embodiments, the mRNA is a codon-optimized mRNA encoding a fusion protein comprising HPV E7 protein and a KEKE domain. In some embodiments, the mRNA is a codon-optimized mRNA encoding a fusion protein comprising HPV E7 protein and a KEKE domain, wherein the mRNA comprises the sequence of SEQ ID NO: 67. In some embodiments, the mRNA is an mRNA encoding for a fusion protein comprising HPV E7 protein and a D-box domain. In some embodiments, the mRNA is an mRNA encoding for a fusion protein comprising HPV E7 protein and a D-box domain, wherein the mRNA comprises the sequence of SEQ ID NO: 62. In some embodiments, the mRNA is a codon-optimized mRNA encoding for a fusion protein comprising HPV E7 protein and a D-box domain. In some embodiments, the mRNA is a codon-optimized mRNA encoding for a fusion protein comprising HPV E7 protein and a D-box domain, wherein the mRNA comprises the sequence of SEQ ID NO: 66. In some embodiments, the mRNA is a codon-optimized mRNA encoding for a fusion protein comprising HPV E7 protein with a mutated nuclear localization sequence (NLS). In some embodiments, the mRNA is a codon-optimized mRNA encoding for a fusion protein comprising HPV E7 protein with a mutated NLS, wherein the mRNA comprises the sequence of SEQ ID NO: 70. In some embodiments, the mRNA is a codon-optimized mRNA encoding for a HPV E7.6 protein. In some embodiments, the mRNA is a codon-optimized mRNA encoding for a HPV E7.6 protein, wherein the mRNA comprises the sequence of SEQ ID NO: 68. In some embodiments, the mRNA is a codon-optimized mRNA encoding for a fusion protein comprising 6 repeats of HPV E7.6. In some embodiments, the mRNA is a codon-optimized mRNA encoding for a fusion protein comprising 6 repeats of HPV E7.6, wherein the mRNA comprises the sequence of SEQ ID NO: 69.

In some embodiments, the mRNA encodes the native Influenza M1 protein. In some embodiments, the mRNA encodes the native Influenza M1 protein, and comprises the sequence of SEQ ID NO: 83. In some embodiments, the mRNA is a codon-optimized mRNA encoding the native Influenza M1 protein. In some embodiments, the mRNA is a codon-optimized mRNA encoding the native Influenza M1 protein, wherein the codon-optimized mRNA comprises the sequence of SEQ ID NO: 84.

In some embodiments, the mRNA encodes the native CMV pp65 protein. In some embodiments, the mRNA is a codon-optimized mRNA encoding the native CMV pp65 protein. In some embodiments, the mRNA is a codon-optimized mRNA encoding the native CMV pp65 protein, wherein the codon-optimized mRNA comprises the sequence of SEQ ID NO: 85.

In some embodiments, the mRNA encodes the MART-1 antigen. In some embodiments, the mRNA is a codon-optimized mRNA encoding the MART-1 antigen.

In some embodiments according to any one of the mRNAs described herein, one or more residues of the mRNA is modified. In some embodiments, one or more residues of the mRNA is one or more of: a phosphorothioate residue, a pseudouridine residue, an N1-methyladenosine residue, a 5-methylcytidine residue, or a morpholino residue.

Proteins and Fragments Thereof, and Antigens

In some embodiments according to any one of the methods, compositions or pluralities of modified PBMCs described herein, the protein is a disease-associated protein. In some embodiments, the protein is a non-self protein. In some embodiments, the protein is a mutated protein associated with cancer, a viral protein, bacterial protein, or fungal protein. In some embodiments, the protein is derived from a lysate, such as a lysate of disease cells. In some embodiments, the protein is derived from a tumor lysate. In some embodiments, the protein comprises one or more of tumor antigens or tumor associated antigens. In some embodiments, the protein is a mutated protein associated with a cancer. In some embodiments, the cancer is head and neck cancer, cervical cancer, vulvar cancer, vaginal cancer, penile cancer, anal cancer, perianal cancer, anogenital cancer, oral cancer or salivary cancer. In some embodiments, the protein comprises one or more antigens, wherein the antigen is a head and neck cancer antigen, a cervical cancer antigen, a vulvar cancer antigen, a vaginal cancer antigen, a penile cancer antigen, an anal cancer antigen, a perianal cancer antigen, an anogenital cancer antigen, an oral cancer antigen, a salivary cancer antigen, a breast cancer antigen, a skin cancer antigen, a bladder cancer antigen, a colon cancer, a rectal cancer antigen, an endometrial cancer antigen, a kidney cancer antigen, a leukemia antigen, a lung cancer antigen, a melanoma antigen, a non-Hodgkin lymphoma antigen, a pancreatic cancer antigen, a prostate cancer antigen, or a thyroid cancer antigen, In some embodiments, the cancer is a solid cancer. In some embodiments, the cancer is a hematologic cancer.

In some embodiments, the cancer is a virus-associated cancer. In some embodiments, the cancer is a HPV-associated cancer. In some embodiments, the cancer is a localized cancer. In some embodiments, the cancer is a metastatic cancer. In some embodiments, the antigen is associated with an infectious disease. In some embodiments, the infectious disease is a viral infectious disease, a fungal infectious disease and/or a bacterial infectious disease. In some embodiments, the infectious disease is associated with Influenza, CMV, HIV, HPV, EBV, MCV, HAV, HBV, HCV, HSV-1, HSV-2, VSV, HHV-6, HHV-7 or HHV-8.

In some embodiments according to any one of the methods, compositions or pluralities of modified PBMCs described herein, the protein comprises one or more antigens. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs. In some embodiments, the one or more mRNAs comprise any one of the modifications described herein. In some embodiments, the one or more mRNA comprise any one of the motifs described herein, including but not limited to any one of the immunoproteasome-targeting motifs described herein.

In some embodiments according to any one of the methods, compositions or pluralities of modified PBMCs described herein, the antigen is a human papillomavirus (HPV) antigen. Papillomaviruses are small nonenveloped DNA viruses with a virion size of ~55 nm in diameter. More than 100 HPV genotypes are completely characterized, and a higher number is presumed to exist. HPV is a known cause of cervical cancers, as well as some vulvar, vaginal, penile, oropharyngeal, anal, and rectal cancers. Although most HPV infections are asymptomatic and clear spontaneously, persistent infections with one of the oncogenic HPV types can progress to precancer or cancer. Other HPV-associated diseases can include common warts, plantar warts, flat warts, anogenital warts, anal lesions, epidermodysplasia, focal epithelial hyperplasia, mouth papillomas, verrucous cysts, laryngeal papillomatosis, squamous intraepithelial lesions (SILs), cervical intraepithelial neoplasia (CIN), vulvar intraepithelial neoplasia (VIN) and vaginal intraepithelial neoplasia (VAIN). Many of the known human papillomavirus (HPV) types cause benign lesions with a subset being oncogenic. Based on epidemiologic and phylogenetic relationships, HPV types are classified into fifteen "high risk types" (HPV 16, 18, 31, 33, 35, 39, 45, 51, 52, 56, 58, 59, 68, 73, and 82) and three "probable high risk types" (HPV 26, 53, and 66), which together are known to manifest as low and high grade cervical changes and cancers, as well as other anogential cancers such as vulval, vaginal, penile, anal, and perianal cancer, as well as head and neck cancers. Recently, the association of high risk types HPV 16 and 18 with breast cancer was also described. Eleven HPV types classified as "low risk types" (HPV 6, 11, 40, 42, 43, 44, 54, 61, 70, 72, and 81) are known to manifest as benign low-grade cervical changes, genital warts and recurrent respiratory papillomatosis. Cutaneous HPV types 5, 8, and 92 are associated with skin cancer. In some HPV-associated cancers, the immune system is depressed and correspondingly, the antitumor response is significantly impaired. See Suresh and Burtness, *Am J Hematol Oncol* 13(6):20-27 (2017). In some embodiments, the antigen is a pool of multiple polypeptides that elicit a response against the same and or different antigens. In some embodiments, an antigen in the pool of multiple antigens does not decrease the immune response directed toward other antigens in the pool of multiple antigens. In some embodiments, the HPV antigen is a polypeptide comprising an antigenic HPV epitope and one or more heterologous peptide sequences. In some embodiments, the HPV antigen complexes with itself, with other antigens, or with the adjuvant. In some embodiments, the HPV is HPV-16 or HPV-18. In some embodiments, the HPV antigen is comprised of an HLA-A*02-specific epitope. In some embodiments, the HPV antigen is comprised of an HLA-B*07-specific epitope. In some embodiments, the HPV antigen is comprised of an HLA-B*35-specific epitope. In some embodiments, the HPV antigen is comprised of an HLA-A*01-specific epitope. In some embodiments, the HPV antigen is an HPV E6 antigen or an HPV E7 antigen. In some embodiments, the antigen comprises a peptide derived from HPV E6 and/or E7. In some embodiments, the antigen comprises an HLA-A*02-restricted peptide derived from HPV E6 and/or E7. In some embodiments, the HPV protein is HPV E6. In some embodiments, the HPV protein is HPV E7. In some embodiments, the protein comprises a peptide derived from HPV E6. In some embodiments, the protein comprises a peptide derived from HPV E7. In some embodiments, the HPV protein is a protein comprising about any one of: 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the amino acid sequence of native (including wild type, naturally-occurring and/or splice variants) of HPV E6. In some embodiments, the HPV protein is a protein comprising 100% of the amino acid sequence of native HPV E6. In some embodiments, the HPV protein is a protein comprising about any one of: 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the amino acid sequence of native (including wild type, naturally-occurring and/or splice variants) HPV E7. In some embodiments, the HPV protein is a protein comprising about 100% of the amino acid sequence of native HPV E7.

Hepatitis B virus (HBV) strains isolated worldwide have been classified into six genomic groups deduced from genome comparisons and indicated as HBV genotypes A to F. Nine serological groups, called hepatitis B surface antigen (HBsAg) subtypes, have also been defined based on discriminating sera and have been designated adw2, adw4, adr, adrq-, ayw1, ayw2, ayw3, ayw4, and ayr. In some embodiments, the HPV antigen is a polypeptide comprising an antigenic HPV epitope and one or more heterologous peptide sequences. In some embodiments, the HPV antigen complexes with itself, with other antigens, or with the adjuvant. In some embodiments, the HBV is of the genotype/subtype of any one of: A/adw2, B/adw2, C/adr, C/adw2, D/ayw3, D/ayw2, E/ayw4, F/adw2, F/adw4, or F/ayw4. In some embodiments, the HBV protein is comprised of an HLA-A*02-specific epitope. In some embodiments, the HBV protein is HBsAg. In some embodiments, the HBV protein is HBc. In some embodiments, the HBV protein is one or more of HBV core protein, HBV surface protein, HBV polymerase, and/or HBV X protein. In some embodiments, the HBV protein is HBeAg. In some embodiments, the protein comprises a peptide derived from HBsAg. In some embodiments, the protein comprises a peptide derived from HBc. In some embodiments, the protein comprises a peptide derived HBeAg. In some embodiments, the HBV protein is a protein comprising about any one of: 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the amino acid sequence of native (including wild type, naturally-occurring and/or splice variants) HBsAg. In some embodiments, the HBV protein is a protein comprising 100% of the amino acid sequence of native HBsAg. In some embodiments, the HBV protein is a protein comprising about any one of: 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the amino acid sequence of native (including wild type, naturally-occurring and/or splice variants) HBeAg. In some embodiments, the HBV protein is a protein comprising 100% of the amino acid sequence of native HBeAg. In some embodiments, the HBV protein is a protein comprising about any one of: 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the amino acid sequence of native (including wild type, naturally-occurring and/or splice variants) HBc. In some embodiments, the HBV protein is a protein comprising 100% of the amino acid sequence of native HBc. In some embodiments, the HBV protein is a protein comprising about any one of: 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the native amino acid sequence of one or more of HBV core protein, HBV surface protein, HBV polymerase, and/or HBV X protein. In some embodiments, the HBV protein is a protein comprising 100% of the native amino acid sequence of one or more of HBV core protein, HBV surface protein, HBV polymerase, and/or HBV X protein.

In some embodiments, the protein is an Influenza protein. In some embodiments, the Influenza protein is derived from Influenza A and/or Influenza B. In some embodiments, the protein is an Influenza M1 protein. In some embodiments, the protein comprises a peptide derived from Influenza M1 protein. In some embodiments, the Influenza protein is a protein comprising about any one of: 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the amino acid sequence of native (including wild type, naturally-occurring and/or splice variants) Influenza M1 protein. In some embodiments, the protein is a modified Influenza M1 protein. In some embodiments, the Influenza protein is a protein comprising 100% of the amino acid sequence of native Influenza M1 protein.

In some embodiments according to any one of the methods, compositions or pluralities of nucleated cells described herein, the modified nucleated cells comprise a plurality of antigens (e.g. two or more antigens derived from a protein) that comprise a plurality of immunogenic epitopes. In further embodiments, following administration to an individual of the modified nucleated cells comprising the plurality of antigens that comprise the plurality of immunogenic epitopes, none of the plurality of immunogenic epitopes decreases an immune response in the individual to any of the other immunogenic epitopes. In some embodiments, the antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the antigen is a polypeptide comprising an immunogenic peptide epitope and one or more heterologous peptide sequences. In some embodiments, the antigen is a polypeptide comprising an immunogenic peptide epitope that is flanked on the N-terminus and/or the C-terminus by heterologous peptide sequences. In some embodiments, the flanking heterologous peptide sequences are derived from disease-associated immunogenic peptides. In some embodiments, the flanking heterologous peptide sequences are non-naturally occurring sequence. In some embodiments, the flanking heterologous peptide sequences are derived from an immunogenic synthetic long peptide (SLP). In some embodiments, the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17. In some embodiments, the antigen is capable of being processed into an MIC class I-restricted peptide and/or an MHC class II-restricted peptide.

In some embodiments, the protein and/or the antigen comprises one or more modifications to enhance the antigen processing and presentation of the protein and/or the antigen.

As used herein, an immunoproteasome-targeting motif is a portion of a protein that is important in regulation of protein degradation rates. In some embodiments, an immunoproteasome-targeting motif enhances the degradation of a protein in an antigen processing pathway. In some embodiments, an immunoproteasome-targeting motif facilitates the localization of a protein to an antigen processing pathway. In some embodiments, an immunoproteasome-targeting motif enhances the processing of the protein in an immunoproteasome complex. An example of an immunoproteasome-targeting motif is a degron. Degrons known to be targeted by anaphase-promoting complex or cyclosome (APC/C) include the destruction box (D box), the KEN box, and the ABBA motif. Proteins containing these motifs interact with APC/C, resulting in protein ubiquitination and destruction by proteasome. Other exemplary immunoproteasome-targeting motifs includes, but are not limited to KEKE motif.

In some embodiments, the protein or fragment thereof further comprises one or more immunoproteasome-targeting motifs, giving rise to a fusion protein of the protein and the one or more immunoproteasome-targeting motifs. In some embodiments, the one or more immunoproteasome-targeting motifs enhance degradation of the protein in the cell and/or presentation of peptides derived from the protein on the surface of the cell compared to degradation of the protein in the cell and/or presentation of peptides derived from the protein on the surface of the cell in the absence of a immunoproteasome-targeting motif.

In some embodiments, the amount of degradation of the fusion protein comprising the one or more protein immunoproteasome-targeting motifs is increased by about any one of: 10%, 20%, 30%, 40%, 50%, 75%, 100%, 2-fold, 3-fold, 4-fold, 5-fold, 10-fold, 25-fold, 50-fold, 100-fold, 200-fold, or 500-fold or more compared to a corresponding protein not comprising the immunoproteasome-targeting motif. In some embodiments, the rate of degradation of the protein encoded by an mRNA comprising the one or more nucleic acid sequences encoding an immunoproteasome-targeting motif is increased by about any one of: 10%, 20%, 30%, 40%, 50%, 75% 100%, 2-fold, 3-fold, 4-fold, 5-fold, 10-fold, 25-fold, 50-fold, 100-fold, 200-fold, or 500-fold or more compared to a corresponding protein not comprising the immunoproteasome-targeting motif.

In some embodiments, the amount of cell-surface presentation of peptides derived from the protein comprising the one or more immunoproteasome-targeting motif is increased by about any one of: 10%, 20%, 30%, 40%, 50%, 75%, 100%, 2-fold, 3-fold, 4-fold, 5-fold, 10-fold, 25-fold, 50-fold, 100-fold, 200-fold, or 500-fold or more compared to a corresponding protein not comprising the immunoproteasome-targeting motif. In some embodiments, the rate of cell-surface presentation of peptides derived from the protein comprising the one or more immunoproteasome-targeting motifs is increased by about any one of: 10%, 20%, 30%, 40%, 50%, 75%, 100%, 2-fold, 3-fold, 4-fold, 5-fold, 10-fold, 25-fold, 50-fold, 100-fold, 200-fold, or 500-fold or more compared to the a corresponding protein not comprising the immunoproteasome-targeting motif.

In some embodiments, the one or more immunoproteasome-targeting motifs is at the N-terminus of the fusion protein. In some embodiments, the one or more immunoproteasome-targeting motifs is at the C-terminus of the fusion protein. In some embodiments, the one or more immunoproteasome-targeting motifs is at the N-terminus and/or the C-terminus of the fusion protein.

In some embodiments, the one or more immunoproteasome-targeting motifs comprises one or more of: a D-box domain, a sec/MITD domain, a KEKE motif.

In some embodiments, the protein is native full-length HPV E7 protein. In some embodiments, the protein is native full-length HPV E7 protein comprising the amino acid sequence of SEQ ID NO: 52. In some embodiments, the protein is translated from a codon-optimized mRNA encoding the native HPV E7 protein. In some embodiments, the protein is translated from a codon-optimized mRNA encoding the native HPV E7 protein, wherein the protein comprises the amino acid sequence of SEQ ID NO: 52. In some embodiments, the protein is native full-length HPV E6 protein. In some embodiments, the protein is native full-length HPV E6 protein comprising the amino acid sequence of SEQ ID NO: 51. In some embodiments, the protein is translated from a codon-optimized mRNA encoding the native HPV E6 protein. In some embodiments, the protein is translated from a codon-optimized mRNA encoding the native HPV E6 protein, wherein protein comprises the amino acid sequence of SEQ ID NO: 51. In some embodiments, the protein is a fusion protein comprising HPV E7 protein and a KEKE domain. In some embodiments, the protein is a fusion protein comprising HPV E7 protein and a KEKE domain, wherein the protein comprises the amino acid sequence of SEQ ID NO: 56. In some embodiments, the protein is a fusion protein comprising HPV E7 protein and a D-box domain. In some embodiments, the protein is a fusion protein comprising HPV E7 protein and a D-box domain, wherein the protein comprises the amino acid sequence of SEQ ID NO: 53. In some embodiments, the protein is a fusion protein comprising HPV E7 protein with a mutated NLS. In some embodiments, the protein is a fusion protein comprising HPV E7 protein with a mutated NLS, wherein the protein comprises the amino acid sequence of SEQ ID NO: 55. In some embodiments, the protein is a HPV E7.6 protein. In some embodiments, the protein is a HPV E7.6 protein, wherein the protein comprises the amino acid sequence of SEQ ID NO: 57. In some embodiments, the protein is a fusion protein comprising 6 repeats of HPV E7.6. In some embodiments, the protein is a fusion protein comprising 6 repeats of HPV E7.6, wherein the protein comprises the amino acid sequence of SEQ ID NO: 58.

Methods of Generating Compositions of Nucleated Cells Comprising a Protein or Fragment Thereof In some aspects, provided are methods for producing nucleated cells comprising a protein or fragment thereof; the method comprising introducing the protein or fragment thereof into the nucleated cells, wherein the protein or fragment thereof stimulates an immune response in an individual in an HLA agnostic manner.

In some aspects, provided are methods for producing nucleated cells comprising a protein or fragment thereof; the method comprising introducing mRNA encoding the protein or fragment thereof into the nucleated cells, wherein the mRNA is expressed to produce the protein or fragment thereof; wherein the protein or fragment thereof stimulates an immune response in an individual in an HLA agnostic manner.

In some aspects, provided are methods for producing nucleated cells comprising a two or more antigens from a protein; the method comprising introducing the two or more antigens into the nucleated cells; wherein the protein or fragment thereof stimulates an immune response in an individual in an HLA agnostic manner.

In some aspects, provided are methods for producing conditioned nucleated cells comprising a protein or fragment thereof; the method comprising introducing the protein or fragment thereof into the conditioned nucleated cells;

wherein the protein or fragment thereof stimulates an immune response in an individual in an HLA agnostic manner.

In some aspects, provided are methods for producing conditioned nucleated cells comprising a protein or fragment thereof; the method comprising introducing mRNA encoding the protein or fragment thereof into the conditioned nucleated cells, wherein the mRNA is expressed to produce the protein or fragment thereof; wherein the protein or fragment thereof stimulates an immune response in an individual in an HLA agnostic manner.

In some aspects, provided are methods for producing conditioned nucleated cells comprising two or more antigens from a protein; the method comprising introducing the two or more antigens into the conditioned nucleated cells; wherein the protein or fragment thereof stimulates an immune response in an individual in an HLA agnostic manner.

In some embodiments, provided are methods for producing nucleated cells comprising two or more antigens derived from a protein; wherein the two or more antigens stimulates an immune response regardless of the HLA haplotype of the individual. In some embodiments, provided are methods for producing nucleated cells comprises two or more antigens derived from a protein; wherein the two or more antigens stimulates an immune response regardless of the HLA haplotype of the individual.

In some embodiments, the cell comprises two or more antigens derived from the protein. In some embodiments, the cell comprises about any one of: 2, 3, 4, 5, 6, 7, 8, 9, 10, 11, 12, 13, 14, 15, 16, 17, 18, 19, 20, 22, 24, 26, 28, 30, 35, 40, 45, 50, 55, 60, 70, 75, 80, 90, 100 or more antigens derived from the protein. In some embodiments, at least two of the antigens comprise partially overlapping amino acid sequences. In some embodiments, the combined amino acid sequences of all the antigens overlaps the amino acid sequence of the protein by about 90% or more. In some embodiments, the combined amino acid sequences of all the antigens overlaps with about any one of: 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the amino acid sequence of the protein. In some embodiments, each amino acid of about 80% of the amino acid sequence of the protein overlaps with at least two antigens derived from the protein. In some embodiments, each amino acid of about 80% of the amino acid sequence of the protein overlaps with at least three antigens derived from the protein. In some embodiments, each amino acid of about 90% of the amino acid sequence of the protein overlaps with at least two antigens derived from the protein. In some embodiments, each amino acid of about 90% of the amino acid sequence of the protein overlaps with at least three antigens derived from the protein. In some embodiments, each amino acid of about 95% of the amino acid sequence of the protein overlaps with at least two antigens derived from the protein. In some embodiments, each amino acid of about 95% of the amino acid sequence of the protein overlaps with at least three antigens derived from the protein.

In some embodiments, the antigen is a polypeptide comprising two or more epitopes of the protein. In some embodiments, embodiments, the immunogenic peptide epitope is fused to an N-terminal flanking polypeptide and/or a C-terminal flanking polypeptide. In some embodiments, the antigen is a one or more epitopes of the protein and one or more heterologous peptide sequences. In some embodiments, the one or more epitopes is flanked on the N-terminus and/or the C-terminus by heterologous peptide sequences. In some embodiments, the flanking heterologous peptide sequences are derived from disease-associated immunogenic peptides. In some embodiments, the flanking heterologous peptide sequences are non-naturally occurring sequence. In some embodiments, the flanking heterologous peptide sequences are derived from an immunogenic synthetic long peptide (SLP). In some embodiments, the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17. In some embodiments, the antigen is capable of being processed into an MHC class I-restricted peptide and/or an MHC class II-restricted peptide.

In some embodiments, the protein is a mutated protein associated with cancer, a viral protein, a bacterial protein or a fungal protein. In some embodiments, the protein is a human papillomavirus (HPV) protein. In some embodiments, the HPV is HPV-16 or HPV-18. In some embodiments, the protein is an HPV E6 or HPV E7 protein. In some embodiments, the protein is a hepatitis B virus (HBV) protein.

In some embodiments, the nucleated cells comprising the protein or fragment thereof are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the protein or fragment thereof to pass through to form a perturbed input nucleated cells; and b) incubating the perturbed input nucleated cells with the protein or fragment thereof to allow the protein or fragment thereof to enter the perturbed input nucleated cells; thereby generating nucleated cells comprising the protein or fragment thereof, wherein the protein or fragment thereof stimulates an immune response in an individual in an HLA agnostic manner. In some embodiments, the nucleated cells comprising the mRNA encoding the protein or fragment thereof are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; thereby generating nucleated cells comprising the mRNA encoding the protein or fragment thereof. In some embodiments, the nucleated cells comprising the protein or fragment thereof are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; wherein the mRNA is expressed to produce the protein or fragment thereof, thereby generating nucleated cells comprising the protein or fragment thereof, wherein the protein or fragment thereof stimulates an immune response in an individual in an HLA agnostic manner.

In some embodiments, the input cell suspension may comprise the input nucleated cells and an antigen. In some embodiments, the input cell suspension comprises the input nucleated cells and the protein or fragment thereof. In some embodiments, the input cell suspension comprises the input nucleated cells and the mRNA encoding the protein or fragment thereof. In some embodiments, the method comprises incubating the nucleated cells with the protein or fragment thereof, or with the mRNA encoding the protein or fragment thereof before, during and/or after passing the cell suspension through the cell-deforming constriction. In some embodiments, the method comprises incubating the nucleated cells with the protein or fragment thereof, or with the mRNA encoding the protein or fragment thereof before passing the cell suspension through the cell-deforming constriction. In some embodiments, the width of the constriction is about 10% to about 99% of the mean diameter of the input nucleated cells. In some embodiments, the width of the constriction is about 10% to about 99% of the mean diameter of the input nucleated cells having the smallest diameter within the population of nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells having the smallest diameter within the population of nucleated cells. In some embodiments, the width of the constriction is about 2 μm to about 5 μm, about 3 μm to about 5 μm, about 2 μm to about 2.5 μm, about 2.2 μm to about 2.5, about 2.5 μm to about 3 μm, about 3 μm to about 3.5 μm, about 3.5 μm to about 4 μm, about 4 μm to about 4.5 μm, about 3.2 μm to about 3.8 μm, about 3.8 μm to about 4.3 μm, about 4.2 μm to about 6 μm, or about 4.2 μm to about 4.8 μm. In some embodiments, the width of the constriction is about 4.5 μm. In some embodiments, the width of the constriction is about or less than any one of 2 μm, 2.2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the cell suspension comprising the input nucleated cells are passed through multiple constrictions wherein the multiple constrictions are arranged in series and/or in parallel.

In some embodiments according to any one of the methods, uses or compositions described herein, the nucleated cells (e.g., PBMCs) are incubated with the adjuvant for a sufficient time for the nucleated cells to condition. In some embodiments, the nucleated cells are incubated with the adjuvant for about 1 to about 24 hours for the nucleated cells to condition. In some embodiments, the nucleated cells are incubated with the adjuvant for about 2 to about 10 hours for the nucleated cells to condition. In some embodiments, the nucleated cells are incubated with the adjuvant for about 3 to about 6 hours for the nucleated cells to condition. In some embodiments, the nucleated cells are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the nucleated cells to condition. In some embodiments, the nucleated cells are incubated with the adjuvant for about 4 hours for the nucleated cells to condition. In some embodiments, the nucleated cells are conditioned before introducing the protein or fragment thereof or the nucleic acid encoding protein or fragment thereof into the nucleated cells. In some embodiments, the nucleated cells are conditioned after introducing the protein or fragment thereof or the nucleic acid encoding the protein or fragment thereof into the nucleated cells. In some embodiments, the adjuvant used for conditioning is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic:polycytidylic acid (poly I:C), a TLR3 agonist, a TLR4 agonist, a TLR7 agonist, a TLR8 agonist, or a TLR9 agonist. Exemplary adjuvants include, without limitation, CpG ODN, interferon-α (IFN-α), polyinosinic: polycytidylic acid (polyI:C), imiquimod (R837), resiquimod (R848), or lipopolysaccharide (LPS). In some embodiments, the adjuvant is a CpG oligodeoxynucleotide (ODN). In some embodiments, the adjuvant is CpG 7909.

In some embodiments, wherein the nucleated cells comprise B cells, one or more co-stimulatory molecules is upregulated in the B cells of the conditioned nucleated cells compared to the B cells of the unconditioned nucleated cells. In some embodiments, the nucleated cells are a plurality of peripheral blood mononuclear cells (PBMCs). In some embodiments, wherein the nucleated cells are a plurality of PBMCs, one or more co-stimulatory molecules is upregulated in the B cells of the conditioned plurality of PBMCs compared to the B cells of the unconditioned plurality of PBMCs. In some embodiments, the co-stimulatory molecule is CD80 and/or CD86. In some embodiments, the conditioned plurality of PBMCs has increased expression of one or more of IFN-γ, IL-6, MCP-1, MIP-1β, IP-10, or TNF-α compared to an unconditioned plurality of PBMCs. In some embodiments, the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to an unconditioned plurality of PBMCs In some embodiments according to any one of the methods, uses or compositions described herein, the nucleated cells are immune cells. In some embodiments, the nucleated cells are human cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the nucleated cells are a plurality of PBMCs. In some embodiments, the conditioned nucleated cells are a conditioned plurality of modified PBMCs. In some embodiments, the plurality of PBMCs comprises two or more of T cell, B cell, NK cell, monocytes, dendritic cells or NK-T cells. In some embodiments, the nucleated cells are one or more of T cells, B cells, NK cells, monocytes, dendritic cells and/or NK-T cells.

In some embodiments, the plurality of PBMCs are further modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of PBMCs are further modified to increase expression of one or more cytokines. In some embodiments, the cytokine is IL-10, IL-15, IL-12, IL-2, IFN-α, IFN-γ, IL-21, or a functional variant thereof. In some embodiments, the cytokine is IFN-α2 or a functional variant thereof. In some embodiments, the cytokine is a variant cytokine (such as a modified cytokine). In some embodiments, the plurality of PBMCs are further modified to increase expression of one or more chimeric membrane-bound cytokines. In some embodiments, the cytokine is modified, and the modified cytokine is a fusion protein comprising the cytokine and a transmembrane domain. In some embodiments, the cytokine is joined to the transmembrane domain by a peptide linker. In some embodiments, the transmembrane domain is a transferrin receptor protein 1 (TFRC) or a tumor necrosis factor (e.g., FasL) transmembrane domain. In some embodiments, the transmembrane domain comprises the amino acid sequence of SEQ ID NO: 81 or SEQ ID NO: 82. In some embodiments, the peptide linker is a $G_4S$ linker or an EAAAK linker. In embodiments, the $G_4S$ linker comprises any one of 2, 3, 4, 5, 6, 7, 8, 9, or 10 repeats of $G_4S$ sequence. In some embodiments, the EAAAK linker comprises any one of 2, 3, 4, 5, 6, 7, 8, 9, or 10 repeats of EAAAK sequence. In some embodiments, the peptide linker is $(G_4S)_3$ (SEQ ID NO: 73) or $(EAAAK)_3$ (SEQ ID NO: 74). In some embodiments, the chimeric membrane-bound cytokine comprises the amino acid sequence of any one of SEQ ID NOs: 77-80. In some embodiments, the plurality of modified PBMCs comprises a nucleic acid that results in increased expression and/or secretion of the one or more cytokines. In some embodiments, the nucleic acid encoding the chimeric membrane-bound cytokine comprises the nucleotide sequence of SEQ ID NO: 71 or 72. In some embodiments, the cytokine is a Signal 3 effector in stimulating T cell activation. In some embodiments, the chimeric membrane-bound cytokine enhances the half-life of the cytokine in an individual compared to a non-membrane-bound cytokine. In some embodiments, the half-life of the chimeric membrane-bound cytokine is increased by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a non-membrane-bound cytokine. In some embodiments, the membrane-bound cytokine prolongs the spatial association of the cytokine with the antigens presented by the nucleated cell introduced with the protein or fragment thereof, by about any one of: 1, 2, 3, 4, 6, 8, 12, 16, 20, 24, 28, 32, 36, 48, 72, 96 or more hours, compared to a corresponding nucleated cell comprising a non-membrane-bound cytokine. In some embodiments, a nucleated cell comprising the protein or fragment thereof and further comprising a membrane-bound cytokine exhibits a local cytokine concentration that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine. In some embodiments, a nucleated cell comprising the protein or fragment thereof and further comprising a membrane-bound cytokine can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine.

Compositions of Nucleated Cells Comprising a Protein or Fragment Thereof

In some aspects, there is provided a composition comprising nucleated cells, wherein the nucleated cells comprises a protein or fragment thereof; wherein the protein or fragment thereof stimulates an immune response in an individual in an HLA agnostic manner. In some aspects, them is provided a composition for stimulating an immune response in an individual, wherein the composition comprises an effective amount of nucleated cells comprising a protein or fragment thereof; wherein the protein or fragment thereof stimulates an immune response in an individual in an HILA agnostic manner. In some embodiments, provided are uses of a composition comprising an effective amount of nucleated cells in the manufacture of a medicament for stimulating an immune response in an individual, wherein the nucleated cells comprises a protein or fragment thereof; wherein the protein or fragment thereof stimulates an immune response in an individual in an HLA agnostic manner.

In some aspects, there is provided a composition comprising nucleated cells, wherein the nucleated cells comprises a mRNA encoding a protein or fragment thereof; wherein the protein or fragment thereof stimulates an immune response in an individual in an HLA agnostic manner. In some aspects, there is provided a composition for stimulating an immune response in an individual, wherein the composition comprises an effective amount of nucleated cells comprising an mRNA encoding a protein or fragment thereof; wherein the protein or fragment thereof stimulates an immune response in an individual in an HLA agnostic manner. In some embodiments, provided are uses of a composition comprising an effective amount of nucleated cells in the manufacture of a medicament for stimulating an immune response in an individual, wherein the nucleated cells comprises an mRNA encoding a protein or fragment thereof; wherein the protein or fragment thereof stimulates an immune response in an individual in an HLA agnostic manner.

In some aspects, there is provided a composition comprising nucleated cells, wherein the nucleated cells comprises two or more antigens derived from a protein; wherein the protein or fragment thereof stimulates an immune response in an individual in an HLA agnostic manner. In some aspects, there is provided a composition for stimulating an immune response in an individual, wherein the composition comprises an effective amount of nucleated cells comprising two or more antigens derived from a protein; wherein the protein or fragment thereof stimulates an immune response in an individual in an HLA agnostic manner. In some embodiments, provided are uses of a composition comprising an effective amount of nucleated cells in the manufacture of a medicament for stimulating an immune response in an individual, wherein the nucleated cells comprises two or more antigens derived from a protein; wherein the protein or fragment thereof stimulates an immune response in an individual in an HLA agnostic manner.

In some aspects, there is provided a composition comprising conditioned nucleated cells, wherein the nucleated cells comprises a protein or fragment thereof; wherein the protein or fragment thereof stimulates an immune response in an individual in an HLA agnostic manner. In some aspects, there is provided a composition for stimulating an immune response in an individual, wherein the composition comprises an effective amount of conditioned nucleated cells comprising a protein or fragment thereof; wherein the protein or fragment thereof stimulates an immune response in an individual in an HLA agnostic manner. In some embodiments, provided are uses of a composition comprising an effective amount of nucleated cells in the manufacture of a medicament for stimulating an immune response in an individual, wherein the nucleated cells comprises a protein or fragment thereof; wherein the protein or fragment thereof stimulates an immune response in an individual in an HLA agnostic manner.

In some aspects, there is provided a composition comprising conditioned nucleated cells, wherein the nucleated cells comprises an mRNA encoding a protein or fragment thereof; wherein the protein or fragment thereof stimulates an immune response in an individual in an HLA agnostic manner. In some aspects, there is provided a composition for stimulating an immune response in an individual, wherein the composition comprises an effective amount of conditioned nucleated cells comprising an mRNA encoding a protein or fragment thereof; wherein the protein or fragment thereof stimulates an immune response in an individual in an HLA agnostic manner. In some embodiments, provided are uses of a composition comprising an effective amount of nucleated cells in the manufacture of a medicament for stimulating an immune response in an individual, wherein the nucleated cells comprises an mRNA encoding a protein or fragment thereof; wherein the protein or fragment thereof stimulates an immune response in an individual in an HLA agnostic manner.

In some aspects, there is provided a composition comprising conditioned nucleated cells, wherein the nucleated cells comprises two or more antigens derived from a protein; wherein the protein or fragment thereof stimulates an immune response in an individual in an HLA agnostic manner. In some aspects, there is provided a composition for stimulating an immune response in an individual, wherein the composition comprises an effective amount of conditioned nucleated cells comprising two or more antigens derived from a protein; wherein the protein or fragment thereof stimulates an immune response in an individual in an HLA agnostic manner. In some embodiments, provided are uses of a composition comprising an effective amount of nucleated cells in the manufacture of a medicament for stimulating an immune response in an individual, wherein the nucleated cells comprises two or more antigens derived from a protein; wherein the protein or fragment thereof stimulates an immune response in an individual in an HILA agnostic manner.

In some aspects, the invention provides a composition for use as a medicine, wherein the composition comprises an effective amount of composition of anucleate cells comprising a protein of fragment whereof, wherein the protein or fragment thereof stimulates an immune response in an individual in an HLA agnostic manner. In some aspects, the invention provides a composition for use as a medicine, wherein the composition comprises an effective amount of composition of anucleate cells comprising an mRNA encoding a protein of fragment whereof, wherein the protein or fragment thereof stimulates an immune response in an individual in an HILA agnostic manner. In some aspects, the invention provides a composition for use as a medicine, wherein the composition comprises an effective amount of composition of anucleate cells comprising a two or more antigens from a protein, wherein the two or more antigens stimulates an immune response in an individual in an HLA agnostic manner.

In some embodiments, the cell comprises two or more antigens derived from the protein. In some embodiments, the cell comprises about any one of: 2, 3, 4, 5, 6, 7, 8, 9, 10, 11, 12, 13, 14, 15, 16, 17, 18, 19, 20, 22, 24, 26, 28, 30, 35, 40, 45, 50, 55, 60, 70, 75, 80, 90, 100 or more antigens derived from the protein. In some embodiments, at least two of the antigens comprise partially overlapping amino acid sequences. In some embodiments, the combined amino acid sequences of all the antigens overlaps the amino acid sequence of the protein by about 90% or more. In some embodiments, the combined amino acid sequences of all the antigens overlaps with about any one of: 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the amino acid sequence of the protein. In some embodiments, each amino acid of about 80% of the amino acid sequence of the protein overlaps with at least two antigens derived from the protein. In some embodiments, each amino acid of about 80% of the amino acid sequence of the protein overlaps with at least three antigens derived from the protein. In some embodiments, each amino acid of about 90% of the amino acid sequence of the protein overlaps with at least two antigens derived from the protein. In some embodiments, each amino acid of about 90% of the amino acid sequence of the protein overlaps with at least three antigens derived from the protein. In some embodiments, each amino acid of about 95% of the amino acid sequence of the protein overlaps with at least two antigens derived from the protein. In some embodiments, each amino acid of about 95% of the amino acid sequence of the protein overlaps with at least three antigens derived from the protein.

In some embodiments, the antigen is a polypeptide comprising two or more epitopes of the protein. In some embodiments, embodiments, the immunogenic peptide epitope is fused to an N-terminal flanking polypeptide and/or a C-terminal flanking polypeptide. In some embodiments, the antigen is a one or more epitopes of the protein and one or more heterologous peptide sequences. In some embodiments, the one or more epitopes is flanked on the N-terminus and/or the C-terminus by heterologous peptide sequences. In some embodiments, the flanking heterologous peptide sequences are derived from disease-associated immunogenic peptides. In some embodiments, the flanking heterologous peptide sequences are non-naturally occurring sequence. In some embodiments, the flanking heterologous peptide sequences are derived from an immunogenic synthetic long peptide (SLP). In some embodiments, the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17. In some embodiments, the antigen is capable of being processed into an MHC class I-restricted peptide and/or an MHC class II-restricted peptide.

In some embodiments, the protein is a mutated protein associated with cancer, a viral protein, a bacterial protein or a fungal protein. In some embodiments, the protein is a human papillomavirus (HPV) protein. In some embodiments, the HPV is HPV-16 or HPV-18. In some embodiments, the protein is an HPV E6 or HPV E7 protein. In some embodiments, the protein is a hepatitis B virus (HBV) protein.

In some embodiments, the nucleated cells comprising the protein or fragment thereof are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the protein or fragment thereof to pass through to form a perturbed input nucleated cells; and b) incubating the perturbed input nucleated cells with the protein or fragment thereof to allow the protein or fragment thereof to enter the perturbed input nucleated cells; thereby generating nucleated cells comprising the protein or fragment thereof. In some embodiments, the nucleated cells comprising the mRNA encoding the protein or fragment thereof are prepared by: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; thereby generating nucleated cells comprising the mRNA encoding the protein or fragment thereof.

In some embodiments, the input cell suspension may comprise the input nucleated cells and an antigen. In some embodiments, the input cell suspension comprises the input nucleated cells and the protein or fragment thereof. In some embodiments, the input cell suspension comprises the input nucleated cells and the mRNA encoding the protein or fragment thereof. In some embodiments, the method comprises incubating the nucleated cells with the protein or fragment thereof, or with the mRNA encoding the protein or fragment thereof before, during and/or after passing the cell suspension through the cell-deforming constriction. In some embodiments, the method comprises incubating the nucleated cells with the protein or fragment thereof, or with the mRNA encoding the protein or fragment thereof before passing the cell suspension through the cell-deforming constriction. In some embodiments, the width of the constriction is about 10% to about 99% of the mean diameter of the input nucleated cells. In some embodiments, the width of the constriction is about 10% to about 99% of the mean diameter of the input nucleated cells having the smallest diameter within the population of nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells having the smallest diameter within the population of nucleated cells. In some embodiments, the width of the constriction is about 2 pnm to about 5 μm, about 3 μm to about 5 μm, about 2 μm to about 2.5 μm, about 2.2 μm to about 2.5, about 2.5 μm to about 3 μm, about 3 μm to about 3.5 μm, about 3.5 μm to about 4 μm, about 4 μm to about 4.5 μm, about 3.2 μm to about 3.8 μm, about 3.8 μm to about 4.3 μm, about 4.2 μm to about 6 μm, or about 4.2 μm to about 4.8 μm. In some embodiments, the width of the constriction is about 4.5 μm. In some embodiments, the width of the constriction is about or less than any one of 2 μm, 2.2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the cell suspension comprising the input nucleated cells are passed through multiple constrictions wherein the multiple constrictions are arranged in series and/or in parallel.

In some embodiments according to any one of the methods, uses or compositions described herein, the nucleated cells (e.g., PBMCs) are incubated with the adjuvant for a sufficient time for the nucleated cells to condition. In some embodiments, the nucleated cells are incubated with the adjuvant for about 1 to about 24 hours for the nucleated cells to condition. In some embodiments, the nucleated cells are incubated with the adjuvant for about 2 to about 10 hours for the nucleated cells to condition. In some embodiments, the nucleated cells are incubated with the adjuvant for about 3 to about 6 hours for the nucleated cells to condition. In some embodiments, the nucleated cells are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the nucleated cells to condition. In some embodiments, the nucleated cells are incubated with the adjuvant for about 4 hours for the nucleated cells to condition. In some embodiments, the nucleated cells are conditioned before introducing the protein or fragment thereof or the nucleic acid encoding protein or fragment thereof into the nucleated cells. In some embodiments, the nucleated cells are conditioned after introducing the protein or fragment thereof or the nucleic acid encoding the protein or fragment thereof into the nucleated cells. In some embodiments, the adjuvant used for conditioning is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), a TLR3 agonist, a TLR4 agonist, a TLR7 agonist, a TLR8 agonist, or a TLR9 agonist. Exemplary adjuvants include, without limitation, CpG ODN, interferon-α (IFN-α), polyinosinic: polycytidylic acid (polyI:C), imiquimod (R837), resiquimod (R848), or lipopolysaccharide (LPS). In some embodiments, the adjuvant is a CpG oligodeoxynucleotide (ODN). In some embodiments, the adjuvant is CpG 7909.

In some embodiments, wherein the nucleated cells comprise B cells, one or more co-stimulatory molecules is upregulated in the B cells of the conditioned nucleated cells compared to the B cells of the unconditioned nucleated cells. In some embodiments, the nucleated cells are a plurality of peripheral blood mononuclear cells (PBMCs). In some embodiments, wherein the nucleated cells are a plurality of PBMCs, one or more co-stimulatory molecules is upregulated in the B cells of the conditioned plurality of PBMCs compared to the B cells of the unconditioned plurality of PBMCs. In some embodiments, the co-stimulatory molecule is CD80 and/or CD86. In some embodiments, the conditioned plurality of PBMCs has increased expression of one or more of IFN-γ, IL-6, MCP-1, MIP-1β, IP-10, or TNF-α compared to an unconditioned plurality of PBMCs. In some embodiments, the expression of one or more of IFN-γ, IL-6, MCP-1, MIP-1β, IP-40, or TNF-α is increased by more than about 1.2-fold, 1.5-fold, 1.8-fold, 2-fold, 3-fold, 4-fold, 5-fold, 8-fold, or more than 10-fold compared to an unconditioned plurality of PBMCs In some embodiments according to any one of the methods, uses or compositions described herein, the nucleated cells are immune cells. In some embodiments, the nucleated cells are human cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, and/or HLA-C*16. In some embodiments, the nucleated cells are a plurality of PBMCs. In some embodiments, the conditioned nucleated cells are a conditioned plurality of modified PBMCs. In some embodiments, the plurality of PBMCs comprises two or more of T cell, B cell, NK cell, monocytes, dendritic cells or NK-T cells. In some embodiments, the nucleated cells are one or more of T cells, B cells, NK cells, monocytes, dendritic cells and/or NK-T cells.

In some embodiments, the plurality of PBMCs are further modified to increase expression of one or more of co-stimulatory molecules. In some embodiments, the co-stimulatory molecule is B7-H2 (ICOSL), B7-4 (CD80), B7-2CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of PBMCs are further modified to increase expression of one or more cytokines. In some embodiments, the cytokine is IL-10, IL-15, IL-12, IL-2, IFN-α, IFN-γ, IL-21, or a functional variant thereof. In some embodiments, the cytokine is IFN-α2 or a functional variant thereof. In some embodiments, the cytokine is a variant cytokine (such as a modified cytokine). In some embodiments, the plurality of PBMCs are further modified to increase expression of one or more chimeric membrane-bound cytokines. In some embodiments, the cytokine is modified, and the modified cytokine is a fusion protein comprising the cytokine and a transmembrane domain. In some embodiments, the cytokine is joined to the transmembrane domain by a peptide linker. In some embodiments, the transmembrane domain is a transferrin receptor protein 1 (TFRC) or a tumor necrosis factor (e.g., FasL) transmembrane domain. In some embodiments, the transmembrane domain comprises the amino acid sequence of SEQ ID NO: 81 or SEQ ID NO: 82. In some embodiments, the peptide linker is a $G_4S$ linker or an EAAAK linker. In embodiments, the $G_4S$ linker comprises any one of 2, 3, 4, 5, 6, 7, 8, 9, or 10 repeats of $G_4S$ sequence. In some embodiments, the EAAAK linker comprises any one of 2, 3, 4, 5, 6, 7, 8, 9, or 10 repeats of EAAAK sequence. In some embodiments, the peptide linker is $(G_4S)_3$ (SEQ ID NO: 73) or $(EAAAK)_3$ (SEQ ID NO: 74). In some embodiments, chimeric membrane-bound cytokine comprises the amino acid sequence of any one of SEQ ID NOs: 77-80. In some embodiments, the plurality of modified PBMCs comprises a nucleic acid that results in increased expression and/or secretion of the one or more cytokines. In some embodiments, the nucleic acid encoding the chimeric membrane-bound cytokine comprises the nucleotide sequence of SEQ ID NO: 71 or 72. In some embodiments, the cytokine is a Signal 3 effector in stimulating T cell activation. In some embodiments, the chimeric membrane-bound cytokine enhances the half-life of the cytokine in an individual compared to a non-membrane-bound cytokine. In some embodiments, the half-life of the chimeric membrane-bound cytokine is increased by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a non-membrane-bound cytokine. In some embodiments, the membrane-bound cytokine prolongs the spatial association of the cytokine with the antigens presented by the nucleated cell introduced with the protein or fragment thereof, by about any one of: 1, 2, 3, 4, 6, 8, 12, 16, 20, 24, 28, 32, 36, 48, 72, 96 or more hours, compared to a corresponding nucleated cell comprising a non-membrane-bound cytokine. In some embodiments, a nucleated cell comprising the protein or fragment thereof and further comprising a membrane-bound cytokine exhibits a local cytokine concentration that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine. In some embodiments, a nucleated cell comprising the protein or fragment thereof and further comprising a membrane-bound cytokine can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine. In some embodiments, the membrane-tethered cytokine is a membrane-bound chemokine.

Methods of Enhancing Activity of an Immune Cell, and Compositions Thereof

In some aspects, provided are methods for enhancing the activity of an immune cell, the methods comprising expressing a nucleic acid encoding a chimeric membrane-bound cytokine in the immune cell. In some embodiments, the cytokine is modified, and the modified cytokine is a fusion protein comprising the cytokine and a transmembrane domain. In some embodiments, the cytokine is joined to the transmembrane domain by a peptide linker. In some embodiments, the transmembrane domain is a transferrin receptor protein 1 (TFRC) or a tumor necrosis factor (e.g., FasL) transmembrane domain. In some embodiments, the transmembrane domain comprises the amino acid sequence of SEQ ID NO: 81 or SEQ ID NO: 82. In some embodiments, the peptide linker is a $G_4S$ linker or an EAAAK linker. In embodiments, the $G_4S$ linker comprises any one of 2, 3, 4, 5, 6, 7, 8, 9, or 10 repeats of $G_4S$ sequence. In some embodiments, the EAAAK linker comprises any one of 2, 3, 4, 5, 6, 7, 8, 9, or 10 repeats of EAAAK sequence. In some embodiments, the peptide linker is $(G_4S)_3$ (SEQ ID NO: 73) or $(EAAAK)_3$ (SEQ ID NO: 74). In some embodiments, the chimeric membrane-bound cytokine comprises the amino acid sequence of SEQ ID NOs: 77-80. In some embodiments, the plurality of modified PBMCs comprises a nucleic acid that results in increased expression and/or secretion of the one or more cytokines. In some embodiments, the nucleic acid encoding the chimeric membrane-bound cytokine comprises the nucleotide sequence of SEQ ID NO: 71 or 72. In some embodiments, the cytokine is a Signal 3 effector in stimulating T cell activation. In some embodiments, the chimeric membrane-bound cytokine enhances the half-life of the cytokine in an individual compared to a non-membrane-bound cytokine. In some embodiments, the half-life of the chimeric membrane-bound cytokine is increased by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a non-membrane-bound cytokine. In some embodiments, the membrane-bound cytokine prolongs the spatial association of the cytokine with the antigens presented by the nucleated cell introduced with the protein or fragment thereof, by about any one of: 1, 2, 3, 4, 6, 8, 12, 16, 20, 24, 28, 32, 36, 48, 72, 96 or more hours, compared to a corresponding nucleated cell comprising a non-membrane-bound cytokine. In some embodiments, a nucleated cell comprising the protein or fragment thereof and further comprising a membrane-bound cytokine exhibits a local cytokine concentration that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine. In some embodiments, a nucleated cell comprising the protein or fragment thereof and further comprising a membrane-bound cytokine can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine.

In some embodiments, the membrane-bound cytokine is a membrane-bound chemokine.

In some aspects, there is provided a composition for enhancing the activity of an immune cell, the composition comprising a chimeric membrane-bound cytokine in the immune cell. In some embodiments, the cytokine is modified, and the modified cytokine is a fusion protein comprising the cytokine and a transmembrane domain. In some embodiments, the cytokine is joined to the transmembrane domain by a peptide linker. In some embodiments, the transmembrane domain is a transferrin receptor protein 1 (TFRC) or a tumor necrosis factor (e.g., FasL) transmembrane domain. In some embodiments, the transmembrane domain comprises the amino acid sequence of SEQ ID NO: 81 or SEQ ID NO: 82. In some embodiments, the peptide linker is a $G_4S$ linker or an EAAAK linker. In embodiments, the $G_4S$ linker comprises any one of 2, 3, 4, 5, 6, 7, 8, 9, or 10 repeats of $G_4S$ sequence. In some embodiments, the EAAAK linker comprises any one of 2, 3, 5, 6, 7, 8, 9, or 10 repeats of EAAAK sequence. In some embodiments, the peptide linker is $(G_4S)_3$ (SEQ ID NO: 73) or $(EAAAK)_3$ (SEQ ID NO: 74). In some embodiments, the chimeric membrane-bound cytokine comprises the amino acid sequence of any one of SEQ ID NOs: 77-80. In some embodiments, the plurality of modified PBMCs comprises a nucleic acid that results in increased expression and/or secretion of the one or more cytokines. In some embodiments, the nucleic acid encoding the chimeric membrane-bound cytokine comprises the nucleotide sequence of SEQ ID NO: 71 or 72. In some embodiments, the cytokine is a Signal 3 effector in stimulating T cell activation. In some embodiments, the chimeric membrane-bound cytokine enhances the half-life of the cytokine in an individual compared to a non-membrane-bound cytokine. In some embodiments, the half-life of the chimeric membrane-bound cytokine is increased by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a non-membrane-bound cytokine. In some embodiments, the membrane-bound cytokine prolongs the spatial association of the cytokine with the antigens presented by the nucleated cell introduced with the protein or fragment thereof, by about any one of: 1, 2, 3, 4, 6, 8, 12, 16, 20, 24, 28, 32, 36, 48, 72, 96 or more hours, compared to a corresponding nucleated cell comprising a non-membrane-bound cytokine. In some embodiments, a nucleated cell comprising the protein or fragment thereof and further comprising a membrane-bound cytokine exhibits a local cytokine concentration that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine. In some embodiments, a nucleated cell comprising the protein or fragment thereof and further comprising a membrane-bound cytokine can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 50)-fold or more compared to a corresponding nucleated cell comprising a non-membrane-bound cytokine.

In some embodiments, the membrane-bound cytokine is a membrane-bound chemokine.

In some embodiments, the plurality of PBMCs are modified to increase expression of one or more cytokines. In some embodiments, the cytokine is IL-10, IL-15, IL-12, IL-2, IFN-α, IFN-γ, IL-21, or a functional variant thereof. In some embodiments, the cytokine is IFN-α2 or a functional variant thereof. In some embodiments, the cytokine is a variant cytokine (such as a modified cytokine), such as a chimeric membrane-bound cytokine. In some embodiments, the plurality of PBMCs are further modified to increase expression of one or more chimeric membrane-bound cytokines (such as membrane bound IL-10, IL-15, IL-12, IL-2, IFN-α, IFN-γ, IL-21).

In some embodiments, the immune cell further comprises an antigen. In some embodiments, the immune cell further comprises an mRNA encoding an antigen. In some embodiments, the antigen is a protein or fragment thereof, wherein the protein or fragment thereof stimulates an immune response regardless of the HLA haplotype of the individual. In some embodiments, the immune cell further comprises two or more antigens derived from a protein. In some embodiments, the two or more antigens stimulates an immune response regardless of the HLA haplotype of the individual. In some embodiments, the protein is a mutated protein associated with cancer, a viral protein, a bacterial protein or a fungal protein. In some embodiments, the protein is a human papillomavirus (HPV) protein. In some embodiments, the HPV is HPV-16 or HPV-18. In some embodiments, the protein is an HPV E6 or HPV E7 protein. In some embodiments, the protein is a hepatitis B virus (HBV) protein.

In some embodiments, provided are methods for enhancing the activity of an immune cell, wherein the immune cells comprising the chimeric membrane-bound cytokine are prepared by: a) passing a cell suspension comprising input immune cells through a cell-deforming constriction, wherein a diameter of the constriction is a function of a diameter of the input immune cells in the suspension, thereby causing perturbations of the input immune cells large enough fora nucleic acid encoding the chimeric membrane-bound cytokine to pass through to form a perturbed input immune cells; and b) incubating the perturbed input immune cells with the nucleic acid encoding the chimeric membrane-bound cytokine to allow the nucleic acid to enter the perturbed input immune cells where the nucleic acid encoding the chimeric membrane-bound cytokine is expressed; thereby generating immune cells comprising a chimeric membrane-bound cytokine. In some embodiments, the nucleic acid encoding the chimeric membrane-bound cytokine is an mRNA encoding the chimeric membrane-bound cytokine.

In some embodiments, provided are methods for enhancing the activity of an immune cell, wherein the immune cells comprising the chimeric membrane-bound cytokine and further comprising an antigen are prepared by: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and an antigen to pass through to form a perturbed input immune cells; and b) incubating the perturbed input immune cells with the nucleic acid encoding the chimeric membrane-bound cytokine and the antigen to allow the nucleic acid and the antigen to enter the perturbed input immune cells where the nucleic acid encoding the chimeric membrane-bound cytokine is expressed; thereby generating immune cells comprising the chimeric membrane-bound cytokine and the antigen. In some embodiments, the nucleic acid encoding the chimeric membrane-bound cytokine is an mRNA encoding the chimeric membrane-bound cytokine.

In some embodiments, provided are methods for enhancing the activity of an immune cell, wherein the immune cells comprising the chimeric membrane-bound cytokine and further comprising an antigen are prepared by: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and a nucleic acid encoding the antigen to pass through to form a perturbed input immune cells; and b) incubating the perturbed input immune cells with the nucleic acid encoding the chimeric membrane-bound cytokine and the nucleic acid encoding the antigen to allow the nucleic acids to enter the perturbed input immune cells where the nucleic acid encoding the chimeric membrane-bound cytokine and the nucleic acid encoding the antigen are expressed; thereby generating immune cells comprising the chimeric membrane-bound cytokine and the antigen. In some embodiments, the nucleic acid encoding the chimeric membrane-bound cytokine and/or the nucleic acid encoding the antigen is a mRNA.

In some embodiments, there is provided a method for enhancing the activity of an immune cell, wherein the immune cells comprising the chimeric membrane-bound cytokine and the two or more antigens derived from a protein are prepared by: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the two or more antigens derived from a protein to pass through to form a perturbed input immune cells; and b) incubating the perturbed input immune cells with the nucleic acid encoding the chimeric membrane-bound cytokine and the two or more antigens derived from a protein to allow the nucleic acid to enter the perturbed input immune cells where the nucleic acid encoding the chimeric membrane-bound cytokine is expressed; thereby generating immune cells comprising a chimeric membrane-bound cytokine and the two or more antigen derived from a proteins.

In some aspects, there is provided a composition for use as a medicine, wherein the composition comprises an effective amount of immune cells comprising a chimeric membrane-bound cytokine. In some aspects, provided are compositions for treating a cancer, an infectious disease, or a viral-associated disease with a composition in an individual, wherein the composition comprises an effective amount of immune cells comprising a chimeric membrane-bound cytokine. In some aspects, provided are methods of treating a cancer, an infectious disease, or a viral-associated disease in an individual, comprising administering a composition comprising an effective amount of immune cells comprising a chimeric membrane-bound cytokine to the individual. In some embodiments, provided are uses of a composition comprising an effective amount of immune cells comprising a chimeric membrane-bound cytokine in the manufacture of a medicament for stimulating an immune response in an individual and/or treating a cancer, an infectious disease, or a viral-associated disease in an individual. In some embodiments according to the methods, compositions, or uses described herein, the immune cells comprising the chimeric membrane-bound cytokine are prepared by: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine to pass through to form a perturbed input immune cells; and b) incubating the perturbed input immune cells with the nucleic acid encoding the chimeric membrane-bound cytokine to allow the nucleic acid to enter the perturbed input immune cells where the nucleic acid encoding the chimeric membrane-bound cytokine is expressed; thereby generating immune cells comprising a chimeric membrane-bound cytokine. In some embodiments, the nucleic acid encoding the chimeric membrane-bound cytokine is an mRNA encoding the chimeric membrane-bound cytokine.

In some aspects, there is provided a composition for use as a medicine, wherein the composition comprises an effective amount of immune cells comprising a chimeric membrane-bound cytokine and an antigen. In some aspects, provided are compositions for treating a cancer, an infectious disease, or a viral-associated disease in an individual, wherein the composition comprises an effective amount of immune cells comprising a chimeric membrane-bound cytokine and an antigen. In some aspects, provided are methods of treating a cancer, an infectious disease, or a viral-associated disease in an individual, comprising administering a composition comprising an effective amount of immune cells comprising a chimeric membrane-bound cytokine and an antigen to the individual. In some embodiments, provided are uses of a composition comprising an effective amount of immune cells comprising a chimeric membrane-bound cytokine and an antigen in the manufacture of a medicament for stimulating an immune response in an individual and/or treating a cancer, an infectious disease, or a viral-associated disease in an individual. In some embodiments according to the methods, compositions or uses described herein, the immune cells comprising the chimeric membrane-bound cytokine and the antigen are prepared by: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the antigen to pass through to form a perturbed input immune cells; and b) incubating the perturbed input immune cells with the nucleic acid encoding the chimeric membrane-bound cytokine and the antigen to allow the nucleic acid and the antigen to enter the perturbed input immune cells where the nucleic acid encoding the chimeric membrane-bound cytokine is expressed; thereby generating immune cells comprising the chimeric membrane-bound cytokine and the antigen. In some embodiments, the nucleic acid encoding the chimeric membrane-bound cytokine is an mRNA encoding the chimeric membrane-bound cytokine.

In some aspects, there is provided a composition for use as a medicine, wherein the composition comprises an effective amount of immune cells a chimeric membrane-bound cytokine and an antigen. In some aspects, provided are compositions for treating a cancer, an infectious disease, or a viral-associated disease in an individual, wherein the composition comprises an effective amount of immune cells comprising a chimeric membrane-bound cytokine and an antigen. In some aspects, provided are methods of treating a cancer, an infectious disease, or a viral-associated disease in an individual, comprising administering a composition comprising an effective amount of immune cells comprising a chimeric membrane-bound cytokine and an antigen to the individual. In some embodiments, provided are uses of a composition comprising an effective amount of immune cells comprising a chimeric membrane-bound cytokine and an antigen in the manufacture of a medicament for stimulating an immune response in an individual and/or treating a cancer, an infectious disease, or a viral-associated disease in an individual. In some embodiments according to the methods, compositions or uses described herein, the immune cells comprising the chimeric membrane-bound cytokine and the antigen are prepared by: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and a nucleic acid encoding the antigen to pass through to form a perturbed input immune cells; and b) incubating the perturbed input immune cells with the nucleic acid encoding the chimeric membrane-bound cytokine and the nucleic acid encoding the antigen to allow the nucleic acids to enter the perturbed input immune cells where the nucleic acid encoding the chimeric membrane-bound cytokine and the nucleic acid encoding the antigen are expressed; thereby generating immune cells comprising the chimeric membrane-bound cytokine and the antigen. In some embodiments, the nucleic acid encoding the chimeric membrane-bound cytokine and/or the nucleic acid encoding the antigen is an mRNA.

In some aspects, there is provided a composition for use as a medicine, wherein the composition comprises an effective amount of immune cells comprising a chimeric membrane-bound cytokine and two or more antigens derived from a protein. In some aspects, provided are compositions for treating a cancer, an infectious disease, or a viral-associated disease in an individual, wherein the composition comprises an effective amount of immune cells comprising a chimeric membrane-bound cytokine and two or more antigens derived from a protein. In some aspects, provided are methods of treating a cancer, an infectious disease, or a viral-associated disease in an individual, comprising administering a composition comprising an effective amount of immune cells comprising a chimeric membrane-bound cytokine and two or more antigens derived from a protein to the individual. In some embodiments, provided are uses of a composition comprising an effective amount of immune cells comprising a chimeric membrane-bound cytokine and two or more antigens derived from a protein in the manufacture of a medicament for stimulating an immune response in an individual and/or treating a cancer, an infectious disease, or a viral-associated disease in an individual. In some embodiments according to the methods, compositions, or uses described herein, the immune cells comprising the chimeric membrane-bound cytokine and the two or more antigens derived from a protein are prepared by: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the two or more antigens derived from a protein to pass through to form a perturbed input immune cells; and b) incubating the perturbed input immune cells with the nucleic acid encoding the chimeric membrane-bound cytokine and the two or more antigens derived from a protein to allow the nucleic acid to enter the perturbed input immune cells where the nucleic acid encoding the chimeric membrane-bound cytokine is expressed; thereby generating immune cells comprising a chimeric membrane-bound cytokine and the two or more antigens derived from a protein.

In some embodiments, the width of the constriction is about 10% to about 99% of the mean diameter of the input nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells having the smallest diameter within the population of nucleated cells. In some embodiments, the width of the constriction is about 2 μm to about 5 μm, about 3 μm to about 5 μm, about 2 μm to about 2.5 μm, about 2.2 μm to about 2.5, about 2.5 μm to about 3 μm, about 3 μm to about 3.5 μm, about 3.5 μm to about 4 μm, about 4 μm to about 4.5 μm, about 3.2 μm to about 3.8 μm, about 3.8 μm to about 4.3 μm, about 4.2 μm to about 6 μm, or about 4.2 μm to about 4.8 μm. In some embodiments, the width of the constriction is about 4.5 μm. In some embodiments, the width of the constriction is about or less than any one of 2 μm, 2.2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the cell suspension comprising the input nucleated cells are passed through multiple constrictions wherein the multiple constrictions are arranged in series and/or in parallel.

In some embodiments according to any one of the methods, uses or compositions described herein, the nucleated cells (e.g., PBMCs) are incubated with the adjuvant for a sufficient time for the nucleated cells to condition. In some embodiments, the nucleated cells are incubated with the adjuvant for about 1 to about 24 hours for the nucleated cells to condition. In some embodiments, the nucleated cells are incubated with the adjuvant for about 2 to about 10 hours for the nucleated cells to condition. In some embodiments, the nucleated cells are incubated with the adjuvant for about 3 to about 6 hours for the nucleated cells to condition. In some embodiments, the nucleated cells are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the nucleated cells to condition. In some embodiments, the nucleated cells are incubated with the adjuvant for about 4 hours for the nucleated cells to condition. In some embodiments, the nucleated cells are conditioned before introducing the protein or fragment thereof or the nucleic acid encoding protein or fragment thereof into the nucleated cells. In some embodiments, the nucleated cells are conditioned after introducing the protein or fragment thereof or the nucleic acid encoding the protein or fragment thereof into the nucleated cells. In some embodiments, the adjuvant used for conditioning is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), a TLR3 agonist, a TLR4 agonist, a TLR7 agonist, a TLR8 agonist, or a TLR9 agonist. Exemplary adjuvants include, without limitation, CpG ODN, interferon-α (IFN-α), polyinosinic: polycytidylic acid (polyI:C), imiquimod (R837), resiquimod (R848), or lipopolysaccharide (LPS). In some embodiments, the adjuvant is a CpG oligodeoxynucleotide (ODN). In some embodiments, the adjuvant is CpG 7909.

In some embodiments, wherein the nucleated cells comprise B cells, one or more co-stimulatory molecules is upregulated in the B cells of the conditioned nucleated cells compared to the B cells of the unconditioned nucleated cells. In some embodiments, the nucleated cells are a plurality of peripheral blood mononuclear cells (PBMCs). In some embodiments, wherein the nucleated cells are a plurality of PBMCs, one or more co-stimulatory molecules is upregulated in the B cells of the conditioned plurality of PBMCs compared to the B cells of the unconditioned plurality of PBMCs. In some embodiments, the co-stimulatory molecule is CD80 and/or CD86. In some embodiments, the conditioned plurality of PBMCs has increased expression of one or more of IFN-γ, IL-6, MCP-1, MIP-1β, IP-10, or TNF-α compared to an unconditioned plurality of PBMCs. In some embodiments, the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to an unconditioned plurality of PBMCs In some embodiments according to any one of the methods, uses or compositions described herein, the nucleated cells are immune cells. In some embodiments, the nucleated cells are human cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the nucleated cells are a plurality of PBMCS. In some embodiments, the conditioned nucleated cells are a conditioned plurality of modified PBMCs. In some embodiments, the plurality of PBMCs comprises two or more of T cell, B cell, NK cell, monocytes, dendritic cells or NK-T cells. In some embodiments, the nucleated cells are one or more of T cells, B cells, NK cells, monocytes, dendritic cells and/or NK-T cells.

Constituent Cells within the Input Nucleated Cells

In some embodiments, the methods disclosed herein provide for the administration to an individual in need thereof an effective amount of compositions of nucleated cells comprising a protein or fragment thereof, wherein the protein or fragment is delivered intracellularly. In some embodiments, the composition of nucleated cells is a composition of immune cells. In some embodiments, the composition of nucleated cells comprises a plurality of PBMCs. In some embodiments, the nucleated cells are one or more of T cells, B cells, NK cells, monocytes, dendritic cells and/or NK-T cells.

In a particular embodiment of the invention, the nucleated cells comprising a protein or fragment thereof are PBMCs. As used herein, PBMCs may be isolated by apheresis such as leukapheresis from whole blood obtained from an individual. Also provided are PBMC compositions reconstituted by mixing different pools of PBMCs from the same individual or different individuals. In other examples, PBMCs may also be reconstituted by mixing different populations of cells into a mixed cell composition with a generated profile. In some embodiments, the populations of cells used for reconstituting PBMCs are mixed populations of cells (such as a mixture of one or more of T cells, B cells, NK cells or monocytes). In some embodiments, the populations of cells used for reconstituting PBMCs are purified populations of cells (such as purified T cells, B cells, NK cells or monocytes). In additional examples, the different populations of cells used in reconstituting a PBMC composition can be isolated from the same individual (e.g. autologous) or isolated from different individuals (e.g. allogenic and/or heterologous).

Therefore, in some embodiments according to the methods described herein, the plurality of PBMCs comprises one or more of T cells, B cells, NK cells, monocytes, dendritic cells or NK-T cells. In some embodiments, the plurality of PBMCs comprises T cells, B cells, NK cells, monocytes, dendritic cells or NK-T cells. In some embodiments, the plurality of PBMCs comprises one or more of CD3+ T cells, CD20+ B cells, CD14+ monocytes, CD56+ NK cells. In some embodiments, the plurality of PBMCs comprises T cells, B cells, NK cells and monocytes, and the ratio of T cells, B cells, NK cells and monocytes to the total number of PBMCs in the plurality of PBMCs is essentially the same as the ratio of T cells, B cells, NK cells and monocytes to the total number of PBMCs in whole blood. In some embodiments, the plurality of PBMCs comprises T cells, B cells, NK cells and monocytes, and the ratio of T cells, B cells, NK cells and monocytes to the total number of PBMCs in the plurality of PBMCs is essentially the same as the ratio of r cells, B cells, NK cells and monocytes to the total number of PBMCs in a leukapheresis product from whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 1%, 2%, 5%, 10% 15%, 20%, 25%, 30%, 40%, or 50% from the ratio of T cells, B cells, NK cells and monocytes to the total number of PBMCs in whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 10% from the ratio of T cells, B cells, NK cells and monocytes to the total number of PBMCs in whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 1%, 2%, 5%, 10% 15%, 20%, 25%, 30%, 40%, or 50% from the ratio of T cells, B cells, NK cells and monocytes to the total number of PBMCs in a leukapheresis product from whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 10% from the ratio of T cells, B cells, NK cells and monocytes to the total number of PBMCs in a leukapheresis product from whole blood.

In some embodiments according to the methods described herein, about 25% to about 70% of the modified PBMCs are T cells. In some embodiments, about 2.5% to about 14% of the modified PBMCs are B cells. In some embodiments, about 3.5% to about 35% of the modified PBMCs are NK cells. In some embodiments, about 4% to about 25% of the modified PBMCs are NK cells.

In some embodiments according to the methods described herein, at least about any one of 15%, 20%, 25%, 30%, 35%, 40%, 45%, 50%, 55%, 60%, 65%, 70%, or 75% of the PBMCs are T cells. In some embodiments, at least about 25% of the PBMCs are T cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the PBMCs are B cells. In some embodiments, at least about 2.5% of the PBMCs are B cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 3% of the PBMCs are NK cells. In some embodiments, at least about 3.5% of the PBMCs are NK cells. In some embodiments, at least about any one of 1%, 2%, 3%, 4%, 5%, 6%, 7%, 8%, 9%, 10%, 12%, 14%, 16%, 18%, 20%, 25%, 30%, 35% or 40% of the PBMCs are monocytes. In some embodiments, at least about 4% of the PBMCs are monocytes. In some embodiments, at least about 25% of the PBMCs are T cells; at least about 2.5% of the PBMCs are B cells; at least about 3.5% of the PBMCs are NK cells; and at least about 4% of the PBMCs are monocytes.

In some embodiments according to the methods described herein, not more than about any one of 40%, 45%, 50%, 55%, 60%, 65%, 70%, 75%, 80%, 85%, or 90% of the PBMCs are T cells. In some embodiments, not more than about 70% of the PBMCs are T cells. In some embodiments, not more than about any one of 5%, 10%, 12%, 14%, 16%, 18%, 20%, 22%, 25%, 30%, 35%, 40%, or 50% of the PBMCs are B cells. In some embodiments, not more than about 14% of the PBMCs are B cells. In some embodiments, not more than about any one of 10%, 15%, 20%, 25%, 30%, 35%, 40%, 45%, 50% or 60% of the PBMCs are NK cells. In some embodiments, not more than about 35% of the PBMCs are NK cells. In some embodiments, not more than about any one of 5%, 10%, 12%, 14%, 16%, 18%, 20%, 22%, 25%, 30%, 35%, 40%, or 50% of the PBMCs are monocytes. In some embodiments, not more than about 4% of the PBMCs are monocytes. In some embodiments, not more than about 25% of the PBMCs are T cells; not more than about 2.5% of the PBMCs are B cells; not more than about 3.5% of the PBMCs are NK cells; and not more than about 4% of the PBMCs are monocytes.

In some embodiments according to the methods described herein, about any one of 20% to 25%, 25% to 30%, 30% to 35%, 35% to 40%, 40% to 45%, 45% to 50%, 50% to 55%, 55% to 60%, 60% to 65%, 65% to 70%, or 70% to 75% of the modified PBMCs are T cells. In some embodiments, about 25% to about 70% of the modified PBMCs are T cells. In some embodiments, about any one of 1% to 2.5%, 2.5% to 4%, 4% to 6%, 6% to 8%, 8% to 10%, 10% to 12%, 12% to 14%, 14% to 16%, 16% to 20% or 20% to 25% of the modified PBMCs are B cells. In some embodiments, about 2.5% to about 14% of the modified PBMCs are B cells. In some embodiments, about any one of 1% to 2%, 2% to 3.5%, 3.5% to 5%, 5% to 8%, 8% to 10%, 10% to 12%, 12% to 14%, 14% to 16%, 16% to 20%, 20% to 25%, 25% to 30%, 30% to 35%, or 35% to 40% of the modified PBMCs are NK cells. In some embodiments, about 3.5% to about 35% of the modified PBMCs are NK cells. In some embodiments, about any one of 2% to 4%, 4% to 6%, 6% to 8%, 8% to 10%, 10% to 12%, 12% to 14%, 14% to 16%, 16% to 20%, 20% to 25%, 25% to 30%, 30% to 35%, or 35% to 40% of the modified PBMCs are monocytes. In some embodiments, about 4% to about 25% of the modified PBMCs are monocytes. In some embodiments, about 25% to about 70% of the modified PBMCs are T cells, about 2.5% to about 14% of the modified PBMCs are B cells, about 3.5% to about 35% of the modified PBMCs are NK cells, and about 4% to about 25% of the modified PBMCs are NK cells.

As used herein, PBMCs can also be generated after manipulating the composition of a mixed cell population of mononuclear blood cells (such as lymphocytes and monocytes). In some instances, the PBMCs are generated after reducing (such as depleting) certain subpopulations (such as B cells) within a mixed cell population of mononuclear blood cells. The composition in a mixed cell population of mononuclear blood cells in an individual can be manipulated to make the cell population more closely resemble a leukapheresis product from whole blood in the same individual. In other examples, the composition in a mixed cell population of mononuclear blood cells (for example, mouse splenocytes) can also be manipulated to make the cell population more closely resemble human PBMCs isolated from a leukapheresis product from human whole blood.

In some embodiments of the invention, the composition of nucleated cells comprising a protein or fragment thereof is a population of cells found in PBMCs. In some embodiments, the composition of nucleated cells comprising a protein or fragment thereof comprises one or more of T cells, B cells, NK cells, monocytes, dendritic cells or NK-T cells. In some embodiments, the composition of nucleated cells comprising a protein or fragment thereof comprises one or more of CD3+ T cells, CD20+ B cells, CD14+ monocytes, CD56+ NK cells. In some embodiments, the composition of nucleated cells comprising a protein or fragment thereof comprises at least about any of 70%, 75%, 80%, 85%, 90%, 95%, or 99% T cells. In some embodiments, the composition of nucleated cells comprising a protein or fragment thereof comprises 100% T cells. In some embodiments, the composition of nucleated cells comprising a protein or fragment thereof comprises at least about any of 70%, 75%, 80%, 85%, 90%, 95%, or 99% B cells. In some embodiments, the composition of nucleated cells comprising a protein or fragment thereof comprises 100% B cells. In some embodiments, the composition of nucleated cells comprising a protein or fragment thereof comprises at least about any of 70%, 75%, 80%, 85%, 90%, 95%, or 99% NK cells. In some embodiments, the composition of nucleated cells comprising a protein or fragment thereof comprises 100% NK cells. In some embodiments, the composition of nucleated cells comprising a protein or fragment thereof comprises at least about any of 70%, 75%, 80%, 85%, 90%, 95%, or 99% monocytes. In some embodiments, the composition of nucleated cells comprising a Protein or fragment thereof comprises 100% monocytes. In some embodiments, the composition of nucleated cells comprising a protein or fragment thereof comprises at least about any of 70%, 75%, 80%, 85%, 90%, 95%, or 99% dendritic cells. In some embodiments, the composition of nucleated cells comprising a protein or fragment thereof comprises 100% dendritic cells. In some embodiments, the composition of nucleated cells comprising a protein or fragment thereof comprises at least about any of 70%, 75%, 80%, 85%, 90%, 95%, or 99% N K-T cells. In some embodiments, the composition of nucleated cells comprising a protein or fragment thereof comprises 100% NK-T cells.

Further Modifications of Nucleated Cells Comprising the Protein or Fragment Thereof In some embodiments according to any one of the methods described herein, the composition of nucleated cells (e.g., PBMCs) further comprises an agent that enhances the viability and/or function of the nucleated cells as compared to a corresponding composition of nucleated cells that does not comprise the agent. In some embodiments, the composition of nucleated cells further comprises an agent that enhances the viability and/or function of the nucleated cells upon freeze-thaw cycle as compared to a corresponding composition of nucleated cells that does not comprise the agent. In some embodiments, the agent is a cryopreservation agent and/or a hypothermic preservation agent. In some embodiments, the cryopreservation agent nor the hypothermic preservation agent cause not more than 10% or 20% of cell death in a composition of nucleated cells comprising the agent compared to a corresponding composition of nucleated cells that does not comprise the agent before any freeze-thaw cycles. In some embodiments, at least about 70%, about 80%, or about 90% of the nucleated cells are viable after up to 1, 2, 3, 4, 5 freeze-thaw cycles. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is human albumin. In some embodiments, the agent is one or more of: a divalent metal cation, glucose, ATP, potassium, glycerol, trehalose, D-sucrose, PEG1500, L-arginine, L-glutamine, or EDTA. In some embodiments, the divalent metal cation is one more of $Mg2+$, $Zn2+$ or $Ca2+$. In some embodiments, the agent is one or more of: sodium pyruvate, adenine, trehalose, dextrose, mannose, sucrose, human serum albumin (HSA), DMSO, HEPES, glycerol, glutathione, inosine, dibasic sodium phosphate, monobasic sodium phosphate, sodium metal ions, potassium metal ions, magnesium metal ions, chloride, acetate, gluoconate, sucrose, potassium hydroxide, or sodium hydroxide. In some embodiments, the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® C5S, Cryostor® CS10, Cryostor® CS15, HEPES, glycerol, glutathione, HypoThermosol®.

In some embodiments according to any one of the methods described herein, the composition of nucleated cells comprises a plurality of modified PBMCs that are further modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of modified PBMCs comprises a nucleic acid that results in increased expression of the one or more co-stimulatory molecules. In some embodiments, the plurality of modified PBMCs comprises an mRNA that results in increased expression of the one or more co-stimulatory molecules. In some embodiments, the co-stimulatory molecule is a Signal 2 mediator in stimulating T cell activation.

In some embodiments according to any one of the methods described herein, the modified PBMCs are further modified to increase expression of one or more cytokines. In some embodiments, the cytokine is one or more of IL-2, IL-12, IL-21, or IFNα2. In some embodiments, the plurality of modified PBMCs comprises a nucleic acid that results in increased expression and/or secretion of the one or more cytokines. In some embodiments, the cytokine is a Signal 3 effector in stimulating T cell activation.

T cell activation initiates an intra-cellular signaling cascade that ultimately results in proliferation, effector function, or death, depending on the intensity of the TCR signal and associated signals. To guard against premature or excessive activation, T cells have a requirement of two independent signals for full activation. Signal 1 is an antigen-specific signal provided by the binding of the TCR to antigenic peptide complexed with MHC. Signal 2 is mediated by either cytokines or the engagement of co-stimulatory molecules such as B7.1 (CD80) and B7.2 (CD86) on the antigen-presenting cell (APC). Signal 3 is mediated by inflammatory cytokines such as IL-2, IL-12 and IFN-α.

In some embodiments according to any one of the methods or compositions described herein, wherein the nucleated cells (such as PBMCs) comprise a protein or fragment thereof, the nucleated cells further comprise one or more agents that mediate Signal 2 t such as a Signal 2 mediator). In some embodiments, wherein the nucleated cells (such as PBMCs) comprise a protein or fragment thereof, the nucleated cells further comprise one or more agents that mediate Signal 3 (such as a Signal 3 effector). In some embodiments, wherein the nucleated cells (such as PBMCs) comprise a protein or fragment thereof, the nucleated cells further comprise one or more agents that mediate Signal 2 (such as a Signal 2 mediator) and one or more agents that mediate Signal 3 (such as a Signal 3 effector).

In some embodiments, the one or more agents that mediate Signal 2 comprises one or more of B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the one or more agents that mediate Signal 2 comprises B7-1 (CD80) and/or B7-2 (CD86). In some embodiments, the one or more agents that mediate Signal 2 comprises one or more mRNAs encoding B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112, In some embodiments, the one or more agents that mediate Signal 2 comprises one or more mRNAs encoding 17-1 (CD80) and/or B7-2 (CD86).

In some embodiments, the one or more agents that mediate Signal 3 comprises one or more cytokines. In some embodiments, the one or more agents that mediate Signal 3 comprises one or more of IL-2, IL-7, IL-10, IL-12, IL-15, IL-21, IFNα2. In some embodiments, the one or more agents that mediate Signal 3 comprise IL-2 and/or IL-12. In some embodiments, the one or more agents that mediate Signal 3 comprises one or more of variants of IL-2, IL-7, IL-12, IL-15, IL-21, IFNα2. In some embodiments, the one or more agents that mediate Signal 3 comprise variants of IL-2 and/or IL-12. In some embodiments, the one or more agents that mediate Signal 3 comprises one or more of variants of IL-2, IL-7, IL-12, IL-15, IL-21, IFNα2. In some embodiments, the one or more agents that mediate Signal 3 comprise membrane-bound IL-2 and/or membrane-bound IL-12. In some embodiments, the one or more agents that mediate Signal 3 comprises one or more of variants of IL-2, IL-7, IL-12, IL-15, IL-21, IFNα2. In some embodiments, the one or more agents that mediate Signal 3 comprise variants of IL-2 and/or IL12.

In some embodiments, a nucleated cell comprising the protein or fragment thereof and further comprising an agent that mediates Signal 2 can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell not comprising an agent that mediates Signal 2. In some embodiments, a nucleated cell comprising the protein or fragment thereof and further comprising an agent that mediates Signal 3 can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell not comprising an agent that mediates Signal 3. In some embodiments, a nucleated cell comprising the protein or fragment thereof and further comprising an agent that mediates Signal 2 and/or an agent that mediates Signal 3 can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell not comprising an agent that mediates Signal 2 or Signal 3. In some embodiments, the enhanced antigen-specific T cell activation is HLA agnostic. In some embodiments, the enhanced antigen-specific T cell activation comprises T cell activation dependent on restriction by one or more of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, and/or HLA-C*16 haplotypes.

In some embodiments, the plurality of PBMCs are further modified to increase expression of one or more cytokines. In some embodiments, the cytokine is IL-10, IL-15, IL-12, IL-2, IFN-α, IFN-γ, IL-21, or a functional variant thereof. In some embodiments, the cytokine is IFN-α2 or a functional variant thereof. In some embodiments, the cytokine is a variant cytokine (such as a modified cytokine), such as a chimeric membrane-bound cytokine. In some embodiments, the plurality of PBMCs are further modified to increase expression of one or more chimeric membrane-bound cytokines (such as membrane bound IL-10, IL-15, IL-12, IL-2, IFN-α, IFN-γ, IL-21). In some embodiments, the cytokine is modified, and the modified cytokine is a fusion protein comprising the cytokine and a transmembrane domain. In some embodiments, the cytokine is joined to the transmembrane domain by a peptide linker. In some embodiments, the transmembrane domain is a transferrin receptor protein 1 (TFRC) or a tumor necrosis factor (e.g., FasL) transmembrane domain. In some embodiments, the transmembrane domain comprises the amino acid sequence of SEQ ID NO: 81 or SEQ ID NO: 82. In some embodiments, the peptide linker is a $G_4S$ linker or an EAAAK linker. In embodiments, the $G_4S$ linker comprises any one of 2, 3, 4, 5, 6, 7, 8, 9, or 10 repeats of $G_4S$ sequence. In some embodiments, the EAAAK linker comprises any one of 2, 3, 4, 5, 6, 7, 8, 9, or 10 repeats of EAAAK sequence. In some embodiments, the peptide linker is $(G_4S)_3$ (SEQ ID NO: 73) or $(EAAAK)_3$ (SEQ ID NO: 74). In some embodiments, the chimeric membrane-bound cytokine comprises the amino acid sequence of any one of SEQ ID NOs: 77-80. In some embodiments, the plurality of modified PBMCs comprises a nucleic acid that results in increased expression and/or secretion of the one or more cytokines. In some embodiments, the nucleic acid encodes a chimeric membrane-bound cytokine comprises the nucleotide sequence of SEQ ID NO: 71 or 72. In some embodiments, the cytokine is a Signal 3 effector in stimulating T cell activation. In some embodiments, the chimeric membrane-bound cytokine enhances the half-life of the cytokine in an individual compared to a non-membrane-bound cytokine. In some embodiments, the half-life of the chimeric membrane-bound cytokine is increased by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a non-membrane-bound cytokine. In some embodiments, the membrane-bound cytokine prolongs the spatial association of the cytokine with the antigens presented by the nucleated cell introduced with the protein or fragment thereof, by about any one of: 1, 2, 3, 4, 6, 8, 12, 16, 20, 24, 28, 32, 36, 48, 72, 96 or more hours, compared to a corresponding nucleated cell comprising a non-membrane-tethered cytokine. In some embodiments, a nucleated cell comprising the protein or fragment thereof and further comprising a membrane-bound cytokine exhibits a local cytokine concentration that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine. In some embodiments, a nucleated cell comprising the protein or fragment thereof and further comprising a membrane-bound cytokine can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 50-fold or more compared to a corresponding nucleated cell comprising a non-membrane-bound cytokine.

In some embodiments, the membrane-bound cytokine is a membrane-bound chemokine.

In some embodiments, the modified PBMCs comprise a further modification to modulate MHC class I expression. In some embodiments, an innate immune response mounted in an individual in response to administration, in an allogeneic context, of the modified PBMCs is reduced compared to an innate immune response mounted in an individual in response to administration, in an allogeneic context, of corresponding modified PBMCs that do not comprise the further modification. In some embodiments, the circulating half-life of the modified PBMCs in an individual to which they were administered is increased compared to the circulating half-life of corresponding modified PBMCs that do not comprise the further modification in an individual to which they were administered. In some embodiments, the circulating half-life of the modified PBMCs in an individual to which they were administered is increased by about any one of 10%, 25%, 50%, 75%, 100%, 2-fold, 3-fold, 4-fold, 5-fold, 10-fold, 25-fold, 50-fold, 100-fold, 200-fold, or 500-fold or more compared to the circulating half-life of corresponding modified PBMCs that do not comprise the further modification in an individual to which they were administered. In some embodiments, the circulating half-life of the modified PBMCs in an individual to which they were administered is essentially the same as the circulating half-life of corresponding modified PBMCs that do not comprise the further modification in an individual to which they were administered.

In some embodiments according to any one of the methods described herein, the process further comprises a step of incubating the composition of nucleated cells with an agent that enhances the viability and/or function of the nucleated cells compared to corresponding nucleated cells prepared without the further incubation step.

Further Modifications of Nucleated Cells to Enhance Antigen-Specific Response in HLA-Agnostic Manner T cell activation initiates an intra-cellular signaling cascade that ultimately results in proliferation, effector function, or death, depending on the intensity of the TCR signal and associated signals. To guard against premature or excessive activation, T cells have a requirement of two independent signals for full activation. Signal 1 is an antigen-specific signal provided by the binding of the TCR to antigenic peptide complexed with MHC. Signal 2 is mediated by either cytokines or the engagement of co-stimulatory molecules such as B7.1 (CD80) and B7.2 (CD86) on the antigen-presenting cell (APC). Signal 3 is mediated by inflammatory cytokines such as IL-2, IL-12 and IFN-α.

In some aspects, provided are methods for enhancing the activity of an immune cell, the methods comprising expressing one or more agents that mediate Signal 2 (such as a Signal 2 mediator) in the immune cell. In some aspects, provided am methods for enhancing the activity of an immune cell, the methods comprising expressing one or more agents that mediate Signal 3 (such as a Signal 3 effector) in the immune cell. In some aspects, provided are methods for enhancing the activity of an immune cell, the methods comprising expressing one or more agents that mediate Signal 2 (such as a Signal 2 mediator) and one or more agents that mediate Signal 3 such as a Signal 3 effector) in the immune cell. In some embodiments, the agent that mediates Signal 3 (such as a Signal 3 effector) in stimulating T cell activation is a cytokine. In some embodiments, the cytokine comprises one or more of IL-2, IL-7, IL-10, IL-12, IL-15, IL-21, IFNα2. In some embodiments, the cytokine comprises IL-2 and/or IL-12. In some embodiments, provided are methods for enhancing the activity of an immune cell, the methods comprising expressing a nucleic acid encoding a chimeric membrane-bound cytokine in the immune cell. In some embodiments, the cytokine is modified, and the modified cytokine is a fusion protein comprising the cytokine and a transmembrane domain. In some embodiments, the cytokine is joined to the transmembrane domain by a peptide linker. In some embodiments, the transmembrane domain is a transferrin receptor protein 1 (TFRC) or a tumor necrosis factor (e.g., FasL) transmembrane domain. In some embodiments, the transmembrane domain comprises the amino acid sequence of SEQ ID NO: 81 or SEQ ID NO: 82. In some embodiments, the peptide linker is a $G_4S$ linker or an EAAAK linker. In embodiments, the $G_4S$ linker comprises any one of 2, 3, 4, 5, 6, 7, 8, 9, or 10 repeats of $G_4S$ sequence. In some embodiments, the EAAAK linker comprises any one of 2, 3, 4, 5, 6, 7, 8, 9, or 10 repeats of EAAAK sequence. In some embodiments, the peptide linker is $(G_4S)_3$ (SEQ ID NO: 73) or $(EAAAK)_3$ (SEQ ID NO: 74). In some embodiments, the chimeric membrane-bound cytokine comprises the amino acid sequence of SEQ ID NOs: 77-80. In some embodiments, the plurality of modified PBMCs comprises a nucleic acid that results in increased expression and/or secretion of the one or more cytokines. In some embodiments, the nucleic acid encoding the chimeric membrane-bound cytokine comprises the nucleotide sequence of SEQ ID NO: 71 or 72. In some embodiments, the cytokine is a Signal 3 effector in stimulating T cell activation. In some embodiments, the chimeric membrane-bound cytokine enhances the half-life of the cytokine in an individual compared to a non-membrane-bound cytokine. In some embodiments, the half-life of the chimeric membrane-bound cytokine is increased by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a non-membrane-bound cytokine. In some embodiments, the membrane-bound cytokine prolongs the spatial association of the cytokine with the antigens presented by the nucleated cell introduced with the protein or fragment thereof, by about any one of: 1, 2, 3, 4, 6, 8, 12, 16, 20, 24, 28, 32, 36, 48, 72, 96 or more hours, compared to a corresponding nucleated cell comprising a non-membrane-bound cytokine. In some embodiments, a nucleated cell comprising the protein or fragment thereof and further comprising a membrane-bound cytokine exhibits a local cytokine concentration that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine. In some embodiments, a nucleated cell comprising the protein or fragment thereof and further comprising a membrane-bound cytokine can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine.

In some aspects, the invention provides methods for stimulating an immune response in an individual, the method comprising administering an effective amount of a composition comprising nucleated cells to an individual, wherein the nucleated cells comprise an mRNA encoding a protein or fragment thereof; wherein the mRNA is expressed, and wherein the protein or fragment thereof stimulates an immune response regardless of the HLA haplotype of the individual. In some aspects, the invention provides methods for vaccinating an individual in need thereof, the method comprising administering an effective amount of a composition comprising nucleated cells to an individual, wherein the nucleated cells comprise an mRNA encoding a protein or fragment thereof; wherein the protein or fragment thereof stimulates an immune response regardless of the HLA haplotype of the individual. In some embodiments, the nucleotide sequence of the mRNA is codon optimized for expression in the nucleated cell.

In some embodiments, wherein the nucleated cells comprise a protein or fragment thereof, the protein or fragment thereof comprises an antigen. In some embodiments, wherein the nucleated cells comprise an mRNA encoding a protein or fragment thereof, the protein or fragment thereof is an antigen. In some embodiments, the antigen stimulates an immune response regardless of the HLA haplotype of the individual. In some embodiments, the nucleated cell comprises two or more antigens derived from a protein. In some embodiments, the two or more antigens stimulates an immune response regardless of the HLA haplotype of the individual. In some embodiments, the protein is a mutated protein associated with cancer, a viral protein, a bacterial protein or a fungal protein. In some embodiments, the protein is a human papillomavirus (HPV) protein. In some embodiments, the HPV is HPV-16 or HPV-18. In some embodiments, the protein is an HPV E6 or HPV E7 protein.

In some embodiments, the protein is a hepatitis B virus (HBV) protein. In some embodiments, the nucleated cells comprise a protein or fragment thereof, or an mRNA encoding a protein or fragment thereof; wherein the protein or fragment thereof is processed into antigenic peptide complexed with MHC, thereby mediating Signal 1 in T cell activation.

In some embodiments, Signal 1 is an antigen-specific signal provided by the binding of the T cell receptor to antigenic peptide complexed with MHC. In some embodiments, the nucleated cells comprise an mRNA encoding a protein or fragment thereof; wherein mRNA is expressed, wherein the protein or fragment thereof stimulates an immune response regardless of the HLA haplotype of the individual. In some embodiments, the nucleated cells comprise a protein or fragment thereof, wherein the protein or fragment thereof stimulates an immune response regardless of the HLA haplotype of the individual. In some embodiments, the nucleated cells comprise a protein or fragment thereof, or an mRNA encoding a protein or fragment thereof; wherein the protein or fragment thereof is processed into antigenic peptide complexed with MHC, thereby mediating Signal 1 in T cell activation.

In some embodiments according to any one of the methods described above, the nucleated cells (such as PBMCs) comprise further modifications to further enhance the immune response to the protein or fragment thereof. In some embodiments the methods of further modifications to the nucleated cells (such as PBMCs) further enhances the immune response to the protein or fragment thereof in an HLA agnostic manner. In some embodiments the methods of further modifications to the nucleated cells (such as PBMCs) further enhances the immune response to the protein or fragment thereof, wherein the enhanced immune response comprises immune response dependent on restriction by one or more HLA haplotypes. In some embodiments the methods of further modifications to the nucleated cells (such as PBMCs) further enhances the immune response to the protein or fragment thereof, wherein the enhanced immune response comprises immune response dependent on restriction by one or more of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16 haplotypes. In some embodiments, wherein the nucleated cells comprise a protein or fragment thereof, or an mRNA encoding a protein or fragment thereof; the protein or fragment thereof is processed into antigenic peptide complexed with MHC, thereby mediating Signal 1 in T cell activation. In some embodiments, the further modifications to the nucleated cells comprises introduction of one or more agents that mediate Signal 2 (such as a Signal 2 mediator). In some embodiments, the further modifications to the nucleated cells comprises introduction of one or more agents that mediate Signal 3 (such as a Signal 3 effector). In some embodiments, the further modifications to the nucleated cells comprises introduction of one or more agents that mediate Signal 2 (such as a Signal 2 mediator) and one or more agents that mediate Signal 3 (such as a Signal 3 mediator).

In some embodiments according to any one of methods or compositions described herein, the agent that mediates Signal 2 (such as a Signal 2 mediator) comprises one or more of B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the agent that mediates Signal 2 comprises CD70, B7-1 (CD80) and/or B7-2 (CD86). In some embodiments, the modified nucleated cells comprises a nucleic acid that results in increased expression of one or more of B7-H2 t ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the modified nucleated cells comprises one or more nucleic acids encoding one or more of B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of modified nucleated cells comprises one or more nucleic acids encoding CD70, B7-1 (CD80) and/or B7-2 (CD86)

In some embodiments according to any one of methods or compositions described herein, the agent that mediates Signal 3 (such as a Signal 3 effector) is a cytokine or a functional variant thereof. In some embodiments, the agent that mediates Signal 3 is an mRNA encoding a cytokine or a functional variant thereof. In some embodiments, the cytokine is IL-40, IL-15, IL-12, IL-2, IFN-α, IFN-γ, IL-21, or a functional variant thereof. In some embodiments, the cytokine is IFN-α2 or a functional variant thereof. In some embodiments, the cytokine is a variant cytokine (such as a modified cytokine), such as a chimeric membrane-bound cytokine. In some embodiments, the cytokine is modified, and the modified cytokine is a fusion protein comprising the cytokine and a transmembrane domain. In some embodiments, the cytokine is joined to the transmembrane domain by a peptide linker. In some embodiments, the transmembrane domain is a transferrin receptor protein 1 (TFRC) or a tumor necrosis factor (e.g., FasL) transmembrane domain. In some embodiments, the transmembrane domain comprises the amino acid sequence of SEQ ID NO: 81 or SEQ ID NO: 82. In some embodiments, the peptide linker is a $G_4S$ linker or an EAAAK linker. In embodiments, the $G_4S$ linker comprises any one of 2, 3, 4, 5, 6, 7, 8, 9, or 10 repeats of $G_4S$ sequence. In some embodiments, the EAAAK linker comprises any one of 2, 3, 4, 5, 6, 7, 8, 9, or 10 repeats of EAAAK sequence. In some embodiments, the peptide linker is $(G_4S)_3$ (SEQ ID NO: 73) or $(EAAAK)_3$ (SEQ ID NO: 74). In some embodiments, the chimeric membrane-bound cytokine comprises the amino acid sequence of any one of SEQ ID NOs: 77-80. In some embodiments, the plurality of modified nucleated cells comprises a nucleic acid that results in increased expression and/or secretion of the one or more cytokines. In some embodiments, the nucleic acid encoding the chimeric membrane-bound cytokine comprises the nucleotide sequence of SEQ ID NO: 71 or 72. In some embodiments, the cytokine is a Signal 3 effector in stimulating T cell activation. In some embodiments, the chimeric membrane-bound cytokine enhances the half-life of the cytokine in an individual compared to a non-membrane-bound cytokine. In some embodiments, the half-life of the chimeric membrane-bound cytokine is increased by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a non-membrane-bound cytokine. In some embodiments, the membrane-bound cytokine prolongs the spatial association of the cytokine with the antigens presented by the nucleated cell introduced with the protein or fragment thereof, by about any one of: 1, 2, 3, 4, 6, 8, 12, 16, 20, 24, 28, 32, 36, 48, 72, 96 or more hours, compared to a corresponding nucleated cell comprising a non-membrane-bound cytokine. In some embodiments, a nucleated cell comprising the protein or fragment thereof and further comprising a membrane-bound cytokine exhibits a local cytokine concentration that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine. In some embodiments, a nucleated cell comprising the protein or fragment thereof and further comprising a membrane-bound cytokine can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell comprising a non-membrane-bound cytokine. In some embodiments, the cytokine is IL-10, IL-15, IL-12, IL-2, IFN-α, IFN-γ, IL-21, or a functional variant thereof. In some embodiments, the cytokine is IFN-α2 or a functional variant thereof. In some embodiments, the cytokine is a variant cytokine (such as a modified cytokine), such as a chimeric membrane-bound cytokine. In some embodiments, the nucleated cells are further modified to increase expression of one or more chimeric membrane-bound cytokines (such as membrane bound IL-10, IL-15, IL-12, IL-2, IFN-α, IFN-γ, and/or IL-21). In some embodiments, the nucleated cell further comprises one or more nucleic acids encoding one or more chimeric membrane-bound cytokines. In some embodiments, the nucleated cell further comprises a nucleic acid encoding membrane bound IL-12. In some embodiments, the nucleated cell further comprises a nucleic acid encoding membrane bound IL-2. In some embodiments, the nucleated cells further comprises a nucleic acid encoding membrane bound IL-2 and membrane bound IL-12.

In some embodiments, provided are methods for stimulating an immune response in an individual, the method comprising administering an effective amount of a composition comprising nucleated cells to an individual, wherein the nucleated cells comprise an mRNA encoding a protein or fragment thereof; wherein the protein or fragment thereof stimulates an immune response regardless of the HL A haplotype of the individual; and wherein the nucleated cells are further modified with agents that mediate Signal 2 and/or agents that mediate Signal 3. In some aspects, the invention provide methods for vaccinating an individual in need thereof, the method comprising administering an effective amount of a composition comprising nucleated cells to an individual, wherein the nucleated cells comprise an mRNA encoding a protein or fragment thereof; wherein the protein or fragment thereof stimulates an immune response regardless of the HLA haplotype of the individual; and wherein the nucleated cells are further modified with agents that mediate Signal 2 and/or agents that mediate Signal 3. In some embodiments, the nucleotide sequence of the mRNA is codon optimized for expression in the nucleated cell.

In some embodiments according to any one of the methods, nucleated cells or compositions provided herein, the nucleated cells comprising a protein or fragment thereof and one or more agents that mediate Signal 2 and/or Signal 3 are prepared by a process comprising: a) passing a cell suspension comprising input immune cells through a cell-deforming constriction, wherein a diameter of the constriction is a function of a diameter of the input immune cells in the suspension, thereby causing perturbations of the input immune cells large enough for the protein or fragment thereof and the one or more agents that mediate Signal 2 and/or Signal 3 to form a perturbed input immune cells; and b) incubating the perturbed input immune cells with the protein or fragment thereof and the one or more agents that mediate Signal 2 and/or Signal 3 to allow the protein or fragment thereof and the one or more agents that mediate Signal 2 and/or Signal 3 to enter the perturbed input immune cells; thereby generating immune cells comprising the protein or fragment thereof and the one or more agents that mediate Signal 2 and/or Signal 3.

In some embodiments, the agent that mediates Signal 2 comprises CD86 and the agent that mediates Signal 3 comprises IL-2. In some embodiments according to any one of the methods, nucleated cells or compositions provided herein, the nucleated cells comprising a protein or fragment thereof and CD86 and IL-2 are prepared by a process comprising: a) passing a cell suspension comprising input immune cells through a cell-deforming constriction, wherein a diameter of the constriction is a function of a diameter of the input immune cells in the suspension, thereby causing perturbations of the input immune cells large enough for the protein or fragment thereof and CD86 and IL-2 to form a perturbed input immune cells; and b) incubating the perturbed input immune cells with the protein or fragment thereof and CD86 and IL-2 to allow the protein or fragment thereof and the CD86 and IL-2 to enter the perturbed input immune cells; thereby generating immune cells comprising the protein or fragment thereof and CD86 and IL-2.

In some embodiments, the agent that mediates Signal 3 is a membrane-bound cytokine. In some embodiments according to any one of the methods, nucleated cells or compositions provided herein, the nucleated cells comprising a protein or fragment thereof and a membrane-bound cytokine are prepared by a process comprising: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and a nucleic acid encoding the protein or fragment thereof to pass through to form a perturbed input immune cells; and b) incubating the perturbed input immune cells with the nucleic acid encoding the chimeric membrane-bound cytokine and the nucleic acid encoding the protein or fragment thereof to allow the nucleic acids to enter the perturbed input immune cells where the nucleic acid encoding the chimeric membrane-bound cytokine and the nucleic acid encoding the protein or fragment thereof are expressed; thereby generating immune cells comprising the chimeric membrane-bound cytokine and the protein or fragment thereof. In some embodiments, the nucleic acid encoding the chimeric membrane-bound cytokine and/or the nucleic acid encoding the protein or fragment thereof are mRNAs. In some embodiments, the protein or fragment thereof comprises one or more antigens.

In some embodiments, the agent that mediates Signal 2 comprises a chimeric membrane-bound cytokine. In some embodiments, provided are methods for enhancing the activity of an immune cell in stimulating an immune response to an antigen, wherein the immune cells comprising the chimeric membrane-bound cytokine and further comprising an antigen are prepared by: a) passing a cell suspension comprising input immune cells through a cell-deforming constriction, wherein a diameter of the constriction is a function of a diameter of the input immune cells in the suspension, thereby causing perturbations of the input immune cells large enough for the antigen and a nucleic acid encoding a chimeric membrane-bound cytokine to pass through to form a perturbed input immune cells; and b) incubating the perturbed input immune cells with the nucleic acid encoding the chimeric membrane-bound cytokine and the antigen to allow the nucleic acid and the antigen to enter the perturbed input immune cells where the nucleic acid encoding the chimeric membrane-bound cytokine is expressed; thereby generating immune cells comprising the chimeric membrane-bound cytokine and the antigen. In some embodiments, the nucleic acid encoding the chimeric membrane-bound cytokine is an mRNA encoding the chimeric membrane-bound cytokine.

In some embodiments, provided are methods for enhancing the activity of an immune cell in stimulating an immune response to an antigen, wherein the immune cells comprising the chimeric membrane-bound cytokine and further comprising an antigen are prepared by: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and a nucleic acid encoding the antigen to pass through to form a perturbed input immune cells; and b) incubating the perturbed input immune cells with the nucleic acid encoding the chimeric membrane-bound cytokine and the nucleic acid encoding the antigen to allow the nucleic acids to enter the perturbed input immune cells where the nucleic acid encoding the chimeric membrane-bound cytokine and the nucleic acid encoding the antigen are expressed; thereby generating immune cells comprising the chimeric membrane-bound cytokine and the antigen. In some embodiments, the nucleic acid encoding the chimeric membrane-bound cytokine and/or the nucleic acid encoding the antigen is an mRNA.

In some embodiments, there is provided a method for enhancing the activity of an immune cell in stimulating an immune response to an antigen, wherein the immune cells comprising the chimeric membrane-bound cytokine and the two or more antigens derived from a protein are prepared by: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the two or more antigens derived from a protein to pass through to form a perturbed input immune cells; and b) incubating the perturbed input immune cells with the nucleic acid encoding the chimeric membrane-bound cytokine and the two or more antigens derived from a protein to allow the nucleic acid to enter the perturbed input immune cells where the nucleic acid encoding the chimeric membrane-bound cytokine is expressed; thereby generating immune cells comprising a chimeric membrane-bound cytokine and the two or more antigen derived from a protein.

In some aspects, there is provided a composition for use as a medicine, wherein the composition comprises an effective amount of nucleated cells comprising a protein or fragment thereof and further comprising one or more agents that mediate Signal 2 and/or Signal 3. In some aspects, provided are compositions for treating a cancer, an infectious disease, or a viral-associated disease with a composition in an individual, wherein the composition comprises an effective amount of nucleated cells comprising a protein or fragment thereof and further comprising one or more agents that mediate Signal 2 and/or Signal 3. In some aspects, provided are methods of treating a cancer, an infectious disease, or a viral-associated disease in an individual, comprising administering a composition comprising an effective amount of nucleated cells comprising a protein or fragment thereof and further comprising one or more agents that mediate Signal 2 and/or Signal 3. In some embodiments, provided are uses of a composition comprising an effective amount of nucleated cells comprising a protein or fragment thereof and further comprising one or more agents that mediate Signal 2 and/or Signal 3 in the manufacture of a medicament for stimulating an immune response in an individual and/or treating a cancer, an infectious disease, or a viral-associated disease in an individual.

In some embodiments, the agent that mediates Signal 3 comprises one or more membrane-bound cytokines. In some embodiments, the agent that mediates Signal 3 comprises membrane-bound IL-2. In some embodiments, the agent that mediates Signal 3 comprises membrane-bound IL-2. In some embodiments, the agent that mediates Signal 3 comprises membrane-bound IL-2 and membrane-bound IL-12. In some embodiments, the agent that mediates Signal 2 comprises CD80. In some embodiments, the agent that mediates Signal 3 comprises CD86. In some embodiments, the agent that mediates Signal 2 comprises CD80 and CD86. In some embodiments, the nucleated cells comprise a protein or fragment thereof, or an mRNA encoding a protein or fragment thereof; wherein the protein or fragment thereof is processed into antigenic peptide complexed with MHC, thereby mediating Signal 1 in T cell activation.

In some embodiments according to any one of the methods, nucleated cells or compositions described herein, the nucleated cells comprising a protein or fragment thereof, CD86 and membrane-bound IL-12, wherein the nucleated cells are prepared by a process comprising: a) passing a cell suspension comprising input immune cells through a cell-deforming construction, wherein a diameter of the constriction is a function of a diameter of the input immune cells in the suspension, thereby causing perturbations of the input immune cells large enough for a nucleic acid encoding CD86, a nucleic acid encoding membrane-bound IL-12 and a nucleic acid encoding the protein or fragment thereof to pass through to form a perturbed input immune cells; and b) incubating the perturbed input immune cells with the nucleic acid encoding CD86, the nucleic acid encoding membrane-bound IL-12 and the nucleic acid encoding the protein or fragment thereof to allow the nucleic acids to enter the perturbed input immune cells where the nucleic acid encoding CD86, the nucleic acid encoding membrane-bound IL-12 and the nucleic acid encoding the protein or fragment thereof are expressed; thereby generating immune cells comprising the protein or fragment thereof, CD86 and membrane-bound IL-12. In some embodiments, the nucleic acid encoding CD86, the nucleic acid encoding membrane-bound IL-12 and/or the nucleic acid encoding the protein or fragment thereof are mRNAs. In some embodiments, the protein or fragment thereof comprises one or more antigens.

In some embodiments according to any one of the methods, nucleated cells or compositions described herein, the nucleated cells comprising a protein or fragment thereof, CD86 and membrane-bound IL-2, wherein the nucleated cells are prepared by a process comprising: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding CD86, a nucleic acid encoding membrane-bound IL-2 and a nucleic acid encoding the protein or fragment thereof to pass through to form a perturbed input immune cells; and b) incubating the perturbed input immune cells with the nucleic acid encoding CD86, the nucleic acid encoding membrane-bound IL-2 and the nucleic acid encoding the protein or fragment thereof to allow the nucleic acids to enter the perturbed input immune cells where the nucleic acid encoding CD86, the nucleic acid encoding membrane-bound IL-2 and the nucleic acid encoding the protein or fragment thereof are expressed; thereby generating immune cells comprising the protein or fragment thereof, CD86 and membrane-bound IL-2. In some embodiments, the nucleic acid encoding CD86, the nucleic acid encoding membrane-bound IL-2 and/or the nucleic acid encoding the protein or fragment thereof are mRNAs. In some embodiments, the protein or fragment thereof comprises one or more antigens.

In some embodiments according to any one of the methods, nucleated cells or compositions described herein, the nucleated cells comprising a protein or fragment thereof, CD86, membrane-bound IL-2 and membrane-bound IL-12, wherein the nucleated cells are prepared by a process comprising: a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding CD86, a nucleic acid encoding membrane-bound IL-2, a nucleic acid encoding membrane-bound IL-12 and a nucleic acid encoding the protein or fragment thereof to pass through to form a perturbed input immune cells; and b) incubating the perturbed input immune cells with the nucleic acid encoding CD86, the nucleic acid encoding membrane-bound IL-2, the nucleic acid encoding membrane-bound IL-12 and the nucleic acid encoding the protein or fragment thereof to allow the nucleic acids to enter the perturbed input immune cells where the nucleic acid encoding CD86, the nucleic acid encoding membrane-bound IL-2, nucleic acid encoding membrane-bound IL-12 and the nucleic acid encoding the protein or fragment thereof are expressed; thereby generating immune cells comprising the protein or fragment thereof, CD86, membrane-bound IL-2 and membrane-bound IL-12. In some embodiments, the nucleic acid encoding CD86, the nucleic acid encoding membrane-bound IL-2, the nucleic acid encoding membrane-bound IL-12 and/or the nucleic acid encoding the protein or fragment thereof are mRNAs. In some embodiments, the protein or fragment thereof comprises one or more antigens.

In some embodiments, the input cell suspension may comprise the input nucleated cells and an antigen. In some embodiments, the input cell suspension comprises the input nucleated cells and the protein or fragment thereof. In some embodiments, the input cell suspension comprises the input nucleated cells and the mRNA encoding the protein or fragment thereof. In some embodiments, the method comprises incubating the nucleated cells with the protein or fragment thereof, or with the mRNA encoding the protein or fragment thereof before, during and/or after passing the cell suspension through the cell-deforming constriction. In some embodiments, the method comprises incubating the nucleated cells with the protein or fragment thereof, or with the mRNA encoding the protein or fragment thereof before passing the cell suspension through the cell-deforming constriction.

In some embodiments, the input cell suspension comprises the input nucleated cells and the protein or fragment thereof as well as the agents that mediate Signal 2 and/or the agents that mediate Signal 3. In some embodiments, the input cell suspension comprises the input nucleated cells and the protein or fragment thereof as well as the mRNAs encoding for agents that mediate Signal 2 and/or the agents that mediate Signal 3. In some embodiments, the input cell suspension comprises the input nucleated cells and the mRNA encoding the protein or fragment thereof as well as the mRNAs encoding for agents that mediate Signal 2 and/or the agents that mediate Signal 3. In some embodiments, the method comprises incubating the nucleated cells with the mRNAs encoding for agents that mediate Signal 2 and/or the agents that mediate Signal 3, as well as with the protein or fragment thereof, or the mRNA encoding the protein or fragment thereof before, during and/or after passing the cell suspension through the cell-deforming constriction. In some embodiments, the method comprises incubating the nucleated cells with the mRNAs encoding for agents that mediate Signal 2 and/or the agents that mediate Signal 3, as well as with the protein or fragment thereof, or the mRNA encoding the protein or fragment thereof before passing the cell suspension through the cell-deforming constriction.

In some embodiments according to any one of the methods, compositions or nucleated cells described herein, the mRNA (such as mRNA encoding for Signal 2 mediator and mRNA encoding for Signal 3 mediator) is an exogenous mRNA. In some embodiments, the mRNA is an in vitro transcribed (IVT) mRNA. In some embodiments, the exogenous mRNA is an in vitro transcribed (IVT) mRNA. In some embodiments, the mRNA encodes for a recombinant protein. In some embodiments, the mRNA is codon-optimized for expression in nucleated cells.

In some embodiments, the width of the constriction is about 10% to about 99% of the mean diameter of the input nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input nucleated cells having the smallest diameter within the population of nucleated cells. In some embodiments, the width of the constriction is about 2 μm to about 5 μm, about 3 μm to about 5 μm, about 2 μm to about 2.5 μm, about 2.2 μm to about 2.5, about 2.5 μm to about 3 μm, about 3 μm to about 3.5 μm, about 3.5 μm to about 4 μm, about 4 μm to about 4.5 μm, about 3.2 μm to about 3.8 μm, about 3.8 μm to about 4.3 μm, about 4.2 μm to about 6 μm, or about 4.2 μm to about 4.8 μm. In some embodiments, the width of the constriction is about 4.5 μm. In some embodiments, the width of the constriction is about or less than any one of 2 μm, 2.2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the cell suspension comprising the input nucleated cells are passed through multiple constrictions wherein the multiple constrictions are arranged in series and/or in parallel.

In some embodiments according to any one of the methods, uses or compositions described herein, the nucleated cells (e.g., PBMCs) are incubated with the adjuvant for a sufficient time for the nucleated cells to condition. In some embodiments, the nucleated cells are incubated with the adjuvant for about 1 to about 24 hours for the nucleated cells to condition. In some embodiments, the nucleated cells are incubated with the adjuvant for about 2 to about 10 hours for the nucleated cells to condition. In some embodiments, the nucleated cells are incubated with the adjuvant for about 3 to about 6 hours for the nucleated cells to condition. In some embodiments, the nucleated cells are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the nucleated cells to condition. In some embodiments, the nucleated cells are incubated with the adjuvant for about 4 hours for the nucleated cells to condition. In some embodiments, the nucleated cells are conditioned before introducing the protein or fragment thereof or the nucleic acid encoding protein or fragment thereof into the nucleated cells. In some embodiments, the nucleated cells are conditioned after introducing the protein or fragment thereof or the nucleic acid encoding the protein or fragment thereof into the nucleated cells. In some embodiments, the adjuvant used for conditioning is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), a TLR3 agonist, a TLR4 agonist, a TLR7 agonist, a TLR8 agonist, or a TLR9 agonist. Exemplary adjuvants include, without limitation, CpG ODN, interferon-α (IFN-α), polyinosinic: polycytidylic acid (polyI:C), imiquimod (R837), resiquimod (R848), or lipopolysaccharide (LPS). In some embodiments, the adjuvant is a CpG oligodeoxynucleotide (ODN). In some embodiments, the adjuvant is CpG 7909.

In some embodiments, wherein the nucleated cells comprise B cells, one or more co-stimulatory molecules is upregulated in the B cells of the conditioned nucleated cells compared to the B cells of the unconditioned nucleated cells. In some embodiments, the nucleated cells are a plurality of peripheral blood mononuclear cells (PBMCs). In some embodiments, wherein the nucleated cells are a plurality of PBMCs, one or more co-stimulatory molecules is upregulated in the B cells of the conditioned plurality of PBMCs compared to the B cells of the unconditioned plurality of PBMCs. In some embodiments, the co-stimulatory molecule is CD80 and/or CD86. In some embodiments, the conditioned plurality of PBMCs has increased expression of one or more of IFN-γ, IL-6, MCP-1, MIP-1β, IP-10, or TNF-α compared to an unconditioned plurality of PBMCs. In some embodiments, the expression of one or more of IFN-γ, IL-6, MCP-1, MIP-1β, IP-40, or TNF-α is increased by more than about 1.2-fold, 1.5-fold, 1.8-fold, 2-fold, 3-fold, 4-fold, 5-fold, 8-fold, or more than 10-fold compared to an unconditioned plurality of PBMCs In some embodiments according to any one of the methods, uses or compositions described herein, the nucleated cells are immune cells. In some embodiments, the nucleated cells are human cells. In some embodiments, the nucleated cells are human cells with a haplotype of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the nucleated cells are a plurality of PBMCS. In some embodiments, the conditioned nucleated cells are a conditioned plurality of modified PBMCs. In some embodiments, the plurality of PBMCs comprises two or more of T cell, B cell, NK cell, monocytes, dendritic cells or NK-T cells. In some embodiments, the nucleated cells are one or more of T cells, B cells, NK cells, monocytes, dendritic cells and/or NK-T cells.

In some embodiments, the nucleated cells comprise a protein or fragment thereof, or an mRNA encoding a protein or fragment thereof; wherein the protein or fragment thereof is processed into antigenic peptide complexed with MHC, thereby mediating Signal 1 in T cell activation. In some embodiments, a nucleated cell comprising the protein or fragment thereof and further comprising one or more agents that mediate Signal 2 (such as a Signal 2 mediator) can induce antigen-specific immune response at an enhanced level as compared to a corresponding nucleated cell not comprising an agent that mediates Signal 2. In some embodiments, a nucleated cell comprising the protein or fragment thereof and further comprising one or more agents that mediate Signal 2 (such as a Signal 2 mediator) can induce antigen-specific immune response at an enhanced level in an HILA agnostic manner as compared to a corresponding nucleated cell not comprising an agent that mediates Signal 2. In some embodiments, a nucleated cell comprising the protein or fragment thereof and further comprising one or more agents that mediate Signal 2 (such as a Signal 2 mediator) can induce antigen-specific immune response at an enhanced level as compared to a corresponding nucleated cell not comprising an agent that mediates Signal 2, wherein the enhanced immune response comprises immune response dependent on restriction by one or more of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16 haplotypes.

In some embodiments, the nucleated cells comprise a protein or fragment thereof, or an mRNA encoding a protein or fragment thereof; wherein the protein or fragment thereof is processed into antigenic peptide complexed with MHC, thereby mediating Signal 1 in T cell activation. In some embodiments, a nucleated cell comprising the protein or fragment thereof and further comprising one or more agents that mediate Signal 2 (such as a Signal 2 mediator) can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell not comprising an agent that mediates Signal 2. In some embodiments, a nucleated cell comprising the protein or fragment thereof and further comprising one or more agents that mediate Signal 2 (such as a Signal 2 mediator) can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more in a HLA-agnostic manner as compared to a corresponding nucleated cell not comprising an agent that mediates Signal 2. In some embodiments, a nucleated cell comprising the protein or fragment thereof and further comprising one or more agents that mediate Signal 2 (such as a Signal 2 mediator) can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more as compared to a corresponding nucleated cell not comprising an agent that mediates Signal 2, wherein the enhanced T cell activation comprises T cell activation dependent on restriction by one or more of HLA-A*02, HLA-A*01, HLA-A*03, HLA-A*24, HLA-A*11, HLA- A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16 haplotypes. In some embodiments, a nucleated cell comprising the protein or fragment thereof and further comprising one or more agents that mediate Signal 2 (such as a Signal 2 mediator) can induce antigen-specific CD8+ T cell activation, wherein the one or more polyfunctional markers of the CD8+ T cell is increased by any one of: 10%, 25%, 50%, 75%, 100%, 2-fold, 3-fold, 4-fold, 5-fold, 10-fold, 25-fold, 50-fold, 100-fold, 200-fold, or 500-fold or more as compared to an antigen-specific CD8+ T cell activated by a nucleated cell not further comprising an agent that mediates Signal 2. In some embodiments, the one or more polyfunctional markers comprises: Granzyme B, IFN-α, IL-2, PD-1, and/or IFN-γ. In some embodiments, a nucleated cell comprising the protein or fragment thereof and further comprising one or more agents that mediate Signal 2 (such as a Signal 2 mediator) can induce antigen-specific CD8+ T cell activation, wherein the proliferation and/or survival of the CD8+ T cell is increased by any one of: 10%, 25%, 50%, 75%, 100%, 2-fold, 3-fold, 4-fold, 5-fold, 10-fold, 25-fold, 50-fold, 100-fold, 200-fold, or 500-fold or more as compared to an antigen-specific CD8+ T cell activated by a nucleated cell not further comprising an agent that mediates Signal 2.

In some embodiments, the nucleated cells comprise a protein or fragment thereof, or an mRNA encoding a protein or fragment thereof; wherein the protein or fragment thereof is processed into antigenic peptide complexed with MHC, thereby mediating Signal 1 in T cell activation. In some embodiments, a nucleated cell comprising the protein or fragment thereof and further comprising one or more agents that mediate Signal 3 (such as a Signal 3 effector) can induce antigen-specific immune response at an enhanced level as compared to a corresponding nucleated cell not comprising an agent that mediates Signal 3. In some embodiments, a nucleated cell comprising the protein or fragment thereof and further comprising one or more agents that mediate Signal 3 (such as a Signal 3 effector) can induce antigen-specific immune response at an enhanced level in an HLA agnostic manner as compared to a corresponding nucleated cell not comprising an agent that mediates Signal 3. In some embodiments, a nucleated cell comprising the protein or fragment thereof and further comprising one or more agents that mediate Signal 3 (such as a Signal 3 effector) can induce antigen-specific immune response at an enhanced level as compared to a corresponding nucleated cell not comprising an agent that mediates Signal 3, wherein the enhanced immune response comprises immune response dependent on restriction by one or more of HLA-A *02, HLA-A *01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16 haplotypes.

In some embodiments, the nucleated cells comprise a protein or fragment thereof, or an mRNA encoding a protein or fragment thereof; wherein the protein or fragment thereof is processed into antigenic peptide complexed with MHC, thereby mediating Signal 1 in T cell activation. In some embodiments, a nucleated cell comprising the protein or fragment thereof and further comprising one or more agents that mediate Signal 3 (such as a Signal 3 effector) can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell not comprising an agent that mediates Signal 3. In some embodiments, a nucleated cell comprising the protein or fragment thereof and further comprising one or more agents that mediate Signal 3 (such as a Signal 3 effector) can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more in a HLA-agnostic manner as compared to a corresponding nucleated cell not comprising an agent that mediates Signal 3. In some embodiments, a nucleated cell comprising the protein or fragment thereof and further comprising one or more agents that mediate Signal 3 (such as a Signal 3 effector) can induce antigen-specific CD8+ T cell activation at an enhanced level as compared to a corresponding nucleated cell not comprising an agent that mediates Signal 3, wherein the enhanced T cell activation comprises T cell activation dependent on restriction by one or more of HLA-A*02, HLA-A*01, HLA-A*03, HLA-A*24, HLA-A*i 1, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16 haplotypes. In some embodiments, a nucleated cell comprising the protein or fragment thereof and further comprising one or more agents that mediate Signal 3 (such as a Signal 3 mediator) can induce antigen-specific CD8+ T cell activation, wherein the one or more polyfunctional markers of the CD8+ T cell is increased by any one of: 10%, 25%, 50%, 75%, 100%, 2-fold, 3-fold, 4-fold, 5-fold, 10-fold, 25-fold, 50-fold, 100-fold, 200-fold, or 500-fold or more as compared to an antigen-specific CD8+ T cell activated by a nucleated cell not further comprising an agent that mediates Signal 3. In some embodiments, the one or more polyfunctional markers comprises: Granzyme B, IFN-α, IL-2, PD-1, and/or IFN-γ. In some embodiments, a nucleated cell comprising the protein or fragment thereof and further comprising one or more agents that mediate Signal 3 (such as a Signal 3 mediator) can induce antigen-specific CD8+ T cell activation, wherein the proliferation and/or survival of the CD8+ T cell is increased by any one of: 10%, 25%, 50%, 75%, 100%, 2-fold, 3-fold, 4-fold, 5-fold, 10-fold, 25-fold, 50-fold, 100-fold, 200-fold, or 500-fold or more as compared to an antigen-specific CD8+ T cell activated by a nucleated cell not further comprising an agent that mediates Signal 3.

In some embodiments, a nucleated cell comprising the protein or fragment thereof and further comprising one or more agents that mediate Signal 2 (such as a Signal 2 mediator) and one or more agents that mediate Signal 3 (such as a Signal 3 effector) can induce antigen-specific immune response at an enhanced level as compared to a corresponding nucleated cell not comprising an agent that mediates Signal 2 or Signal 3. In some embodiments, a nucleated cell comprising the protein or fragment thereof and further comprising one or more agents that mediate Signal 2 (such as a Signal 2 mediator) and one or more agents that mediate Signal 3 (such as a Signal 3 mediator) can induce antigen-specific immune response at an enhanced level in an HLA agnostic manner as compared to a corresponding nucleated cell not comprising an agent that mediates Signal 2 or Signal 3.

In some embodiments, the nucleated cells comprise a protein or fragment thereof, or an mRNA encoding a protein or fragment thereof; wherein the protein or fragment thereof is processed into antigenic peptide complexed with MHC, thereby mediating Signal 1 in T cell activation. In some embodiments, a nucleated cell comprising the protein or fragment thereof and further comprising one or more agents that mediate Signal 2 (such as a Signal 2 mediator) and one or more agents that mediate Signal 3 (such as a Signal 3 effector) can induce antigen-specific immune response at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell not comprising an agent that mediates Signal 2 or Signal 3. In some embodiments, a nucleated cell comprising the protein or fragment thereof and further comprising one or more agents that mediate Signal 2 (such as a Signal 2 mediator) and one or more agents that mediate Signal 3 (such as a Signal 3 effector) can induce antigen-specific immune response at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more in a HLA-agnostic manner as compared to a corresponding nucleated cell not comprising an agent that mediates Signal 2 or Signal 3. In some embodiments, a nucleated cell comprising the protein or fragment thereof and further comprising one or more agents that mediate Signal 2 (such as a Signal 2 mediator) and one or more agents that mediate Signal 3 such as a Signal 3 effector) can induce antigen-specific immune response at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more as compared to a corresponding nucleated cell not comprising an agent that mediates Signal 2 or Signal 3, wherein the enhanced immune response comprises immune response dependent on restriction by one or more of HLA-A*02, HLA-A*01, HLA-A*03, HLA-A*24, HLA-A*l 1, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16 haplotypes.

In some embodiments, the nucleated cells comprise a protein or fragment thereof, or an mRNA encoding a protein or fragment thereof; wherein the protein or fragment thereof is processed into antigenic peptide complexed with MHC, thereby mediating Signal 1 in T cell activation. In some embodiments, a nucleated cell comprising the protein or fragment thereof and further comprising one or more agents that mediate Signal 2 (such as a Signal 2 mediator) and one or more agents that mediate Signal 3 (such as a Signal 3 mediator) can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more compared to a corresponding nucleated cell not comprising an agent that mediates Signal 2 or Signal 3. In some embodiments, a nucleated cell comprising the protein or fragment thereof and further comprising one or more agents that mediate Signal 2 (such as a Signal 2 effector) and one or more agents that mediate Signal 3 (such as a Signal 3 effector) can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more in a HLA-agnostic manner as compared to a corresponding nucleated cell not comprising an agent that mediates Signal 2 or Signal 3. In some embodiments, a nucleated cell comprising the protein or fragment thereof and further comprising one or more agents that mediate Signal 2 (such as a Signal 2 mediator) and one or more agents that mediate Signal 3 (such as a Signal 3 mediator) can induce antigen-specific CD8+ T cell activation at a level that is higher by about any one of: 10%, 25%, 50%, 75%, 100%, 2-fold, 3-fold, 4-fold, 5-fold, 10-fold, 25-fold, 50-fold, 100-fold, 200-fold, or 500-fold or more as compared to a corresponding nucleated cell not comprising an agent that mediates Signal 2 or Signal 3, wherein the enhanced r cell activation comprises T cell activation dependent on restriction by one or more of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16 haplotypes. In some embodiments, a nucleated cell comprising the protein or fragment thereof and further comprising one or more agents that mediate Signal 2 (such as a Signal 2 mediator) and one or more agents that mediate Signal 3 (such as a Signal 3 mediator) can induce antigen-specific CD8+ T cell activation, wherein the one or more polyfunctional markers of the CD8+ T cell is increased by any one of: 10%, 25%, 50%, 75%, 100%, 2-fold, 3-fold, 4-fold, 5-fold, 10-fold, 25-fold, 50-fold, 100-fold, 200-fold, or 500-fold or more as compared to an antigen-specific CD8+ T cell activated by a nucleated cell not further comprising an agent that mediates Signal 2 or Signal 3. In some embodiments, the one or more polyfunctional markers comprises: Granzyme B, IFN-α, IL-2, PD-1, and/or IFN-γ. In some embodiments, a nucleated cell comprising the protein or fragment thereof and further comprising one or more agents that mediate Signal 2 (such as a Signal 2 mediator) and one or more agents that mediate Signal 3 (such as a Signal 3 mediator) can induce antigen-specific CD8+ T cell activation, wherein the proliferation and/or survival of the CD8+ T cell is increased by any one of: 10%, 25%, 50%, 75%, 100%, 2-fold, 3-fold, 4-fold, 5-fold, 10-fold, 25-fold, 50-fold, 100-fold, 200-fold, or 500-fold or more as compared to an antigen-specific CD8+ T cell activated by a nucleated cell not further comprising an agent that mediates Signal 2 or Signal 3.

Adjuvants

As used herein, the term "adjuvant" can refer to a substance which either directly or indirectly modulates and/or engenders an immune response. In some embodiments of the invention, an adjuvant is used to condition a population of nucleated cells such as a population of PBMCs (i.e., the cells are incubated with an adjuvant prior to administration to an individual). In some instances, the adjuvant is administered in conjunction with a protein or fragment thereof to effect enhancement of an immune response to the protein or fragment thereof as compared to protein or fragment thereof alone. Therefore, adjuvants can be used to boost elicitation of an immune cell response (e.g. T cell response) to a protein or fragment thereof. Exemplary adjuvants include, without limitation, stimulator of interferon genes (STING) agonists, retinoic acid-inducible gene I (RIG-I) agonists, and agonists for TLR3, TLR4, TLR7, TLR8 and/or TLR9. Exemplary adjuvants include, without limitation, CpG ODN, interferon-α (IFN-α), polyinosinic:polycytidylic acid (polyI:C), imiquimod (R837), resiquimod (R848), or lipopolysaccharide (LPS). In some embodiments, the adjuvant is CpG ODN, LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In particular embodiments, the adjuvant is a CpG ODN. In some embodiments, the adjuvant is a CpG ODN. In some embodiments, the CpG ODN is a Class A CpG ODN, a Class B CpG ODN, or a Class C CpG ODN. In some embodiments, the CpG ODN adjuvant comprise of a selection from the group of CpG ODN 1018, CpG ODN 1585, CpG ODN 2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03. In some embodiments, the CpG ODN adjuvant is CpG ODN 1826 (TCCATGACGTTCCTGACGTT (SEQ ID NO:30)) or CpG ODN 2006 (also known as CpG 7909) (TCGTCGTTTTGTCGTTTTCTCGTT (SEQ ID NO:31)) oligonucleotide. In some embodiments, the adjuvant is CpG 7909. In some embodiments, the RIG-I agonist comprises polyinosinic:polycytidylic acid (polyI:C). Multiple adjuvants can also be used in conjunction with the antigens to enhance the elicitation of immune response. In some embodiments, the modified PBMCs comprise more than one adjuvant. Multiple adjuvants can also be used in conjunction with the antigens to enhance the elicitation of immune response. In some embodiments, the modified PBMCs comprise more than one adjuvant. In some embodiments, the modified PBMCs comprise any combination of the adjuvants CpG ODN, LPS, IFN-α, IFN-β, IFN-γ, alpha-Galactosyl Ceramide, STING agonists, cyclic dinucleotides (CDN), RIG-I agonists, polyinosinic-polycytidylic acid, a TLR3 agonist, a TLR4 agonist, a TLR7 agonist, a TLR8 agonist, or a TLR9 agonist.

Constrictions Used in Generating Compositions of Nucleated Cells Comprising a Protein or Fragment Thereof In some embodiments, the invention provides compositions of nucleated cells comprising a protein or fragment thereof for stimulating an immune response. In some embodiments, the nucleated cells are immune cells; for example, a plurality of PBMCs or one or more of T cell, B cell, NK cell, monocytes, dendritic cells or NK-T cells. In some embodiments, the protein or fragment thereof is delivered to the nucleated cells intracellularly.

In some embodiments, the protein or fragment thereof is introduced into the nucleated cells by passing the cell through a constriction such that transient pores are introduced to the membrane of the cell thereby allowing the protein or fragment thereof to enter the cell. Examples of constriction-based delivery of compounds into a cell are provided by WO 2013/059343, WO 2015/023982, WO 2016/070136, WO2017041050, WO2017008063, WO 2017/192785, WO 2017/192786, WO 2019/178005, WO 2019/178006, WO 2020/072833, PCT/US2020/15098, and PCT/US2020/020194.

In some embodiments, the protein or fragment thereof is delivered into the nucleated cells to produce the nucleated cells of the invention by passing a cell suspension comprising the nucleated cells (e.g., PBMCs) through a constriction, wherein the constriction deforms the cells thereby causing a perturbation of the cells such that a protein or fragment thereof enters the cells. In some embodiments, the constriction is contained within a microfluidic channel. In some embodiments, multiple constrictions can be placed in parallel and/or in series within the microfluidic channel.

In some embodiments, the constriction within the microfluidic channel includes an entrance portion, a center point, and an exit portion. In some embodiments, the length, depth, and width of the constriction within the microfluidic channel can vary. In some embodiments, the width of the constriction within the microfluidic channel is a function of the diameter of the nucleated cells. Methods to determine the diameter of nucleated cells are known in the art; for example, high-content imaging, cell counters or flow cytometry.

In some embodiments of the constriction-based delivery of a protein or fragment thereof to nucleated cells, the width of the constriction is about 3 μm to about 15 μm. In some embodiments, the width of the constriction is about 3 μm to about 10 μm. In some embodiments, the width of the constriction is about 3 μm to about 6 μm. In some embodiments, the width of the constriction is about 4.2 μm to about 6 μm. In some embodiments, the width of the constriction is about 4.2 μm to about 4.8 μm. In some embodiments, the width of the constriction is about 3 μm to about 5 μm. In some embodiments, the width of the constriction is about 3 μm to about 3.5 μm. In some embodiments, the width of the constriction is about 3.5 μm to about 4 μm. In some embodiments, the width of the constriction is about 4 μm to about 4.5 μm. In some embodiments, the width of the constriction is about 3.2 μm to about 3.8 μm. In some embodiments, the width of the constriction is about 3.8 μm to about 4.3 μm. In some embodiments, the width of the constriction is about or less than any one of 2 μm, 2.5 μm, 3 μm, 3.5 μm, 4 μm, 4.5 μm, 5 μm, 5.5 μm, 6 μm, 6.5 μm, 7 μm, 7.5 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the width of the constriction is about or less than any one of 3.0 μm, 3.1 μm, 3.2 μm, 3.3 μm, 3.4 μm, 3.5 μm, 3.6 μm, 3.7 μm, 3.8 μm, 3.9 μm, 4.0 μm, 4.1 μm, 4.2 μm, 4.3 μm, 4.4 μm, 4.5 μm, 4.6 μm, 4.7 μm, 4.8 μm, 4.9 μm, or 5.0 μm. In some embodiments, the width of the constriction is about 4.5 μm.

In some embodiments of the invention, the composition comprises a plurality of nucleated cells (e.g., a plurality of PBMCs) within the population of nucleated cells. In some embodiments, the width of the constriction is about 10% to about 99% of the mean diameter of a subpopulation of nucleated cells having the smallest diameter within the population of nucleated cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of a subpopulation of nucleated cells having the smallest diameter within the population of nucleated cells. In some embodiments, the width of the constriction is any one of about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of a subpopulation of nucleated cells having the smallest diameter within the population of nucleated cells. In some embodiments, the width of the constriction is any one of about 10%, 15%, 20%, 25%, 30%, 35%, 40%, 45%, 50%, 55%, 60%, 65%, 70%, 75%, 80%, 85%, 90%, 95%, or 99% of the mean diameter of a subpopulation of nucleated cells having the smallest diameter within the population of nucleated cells. In some embodiments, the subpopulation of nucleated cells having the smallest mean diameter within a plurality of input PBMCs is a population of lymphocytes, wherein the diameter of the population of lymphocytes is about 6 μm to about 10 μm. In some embodiments, the mean diameter of the population of lymphocytes is about 7 μm. In some embodiments, the population of lymphocytes is a population of T cells. In some embodiments, the lymphocytes are T cells. In some embodiments, the subpopulation of nucleated cells having the smallest mean diameter within the plurality of input PBMCs are T cells.

In some embodiments of the invention, the composition comprises a plurality of nucleated cells (e.g., a plurality of PBMCs) within the population of nucleated cells. In some embodiments, the width of the constriction is about 10% to about 99% of the mean diameter of a subpopulation of nucleated cells having the largest diameter within the population of nucleated cells. In some embodiments, the width of the constriction is any one of about 10% to about 90%, about 10% to about 80%, about 10% to about 70%, about 20% to about 60%, about 40% to about 60%, about 30% to about 45%, about 15% to about 30%, about 15% to about 20%, about 20% a to about 25%, about 25% to about 30%, about 20% to about 30%, about 30% to about 70%, or about 30% to about 60% of the mean diameter of a subpopulation of nucleated cells having the largest diameter within the population of nucleated cells. In some embodiments, the width of the constriction is any one of about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of a subpopulation of nucleated cells having the largest diameter within the population of nucleated cells. In some embodiments, the width of the constriction is any one of about 5%, 10%, 15%, 20%, 25%, 30%, 35%, 40%, 45%, 50%, 55%, 60%, 65%, 70%, 75%, 80%, 85%, 90%, 95%, or 99% of the mean diameter of a subpopulation of nucleated cells having the largest diameter within the population of nucleated cells. In some embodiments, the subpopulation of nucleated cells having the largest mean diameter within a plurality of input PBMCs is a population of monocytes, wherein the diameter of the population of monocytes is about 15 μm to about 25 μm. In some embodiments, the mean diameter of the population of monocytes is about 18 μm. In some embodiments, the subpopulation of nucleated cells having the largest mean diameter within the plurality of input PBMCs are monocytes.

A number of parameters may influence the delivery of a compound to nucleated cells for stimulating an immune response by the methods described herein. In some embodiments, the cell suspension is contacted with the compound before, concurrently, or after passing through the constriction. The nucleated cells may pass through the constriction suspended in a solution that includes the compound to deliver, although the compound can be added to the cell suspension after the nucleated cells pass through the constriction. In some embodiments, the compound to be delivered is coated on the constriction.

Examples of parameters that may influence the delivery of the compound into the nucleated cells include, but are not limited to, the dimensions of the constriction, the entrance angle of the constriction, the surface properties of the constrictions (e.g., roughness, chemical modification, hydrophilic, hydrophobic, etc.), the operating flow speeds (e.g., cell transit time through the constriction), the cell concentration, the concentration of the compound in the cell suspension, buffer in the cell suspension, and the amount of time that the nucleated cells recover or incubate after passing through the constrictions can affect the passage of the delivered compound into the nucleated cells. Additional parameters influencing the delivery of the compound into the nucleated cells can include the velocity of the nucleated cells in the constriction, the shear rate in the constriction, the viscosity of the cell suspension, the velocity component that is perpendicular to flow velocity, and time in the constriction. In addition, multiple chips comprising channels in series and/or in parallel may impact delivery to nucleated cells. Multiple chips in parallel may be useful to enhance throughput. Such parameters can be designed to control delivery of the compound. In some embodiments, the cell concentration ranges from about 10 to at least about $10^{12}$ cells/mL or any concentration or range of concentrations therebetween. In some embodiments, delivery compound concentrations can range from about 10 ng/mL to about 1 g/mL or any concentration or range of concentrations therebetween. In some embodiments, delivery compound concentrations can range from about 1 pM to at least about 2 M or any concentration or range of concentrations therebetween.

In some embodiments, the concentration of protein or fragment thereof incubated with the nucleated cells is between about 0.01 μM and about 10 mM. For example, in some embodiments, the concentration of protein or fragment thereof incubated with the nucleated cells is any of less than about 0.01 μM, about 0.1 μM, about 1 μM, about 10 μM, about 100 μM, about 1 mM or about 10 mM. In some embodiments, the concentration of protein or fragment thereof incubated with the nucleated cells is greater than about 10 mM. In some embodiments, the concentration of protein or fragment thereof incubated with the nucleated cells is any of between about 0.01 μM and about 0.1 μM, between about 0.1 μM and about 1 μM, between about 1 μM and about 10 μM, between about 10 μM and about 100 μM, between about 100 μM and about 1 mM, or between 1 mM and about 10 mM. In some embodiments, the concentration of protein or fragment thereof incubated with the nucleated cells is between about 0.1 μM and about 1 mM. In some embodiments, the concentration of protein or fragment thereof incubated with the nucleated cells is between about 0.1 μM and about 10 μM. In some embodiments, the concentration of protein or fragment thereof incubated with the nucleated cells is 1 μM.

In some embodiments, the nucleated cells comprise the nucleic acid encoding the protein or fragment thereof at a concentration between about 1 nM and about 1 mM. In some embodiments, the nucleated cells comprises the nucleic acid encoding the protein or fragment thereof at a concentration of any of less than about 0.1 nM, about 1 nM, about 0.01 μM, about 0.1 μM, about 1 μM, about 10 μM, about 100 μM, about 1 mM or about 10 mM. In some embodiments, the nucleated cells comprise the nucleic acid encoding the protein or fragment thereof at a concentration of greater than about 10 mM. In some embodiments, the nucleated cells comprise the nucleic acid encoding the protein or fragment thereof at a concentration of any of between about 0.1 nM to about 1 nM, about 1 nM to about 10 nM, about 10 nM to about 100 nM, about 0.1 μM and about 1 μM, between about 1 μM and about 10 μM, between about 10 μM and about 100 μM, between about 100 μM and about 1 mM, or between 1 mM and about 10 mM. In some embodiments, the nucleated cells comprise the nucleic acid encoding the protein or fragment thereof at a concentration between about 10 nM and about 100 nM. In some embodiments, the nucleated cells comprise the nucleic acid encoding the protein or fragment thereof at a concentration between about 1 nM and about 10 nM. In some embodiments, the nucleated cells comprise the protein or fragment thereof at a concentration of about 50 nM. In some embodiments, the nucleic acid is an mRNA.

Conditioning of Nucleated Cells

In some embodiments according to any one of methods described herein; the nucleated cells (e.g., PBMCs) comprising a protein or fragment thereof are conditioned. In further embodiments, the nucleated cells are matured. In some embodiments, the nucleated cells are conditioned subsequent to constriction mediated delivery. In some embodiments, the nucleated cells comprising the protein or fragment thereof is incubated with an adjuvant for a sufficient time for the cells comprising the constriction-delivered protein or fragment thereof to condition, thereby generating a composition of conditioned cells comprising the protein or fragment thereof. In some embodiments, the nucleated cells are conditioned subsequent to constriction-mediated delivery. In some embodiments, the nucleated cells comprising the constriction-delivered protein or fragment thereof are incubated with an adjuvant for a sufficient time for the nucleated cells comprising the constriction-delivered protein or fragment thereof to condition, thereby generating a composition of conditioned nucleated cells comprising the protein or fragment thereof. In some aspects, there is provided a composition of conditioned nucleated cells comprising an protein or fragment thereof, prepared by a process comprising the steps of: a) passing a cell suspension through a cell-deforming constriction, wherein a width of the constriction is a function of the nucleated cells in the suspension, thereby causing perturbations of the nucleated cells large enough for the protein or fragment thereof to pass through to form perturbed nucleated cells; b) incubating the perturbed nucleated cells with the protein or fragment thereof for a sufficient time to allow the protein or fragment thereof to enter the perturbed nucleated cells, thereby generating modified nucleated cells comprising the protein or fragment thereof; and c) incubating the modified nucleated cells comprising the constriction-delivered protein or fragment thereof with an adjuvant for a sufficient time for the modified nucleated cells comprising the constriction-delivered protein or fragment thereof to condition, thereby generating the composition of conditioned nucleated cells comprising the protein or fragment thereof. In some aspects, there is provided a composition of conditioned nucleated cells comprising a protein or fragment thereof, prepared by a process comprising the steps of: a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells, thereby generating nucleated cells comprising the mRNA encoding the protein or fragment thereof; and c) incubating the modified nucleated cells comprising the constriction-delivered mRNA with an adjuvant for a sufficient time for the modified nucleated cells comprising the constriction-delivered mRNA thereof to condition, wherein the mRNA is expressed to produce the protein or fragment thereof; thereby generating the composition of conditioned nucleated cells comprising the protein or fragment thereof. In some embodiments, the protein or fragment thereof stimulates an immune response in an individual in an HLA agnostic manner. In some embodiments, the process further comprises isolating the modified nucleated cells comprising the protein or fragment thereof from the cell suspension before incubation with the adjuvant to condition the modified nucleated cells.

In some embodiments, the nucleated cells (e.g., PBMCs) are conditioned prior to constriction-mediated delivery. In some embodiments, the nucleated cells are incubated with an adjuvant for a sufficient time for the nucleated cells to condition, thereby conditioning nucleated cells. In some embodiments, there is provided a composition of conditioned nucleated cells comprising a protein or fragment thereof, prepared by a process comprising the steps of: a) incubating nucleated cells with an adjuvant for a sufficient time for the nucleated cells to condition, thereby generating conditioned nucleated cells; b) passing a cell suspension comprising the conditioned nucleated cells through a cell-deforming constriction, wherein a width of the constriction is a function of a diameter of the nucleated cells in the suspension, thereby causing perturbations of the nucleated cells large enough for the protein or fragment thereof to pass through to form conditioned perturbed nucleated cells; and c) incubating the conditioned perturbed nucleated cells with the protein or fragment thereof for a sufficient time to allow the protein or fragment thereof to enter the conditioned perturbed nucleated cells, thereby generating the conditioned nucleated cells comprising the protein or fragment thereof. In some aspects, there is provided a composition of conditioned nucleated cells comprising a protein or fragment thereof, prepared by a process comprising the steps of: a) incubating nucleated cells with an adjuvant for a sufficient time for the nucleated cells to condition, thereby generating conditioned nucleated cells; b) passing a cell suspension comprising the conditioned nucleated cells through a cell-deforming constriction, wherein a width of the constriction is a function of a diameter of the nucleated cells in the suspension, thereby causing perturbations of the nucleated cells large enough for the mRNA encoding the protein or fragment thereof to pass through to form conditioned perturbed nucleated cells; and c) incubating the conditioned perturbed nucleated cells with the mRNA encoding the protein or fragment thereof for a sufficient time to allow the mRNA encoding the protein or fragment thereof to enter the conditioned perturbed nucleated cells, wherein the mRNA is expressed to produce the protein or fragment thereof, thereby generating the conditioned nucleated cells comprising the protein or fragment thereof. In some embodiments, the protein or fragment thereof stimulates an immune response in an individual in an HLA agnostic manner. In some embodiments, the process further comprises isolating the conditioned nucleated cells from the adjuvant before passing the conditioned nucleated cells through a cell-deforming constriction.

In some embodiments according to any one of methods described herein, the nucleated cells (e.g., PBMCs) comprising the protein or fragment thereof are incubated with the adjuvant for about 1 to about 24 hours for the nucleated cells to condition. In some embodiments, the nucleated cells are incubated with the adjuvant for about 2 to about 10 hours for the nucleated cells to condition. In some embodiments, the nucleated cells are incubated with the adjuvant for about 3 to about 6 hours for the nucleated cells to condition. In some embodiments, the nucleated cells are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the nucleated cells to condition. In some embodiments, the nucleated cells are incubated with the adjuvant for about 4 hours for the nucleated cells to condition.

In some embodiments, there is provided a conditioned plurality of PBMCs comprising a protein or fragment thereof, prepared by incubating the plurality of PBMCs comprising the protein or fragment thereof with an adjuvant for a sufficient time for the PBMCs to condition, thereby generating the conditioned plurality of PBMCs comprising the protein or fragment thereof. In some embodiments, there is provided a conditioned plurality of PBMCs comprising a protein or fragment thereof, prepared by incubating the plurality of PBMCs with an adjuvant fora sufficient time for the PBMCs to condition prior to introducing the protein or fragment thereof to the PBMCs, thereby generating the conditioned plurality of PBMCs comprising the protein or fragment thereof.

In some embodiments according to any of the conditioned plurality of PBMCs described herein, the plurality of PBMCs is incubated with the adjuvant for about 1 to about 24 hours for the PBMCs to condition. In some embodiments, the plurality of PBMCs is incubated with the adjuvant for about 2 to about 10 hours for the PBMCs to condition. In some embodiments, the plurality of PBMCs is incubated with the adjuvant for about 3 to about 6 hours for the PBMCs to condition. In some embodiments, the plurality of PBMCs is incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the PBMCs to condition. In some embodiments, the plurality of PBMCs is incubated with the adjuvant for about 4 hours for the PBMCs to condition.

In some embodiments according to any one of the conditioned plurality of PBMCs described herein, one or more co-stimulatory molecules are upregulated in the conditioned plurality of modified PBMCs compared to an unconditioned plurality of modified PBMCs. In some embodiments, one or more co-stimulatory molecules are upregulated in a subpopulation of cells in the conditioned plurality of modified PBMCs compared to the subpopulation of cells in an unconditioned plurality of modified PBMCs. In some embodiments, one or more co-stimulatory molecules are upregulated in the B cells of the conditioned plurality of modified PBMCs compared to the B cells in an unconditioned plurality of modified PBMCs. In some embodiments, the co-stimulatory molecule is CD80 and/or CD86. In some embodiments, the co-stimulatory molecule is CD86. In some embodiments, the CD80 and/or CD86 is upregulated in the B cells of the conditioned plurality of modified PBMCs by more than about 1.2-fold, 1.5-fold, 1.8-fold, 2-fold, 3-fold, 4-fold, 5-fold, 8-fold, or more than 10-fold compared to the B cells in an unconditioned plurality of modified PBMCs. In some embodiments, the CD80 and/or CD86 is upregulated in the B cells of the conditioned plurality of modified PBMCs by any of about 1.2-fold to about 1.5-fold, about 15-fold to about 18-fold, about 1.8-fold to about 2-fold, about 2-fold to about 3-fold, about 3-fold to about 4-fold, about 4-fold to about 5-fold, about 5-fold to about 8-fold, about 8-fold to about 10-fold, about 10-fold to about 20-fold, about 20-fold to about 50-fold, about 50-fold to about 100-fold, about 100-fold to about 200-fold, about 200-fold to about 500-fold, or more than about 500-fold compared to the B cells in an unconditioned plurality of modified PBMCs. In some embodiments, the expression of one or more of IFN-γ, IL-6, MCP-1, MIP-1β, IP-10, or TNF-α is increased in the conditioned plurality of modified PBMCs compared to an unconditioned plurality of modified PBMCs. In some embodiments, the expression of one or more of IFN-γ, IL-6, MCP-1, MIP-1β, IP-10, or TNF-α is increased a subpopulation of cells in the conditioned plurality compared to the subpopulation of cells in an unconditioned plurality of modified PBMCs. In some embodiments, the expression of one or more of IFN-γ, IL-6, MCP-1, MIP-1β, IP-10, or TNF-α is increased by about 1.2-fold, 1.5-fold, 1.8-fold, 2-fold, 3-fold, 4-fold, 5-fold, 8-fold, or more than 10-fold in the conditioned plurality of modified PBMCs compared to an unconditioned plurality of modified PBMCs. In some embodiments, the expression of one or more of IFN-γ, IL-6, MCP-1, MIP-1β, IP-10, or TNF-α is increased by any of about 1.2-fold to about 1.5-fold, about 1.5-fold to about 1.8-fold, about 1.8-fold to about 2-fold, about 2-fold to about 3-fold, about 3-fold to about 4-fold, about 4-fold to about 5-fold, about 5-fold to about 8-fold, about 8-fold to about 10-fold, about 10-fold to about 20-fold, about 20-fold to about 50-fold, about 50-fold to about 100-fold, about 100-fold to about 200-fold, about 200-fold to about 500-fold, or more than about 500-fold in the conditioned plurality of modified PBMCs compared to an unconditioned plurality of modified PBMCs.

Systems and Kits

In some aspects, the invention provides a system comprising one or more of the constriction, an immune cell suspension, protein or fragment thereof or adjuvants for use in the methods disclosed herein. The system can include any embodiment described for the methods disclosed above, including microfluidic channels or a surface having pores to provide cell-deforming constrictions, cell suspensions, cell perturbations, delivery parameters, compounds, and/or applications etc. In some embodiment, the cell-deforming constrictions are sized for delivery to immune cells. In some embodiments, the delivery parameters, such as operating flow speeds, cell and compound concentration, velocity of the cell in the constriction, and the composition of the cell suspension (e.g., osmolarity, salt concentration, serum content, cell concentration, pH, etc.) are optimized for maximum response of a compound for suppressing an immune response or inducing tolerance.

Also provided are kits or articles of manufacture for use in treating individuals with a cancer or an infection. In some embodiments, the kit comprises a modified immune cell comprising intracellularly a protein or fragment thereof and intracellularly an adjuvant. In some embodiments, the kit comprises one or more of the constriction, an immune cell suspension, protein or fragment thereof or adjuvants for use in generating modified immune cells for use in treating an individual with cancer or infection. In some embodiments, the kits comprise the compositions described herein (e.g. a microfluidic channel or surface containing pores, cell suspensions, and/or compounds) in suitable packaging. Suitable packaging materials are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The invention also provides kits comprising components of the methods described herein and may further comprise instructions for perfuming said methods treat an individual in need thereof and/or instructions for introducing a protein or fragment thereof and an adjuvant into an immune cell. The kits described herein may further include other materials, including other buffers, diluents, filters, needles, syringes, and package inserts with instructions for performing any methods described herein; e.g., instructions for treating an individual in need thereof or instructions for modifying an immune cell to contain intracellularly a protein or fragment thereof and intracellularly an adjuvant.

EXEMPLARY EMBODIMENTS

Embodiment 1. A method for stimulating an immune response in an individual, the method comprising administering an effective amount of a composition comprising nucleated cells to an individual, wherein the nucleated cells comprises a protein or fragment thereof; wherein the protein or fragment thereof stimulates an immune response regardless of the HLA haplotype of the individual.

Embodiment 2. A method for vaccinating an individual in need thereof, the method comprising administering an effective amount of a composition comprising nucleated cells to an individual, wherein the nucleated cells comprises a protein or fragment thereof; wherein the protein or fragment thereof stimulates an immune response regardless of the HLA haplotype of the individual.

Embodiment 3. The method of embodiment 1 or 2, wherein the protein or fragment thereof further comprises one or more immunoproteasome-targeting motifs, generating a fusion protein of the protein and the one or more immunoproteasome-targeting motifs.

Embodiment 4. A method for stimulating an immune response in an individual, the method comprising administering an effective amount of a composition comprising nucleated cells to an individual, wherein the nucleated cells comprise a mRNA encoding a protein or fragment thereof; wherein the protein or fragment thereof stimulates an immune response regardless of the HLA haplotype of the individual.

Embodiment 5. A method for vaccinating an individual in need thereof, the method comprising administering an effective amount of a composition comprising nucleated cells to an individual, wherein the nucleated cells comprise a mRNA encoding a protein or fragment thereof; wherein the protein or fragment thereof stimulates an immune response regardless of the HLA haplotype of the individual.

Embodiment 6. The method of embodiment 4 or 5 wherein the nucleotide sequence of the mRNA is codon optimized for expression in the nucleated cell.

Embodiment 7. The method of any one of embodiments 4-6, wherein the mRNA comprises one or more nucleic acid sequences encoding a immunoproteasome-targeting motif, wherein translation of the mRNA generates a fusion protein of the protein and the one or more immunoproteasome-targeting motifs.

Embodiment 8. The method of embodiment 3 or 6, wherein the one or more immunoproteasome-targeting motifs enhance degradation of the protein in the cell and/or presentation of peptides derived from the protein on the surface of the cell compared to degradation of the protein in the cell and/or presentation of peptides derived from the protein on the surface of the cell in the absence of a immunoproteasome-targeting motif.

Embodiment 9. The method of embodiment 8, wherein the one or more immunoproteasome-targeting motifs is at the N-terminus and/or the C-terminus of the fusion protein.

Embodiment 10. The method of embodiments 7-9 where the one or more immunoproteasome-targeting motifs is a destruction box (D-box) domain, a KEKE domain, and/or a sec/MITD domain.

Embodiment 11. The method of any one of embodiments 4-10, wherein one or more residues of the mRNA is modified.

Embodiment 12. The method of embodiment 11, wherein one or more residues of the mRNA is a phosphorothioate residue, a pseudouridine residue, an N1-methyladenosine residue, a 5-methylcytidine residue, or a morpholino residue.

Embodiment 13. A method for stimulating an immune response in an individual, the method comprising administering an effective amount of a composition comprising nucleated cells to an individual, wherein the nucleated cells comprises two or more antigens derived from a protein; wherein the two or more antigens stimulates an immune response regardless of the HLA haplotype of the individual.

Embodiment 14. A method for vaccinating an individual in need thereof, the method comprising administering an effective amount of a composition comprising nucleated cells to an individual, wherein the nucleated cells comprises two or more antigens derived from a protein; wherein the two or more antigens stimulates an immune response regardless of the HLA haplotype of the individual.

Embodiment 15. The method of embodiment 13 or 14, where the cells comprise three, four, five, six, seven, eight, nine, ten or more than ten antigens derived from the protein.

Embodiment 16. The method of any one of embodiments 13-15, wherein at least two of the antigens comprise partially overlapping amino acid sequences.

Embodiment 17. The method of embodiment 16, wherein the combined amino acid sequences of all the antigens overlaps the amino acid sequence of the protein by about 90% or more.

Embodiment 18. The method of any one of embodiments 13-17, wherein the antigen is a polypeptide comprising two or more epitopes of the protein.

Embodiment 19. The method of any one of embodiments 13-18, wherein the antigen is a polypeptide comprising one or more epitopes of the protein and one or more heterologous peptide sequences.

Embodiment 20. The method of any one of embodiments 13-19, wherein one or more epitopes is flanked on the N-terminus and/or the C-terminus by one or more heterologous peptide sequences.

Embodiment 21. The method of embodiment 20, wherein the N-terminal and/or C-terminal flanking polypeptides are derived from an immunogenic synthetic long peptide (SLP).

Embodiment 22. The method of embodiment 21, wherein the N-terminal and/or C-terminal flanking polypeptides are derived from a disease-associated immunogenic SLP.

Embodiment 23. The method of any one of embodiments 1-22, wherein the protein is a mutated protein associated with cancer, a product of an oncogene, a neoantigen, a viral protein, a bacterial protein or a fungal protein.

Embodiment 24. The method of any one of embodiments 1, 3, 4, 6-13, 15-23, wherein the stimulating an immune response in an individual is used for the treatment of a cancer, an infectious disease, or a viral-associated disease.

Embodiment 25. The method of embodiment 24, wherein the viral-associated disease is a disease associated with human papillomavirus (HPV), hepatitis A virus (HAV), hepatitis B virus (HBV), hepatitis C virus (HCV), herpes simplex virus 1 (HSV-1), herpes simplex virus (HSV-2), varicella-zoster virus (VZV), human herpesvirus 6 (HHV-6), human herpesvirus 7 (HHV-7), human herpesvirus 8 (HHV-8), cytomegalovirus (CMV), human immunodeficiency virus (HIV), Epstein Barr virus (EBV) or influenza.

Embodiment 26. The method of embodiment any one of embodiments 1-24, wherein the protein is a human papillomavirus (HPV) protein.

Embodiment 27. The method of embodiment 26, wherein the HPV is HPV-16 or HPV-18.

Embodiment 28. The method of embodiment 26 or 27, wherein the protein is an HPV E6 or HPV E7 protein.

Embodiment 29. The method of any one of embodiments 1-24, wherein the protein is a hepatitis B vims (HBV) protein.

Embodiment 30. The method of embodiment 29, wherein the HBV protein is a core protein, a small surface antigen, a medium surface antigen, a large surface antigen, an e antigen, an X antigen, or a polymerase protein.

Embodiment 31. The method of any one of embodiments 1-30, wherein the composition further comprises an adjuvant.

Embodiment 32. The method of any one of embodiments 1-31, wherein the composition is administered in conjunction with an adjuvant.

Embodiment 33. The method of embodiment 31 or 32, wherein the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR 9 agonist.

Embodiment 34. The method of any one of embodiments 1-3 and 23-33, wherein the nucleated cells comprising the protein or fragment thereof are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the protein or fragment thereof to pass through to form a perturbed input nucleated cells; and b) incubating the perturbed input nucleated cells with the protein or fragment thereof to allow the protein or fragment thereof to enter the perturbed input nucleated cells; thereby generating nucleated cells comprising the protein or fragment thereof.

Embodiment 35. The method of any one of embodiments 4-11, wherein the nucleated cells comprising the mRNA encoding the protein or fragment thereof are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; thereby generating nucleated cells comprising the mRNA encoding the protein or fragment thereof.

Embodiment 36. The method of any one of embodiments 12-33, wherein the nucleated cells comprising two or more antigens are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the two or more antigens to pass through to form a perturbed input nucleated cells; and b) incubating the perturbed input nucleated cells with the two or more antigens to allow the two or more antigens to enter the perturbed input nucleated cells; thereby generating nucleated cells comprising two or more antigens.

Embodiment 37. The method of any one of embodiments 34-36, wherein the method comprises (a) incubating the nucleated cells with the protein or fragment thereof before, during and/or after passing the cell suspension through the cell-deforming constriction;

(b) incubating the nucleated cells with the mRNA encoding the protein or fragment thereof before, during and/or after passing the cell suspension through the cell-deforming constriction; or (c) incubating the nucleated cells with the two or more antigens before, during and/or after passing the cell suspension through the cell-deforming constriction.

Embodiment 38. The method of any one of embodiments 34-36, wherein the method comprises (a) incubating the nucleated cells with the protein or fragment thereof before passing the cell suspension through the cell-deforming constriction;

(b) incubating the nucleated cells with the mRNA encoding the protein or fragment thereof before passing the cell suspension through the cell-deforming constriction; or (c) incubating the nucleated cells with the two or more antigens before passing the cell suspension through the cell-deforming constriction.

Embodiment 39. The method of any one of embodiments 34-38, wherein the width of the constriction is about 10% to about 99% of the mean diameter of the input nucleated cells.

Embodiment 40. The method of any one of embodiments 34-39, wherein the width of the constriction is about 3.0 μm to about 4.2 μm or about 3.0 μm to about 4.8 μm or about 3.0 μm to about 6 μm or about 4.2 μm to about 4.8 μm or about 4.2 μm to about 6 μm.

Embodiment 41. The method of any one of embodiments 34-40, wherein the width of the constriction is about 3.5 μm.

Embodiment 42. The method of any one of embodiments 34-41, wherein the width of the constriction is about 4.5 μm or about 4.0 μm.

Embodiment 43. The method of any one of embodiments 34-42, wherein the cell suspension comprising the plurality of input nucleated cells are passed through multiple constrictions wherein the multiple constrictions are arranged in series and/or in parallel.

Embodiment 44. The method of any one of embodiments 1-43, wherein the nucleated cells are autologous or allogeneic to the individual.

Embodiment 45. The method of any one of embodiments 1-44, wherein the nucleated cells are immune cells.

Embodiment 46. The method of any one of embodiments 1.45, wherein the nucleated cells are a plurality of peripheral blood mononuclear cells (PBMCs).

Embodiment 47. The method of embodiment 46, wherein the plurality of PBMCs comprise two or more of T cell, B cell, NK cell, monocytes, dendritic cells or NK-T cells.

Embodiment 48. The method of any one of embodiments 1-47, wherein the nucleated cells are one or more of T cells, B cells, NK cells, monocytes, dendritic cells and/or NK-T cells.

Embodiment 49. The method of any one of embodiments 1-48, wherein the nucleated cells are conditioned with an adjuvant to form conditioned cells.

Embodiment 50. The method of embodiment 49, wherein the nucleated cells are incubated with the adjuvant for about 1 hour to about 24 hours, about 2 hours to about 10 hours, about 3 hours to about 6 hours, or about 4 hours for the cells to condition.

Embodiment 51. The method of embodiment 49 or 50, wherein the nucleated cells are conditioned before or after introducing the protein or fragment thereof or the mRNA encoding the protein or fragment thereof into the nucleated cells.

Embodiment 52. The method of any one of embodiments 49-51, wherein the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR 9 agonist.

Embodiment 53. The method of any one of embodiments 48-51, wherein the adjuvant is a CpG oligodeoxynucleotide (ODN).

Embodiment 54. The method of any one of embodiments 49-53, wherein the adjuvant is CpG 7909.

Embodiment 55. The method of any one of embodiments 49-54, wherein the conditioned cells are a conditioned plurality of PBMCs.

Embodiment 56. The method of embodiment 55, wherein the plurality of PBMCs are modified to increase expression of one or more of co-stimulatory molecules.

Embodiment 57. The method of embodiment 56, wherein the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112.

Embodiment 58. The method of embodiment 56, wherein the co-stimulatory molecule is CD86.

Embodiment 59. The method of any one of embodiments 55-58, wherein the plurality of PBMCs are modified to increase expression of one or more cytokines.

Embodiment 60. The method of any one of embodiments 55-59, wherein the plurality of PBMCs are modified to comprise a chimeric membrane-bound cytokine.

Embodiment 61. The method of embodiment 60, wherein the chimeric membrane-bound cytokine is a fusion protein comprising the cytokine and a transmembrane domain.

Embodiment 62. The method of embodiment 61, wherein the cytokine is joined to the transmembrane domain by a peptide linker.

Embodiment 63. The method of embodiment 62 wherein the peptide linker is (G4S)3 (SEQ ID NO:73) or (EAAAK)3 (SEQ ID NO:74).

Embodiment 64. The method of any one of embodiments 59-63, wherein the cytokine is a Type I cytokine.

Embodiment 65. The method of any one of embodiments 59-64, wherein the cytokine is IL-15, IL-12, IL-2, IFN α, IFN β, or IL-21 or functional variant thereof.

Embodiment 66. The method of embodiment 65, wherein the cytokine is IL-2 or a functional variant thereof and/or IL-12 or a functional variant thereof.

Embodiment 67. The method of any one of embodiments 60-65, wherein the chimeric membrane-bound cytokine comprises the amino acid sequence of SEQ ID NOs:77-80.

Embodiment 68. The method of any one of embodiments 56-67, wherein the plurality of PBMCs is modified to increase expression of one or more cytokines and/or one or more co-stimulatory molecules.

Embodiment 69. The method of embodiment 68, wherein the plurality of PBMCs comprises increased expression of one or more cytokines and/or one or more of co-stimulatory molecules, wherein the plurality of PBMCs are prepared by a process comprising:

a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the protein or fragment thereof, and one or more mRNAs encoding one or more cytokines and/or one or more mRNAs encoding one or more co-stimulatory molecules to pass through to form perturbed input nucleated cells; and b) incubating the perturbed input nucleated cells with the protein or fragment thereof to allow the protein or fragment thereof, and one or more mRNAs encoding one or more cytokines and/or one or more mRNAs encoding one or more co-stimulatory molecules to enter the perturbed input nucleated cells; wherein the mRNAs are expressed, thereby generating nucleated cells comprising the protein or fragment thereof, the one or more cytokines and/or the one or more co-stimulatory molecules.

Embodiment 70. The method of embodiment 68, wherein the plurality of PBMCs comprises increased expression of one or more cytokines and/or one or more of co-stimulatory molecules, wherein the plurality of PBMCs are prepared by a process comprising:

a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof, and one or more mRNAs encoding one or more cytokines and/or one or more mRNAs encoding one or more co-stimulatory molecules to pass through to form perturbed input nucleated cells; and b) incubating the perturbed input nucleated cells with the mRNA encoding the protein or fragment thereof to allow the mRNA encoding the protein or fragment thereof, and one or more mRNAs encoding one or more cytokines and/or one or more mRNAs encoding one or more co-stimulatory molecules to enter the perturbed input nucleated cells; wherein the mRNAs are expressed thereby generating nucleated cells comprising the protein or fragment thereof, the one or more cytokines and/or the one or more co-stimulatory molecules.

Embodiment 71. The method of embodiment 68, wherein the plurality of PBMCs comprises increased expression of one or more cytokines and/or one or more of co-stimulatory molecules, wherein the plurality of PBMCs are prepared by a process comprising:

a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the two or more antigens, and one or more mRNAs encoding one or more cytokines and/or one or more mRNAs encoding one or more co-stimulatory molecules to pass through to form perturbed input nucleated cells; and b) incubating the perturbed input nucleated cells with the two or more antigens, and one or more mRNAs encoding one or more cytokines and/or one or more mRNAs encoding one or more co-stimulatory molecules to allow the two or more antigens, and one or more mRNAs encoding one or more cytokines and/or one or more mRNAs encoding one or more co-stimulatory molecules to enter the perturbed input nucleated cells; wherein the mRNAs are expressed, thereby generating nucleated cells comprising two or more antigens, the one or more cytokines and/or the one or more co-stimulatory molecules.

Embodiment 72. The method of any one of embodiments 69-71, wherein the method comprises (a) incubating the nucleated cells with the protein or fragment thereof, the one or more mRNAs encoding one or more cytokines and/or the one or more mRNAs encoding one or more co-stimulatory molecules before, during and/or after passing the cell suspension through the cell-deforming constriction;

(b) incubating the nucleated cells with the mRNA encoding the protein or fragment thereof, the one or more mRNAs encoding one or more cytokines and/or the one or more mRNAs encoding one or more co-stimulatory molecules before, during and/or after passing the cell suspension through the cell-deforming constriction; or (c) incubating the nucleated cells with the two or more antigens, the one or more mRNAs encoding one or more cytokines and/or the one or more mRNAs encoding one or more co-stimulatory molecules before, during and/or after passing the cell suspension through the cell-deforming constriction.

Embodiment 73. The method of any one of embodiments 69-71, wherein the method comprises (a) incubating the nucleated cells with the protein or fragment thereof, the one or more mRNAs encoding one or more cytokines and/or the one or more mRNAs encoding one or more co-stimulatory molecules before passing the cell suspension through the cell-deforming constriction;

(b) incubating the nucleated cells with the mRNA encoding the protein or fragment thereof, the one or more mRNAs encoding one or more cytokines and/or the one or more mRNAs encoding one or more co-stimulatory molecules before, during and/or after passing the cell suspension through the cell-deforming constriction; or (c) incubating the nucleated cells with the two or more antigens, the one or more mRNAs encoding one or more cytokines and/or the one or more mRNAs encoding one or more co-stimulatory molecules before passing the cell suspension through the cell-deforming constriction.

Embodiment 74. The method any one of embodiments 55-73, wherein one or more co-stimulatory molecules is upregulated in the B cells of the conditioned plurality of PBMCs compared to the B cells in the plurality of nonconditioned PBMCs, wherein the co-stimulatory molecule is CD80 and/or CD86.

Embodiment 75. The method of any one of embodiments 55-74, wherein the plurality of PBMCs have increased expression of one or more of IFN-γ, IL-6, MCP-1, MIP-1β, IP-10, or TNF-α compared to a plurality of unconditioned PBMCs.

Embodiment 76. The method of embodiment 75, wherein the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to the plurality of unconditioned PBMCs.

Embodiment 77. The method of any one of embodiments 1-76, wherein the composition comprising nucleated cells is administered a plurality of times.

Embodiment 78. The method of any one of embodiments 1-77, wherein the composition is administered intravenously.

Embodiment 79. The method of any one of embodiments 1-78, wherein the individual is a human.

Embodiment 80. The method of any one of embodiments 1-79, wherein the composition is administered prior to, concurrently with, or following administration of another therapy.

Embodiment 81. The method of embodiment 80, wherein another therapy is a chemotherapy, a radiation therapy, an antibody, a cytokine, an immune checkpoint inhibitor, or a bispecific polypeptide used in immune-oncology therapy.

Embodiment 82. A composition comprising nucleated cells, wherein the nucleated cells comprises a protein or fragment thereof; wherein the protein or fragment thereof stimulates an immune response in an individual in an HLA agnostic manner.

Embodiment 83. The composition of embodiment 82, wherein the protein or fragment thereof further comprises one or more immunoproteasome-targeting motifs, generating a fusion protein of the protein and the one or more immunoproteasome-targeting motifs.

Embodiment 84. A composition comprising nucleated cells, wherein the nucleated cells comprises a mRNA encoding a protein or fragment thereof; wherein the protein or fragment thereof stimulates an immune response in an individual in an HLA agnostic manner.

Embodiment 85. The composition of embodiment 84 wherein the nucleotide sequence of the mRNA is codon optimized for expression in the nucleated cell.

Embodiment 86. The composition of embodiment 84 or 85, wherein the mRNA comprises one or more nucleic acid sequences encoding a immunoproteasome-targeting motif, wherein translation of the mRNA generates a fusion protein of the protein and the one or more immunoproteasome-targeting motif.

Embodiment 87. The composition of embodiment 83 or 86, wherein the one or more immunoproteasome-targeting motifs enhance degradation of the protein in the cell and/or presentation of peptides derived from the protein on the surface of the cell compared to degradation of the protein in the cell and/or presentation of peptides derived from the protein on the surface of the cell in the absence of a immunoproteasome-targeting motif.

Embodiment 88. The composition of embodiment 87, wherein the one or more immunoproteasome-targeting motifs is at the N-terminus and/or the C-terminus of the fusion protein.

Embodiment 89. The composition of embodiments 86-88 where the one or more immunoproteasome-targeting motifs is a destruction box (D-box) domain, a KEKE domain, and/or a sec/MITD domain.

Embodiment 90. The composition of any one of embodiments 84-89, wherein one or more residues of the mRNA is modified.

Embodiment 91. The composition of embodiment 90, wherein one or more residues of the mRNA is a phosphorothioate residue, a pseudouridine residue, an N1-methyladenosine residue, a 5-methylcytidine residue, or a morpholino residue.

Embodiment 92. A composition comprising nucleated cells, wherein the nucleated cells comprises two or more antigens derived from a protein; wherein the protein or fragment thereof stimulates an immune response in an individual in an HLA agnostic manner.

Embodiment 93. The composition of embodiment 92, where the cells comprise three, four, five, six, seven, eight, nine, ten or more than ten antigens derived from the protein.

Embodiment 94. The composition of embodiment 92 or 93, wherein at least two of the antigens comprise partially overlapping amino acid sequences.

Embodiment 95. The composition of embodiment 94, wherein the combined amino acid sequences of all the antigens overlaps the amino acid sequence of the protein by about 90% or more.

Embodiment 96. The composition of any one of embodiments 92-95, wherein antigen is a polypeptide comprising two or more epitopes of the protein.

Embodiment 97. The composition of any one of embodiments 92-96, wherein antigen is a polypeptide comprising one or more epitopes of the protein and one or more heterologous peptide sequences.

Embodiment 98. The composition of any one of embodiments 92-97, wherein one or more epitopes is flanked on the N-terminus and/or the C-terminus by one or more heterologous peptide sequences.

Embodiment 99. The composition of embodiment 98, wherein the N-terminal and/or C-terminal flanking polypeptides are derived from an immunogenic synthetic long peptide (SLP).

Embodiment 100. The composition of embodiment 99, wherein the N-terminal and/or C-terminal flanking polypeptides are derived from a disease-associated immunogenic SLP.

Embodiment 101. The composition of any one of embodiments 82-100, wherein the protein is a mutated protein associated with cancer, a product of an oncogene, a neoantigen, a viral protein, a bacterial protein or a fungal protein.

Embodiment 102. The composition of any one of embodiments 82-101, wherein the stimulating an immune response in an individual is used for the treatment of a cancer, an infectious disease, or a viral-associated disease.

Embodiment 103. The composition of embodiment 102, wherein the viral-associated disease is a disease associated with human papillomavirus (HPV), hepatitis A virus (HAV), hepatitis B virus (HBV), hepatitis C virus (HCV), herpes simplex virus 1 (HSV-1), herpes simplex virus (HSV-2), varicella-zoster virus (VZV), human herpesvirus 6 (HHV-6), human Herpesvirus 7 (HHV-7), human herpesvirus 8 (HHV-8), cytomegalovirus (CMV), human immunodeficiency virus (HIV), Epstein Barr virus (EBV), or influenza.

Embodiment 104. The composition of embodiment any one of embodiments 82-103, wherein protein is a human papillomavirus (HPV) protein.

Embodiment 105. The composition of embodiment 104, wherein the HPV is HPV-16 or HPV-18.

Embodiment 106. The composition of embodiment 104 or 105, wherein the protein is an HPV E6 or HPV E7 protein.

Embodiment 107. The composition of any one of embodiments 82-103, wherein protein is a hepatitis B virus (HBV) protein.

Embodiment 108. The composition of embodiment 107, wherein the HBV protein is a core protein, a small surface antigen, a medium surface antigen, a large surface antigen, an e antigen, an X antigen, or a polymerase protein.

Embodiment 109. The composition of any one of embodiments 82-108, wherein the composition further comprises an adjuvant.

Embodiment 110. The composition of embodiment 109, wherein the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR 9 agonist.

Embodiment 111. The composition of any one of embodiments 82 and 101-110, wherein the nucleated cells comprising the protein or fragment thereof are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the protein or fragment thereof to pass through to form a perturbed input nucleated cells; and b) incubating the perturbed input nucleated cells with the protein or fragment thereof to allow the protein or fragment thereof to enter the perturbed input nucleated cells; thereby generating nucleated cells comprising the protein or fragment thereof.

Embodiment 112. The composition of any one of embodiments 84-91, and 101-110 wherein the nucleated cells comprising the mRNA encoding the protein or fragment thereof are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; thereby generating nucleated cells comprising the mRNA encoding the protein or fragment thereof.

Embodiment 113. The composition of any one of embodiments 92-110, wherein the nucleated cells comprising two or more antigens are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the two or more antigens to pass through to form a perturbed input nucleated cells; and b) incubating the perturbed input nucleated cells with the two or more antigens to allow the two or more antigens to enter the perturbed input nucleated cells; thereby generating nucleated cells comprising two or more antigens.

Embodiment 114. The composition of any one of embodiments 111-113, wherein the process of preparing the nucleated cells comprises:

(a) incubating the nucleated cells with the protein or fragment thereof before, during and/or after passing the cell suspension through the cell-deforming constriction;

(b) incubating the nucleated cells with the mRNA encoding the protein or fragment thereof before, during and/or after passing the cell suspension through the cell-deforming constriction; or (c) incubating the nucleated cells with the two or more antigens before, during and/or after passing the cell suspension through the cell-deforming constriction.

Embodiment 115. The method of any one of embodiments 111-113, wherein the process of preparing the nucleated cells comprises:

(a) incubating the nucleated cells with the protein or fragment thereof before passing the cell suspension through the cell-deforming constriction;

(b) incubating the nucleated cells with the mRNA encoding the protein or fragment thereof before passing the cell suspension through the cell-deforming constriction; or (c) incubating the nucleated cells with the two or more antigens before passing the cell suspension through the cell-deforming constriction.

Embodiment 116. The composition of any one of embodiments 111-115, wherein the width of the constriction is about 10% to about 99% of the mean diameter of the input nucleated cells.

Embodiment 117. The composition of any one of embodiments 111-116, wherein the width of the constriction is about 3.0 μm to about 4-2 μm or about 3.0 μm to about 4.8 μm or about 3-0 μm to about 6 μm or about 4.2 μm to about 4.8 μm or about 4.2 μm to about 6 μm.

Embodiment 118. The composition of any one of embodiments 111-117, wherein the width of the constriction is about 3.5 μm.

Embodiment 119. The composition of any one of embodiments 111-118, wherein the width of the constriction is about 4.5 μm or about 4.0 μm.

Embodiment 120. The composition of any one of embodiments 111-119, wherein the cell suspension comprising the plurality of input nucleated cells are passed through multiple constrictions wherein the multiple constrictions are arranged in series and/or in parallel.

Embodiment 121. The composition of any one of embodiments 82-120, wherein the nucleated cells are autologous or allogeneic to the individual.

Embodiment 122. The composition of any one of embodiments 82-121, wherein the nucleated cells are immune cells.

Embodiment 123. The composition of any one of embodiments 82-122, wherein the nucleated cells are a plurality of peripheral blood mononuclear cells (PBMCs).

Embodiment 124. The composition of embodiment 123, wherein the plurality of PBMCs comprise two or more of T cell, B cell, NK cell, monocytes, dendritic cells or NK-T cells.

Embodiment 125. The composition of any one of embodiments 82-124, wherein the nucleated cells are one or more of T cells, B cells, NK cells, monocytes, dendritic cells and/or NK-T cells.

Embodiment 126. The composition of any one of embodiments 82-125, wherein the nucleated cells are conditioned with an adjuvant to form conditioned cells.

Embodiment 127. The composition of embodiment 126, wherein the nucleated cells are incubated with the adjuvant for about 1 hour to about 24 hours, about 2 hours to about 10 hours, about 3 hours to about 6 hours, or about 4 hours for the cells to condition.

Embodiment 128. The composition of embodiment 126 or 127, wherein the nucleated cells are conditioned before or after introducing the protein or fragment thereof or the mRNA encoding the protein or fragment thereof into the nucleated cells.

Embodiment 129. The composition of any one of embodiments 126-128, wherein the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR 9 agonist.

Embodiment 130. The composition of any one of embodiments 126-129, wherein the adjuvant is a CpG oligodeoxynucleotide (ODN).

Embodiment 131. The composition of any one of embodiments 126-130, wherein the adjuvant is CpG 7909.

Embodiment 132. The composition of any one of embodiments 126-131, wherein the conditioned cells are a conditioned plurality of PBMCs.

Embodiment 133. The composition of embodiment 132, wherein the plurality of PBMCs are modified to increase expression of one or more of co-stimulatory molecules.

Embodiment 134. The composition of embodiment 133, wherein the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112.

Embodiment 135. The composition of embodiment 134, wherein the co-stimulatory molecule is CD86.

Embodiment 136. The composition of any one of embodiments 132-135, wherein the plurality of PBMCs are modified to increase expression of one or more cytokines.

Embodiment 137. The composition of any one of embodiments 132-136, wherein the plurality of PBMCs are modified to comprise a chimeric membrane-bound cytokine.

Embodiment 138. The composition of embodiment 137, wherein the chimeric membrane-bound cytokine is a fusion protein comprising the cytokine and a transmembrane domain.

Embodiment 139. The composition of embodiment 138, wherein the cytokine is joined to the transmembrane domain by a peptide linker.

Embodiment 140. The composition of embodiment 139 wherein the peptide linker is (G4S)3 (SEQ ID NO:73) or (EAAAK)3 (SEQ ID NO:74).

Embodiment 141. The composition of any one of embodiments 136-140, wherein the cytokine is a Type I cytokine.

Embodiment 142. The composition of any one of embodiments 136-141, wherein the cytokine is IL-15, IL-12, IL-2, IFN α, IFN β, or IL-21 or functional variant thereof.

Embodiment 143. The method of embodiment 142, wherein the cytokine is IL-2 or a functional variant thereof and/or IL-12 or a functional variant thereof.

Embodiment 144. The composition of any one of embodiments 137-143, wherein the chimeric membrane-bound cytokine comprises the amino acid sequence of SEQ ID NOs:77-80.

Embodiment 145. The composition of any one of embodiments 133-144, wherein the plurality of PBMCs is modified to increase expression of one or more cytokines and/or one or more co-stimulatory molecules Embodiment 146. The composition of embodiment 145, wherein the plurality of PBMCs comprises increased expression of one or more cytokines and/or one or more of co-stimulatory molecules, wherein the plurality of PBMCs are prepared by a process comprising:

a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the protein or fragment thereof, and one or more mRNAs encoding one or more cytokines and/or one or more mRNAs encoding one or more co-stimulatory molecules to pass through to form perturbed input nucleated cells; and b) incubating the perturbed input nucleated cells with the protein or fragment thereof to allow the protein or fragment thereof, and one or more mRNAs encoding one or more cytokines and/or one or more mRNAs encoding one or more co-stimulatory molecules to enter the perturbed input nucleated cells; wherein the mRNAs are expressed, thereby generating nucleated cells comprising the protein or fragment thereof, the one or more cytokines and/or the one or more co-stimulatory molecules.

Embodiment 147. The composition of embodiment 145, wherein the plurality of PBMCs comprises increased expression of one or more cytokines and/or one or more of co-stimulatory molecules, wherein the plurality of PBMCs are prepared by a process comprising:

a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof, and one or more mRNAs encoding one or more cytokines and/or one or more mRNAs encoding one or more co-stimulatory molecules to pass through to form perturbed input nucleated cells; and b) incubating the perturbed input nucleated cells with the mRNA encoding the protein or fragment thereof to allow the mRNA encoding the protein or fragment thereof, and one or more mRNAs encoding one or more cytokines and/or one or more mRNAs encoding one or more co-stimulatory molecules to enter the perturbed input nucleated cells; wherein the mRNAs are expressed thereby generating nucleated cells comprising the protein or fragment thereof, the one or more cytokines and/or the one or more co-stimulatory molecules.

Embodiment 148. The composition of embodiment 145, wherein the plurality of PBMCs comprises increased expression of one or more cytokines and/or one or more of co-stimulatory molecules, wherein the plurality of PBMCs are prepared by a process comprising:

a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the two or more antigens, and one or more mRNAs encoding one or more cytokines and/or one or more mRNAs encoding one or more co-stimulatory molecules to pass through to form perturbed input nucleated cells; and b) incubating the perturbed input nucleated cells with the two or more antigens, and one or more mRNAs encoding one or more cytokines and/or one or more mRNAs encoding one or more co-stimulatory molecules to allow the two or more antigens, and one or more mRNAs encoding one or more cytokines and/or one or more mRNAs encoding one or more co-stimulatory molecules to enter the perturbed input nucleated cells; wherein the mRNAs are expressed, thereby generating nucleated cells comprising two or more antigens, the one or more cytokines and/or the one or more co-stimulatory molecules.

Embodiment 149. The composition of any one of embodiments 146-148, wherein the process of preparing the plurality of PBMCs comprises:

(a) incubating the plurality of PBMCs with the protein or fragment thereof, the one or more mRNAs encoding one or more cytokines and/or the one or more mRNAs encoding one or more co-stimulatory molecules before, during and/or after passing the cell suspension through the cell-deforming constriction;

(b) incubating the plurality of PBMCs with the mRNA encoding the protein or fragment thereof, the one or more mRNAs encoding one or more cytokines and/or the one or more mRNAs encoding one or more co-stimulatory molecules before, during and/or after passing the cell suspension through the cell-deforming constriction; or (c) incubating the plurality of PBMCs with the two or more antigens, the one or more mRNAs encoding one or more cytokines and/or the one or more mRNAs encoding one or more co-stimulatory molecules before, during and/or after passing the cell suspension through the cell-deforming constriction.

Embodiment 150. The composition of any one of embodiments 146-148, wherein the process of preparing the plurality of PBMCs comprises:

(a) incubating the plurality of PBMCs with the protein or fragment thereof, the one or more mRNAs encoding one or more cytokines and/or the one or more mRNAs encoding one or more co-stimulatory molecules before passing the cell suspension through the cell-deforming constriction;

(b) incubating the plurality of PBMCs with the mRNA encoding the protein or fragment thereof, the one or more mRNAs encoding one or more cytokines and/or the one or more mRNAs encoding one or more co-stimulatory molecules before, during and/or after passing the cell suspension through the cell-deforming constriction; or (c) incubating the plurality of PBMCs with the two or more antigens, the one or more mRNAs encoding one or more cytokines and/or the one or more mRNAs encoding one or more co-stimulatory molecules before passing the cell suspension through the cell-deforming constriction.

Embodiment 151. The composition of any one of embodiments 132-150, wherein one or more co-stimulatory molecules is upregulated in the B cells of the conditioned plurality of PBMCs compared to the B cells in the plurality of nonconditioned PBMCs, wherein the co-stimulatory molecule is CD80 and/or CD86.

Embodiment 152. The composition of any one of embodiments 132-151, wherein the plurality of PBMCs have increased expression of one or more of IFN-γ, IL-6, MCP-1, MIP-1β, IP-10, or TNF-α compared to a plurality of unconditioned PBMCs.

Embodiment 153. The composition of embodiment 152, wherein the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to the plurality of unconditioned PBMCs.

Embodiment 154. A composition for stimulating an immune response in an individual, wherein the composition comprises an effective amount of composition of any one of embodiments 82-153; wherein the composition stimulates an immune response in an individual in an HLA agnostic manner.

Embodiment 155. A composition for use as a medicine, wherein the composition comprises an effective amount of composition of any one of embodiments 82-153.

Embodiment 156. A composition for treating a cancer, an infectious disease, or a viral-associated disease in an individual, wherein the composition comprises an effective amount of composition of any one of embodiments 82-153.

Embodiment 157. The composition of any one of embodiments 154-156, wherein the composition further comprises an adjuvant.

Embodiment 158. The composition of any one of embodiments 154-157, wherein the composition is administered in conjunction with an adjuvant.

Embodiment 159. The composition of embodiment 157 or 158, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, a TLR3 agonist, a TLR4 agonist, a TLR7 agonist, a TLR8 agonist, or a TLR9 agonist.

Embodiment 160. The composition of any one of embodiments 157-159, wherein the composition comprising nucleated cells is administered a plurality of times.

Embodiment 161. The composition of any one of embodiments 157-160, wherein the composition is administered intravenously.

Embodiment 162. The composition of any one of embodiments 157-161, wherein the individual is a human.

Embodiment 163. The composition of any one of embodiments 157-162, wherein the composition is administered prior to, concurrently with, or following administration of another therapy.

Embodiment 164. The composition of embodiment 163, wherein another therapy is a chemotherapy, a radiation therapy, an antibody, a cytokine, an immune checkpoint inhibitor, or a bispecific polypeptide used in immune-oncology therapy.

Embodiment 165. Use of a composition in the manufacture of a medicament for stimulating an immune response in an individual, wherein the composition comprises an effective amount of composition of any one of embodiments 82-153; wherein the composition stimulates an immune response in an individual in an HLA agnostic manner.

Embodiment 166. Use of a composition in the manufacture of a medicament for treating a cancer, an infectious disease, or a viral-associated disease in an individual, wherein the composition comprises an effective amount of composition of any one of embodiments 82-153.

Embodiment 167. The use of embodiment 165 or 166, wherein the composition further comprises an adjuvant.

Embodiment 168. The composition of any one of embodiments 165-167, wherein the composition is formulated for administration in conjunction with an adjuvant.

Embodiment 169. The use of embodiment 167 or 168, wherein the adjuvant is a CpG oligodeoxynucleotide (ODN), LPS, IFN-α, IFN-s, IFN-γ, alpha-Galactosyl Ceramide, STING agonists, cyclic dinucleotides (CDN), RIG-I agonists, polyinosinic-polycytidylic acid, a TLR3 agonist, a TLR4 agonist, a TLR7 agonist, a TLR8 agonist, or a TLR9 agonist.

Embodiment 170. The use of any one of embodiments 167-169, wherein the composition comprising nucleated cells is administered a plurality of times.

Embodiment 171. The use of any one of embodiments 167-170, wherein the composition is administered intravenously.

Embodiment 172. The use of any one of embodiments 167-171, wherein the individual is a human.

Embodiment 173. The use of any one of embodiments 167-172, wherein the composition is administered prior to, concurrently with, or following administration of another therapy.

Embodiment 174. The use of embodiment 173, wherein another therapy is a chemotherapy, a radiation therapy, an antibody, a cytokine, an immune checkpoint inhibitor, or a bispecific polypeptide used in immune-oncology therapy.

Embodiment 175. A kit for use in the method of any one of embodiments 1-81.

Embodiment 176. A kit comprising the composition of any one of embodiments 82-153.

Embodiment 177. The kit of embodiment 175 or 176, wherein the kit further comprises one or more of buffers, diluents, filters, needles, syringes, or package inserts with instructions for administering the composition to an individual to stimulate an immune response in an HLA agnostic manner.

Embodiment 178. A method for producing nucleated cells comprising a protein or fragment thereof; the method comprising introducing the protein or fragment thereof into the nucleated cells, wherein the protein or fragment thereof stimulates an immune response in an individual in an HLA agnostic manner.

Embodiment 179. A method for producing nucleated cells comprising a protein or fragment thereof; the method comprising introducing mRNA encoding the protein or fragment thereof into the nucleated cells, wherein the mRNA is expressed to produce the protein or fragment thereof; wherein the protein or fragment thereof stimulates an immune response in an individual in an HLA agnostic manner.

Embodiment 180. A method for producing nucleated cells comprising a two or more antigens from a protein; the method comprising introducing the two or more antigens into the nucleated cells; wherein the protein or fragment thereof stimulates an immune response in an individual in an HLA agnostic manner.

Embodiment 181. The method of embodiment 178, wherein introducing the protein or fragment thereof to the nucleate cell intracellularly comprises a) passing a cell suspension comprising input nucleated cells through a cell-deforming constriction, wherein a diameter of the constriction is a function of a diameter of the input nucleated cells in the suspension, thereby causing perturbations of the input nucleate cells large enough for the protein or fragment thereof to pass through to form a perturbed input nucleated cells; and
b) incubating the perturbed input nucleated cells with the protein or fragment thereof to allow the protein or fragment thereof to enter the perturbed input nucleated cells; thereby generating nucleated cells comprising the protein or fragment thereof.

Embodiment 182. The method of embodiment 179 wherein the nucleated cells comprising the mRNA encoding the protein or fragment thereof are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the mRNA encoding the protein or fragment thereof to pass through to form a perturbed input nucleated cells; and b) incubating the perturbed input nucleated cells with the mRNA encoding the protein or fragment thereof to allow the mRNA encoding the protein or fragment thereof to enter the perturbed input nucleated cells; thereby generating nucleated cells comprising the mRNA encoding the protein or fragment thereof.

Embodiment 183. The method of embodiment 180, wherein the nucleated cells comprising two or more antigens are prepared by a) passing a cell suspension comprising input nucleated cells through a cell-deforming constriction, wherein a diameter of the constriction is a function of a diameter of the input nucleated cells in the suspension, thereby causing perturbations of the input nucleated cells large enough for the two or more antigens to pass through to form a perturbed input nucleated cells; and b) incubating the perturbed input nucleated cells with the two or more antigens to allow the two or more antigens to enter the perturbed input nucleated cells; thereby generating nucleated cells comprising two or more antigens.

Embodiment 184. The method of any one of embodiments 181-183, wherein the method comprises:

(a) incubating the nucleated cells with the protein or fragment thereof before, during and/or after passing the cell suspension through the cell-deforming constriction;

(b) incubating the nucleated cells with the mRNA encoding the protein or fragment thereof before, during and/or after passing the cell suspension through the cell-deforming constriction; or (c) incubating the nucleated cells with the two or more antigens before, during and/or after passing the cell suspension through the cell-deforming constriction.

Embodiment 185. The method of any one of embodiments 181-183, wherein the method comprises:

(a) incubating the nucleated cells with the protein or fragment thereof before passing the cell suspension through the cell-deforming constriction;

(b) incubating the nucleated cells with the mRNA encoding the protein or fragment thereof before passing the cell suspension through the cell-deforming constriction; or (c) incubating the nucleated cells with the two or more antigens before passing the cell suspension through the cell-deforming constriction.

Embodiment 186. The method of any one of embodiments 181-185, wherein the width of the constriction is about 10% to about 99% of the mean diameter of the input nucleated cells.

Embodiment 187. The method of any one of embodiments 181-186, wherein the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm.

Embodiment 188. The method of any one of embodiments 181-187, wherein the width of the constriction is about 3.5 μm.

Embodiment 189. The method of any one of embodiments 181-188, wherein the width of the constriction is about 4.5 μm.

Embodiment 190. The method of any one of embodiments 181-189, wherein the cell suspension comprising the plurality of input nucleated cells are passed through multiple constrictions wherein the multiple constrictions are arranged in series and/or in parallel.

Embodiment 191. The method of any one of embodiments 178-190, wherein the method further comprising conditioning the nucleated cells with an adjuvant to form conditioned cells.

Embodiment 192. The method of embodiment 191, wherein the nucleated cells are incubated with the adjuvant for about 1 hour to about 24 hours, about 2 hours to about 10 hours, about 3 hours to about 6 hours, or about 4 hours for the cells to condition.

Embodiment 193. The method of embodiment 191 or 192, wherein the nucleated cells are conditioned before or after introducing the protein or fragment thereof, the mRNA encoding the protein or fragment thereof, or the two or more antigens from a protein into the nucleated cells.

Embodiment 194. A method for enhancing the activity of an immune cell, the methods comprising expressing a nucleic acid encoding a chimeric membrane-bound cytokine in the immune cell.

Embodiment 195. The method of embodiment 193, wherein the chimeric membrane-bound cytokine is a fusion protein comprising a transmembrane domain and a cytokine.

Embodiment 196. The method of embodiment 194 or 195, wherein the transmembrane domain is a transferrin receptor protein 1 (TFRC) or a tumor necrosis factor transmembrane domain.

Embodiment 197. The method of any one of embodiments 194-196, wherein the cytokine is a Type I cytokine.

Embodiment 198. The method of any one of embodiments 194-197, wherein the cytokine is IL-15, IL-12, IL-2, IFN α, IFN β, or IL-21 or functional variant thereof.

Embodiment 199. The method of any one of embodiments 194-198, wherein the cytokine is joined to the transmembrane domain by a peptide linker.

Embodiment 200. The method of embodiment 199, wherein the peptide linker is (G4S)3 (SEQ ID NO:73) or (EAAAK)3 (SEQ ID NO:74).

Embodiment 201. The method of any one of embodiments 194-200, wherein the chimeric membrane-bound cytokine comprises the amino acid sequence of SEQ ID NOs:77-80.

Embodiment 202. The method of any one of embodiments 194-201, wherein the immune cell further comprises an antigen.

Embodiment 203. The method of any one of embodiments 194-201, wherein the immune cell further comprises a mRNA encoding an antigen.

Embodiment 204. The method of embodiment 202 or 203, wherein the antigen is a protein or fragment thereof, wherein the protein or fragment thereof stimulates an immune response regardless of the HLA haplotype of the individual.

Embodiment 205. The method of any one of embodiments 194-201, wherein the immune cell further comprises two or more antigens derived from a protein.

Embodiment 206. The method of embodiment 205, wherein the two or more antigens stimulates an immune response regardless of the HLA haplotype of the individual.

Embodiment 207. The method of any one of embodiments 204-206, wherein the protein is a mutated protein associated with cancer, a product of an oncogene, a neoantigen, a viral protein, a bacterial protein or a fungal protein.

Embodiment 208. The method of any one of embodiments 204-207, wherein the protein is a human papillomavirus (HPV) protein.

Embodiment 209. The method of embodiment 208, wherein the HPV is HPV-16 or HPV-18.

Embodiment 210. The method of embodiment 208 or 209, wherein the protein is an HPV E6 or HPV E7 protein.

Embodiment 211. The method of any one of embodiments 204-207, wherein the protein is a hepatitis B virus (HBV) protein.

Embodiment 212. The method of embodiment 211, wherein the HBV protein is a core protein, a small surface antigen, a medium surface antigen, a large surface antigen, an e antigen, an X antigen, or a polymerase protein.

Embodiment 213. The method of any one of embodiments 194-212, wherein the immune cells are a plurality of peripheral blood mononuclear cells (PBMCs).

Embodiment 214. The method of embodiment 213, wherein the plurality of PBMCs comprise two or more of T cell, B cell, NK cell, monocytes, dendritic cells or NK-T cells.

Embodiment 215. The method of any one of embodiments 194-214, wherein the immune cells are one or more of T cells, B cells, NK cells, monocytes, dendritic cells and/or NK-T cells.

Embodiment 216. The method of any one of embodiments 194-215, wherein the nucleated cells are conditioned with an adjuvant to form conditioned cells.

Embodiment 217. The method of embodiment 216, wherein the nucleated cells are incubated with the adjuvant for about 1 hour to about 24 hours, about 2 hours to about 10 hours, about 3 hours to about 6 hours, or about 4 hours for the cells to condition.

Embodiment 218. The method of embodiment 216 or 217, wherein the nucleated cells are conditioned before or after introducing the protein or fragment thereof or the mRNA encoding the protein or fragment thereof into the nucleated cells.

Embodiment 219. The method of any one of embodiments 216-218, wherein the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR9 agonist.

Embodiment 220. The method of any one of embodiments 216-219, wherein the adjuvant is a CpG oligodeoxynucleotide (ODN).

Embodiment 221. The method of any one of embodiments 194-220, wherein the immune cells comprising the chimeric membrane-bound cytokine are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine to pass through to form a perturbed input immune cells; and b) incubating the perturbed input immune cells with the nucleic acid encoding the chimeric membrane-bound cytokine to allow the nucleic acid to enter the perturbed input immune cells where the nucleic acid encoding the chimeric membrane-bound cytokine is expressed; thereby generating immune cells comprising a chimeric membrane-bound cytokine.

Embodiment 222. The method of embodiment 221, wherein the nucleic acid encoding the chimeric membrane-bound cytokine is a mRNA encoding the chimeric membrane-bound cytokine.

Embodiment 223. The method of any one of embodiments 202, 204 and 207-222, wherein the immune cells comprising the chimeric membrane-bound cytokine and an antigen are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the antigen to pass through to form a perturbed input immune cells; and b) incubating the perturbed input immune cells with the nucleic acid encoding the chimeric membrane-bound cytokine and the antigen to allow the nucleic acid and the antigen to enter the perturbed input immune cells where the nucleic acid encoding the chimeric membrane-bound cytokine is expressed; thereby generating immune cells comprising a chimeric membrane-bound cytokine and an antigen.

Embodiment 224. The method of embodiment 203, 204 and 207-222 wherein the immune cells comprising the chimeric membrane-bound cytokine and an mRNA encoding a protein or fragment thereof are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and a nucleic acid encoding the antigen to pass through to form a perturbed input immune cells; and b) incubating the perturbed input immune cells with the nucleic acid encoding the chimeric membrane-bound cytokine and the nucleic acid encoding the antigen to allow the nucleic acid to enter the perturbed input immune cells where the nucleic acid encoding the chimeric membrane-bound cytokine and the nucleic acid encoding the antigen is expressed; thereby generating immune cells comprising a chimeric membrane-bound cytokine and an antigen.

Embodiment 225. The method of embodiment 223 or 224, wherein the nucleic acid encoding the chimeric membrane-bound cytokine and/or the nucleic acid encoding the antigen is a mRNA.

Embodiment 226. The method of any one of embodiments 202, 204 and 207-222, wherein the immune cells comprising the chimeric membrane-bound cytokine and the two or more antigens derived from a protein are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the two or more antigens derived from a protein to pass through to form a perturbed input immune cells; and b) incubating the perturbed input immune cells with the nucleic acid encoding the chimeric membrane-bound cytokine and the two or more antigens derived from a protein to allow the nucleic acid to enter the perturbed input immune cells where the nucleic acid encoding the chimeric membrane-bound cytokine is expressed; thereby generating immune cells comprising a chimeric membrane-bound cytokine and an antigen.

Embodiment 227. The method of any one of embodiments 221-226, wherein the method comprises:

(a) incubating the immune cells with the nucleic acid encoding the chimeric membrane-bound cytokine before, during and/or after passing the cell suspension through the cell-deforming constriction (b) incubating the immune cells with the nucleic acid encoding the chimeric membrane-bound cytokine and the antigen before, during and/or after passing the cell suspension through the cell-deforming constriction;

(c) incubating the immune cells with the nucleic acid encoding the chimeric membrane-bound cytokine and the nucleic acid encoding the antigen before, during and/or after passing the cell suspension through the cell-deforming constriction; or (d) incubating the immune cells with the nucleic acid encoding the chimeric membrane-bound cytokine and the two or more antigens before, during and/or after passing the cell suspension through the cell-deforming constriction.

Embodiment 228. The method of any one of embodiments 221-226, wherein the method comprises:

(a) incubating the immune cells with the nucleic acid encoding the chimeric membrane-bound cytokine before passing the cell suspension through the cell-deforming constriction;

(b) incubating the immune cells with the nucleic acid encoding the chimeric membrane-bound cytokine and the antigen before passing the cell suspension through the cell-deforming constriction;

(c) incubating the immune cells with the nucleic acid encoding the chimeric membrane-bound cytokine and the nucleic acid encoding the antigen before passing the cell suspension through the cell-deforming constriction; or (d) incubating the immune cells with the nucleic acid encoding the chimeric membrane-bound cytokine and the two or more antigens before passing the cell suspension through the cell-deforming constriction.

Embodiment 229. The method of any one of embodiments 221-228, wherein the width of the constriction is about 10% to about 99% of the mean diameter of the input nucleated cells.

Embodiment 230. The method of any one of embodiments 221-229, wherein the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm.

Embodiment 231. The method of any one of embodiments 221-230, wherein the width of the constriction is about 3.5 μm.

Embodiment 232. The method of any one of embodiments 221-231, wherein the width of the constriction is about 4.5 μm.

Embodiment 233. The method of any one of embodiments 221-232, wherein the cell suspension comprising the plurality of input nucleated cells are passed through multiple constrictions wherein the multiple constrictions are arranged in series and/or in parallel.

Embodiment 234. A composition for enhancing the activity of an immune cell, the composition comprising a chimeric membrane-bound cytokine in the immune cell.

Embodiment 235. The composition of embodiment 234, wherein the chimeric membrane-bound cytokine is a fusion protein comprising a transmembrane domain and a cytokine.

Embodiment 236. The composition of any one of embodiments 234-235, wherein the transmembrane domain is a transferrin receptor protein 1 (TFRC) or a tumor necrosis factor transmembrane domain.

Embodiment 237. The composition of any one of embodiments 234-236, wherein the cytokine is a Type I cytokine.

Embodiment 238. The composition of any one of embodiments 234-237, wherein the cytokine is IL-45, IL-12, IL-2, IFN α, IFN β, or IL-21 or functional variant thereof.

Embodiment 239. The composition of any one of embodiments 234-238, wherein the cytokine is joined to the transmembrane domain by a peptide linker.

Embodiment 240. The composition of embodiment 239, wherein the peptide linker is (G4S)3 (SEQ ID NO:73) or (EAAAK)3 (SEQ ID NO:74).

Embodiment 241. The composition of any one of embodiments 234-240, wherein the chimeric membrane-bound cytokine comprises the amino acid sequence of SEQ ID NOs:77-80.

Embodiment 242. The composition of any one of embodiments 234-241, wherein the immune cell further comprises an antigen.

Embodiment 243. The composition of any one of embodiments 234-242, wherein the immune cell further comprises a mRNA encoding an antigen.

Embodiment 244. The composition of embodiment 242 or 243, wherein the antigen is a protein or fragment thereof, wherein the protein or fragment thereof stimulates an immune response regardless of the HLA haplotype of the individual.

Embodiment 245. The composition of any one of embodiments 233-241, wherein the immune cell further comprises two or more antigens derived from a protein.

Embodiment 246. The composition of embodiment 245, wherein the two or more antigens stimulates an immune response regardless of the HLA haplotype of the individual.

Embodiment 247. The composition of any one of embodiments 244-246, wherein the protein is a mutated protein associated with cancer, a product of an oncogene, a neoantigen, a viral protein, a bacterial protein or a fungal protein.

Embodiment 248. The composition of embodiment any one of embodiments 244-247, wherein protein is a human papillomavirus (HPV) protein.

Embodiment 249. The composition of embodiment 248, wherein the HPV is HPV-16 or HPV-18.

Embodiment 250. The composition of embodiment 248 or 249, wherein the protein is an HPV E6 or HPV E7 protein.

Embodiment 251. The composition of any one of embodiments 244-247, wherein protein is a hepatitis B vims (HBV) protein.

Embodiment 252. The composition of embodiment 251, wherein the HBV protein is a core protein, a small surface antigen, a medium surface antigen, a large surface antigen, an e antigen, an X antigen or a polymerase protein.

Embodiment 253. The composition of any one of embodiments 233-252, wherein the immune cells are a plurality of peripheral blood mononuclear cells (PBMCs).

Embodiment 254. The composition of embodiment 253, wherein the plurality of PBMCs comprise two or more of T cell, B cell, NK cell, monocytes, dendritic cells or NK-T cells.

Embodiment 255. The composition of any one of embodiments 233-254, wherein the immune cells are one or more of T cells, B cells, NK cells, monocytes, dendritic cells and/or NK-T cells.

Embodiment 256. The composition of any one of embodiments 233-255, wherein the nucleated cells are conditioned with an adjuvant to form conditioned cells.

Embodiment 257. The composition of embodiment 256, wherein the nucleated cells are incubated with the adjuvant for about 1 hour to about 24 hours, about 2 hours to about 10 hours, about 3 hours to about 6 hours, or about 4 hours for the cells to condition.

Embodiment 258. The composition of embodiment 256 or 257, wherein the nucleated cells are conditioned before or after introducing the protein or fragment thereof or the mRNA encoding the protein or fragment thereof into the nucleated cells.

Embodiment 259. The composition of any one of embodiments 256-258, wherein the adjuvant is a CpG oligodeoxynucleotide (ODN), LPS, IFN-α, STING agonists, RIG-I agonists, polyinosinic-polycytidylic acid, a TLR3 agonist, a TLR4 agonist, a TLR7 agonist, a TLR8 agonist, or a TLR 9 agonist.

Embodiment 260. The composition of any one of embodiments 256-259, wherein the adjuvant is a CpG oligodeoxynucleotide (ODN).

Embodiment 261. The composition of any one of embodiments 234-260, wherein the immune cells comprising the chimeric membrane-bound cytokine are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine to pass through to form a perturbed input immune cells; and b) incubating the perturbed input immune cells with the nucleic acid encoding the chimeric membrane-bound cytokine to allow the nucleic acid to enter the perturbed input immune cells where the nucleic acid encoding the chimeric membrane-bound cytokine is expressed; thereby generating immune cells comprising a chimeric membrane-bound cytokine.

Embodiment 262. The composition of embodiment 261, wherein the nucleic acid encoding the chimeric membrane-bound cytokine is a mRNA encoding the chimeric membrane-bound cytokine.

Embodiment 263. The composition of any one of embodiments 242, 244, and 247-262, wherein the immune cells comprising the chimeric membrane-bound cytokine are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the antigen to pass through to form a perturbed input immune cells; and b) incubating the perturbed input immune cells with the nucleic acid encoding the chimeric membrane-bound cytokine and the antigen to allow the nucleic acid to enter the perturbed input immune cells where the nucleic acid encoding the chimeric membrane-bound cytokine is expressed; thereby generating immune cells comprising a chimeric membrane-bound cytokine and an antigen.

Embodiment 264. The composition of embodiment 243, 244, and 247-262, wherein the immune cells comprising the chimeric membrane-bound cytokine are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and a nucleic acid encoding the antigen to pass through to form a perturbed input immune cells; and b) incubating the perturbed input immune cells with the nucleic acid encoding the chimeric membrane-bound cytokine and the nucleic acid encoding the antigen to allow the nucleic acid to enter the perturbed input immune cells where the nucleic acid encoding the chimeric membrane-bound cytokine and the nucleic acid encoding the antigen is expressed; thereby generating immune cells comprising a chimeric membrane-bound cytokine and an antigen.

Embodiment 265. The composition of embodiment 263 or 264, wherein the nucleic acid encoding the chimeric membrane-bound cytokine and/or the nucleic acid encoding the antigen is a mRNA.

Embodiment 266. The composition of any one of embodiments 245-262, wherein the immune cells comprising the chimeric membrane-bound cytokine and the two or more antigens derived from a protein are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine and the two or more antigens derived from a protein to pass through to form a perturbed input immune cells; and b) incubating the perturbed input immune cells with the nucleic acid encoding the chimeric membrane-bound cytokine and the two or more antigens derived from a protein to allow the nucleic acid to enter the perturbed input immune cells where the nucleic acid encoding the chimeric membrane-bound cytokine is expressed; thereby generating immune cells comprising a chimeric membrane-bound cytokine and two or more antigens.

Embodiment 267. The composition of any one of embodiments 261-266, wherein the process of deriving the immune cells comprises:

(a) incubating the immune cells with the nucleic acid encoding the chimeric membrane-bound cytokine before, during and/or after passing the cell suspension through the cell-deforming constriction (b) incubating the immune cells with the nucleic acid encoding the chimeric membrane-bound cytokine and the antigen before, during and/or after passing the cell suspension through the cell-deforming constriction;

(c) incubating the immune cells with the nucleic acid encoding the chimeric membrane-bound cytokine and the nucleic acid encoding the antigen before, during and/or after passing the cell suspension through the cell-deforming constriction; or (d) incubating the immune cells with the nucleic acid encoding the chimeric membrane-bound cytokine and the two or more antigens before, during and/or after passing the cell suspension through the cell-deforming constriction.

Embodiment 268. The method of any one of embodiments 261-266, wherein the process of deriving the immune cells comprises:

(a) incubating the immune cells with the nucleic acid encoding the chimeric membrane-bound cytokine before passing the cell suspension through the cell-deforming constriction;

(b) incubating the immune cells with the nucleic acid encoding the chimeric membrane-bound cytokine and the antigen before passing the cell suspension through the cell-deforming constriction;

(c) incubating the immune cells with the nucleic acid encoding the chimeric membrane-bound cytokine and the nucleic acid encoding the antigen before passing the cell suspension through the cell-deforming constriction; or (d) incubating the immune cells with the nucleic acid encoding the chimeric membrane-bound cytokine and the two or more antigens before passing the cell suspension through the cell-deforming constriction.

Embodiment 269. The composition of any one of embodiments 261-268, wherein the width of the constriction is about 10% to about 99% of the mean diameter of the input nucleated cells.

Embodiment 270. The composition of any one of embodiments 261-269, wherein the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm.

Embodiment 271. The composition of any one of embodiments 261-270, wherein the width of the constriction is about 3.5 μm.

Embodiment 272. The composition of any one of embodiments 261-271, wherein the width of the constriction is about 4.5 μm.

Embodiment 273. The composition of any one of embodiments 261-272, wherein the cell suspension comprising the plurality of input nucleated cells are passed through multiple constrictions wherein the multiple constrictions are arranged in series and/or in parallel.

Embodiment 274. A composition for use as a medicine, wherein the composition comprises an effective amount of composition of any one of embodiments 234-273.

Embodiment 275. A composition for treating a cancer, an infectious disease, or a viral-associated disease in an individual, wherein the composition comprises an effective amount of composition of any one of embodiments 210-248.

Embodiment 276. A kit for use in the method of any one of embodiments 194-233.

Embodiment 277. A kit comprising the composition of any one of embodiments 234-275.

Embodiment 278. The kit of embodiment 250 or 249, wherein the kit further comprises one or more of buffers, diluents, filters, needles, syringes, or package inserts with instructions for enhancing the activity of an immune cell.

Embodiment 279. A method of producing immune cells comprising a chimeric membrane-bound cytokine, the method comprising introducing a nucleic acid encoding the chimeric membrane-bound cytokine to the immune cells.

Embodiment 280. The method of embodiment 279, wherein the immune cells comprising the chimeric membrane-bound cytokine are prepared by a) passing a cell suspension comprising input immune cells through a cell-deforming constriction, wherein a diameter of the constriction is a function of a diameter of the input immune cells in the suspension, thereby causing perturbations of the input immune cells large enough for a nucleic acid encoding the chimeric membrane-bound cytokine to pass through to form a perturbed input immune cells; and b) incubating the perturbed input immune cells with the nucleic acid encoding the chimeric membrane-bound cytokine to allow the nucleic acid to enter the perturbed input immune cells where the nucleic acid encoding the chimeric membrane-bound cytokine is expressed; thereby generating immune cells comprising a chimeric membrane-bound cytokine.

Embodiment 281. The method of embodiment 280, wherein the method comprises incubating the immune cells with the nucleic acid encoding the chimeric membrane-bound cytokine thereof before, during and/or after passing the cell suspension through the cell-deforming constriction.

Embodiment 282. The method of embodiment 280, wherein the method comprises incubating the immune cells with the nucleic acid encoding the chimeric membrane-bound cytokine before passing the cell suspension through the cell-deforming constriction.

Embodiment 283. The method of embodiment 280, 281 or 282, wherein the nucleic acid encoding the chimeric membrane-bound cytokine is a mRNA encoding the chimeric membrane-bound cytokine.

Embodiment 284. The method of any one of embodiments 280-283, wherein the width of the constriction is about 10% to about 99% of the mean diameter of the input nucleated cells.

Embodiment 285. The method of any one of embodiments 280-284, wherein the width of the constriction is about 3.5 μm to about 4.2 μm or about 3.5 μm to about 4.8 μm or about 3.5 μm to about 6 μm or about 4.2 μm to about 4.8 μm or about 4.2 μm to about 6 μm.

Embodiment 286. The method of any one of embodiments 280-285, wherein the width of the constriction is about 3.5 μm.

Embodiment 287. The method of any one of embodiments 280-286, wherein the width of the constriction is about 4.5 μm.

Embodiment 288. The method of any one of embodiments 280-287, wherein the cell suspension comprising the plurality of input nucleated cells are passed through multiple constrictions wherein the multiple constrictions are arranged in series and/or in parallel.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1

To determine if mRNA encoding for a chimeric membrane-bound cytokine can be translated and trafficked to the membrane of immune cells, human donor PBMCs were squeeze squeeze-loaded with mRNA encoding for a chimeric membrane-bound cytokine and the presence of the cytokine on the surface of immune cells was monitored by flow cytometry.

Methods

Figure 1:
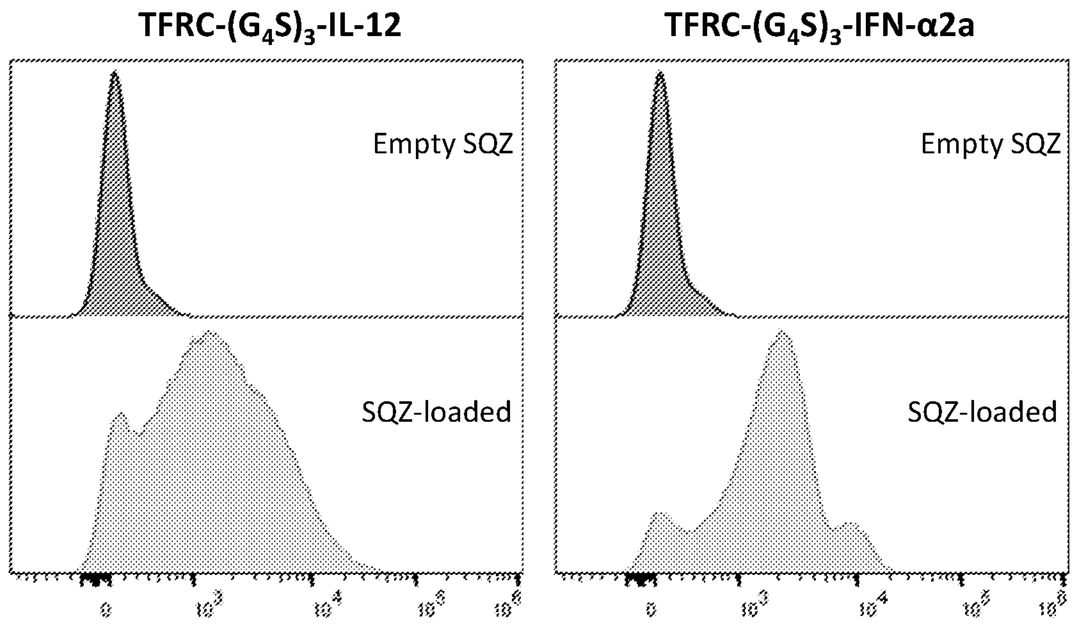
FIG. 1 is a fluorescence plot shows the surface expression of membrane-bound cytokines (IL-12, IFN-α2a) in PBMCs squeeze-loaded with mRNAs encoding the membrane-bound cytokines. $(G_4S)_3$ is SEQ ID NO: 73.

Human PBMCs were prepared at a density of $2\times10^7$/mL, and squeeze squeeze-processed at room temperature through a constriction of 3.5 μm width, 10 μm length, and 70 μm depth at 60 psi with 250 μg/ml of the respective mRNA encoding for a chimeric membrane-bound cytokine (either TFRC-$(G_4S)_3$-IL-12, or TFRC-$(G_4S)_3$-IFN-α2a) or with no cargo (empty squeezesqueeze) in Opti-MEM medium. Following squeeze squeeze-processing, the squeeze squeeze-loaded PBMCs were centrifuged, and the supernatant was discarded. The cells were subsequently washed twice in R10+ medium (RPMI, 10% FBS, 1% Pen/Strep, 1×ITS-A, 50 μM β-ME, 1×MEM NEAA), before resuspension in fresh R10+ medium. The cells were incubated for four hours at 37° C. and then incubated with the respective fluorescent antibodies (either AF488 anti-human IL-2, V450 anti-human IFN-α2b, or Pacific Blue anti-human p40 [IL-12]). To assess mRNA translation and trafficking to the membrane surface, fluorescence intensity of the antibodies bound to the immune cells was analyzed using an Attune N×T Acoustic Focusing Cytometer Results As shown in FIG. 1, human PBMCs squeeze-loaded with mRNA encoding for TFRC-$(G_4S)_3$-IL-12, or TFRC-$(G_4S)_3$-IFN-α2a resulted in an increase in the mean fluorescent intensity (MFI) of IL-12, and IFN-α2a for live immune cells in the squeeze-loaded sample compared to the empty squeeze sample. The results demonstrate human PBMCs squeeze-loaded with mRNA encoding for chimeric membrane-bound cytokines can translate the mRNAs and traffic the encoded proteins to the surface of immune cells.

Example 2

To determine if the chimeric membrane-bound cytokines retain their signaling functionality, human donor PBMCs were squeeze-loaded with mRNA encoding for a chimeric membrane-bound cytokine and co-cultured with cytokine-specific HEK-Blue reporter cells (InvivoGen).

Methods

Human PBMCs were prepared at a density of $2\times10^7$/mL, and squeeze-processed at room temperature through a constriction of 3.5 μm width, 10 μm length, and 70 μm depth at 60 psi with 250 μg/ml of the respective mRNA encoding for a chimeric membrane-bound cytokine (either TFRC-$(G_4S)_3$-IL-12, or TFRC-$(G_4S)_3$-IFN-α2a) or with no cargo (empty squeeze) in Opti-MEM medium. Following squeeze-processing, the squeeze-loaded PBMCs were centrifuged, and the supernatant was discarded. The cells were subsequently washed twice in test medium (DMEM, 10% FBS, 1× Pen/Strep, 2 mM L-glutamine), before resuspension in fresh test medium.

Logarithmically growing HEK-Blue IL-12, HEK-Blue IL-2, and HEK-Blue IFN-α/β (InvivoGen) reporter cells were harvested from culture flasks by rinsing flasks with PBS and co-cultured with the respective squeeze-loaded PBMCs or empty squeeze PBMCs in 96-well plates. The co-culture was incubated overnight at 37° C. before the culture supernatants was harvested. The binding of the respective cytokine to receptor, and activation of respective signaling pathway in the HEK-Blue reporter cells results in secretion of alkaline phosphatase in the culture supernatant. Secreted alkaline phosphatase (SEAP) was detected via a QUANTI-blue assay according to the manufacturer's protocol. The $OD_{630}$ of the HEK-Blue reporter cells alone was subtracted from $OD_{630}$ value for the empty squeeze and squeeze-loaded samples.

Results

Figure 2:
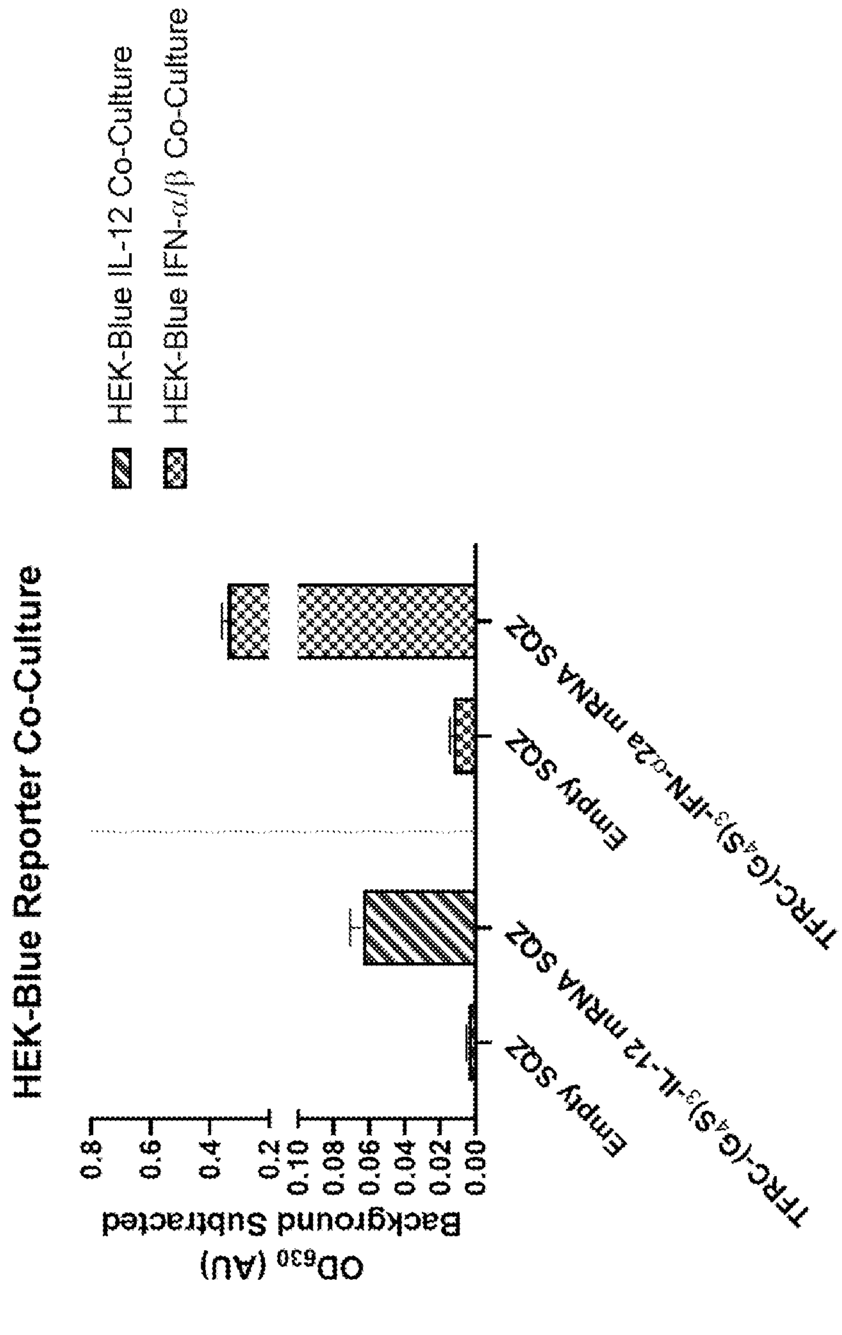
FIG. 2 is a graph showing the cytokine signaling activity by membrane-bound cytokines (IL-12, IFN-α2a) in PBMCs squeeze-loaded with mRNAs encoding the membrane-bound cytokines. $(G_4S)_3$ is SEQ ID NO: 73.

As shown in FIG. 2, human PBMCs squeeze-loaded with mRNA encoding for TFRC-$(G_4S)_3$-IL-12, or TFRC-$(G_4S)_3$-IFN-α2a were able to activate the respective signaling pathways, as shown by an increase in SEAP in the culture supernatant upon co-culture with the HEK-Blue IL-2, HEK-Blue IL-12, and HEK-Blue IFN-α/β, respectively. The results demonstrate that human PBMCs squeeze-loaded with mRNA encoding for chimeric membrane-bound cytokines produce chimeric cytokines that are functionally capable of binding to and signaling through their cognate receptors.

Example 3

To determine if mRNA encoding for a membrane-bound IL-2 can be translated, trafficked to the membrane of immune cells, human donor PBMCs were squeeze-loaded with mRNA encoding fora membrane-bound 11-2 and the presence of IL-2 on the surface of immune cells was monitored by flow cytometry over a time course of 50 hours.

Methods

Human PBMCs were prepared at a density of $2\times10^7$/mL, and squeeze-processed at room temperature through a constriction of 3.5 μm width, 10 μm length, and 70 μm depth at 60 psi with 250 μg/ml of the respective mRNA encoding for membrane-bound IL-2 (either TFRC-$(G_4S)_3$-IL-2, TFRC-$(EA_3K)_3$-IL-2, FasL-$(G_4S)_3$-IL-2, or FasL-$(EA_3K)_3$-IL-2) or untouched PBMCs (no contact) in Opti-MEM medium, Following squeeze processing, the squeeze-loaded PBMCs were centrifuged, and the supernatant was discarded. The cells were subsequently washed twice in X-VIVO 15+ medium (X-VIVO 15, 5% human serum, and 1×ITS-A), before resuspension in fresh X-VIVO 15+ medium. The cells were incubated for 48 hours at 37° C. Separate cultures were harvested at 4, 18, 24, and 48 hours post-squeeze processing. To assess expression of membrane-bound IL-2, Cells were incubated with the respective BV421 anti-human IL-2 antibody and fluorescence intensity of the antibodies bound to the immune cells was analyzed using an Attune N×T Acoustic Focusing Cytometer.

Results

Figure 3:
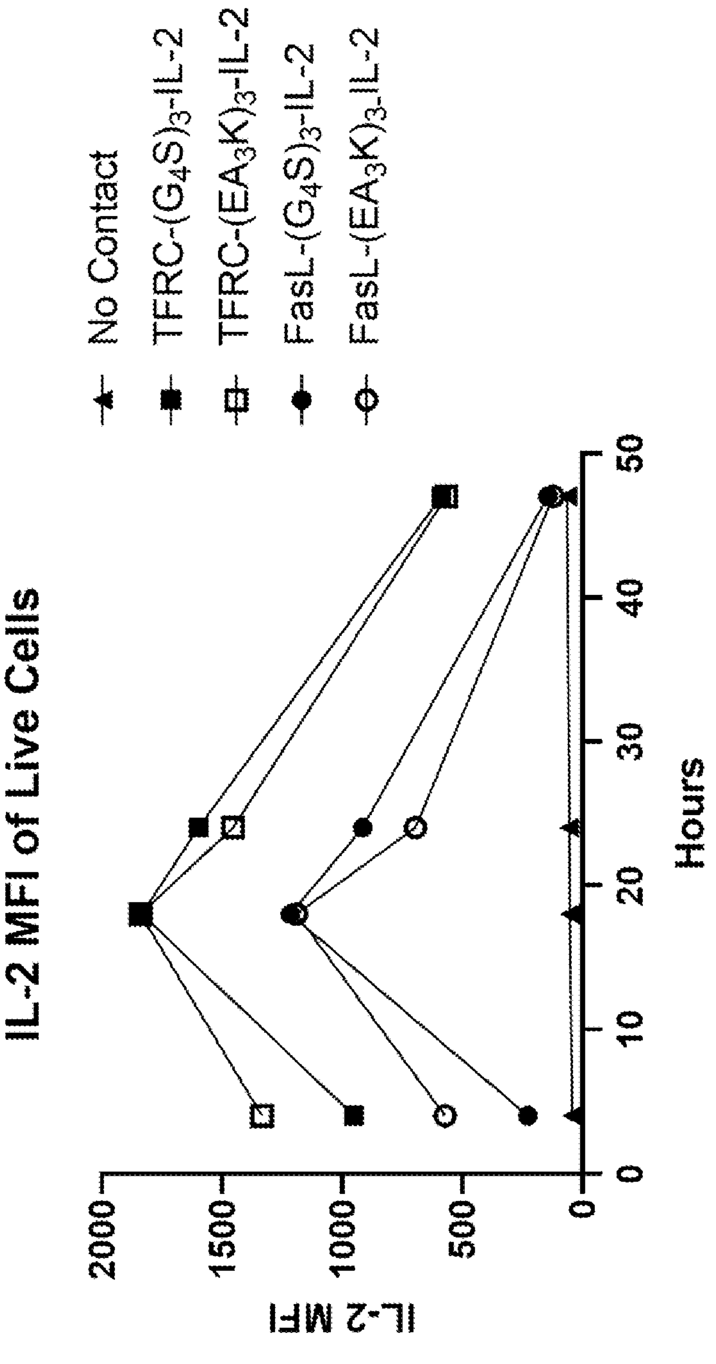
FIG. 3 is a graph showing the duration of surface expression of membrane-bound IL-2 in PBMCs squeeze-loaded with mRNAs encoding the membrane-bound IL-2. $(G_4S)_3$ is SEQ ID NO: 73, $(EA_3K)_3$ is SEQ ID NO:74.

As shown in FIG. 3, human PBMCs squeeze-loaded with mRNA encoding for membrane-bound IL-2 resulted in an increase in the mean fluorescent intensity (MFI) of IL-2 for live immune cells in the squeeze-loaded sample compared to the empty squeeze sample at each time point (4, 18, 24, and 48 hours post-squeeze). The results demonstrate human PBMCs squeeze-loaded with mRNA encoding for chimeric membrane-bound cytokines can translate and traffic the encoded proteins to the surface of immune cells, and that the IL-2 can be detected the surface of immune cells for >24 hours subsequent to squeeze processing.

Example 4

To determine if the chimeric membrane-bound cytokines retain their signaling functionality, human donor PBMCs were squeeze-loaded with mRNA encoding for membrane-bound IL-2 and co-cultured with HEK-Blue IL-2 reporter cells.

Methods

Human PBMCs were prepared at a density of $2\times10^7$/mL, and squeeze-processed at room temperature through a constriction of 3.5 μm width, 10 μm length, and 70 μm depth at 60 psi with 250 μg/ml of the respective mRNA encoding for membrane-bound IL-2 (either TFRC-$(G_4S)_3$-IL-2, TFRC-$(EA_3K)_3$-IL-2, FasL-$(G_4S)_3$-IL-2, or FasL-$(EA_3K)_3$-IL-2)

or with no cargo (empty squeeze) in Opti-MEM medium. Following squeeze-processing, the squeeze-loaded PBMCs were centrifuged, and the supernatant was discarded. The cells were subsequently washed twice in test medium (DMEM, 10% FBS, 1× Pen/Strep, 2 mM L-glutamine), before resuspension in fresh test medium.

Figure 4:
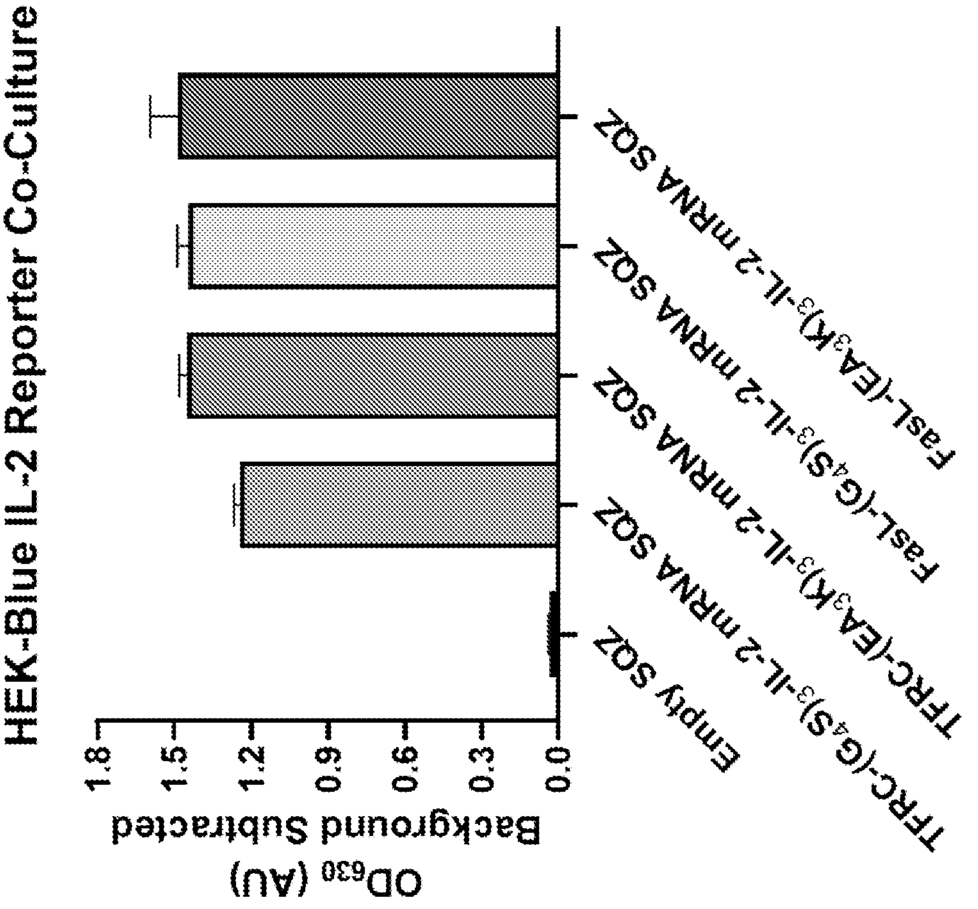
FIG. 4 is a graph showing the cytokine signaling activity by membrane-bound IL-2 in PBMCs squeeze-loaded with mRNAs encoding the membrane-bound IL-2. $(G_4S)_3$ is SEQ ID NO: 86, $(G_4S)_3$ is SEQ ID NO: 73, $(EA_3K)_3$ is SEQ ID NO:74.

Logarithmically growing HEK-Blue IL-2 reporter cells (InvivoGen) were harvested from culture flasks by rinsing flasks with PBS and co-cultured with the squeeze-loaded PBMCs or empty squeeze PBMCs in a 96-well plate. The co-culture was incubated overnight at 37° C. before the culture supernatants was harvested. The binding of IL-2 to its receptor, and activation of IL-2 signaling pathway in the HEK-Blue IL-2 reporter cells results in secretion of alkaline phosphatase in the culture supernatant. Secreted alkaline phosphatase (SEAP) was detected via a QUANTI-blue assay according to the manufacturer's protocol. The $OD_{640}$ of the HEK-Blue reporter cells alone was subtracted from $OD_{640}$ value for the empty squeeze and squeeze-loaded samples Results As shown in FIG. 4, human PBMCs squeeze-loaded with mRNA encoding for TFRC-$(G_4S)_3$-IL-2, TFRC-$(EA_3K)_3$-IL-2, FasL-$(G_4S)_3$-IL-2, or FasL-$(EA_3K)_3$-IL-2 were able to activate IL-2 signaling pathway, as shown by the increase in SEAP in the culture supernatant upon co-culture with HEK Blue IL-2 reporter cells, compared to non-activation by the empty squeeze PBMCs. The results demonstrate that human PBMCs squeeze-loaded with mRNA encoding for membrane-bound IL-2 produce chimeric IL-2 on the surface of immune cells that are functionally capable of binding to and signaling through the IL-2 receptor.

Example 5

To determine if immune cells squeeze-loaded with recombinant E7 (HPV16) protein can elicit an antigen-specific T cell response, human donor HLA-A*02+ PBMCs were squeeze-loaded with E7 protein and the ability to stimulate E7-specific T cells was measured by IFN-γ ELISA.

Methods

Human PBMCs from an HLA-A*02+ donor were prepared at a density of $10\times10^6$/mL, and squeeze-processed through a constriction of 4.5 μm width, 10 μm length, and 70 μm depth at 60 psi with 32 μg/ml of recombinant E7 protein (Abcam plc.), 50 μM E7.6 synthetic long peptide (SLP), or with no cargo (empty squeeze) in RPMI 164-0 medium. The microfluidic squeeze device was chilled on ice for 15 minutes prior to squeeze-processing. Following squeeze-processing, the squeeze-loaded PBMCs were centrifuged, and the supernatant was discarded. The cells were subsequently washed twice in co-culture medium (X-VIVO 15+5% human serum), before resuspension in fresh co-culture medium.

$1.2\times10^5$ squeeze-loaded PBMCs were then placed in co-culture with $3\times10^4$ HLA-A*02+$E7_{11-20}$ responder T cells (Cellero) in a 96-well plate. As a positive control, 0.02 μM of the minimal epitope. $E7_{11-20}$, was added directly to untreated PBMCs and responder cells in the 96-well plate ($E7_{11-20}$ peptide spike). After incubating the co-culture for 6 hours at 37° C., co-culture supernatants were harvested. An IFNγ ELISA was conducted according to the manufacturer's protocol to determine the concentration of IFNγ in the culture supernatant for each sample.

Results

Figure 5:
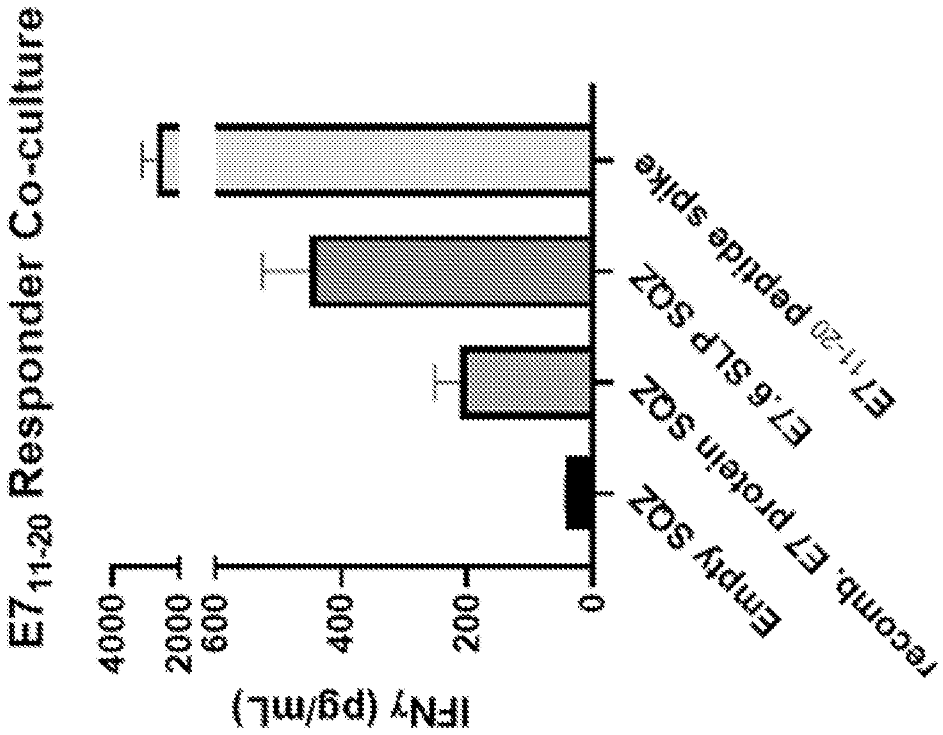
FIG. 5 is a graph showing the amount of IFN-γ secretion by $E7_{11-20}$ responder T cells upon co-culture with PBMCs loaded with recombinant E7 protein, or with an E7.6 SLP.

As shown in FIG. 5, human PBMCs squeeze-loaded with recombinant E7 protein and co-cultured with $E7_{11-20}$ responder T cells led to an increase in IFNγ production compared to the empty squeeze control. The results demonstrate that human PBMCs squeeze-loaded with full-length recombinant E7 protein can elicit a $E7_{11-20}$ peptide-specific T cell response.

Example 6

To determine the amount of E6 protein generated from native or codon-optimized E6 mRNA, human PBMCs were squeeze-loaded with the respective native or codon-optimized E6 mRNAs, and the level of expression was measured with Western blot.

Methods

Human PBMCs from two different HLA-A*02+ donors (237 and 246) were prepared at a density of $2\times10^7$/mL and squeeze-processed at room temperature through a constriction of 3.5 min width, 10 μm length and 70 μm depth at 60 psi with 250 μg/mL of respective E6 mRNA (native or codon-optimized) in Opti-MEM medium. Following squeeze processing, squeeze-loaded hPBMCs were centrifuged, and supernatant was discarded. The cells were subsequently washed twice in XVIVO 15 medium containing 5% human serum before resuspension in fresh XVIVO 15 medium containing 5% human serum.

$2.5\times10^6$ cells were then placed into a 96-well ULA plate and incubated for 90 minutes at 37° C. After 90 min incubation, the cells were harvested and centrifuged. Cell lysates were generated and used for western blot. The presence of E6 protein was detected via using a specific antibody against E6.

Results

Figure 6:
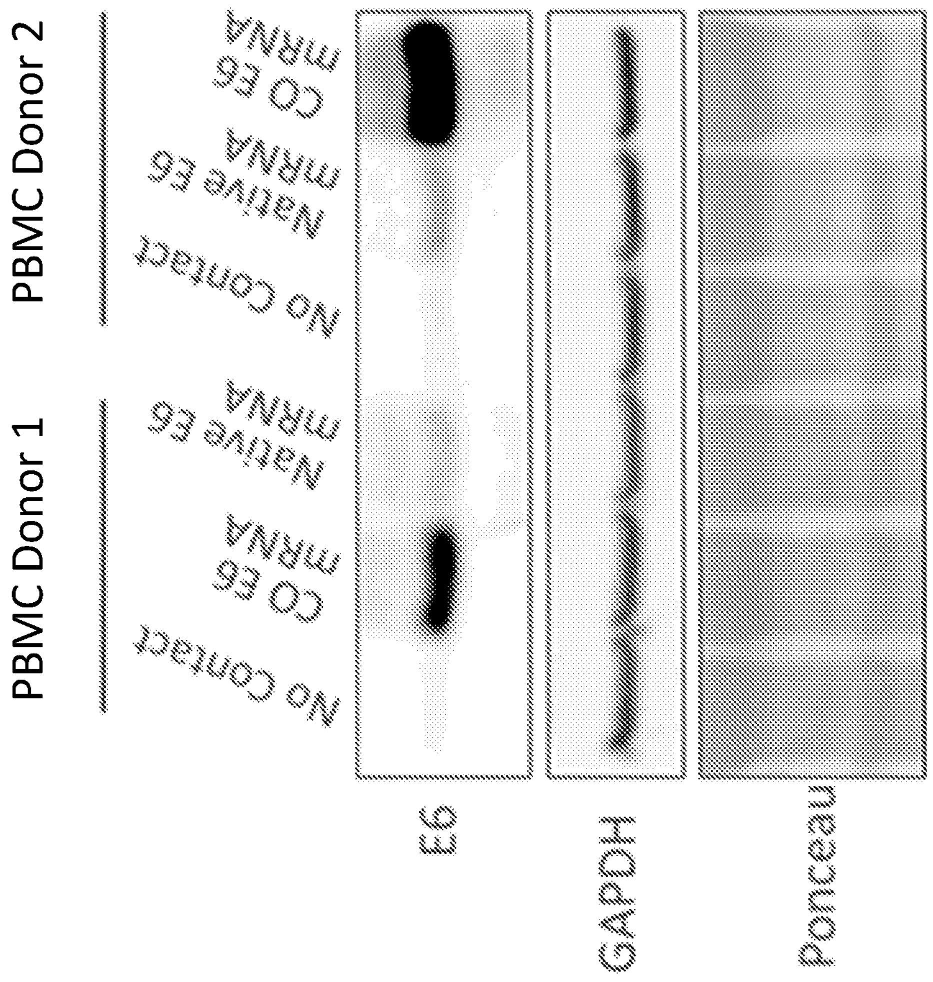
FIG. 6 is a Western Blot showing the amount of E6 protein expression by PBMCs squeeze-loaded with native E6 mRNA or codon-optimized E6 mRNA.

As shown in FIG. 6, E6 protein was successfully detected in squeeze-loaded PBMCs from two different HLA-A*02+ donors (237 and 246) after 90 minutes of squeeze loading. Moreover, codon optimization of E6 mRNA increased mRNA translation as compared to native E6 mRNA.

Example 7

To determine translation kinetics of codon-optimized E6 mRNA, human PBMCs were squeeze-loaded with the respective native or codon-optimized E6 mRNAs, and the level of expression over a time course of 24 hours was measured with Western blot.

Methods

Human PBMCs from two different HLA-A*02+ donors (224 and 239) were prepared at a density of $2\times10^7$/mL and squeeze-processed at room temperature through a constriction of 3.5 m width, 10 μm length and 70 μm depth at 60 psi with 250 μg/mL of codon-optimized E6 mRNA in Opti-MEM medium. Following squeeze processing, squeeze-loaded hPBMCs were centrifuged, and supernatant was discarded. The cells were subsequently washed twice in XVIVO 15 medium containing 5% human serum before resuspension in fresh XVIVO 15 medium containing 5% human serum.

$2.5\times10^6$ cells were then placed into a 96-well ULA plate and incubated for various time points (2, 6, and 24 hours) at 37° C. After each time point, the cells were harvested and centrifuged. Cell lysates were generated and used for western blot. The presence of E6 protein was detected via using a specific antibody against E6.

Results

Figure 7:
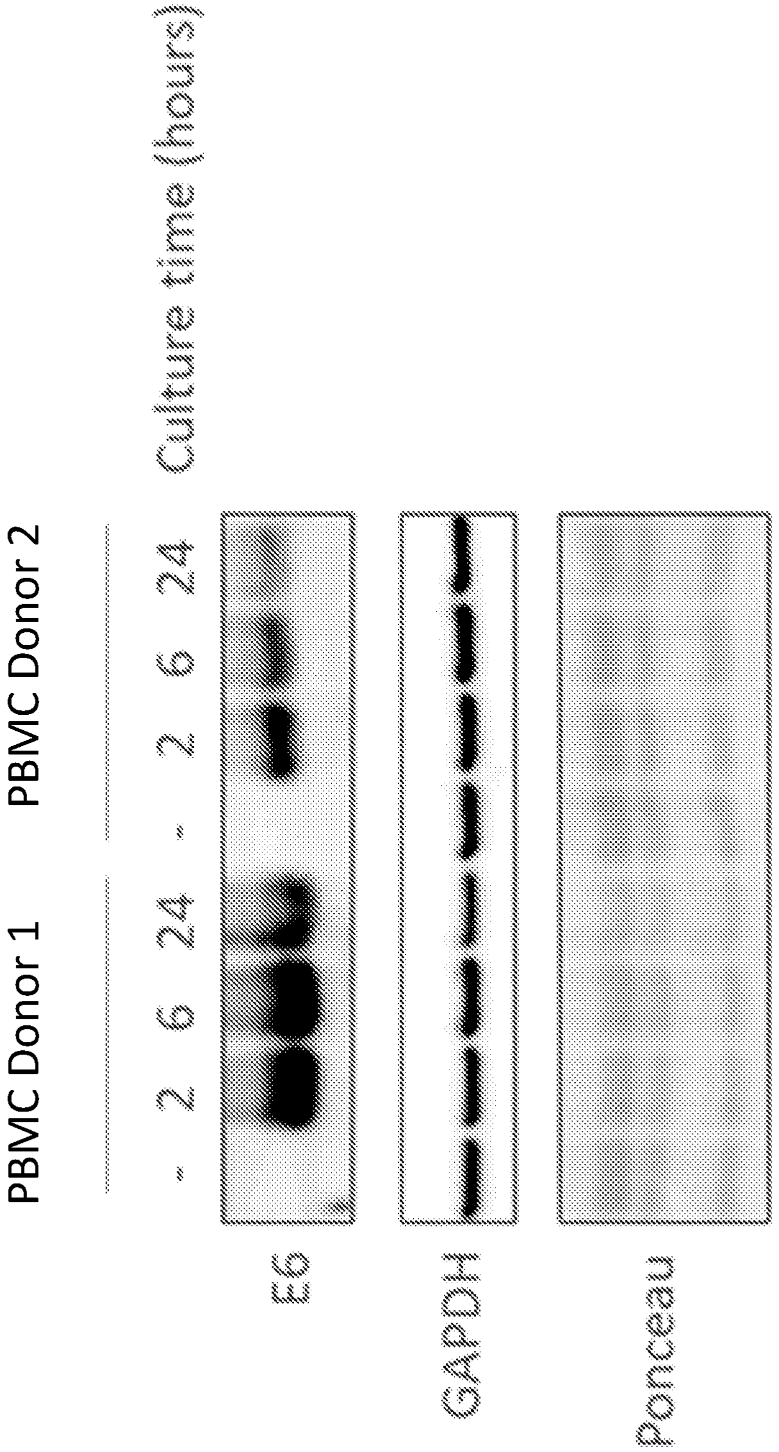
FIG. 7 is a Western Blot showing the kinetics of translation and expression of E6 protein by PBMCs squeeze-loaded with a codon-optimized E6 mRNA.

As shown in FIG. 7, E6 protein was successfully detected in squeeze-loaded PBMCs from two different HLA-A*02+ donors (224 and 239) at each time point assessed in this study. These results indicate that codon optimization could be used to facilitate or enhance mRNA translation of E6.

Example 8

To determine the kinetics of E7 protein following delivery of modified mRNA encoding E7, human PBMCs were squeeze-loaded with the respective native or codon-optimized E7 mRNAs with or without immunoproteasome-targeting motifs, and the level of expression over a time course of 6 hours was measured with Western blot.

Methods

Human PBMCs from HLA-A*02+ donor were prepared at a density of $2\times10^7$/mL and squeeze-processed at room temperature through a constriction of 3.5 μm width, 10 μm length and 70 μm depth at 60 psi with 250 μg/mL of respective E7 mRNA (native, D-box immunoproteasome-targeting motif, two different version of codon-optimized) in Opti-MEM medium. Following squeeze processing, squeeze-loaded hPBMCs were centrifuged, and supernatant was discarded. The cells were subsequently washed twice in XVIVO 15 medium containing 5% human serum before resuspension in fresh XVIVO 15 medium containing 5% human serum.

$2.5\times10^6$ cells were then placed into a 96-well ULA plate and incubated for up to 6 hours at 37° C. After the time point of 1-hour and 6-hour, the cells were harvested and centrifuged. Cell lysates were generated and used for western blot. The presence of E7 protein was detected via using a specific antibody against E7.

Results

Figure 8:
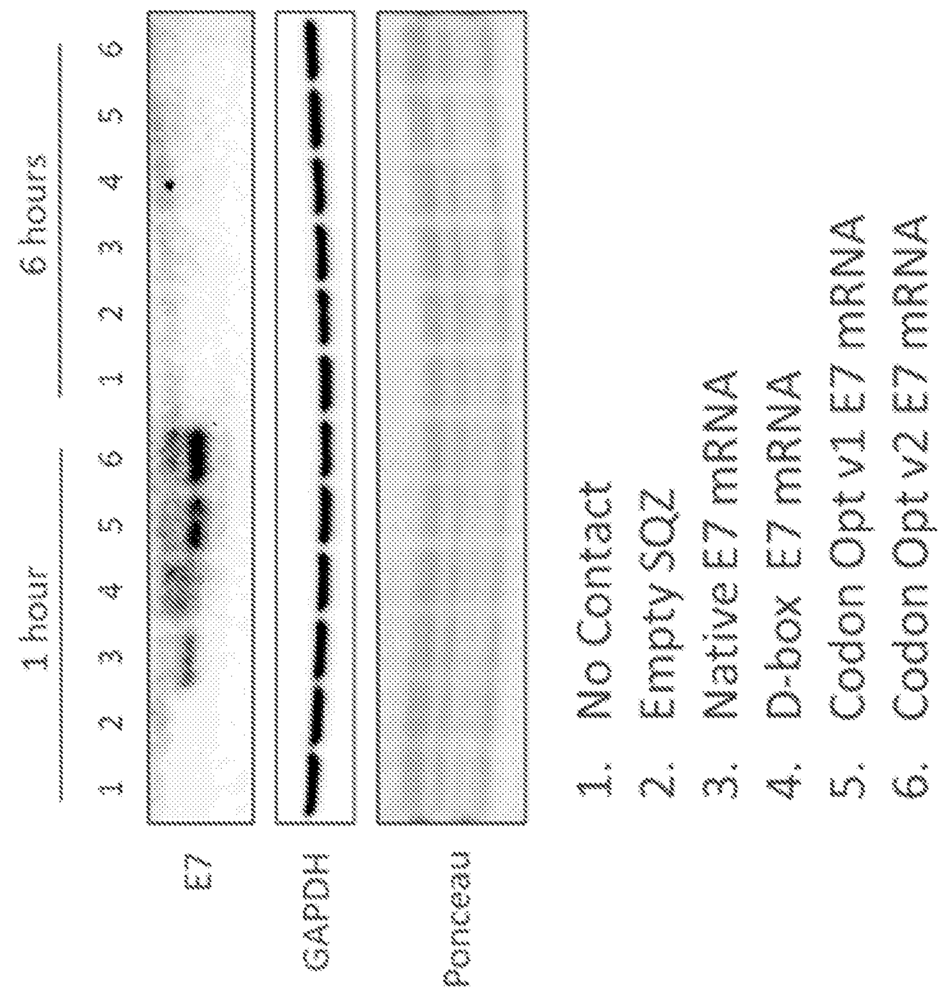
FIG. 8 is a Western Blot showing the kinetics of E6 protein by PBMCs squeeze-loaded with native E7 mRNA, codon-optimized E7 mRNA, or E7 mRNA that further encodes a D-box domain.

As shown in FIG. 8, E7 protein was successfully detected in squeeze-loaded PBMCs from HLA-A*02+ donor for each sample (native, D-box, codon optimized version 1 and version 2) after 1 hour of squeeze loading. Moreover, codon optimization of E7 mRNA increased mRNA translation as compared to native E7 mRNA. In addition. D-box motif containing E7 mRNA exhibited faster protein degradation compared to the native E7 mRNA. E7 protein was undetectable at 6 hours after squeeze loading.

Example 9

In order to determine if immune cells of a specific HLA haplotype squeeze-loaded with an E7 mRNA can induce an antigen-specific T cell response, human donor HLA-A*02, PBMCs were squeeze-loaded with various mRNA constructs encoding full-length E7 and the ability to stimulate $E7_{11-20}$-specific responder T cells was measured using an IFN-7 ELISA assay.

Methods

Human PBMCs from HLA-A*02+ donor were prepared at a density of $2\times10^7$/mL, and squeeze-processed at room temperature through a constriction of 3.5 μm width, 10 μm length and 70 μm depth at 60 psi with 250 μg/mL of various E7 mRNAs in Opti-MEM medium. Following squeeze-processing, the squeeze-loaded PBMCs were centrifuged, and the supernatant was discarded. The cells were subsequently washed twice in XVIVO 15 medium containing 5% human serum, before resuspension in XVIVO 15 medium containing 5% human serum.

$1.2\times10^5$ squeeze-loaded PBMCs were then placed in co-culture with $3\times10^4$ $E7_{11-20}$ responder T cells purchased from Cellero in a 96-well ULA plate. As a positive control, 20 nM $E7_{11-20}$ minimal epitope was added directly to untreated PBMCs and responder cells in the co-culture plate (peptide spike). The plate was incubated 6 hours or overnight at 37° C. and then developed/quantified according to manufacturer's instructions.

Results

Figure 9:
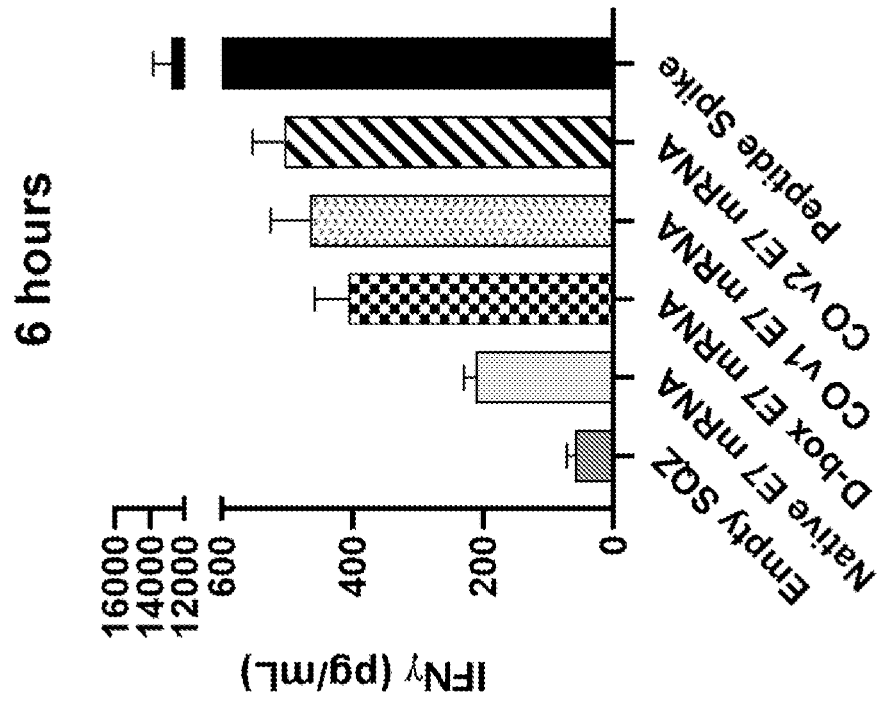
FIG. 9 is a graph showing the amount of IFN-γ secretion by $E7_{11-20}$ responder T cells upon co-culture with PBMCs squeeze-loaded with native E7 mRNA, codon-optimized E7 mRNA, or E7 mRNA that further encodes a D-box domain.

As shown in FIG. 9, HLA-A*02+ human PBMCs squeeze-loaded with various E7 mRNA constructs led to increased IFNγ secretion by $E7_{11-20}$-specific responder T cells upon co-culture for 6 hours. Furthermore, E7 mRNA constructs further encoding an immunoproteasome-targeting motif (D-box E7) or with codon optimization (CO v1 and CO v2) led to increased IFNγ secretion as compared to native E7 mRNA construct. These results demonstrate HLA-A*02+ human PBMCs squeeze-loaded with an E7 mRNA can induce an antigen-specific T cell response and this can be further enhanced by codon optimization or adding immunoproteasome-targeting motif to E7 mRNA.

Example 10

In order to determine if immune cells of a specific HLA haplotype squeeze-loaded with an E7 mRNA can induce an antigen-specific T cell response, human donor HLA-A*02. PBMCs were squeeze-loaded with various mRNA constructs encoding full-length E7 and the ability to stimulate $E7_{11-20}$-specific responder T cells was measured using an IFN-γ ELISA assay.

Methods

Human PBMCs from HLA-A*02+ donor were prepared at a density of $2\times10^7$/mL, and squeeze-processed at room temperature through a constriction of 3.5 μm width, 10 μm length and 70 μml depth at 60 psi with 250 μg/mL of various E7 mRNAs in Opti-MEM medium. Following squeeze-processing, the squeeze-loaded PBMCs were centrifuged, and the supernatant was discarded. The cells were subsequently washed twice in XVIVO 15 medium containing 5% human serum, before resuspension in XVIVO 15 medium containing 5% human serum.

$1.2\times10^5$ squeeze-loaded PBMCs were then placed in co-culture with $3\times10^4$ $E7_{11-20}$ responder T cells purchased from Cellero in a 96-well ULA plate. As a positive control, 20 nM $E7_{11-20}$ terminal epitope was added directly to untreated PBMCs and responder cells in the co-culture plate (peptide spike). The plate was incubated 6 hours or overnight at 37° C. and then developed/quantified according to manufacturer's instructions.

Results

Figure 10B:
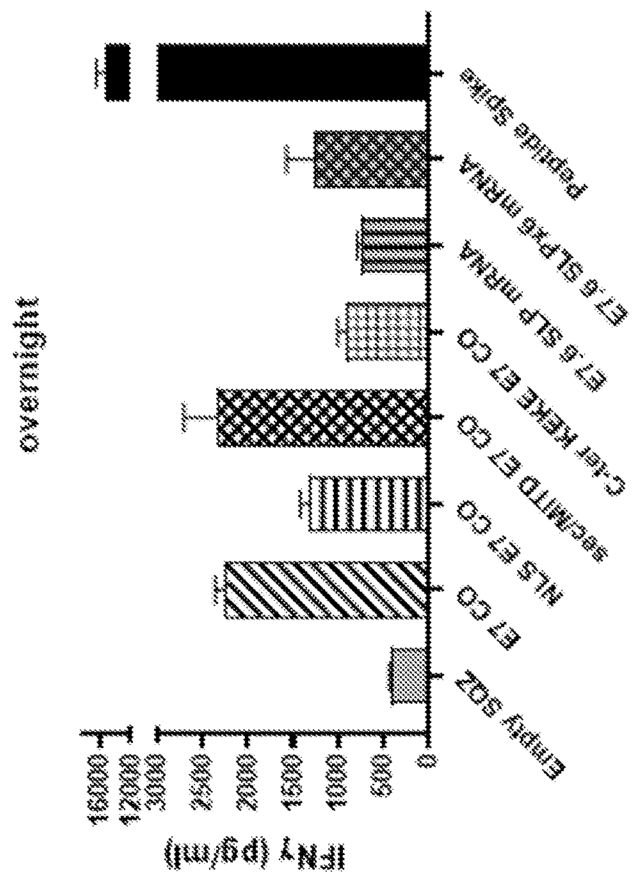
FIGS. 10A and 10B are graphs showing the amount of IFN-γ secretion by $E7_{11-20}$ responder T cells upon a 6-hour or overnight co-culture, respectively, with PBMCs squeeze-loaded with the indicated mRNAs encoding the E7 protein or E7 SLP.
Figure 10A:
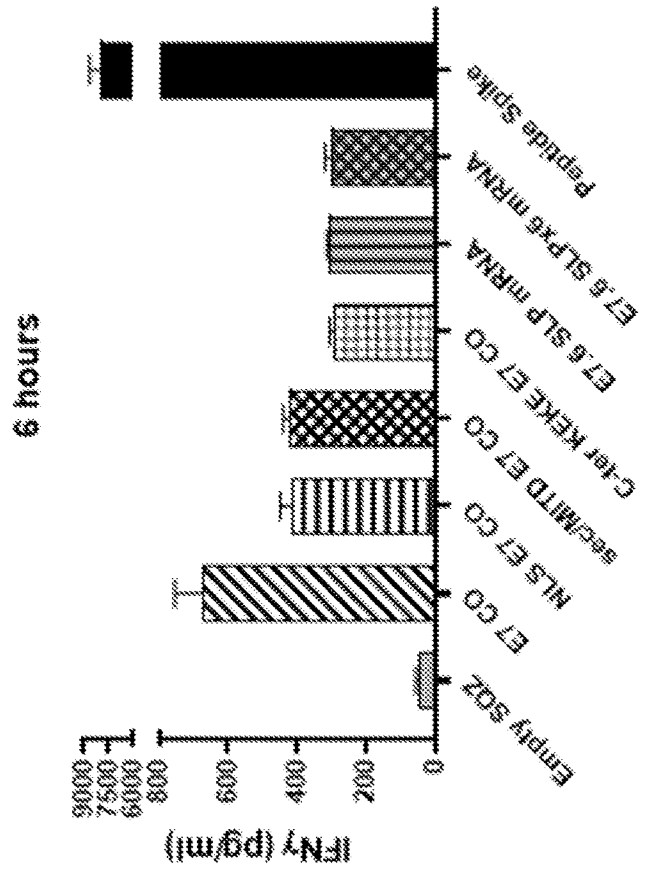

As shown in FIGS. 10A and 10B, HLA-A*02+ human PBMCs squeeze-loaded with various E7 mRNA constructs (E7 CO: codon-optimized E7 mRNA; NLS E7 CO: codon-optimized E7 mRNA further encoding mutated NLS; sec/MITD E7 CO codon-optimized E7 mRNA further encoding sec/MITD localization domain; C-ter KEKE E7 CO: codon-optimized E7 mRNA further encoding C-terminal KEKE immunoproteasome-targeting motif; mRNA encoding E7.6 SLP. mRNA encoding 6× repeats of E7.6 SLP) led to IFNγ secretion detected both after 6 hours and overnight of co-culture.

Example 11

In order to determine if immune cells of a specific HLA haplotype squeeze-loaded with an E7 mRNA can induce an antigen-specific T cell response, human donor HLA-A*02+ PBMCs were squeeze-loaded with various mRNA constructs encoding full-length E7 and the ability to stimulate $E7_{11-20}$-specific responder T cells was measured using an IFN-γ ELISA assay.

Methods

Human PBMCs from HLA-A*02+ donor were prepared at a density of $2\times10^7$/mL, and squeeze-processed at room temperature through a constriction of 3.5 μm width, 10 μm length and 70 μm depth at 60 psi with 250 μg/mL of various E7 mRNAs in Opti-MEM medium. Following squeeze-processing, the squeeze-loaded PBMCs were centrifuged, and the supernatant was discarded. The cells were subsequently washed twice in XVIVO 15 medium containing 5% human serum, before resuspension in XVIVO 15 medium containing 5% human serum.

$1.2\times10^5$ squeeze-loaded PBMCs were then placed in co-culture with $3\times10^4$ $E7_{11-20}$ responder T cells purchased from Cellero in a 96-well ULA plate. As a positive control, 20 nM $E7_{11-20}$ minimal epitope was added directly to untreated PBMCs and responder cells in the co-culture plate (peptide spike). The plate was incubated 6 hours or overnight at 37° C. and then developed/quantified according to manufacturer's instructions.

Results

Figure 11B:
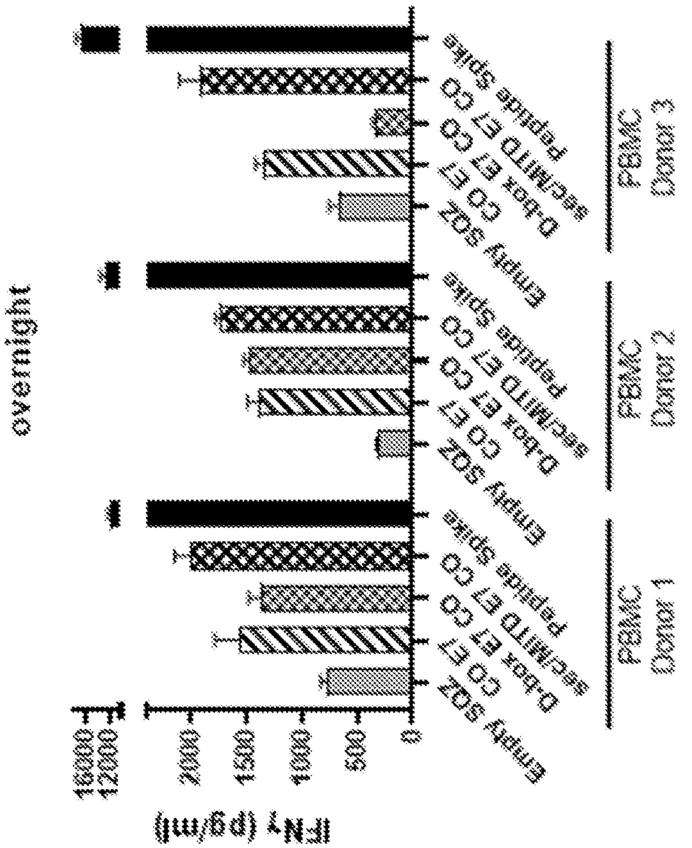
FIGS. 11A and 11B are graphs showing the amount of IFN-γ secretion by $E7_{11-20}$ responder T cells upon a 6-hour or overnight co-culture, respectively, with PBMCs squeeze-loaded with the indicated mRNAs encoding the E7 protein.
Figure 11A:
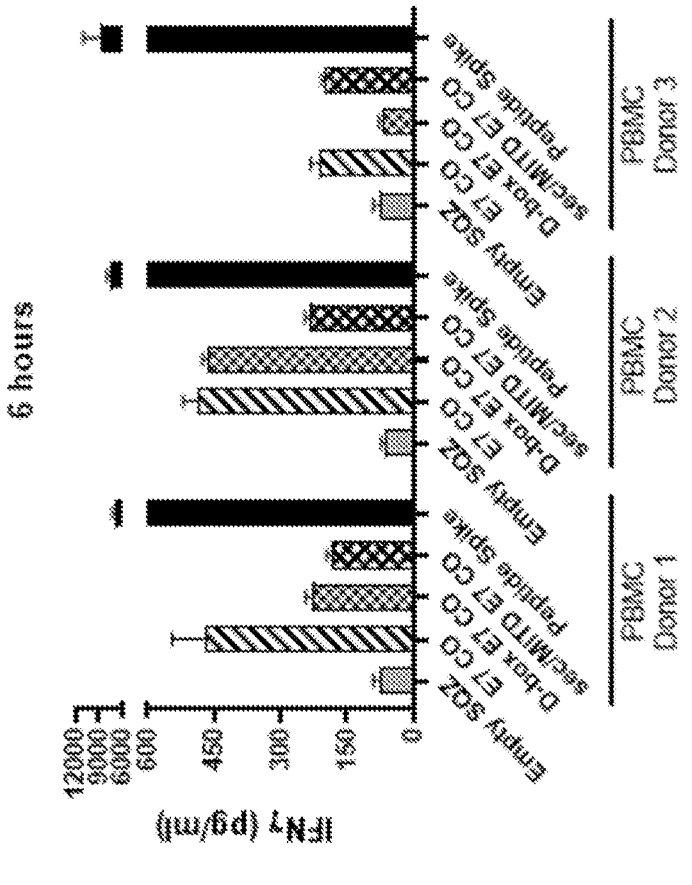

As shown in FIGS. 11A and 11B, HLA-A*02+ human PBMCs squeeze-loaded with various E7 mRNA constructs led to IFNγ secretion by $E7_{11-20}$-specific responder T cells upon co-culture for 6 hours or overnight. Moreover, this induction of $E7_{11-20}$-specific T cell response can be observed consistently from multiple HLA-A*02+ human PBMC donors squeeze-loaded with various E7 mRNA constructs. The results demonstrate different HLA-A*02+ human PBMC donors squeeze-loaded with an E7 mRNA can induce an antigen-specific T cell response.

Example 12

To determine if co-delivery of Signal 2 and Signal 3 mediators can enhance the ability to stimulate T cell responses by antigen presenting cells squeeze-loaded with an antigen, human donor HLA-A*02+ PBMCs were squeeze-loaded with different mRNAs encoding effectors mediating Signal 1, Signal 2, and/or Signal 3 respectively. The activation of CD3+ CD8+ responder cells was measured via intracellular cytokine staining (ICS). The effect of various mRNA squeeze-loaded cells restimulated with peptide were compared to that of cells incubated with CMV pp65 peptide (peptide spike control).

Methods

Human PBMCs isolated from a CMV+ HLA-A*02+ leukopak were stained with CMVpp65 tetramer specific to NLVPMVATV (495.503 aa; SEQ ID NO:88) to determine that these PBMCs have pre-existing pp65-specific CD8 T cells. Subsequently the PBMCs were prepared at a density of $2\times10^7$ cells/mL and combined with mRNA encoding CMV pp65 (Signal 1), mRNA encoding CD86 (Signal 2), and/or mRNA encoding membrane-bound interleukin-12 (mbIL-12) (Signal 3). The cells were squeeze processed in the presence of the mRNA(s) at room temperature using a Cell Squeeze® system and chip through a constriction of 3.5 μm width, 10 μm length, and 70 μm depth at 60 psi in RPMI medium. PBMCs squeeze processed with empty payload (Empty squeeze) and further incubated with 10 nM CMV pp65 peptide was used as a control. The following concentrations and mixtures of each mRNA were tested.

TABLE 1

| Sample | Signal 1 (CO pp65 mRNA) | Signal 2 (CO CD86 mRNA) | Signal 3 (CO mbIL-12 mRNA) |
|---|---|---|---|
| Empty SQZ | — | — | — |
| A | 25 μg/mL | — | — |
| B | 50 μg/mL | — | — |
| C | 100 μg/mL | — | — |
| D | 25 μg/mL | 250 μg/mL | — |
| E | 50 μg/mL | 250 μg/mL | — |
| F | 100 μg/mL | 250 μg/mL | — |
| G | 25 μg/mL | 250 μg/mL | 250 μg/mL |
| H | 50 μg/mL | 250 μg/mL | 250 μg/mL |
| I | 100 μg/mL | 250 μg/mL | 250 μg/mL |
| J | Empty SQZ cells + 10 nM pp65 CMV peptide spike | | |

For example, for Sample G, a total volume of 225 uL of cells in a cell suspension was squeeze processed with mRNAs at the following concentrations: 25 ug/mL of CMV pp65 mRNA, 250 ug/mL of CD86 mRNA, and/or 250 ug/mL of membrane-bound interleukin-12 mRNA.

Following squeeze-processing, the squeeze-loaded PBMCs were transferred to RPMI+10% fetal bovine serum and incubated for 5 days at 37° C. At the final day of incubation, the resulting cells were re-stimulated with 1 μM CMV pp65 peptide, or left without re-stimulation, and their activation and activity was measured via ICS. TNF-α, IFN-γ, IL-2, PD-1, and Granzyme B were assessed in CD3+ CD8+ responder cells.

Results

Figure 12A:
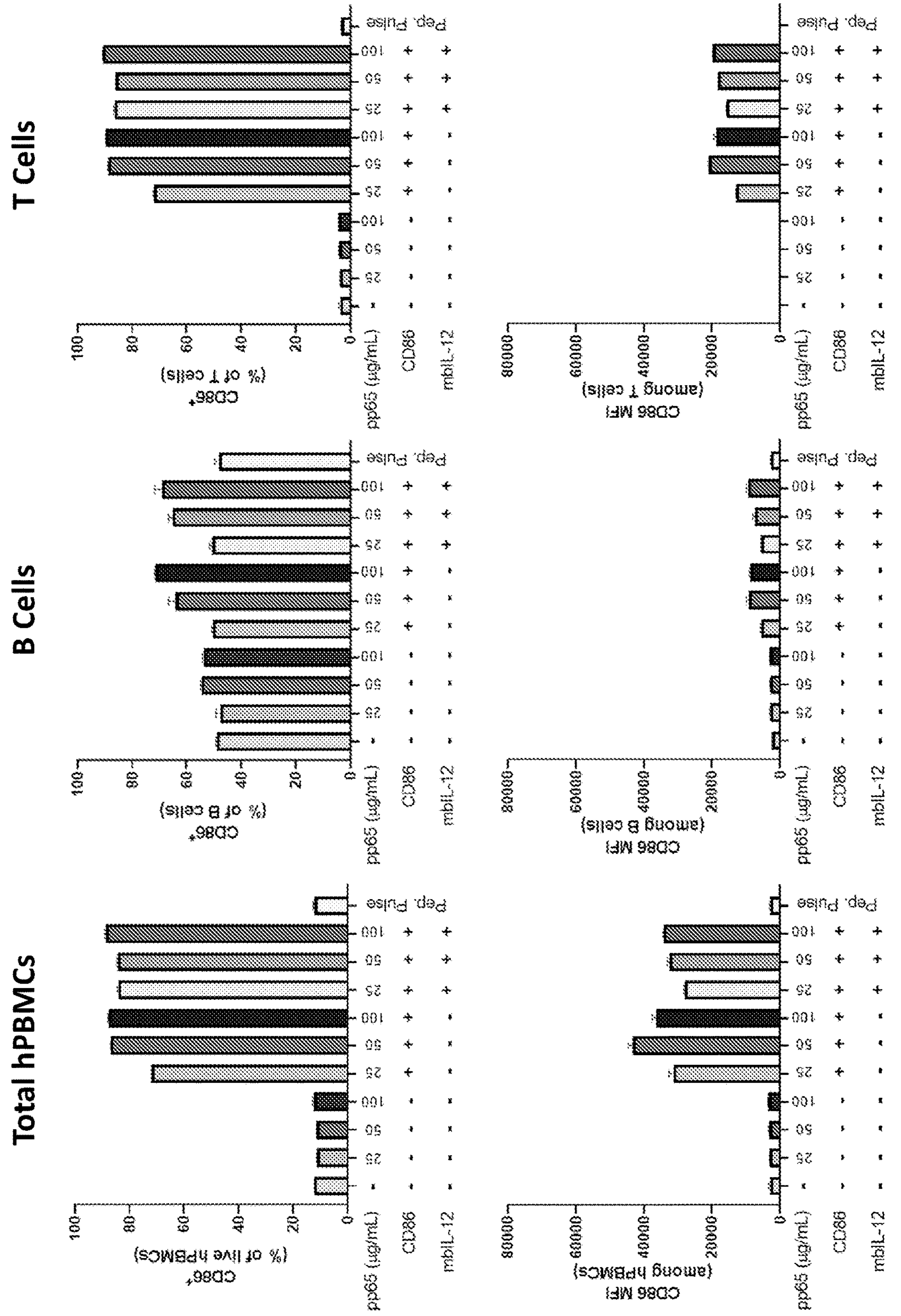
FIGS. 12A, B contain graphs showing CD-86 expression in PBMCs and constituent cell types within PBMCs that are squeeze-loaded with the indicated amount of mRNAs encoding for CMV pp65 antigen, CD86 and/or membrane-bound IL-12 (mbIL-12).
Figure 12B:
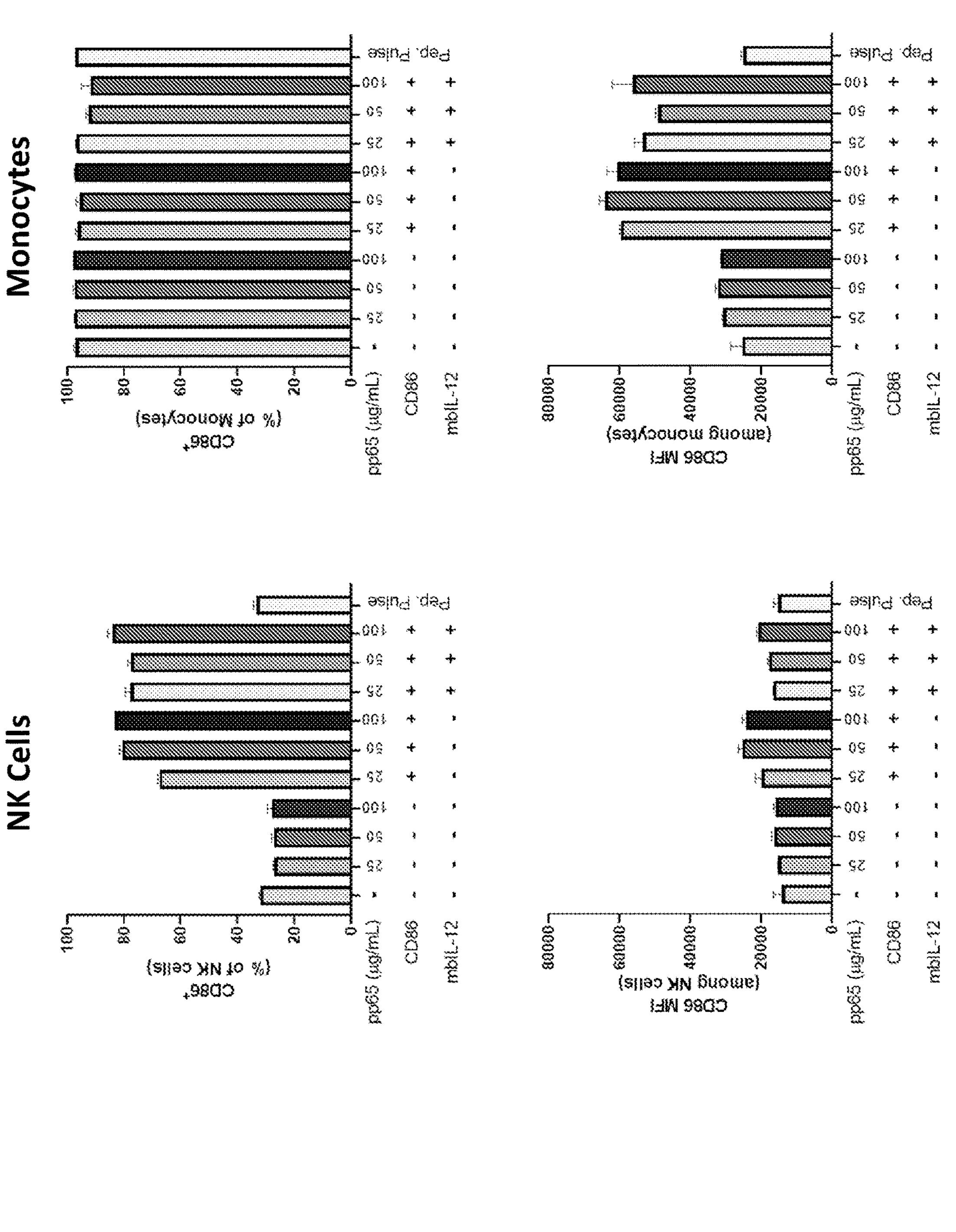
Figure 13A:
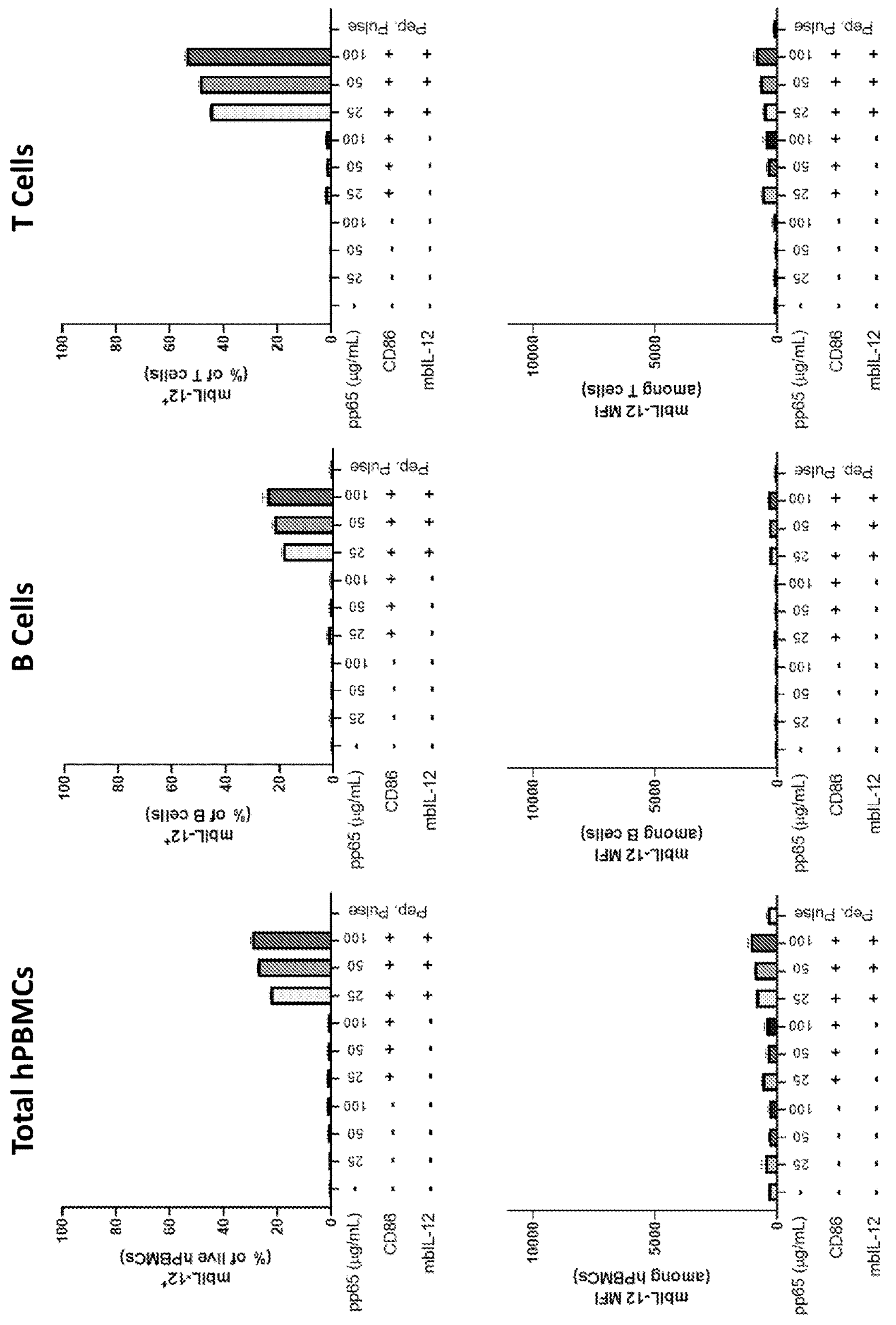
FIGS. 13A, B contain graphs showing membrane-bound IL-42 (mbIL-12) expression in PBMCs and constituent cell types within PBMCs that are squeeze-loaded with the indicated amount of mRNA sencoding for CMV pp65 antigen, CD86 and/or mbIL-12.
Figure 13B:
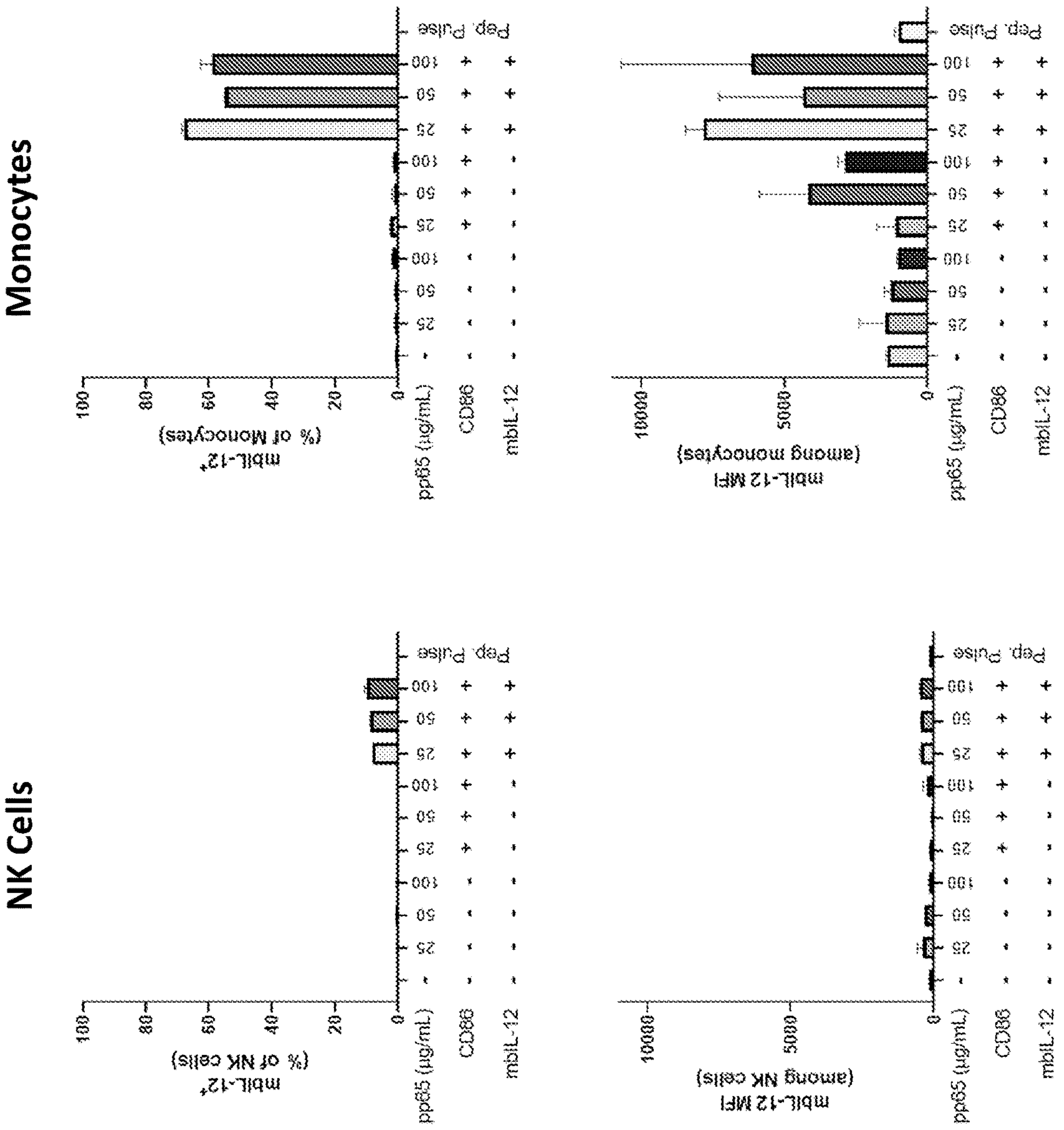

As shown by intracellular staining, there was successful translation of CD86 mRNA (FIGS. 12A, B) and mbIL-12 mRNA (FIGS. 13A, B) at 24 hours subsequent to squeeze-mediated delivery of mRNAs encoding CD86 or mbIL-12 respectively.

Figure 14:
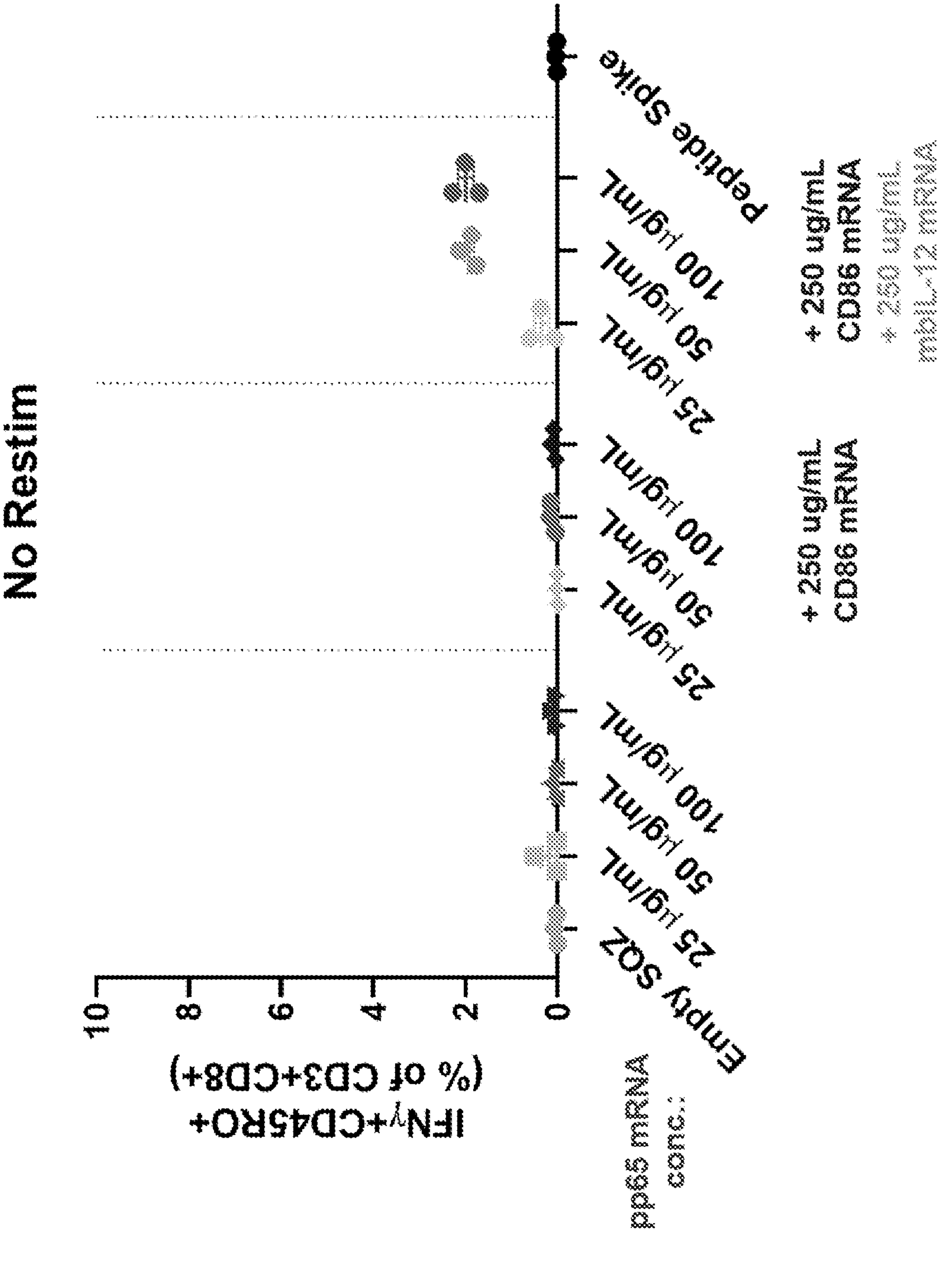
FIG. 14 is a graph showing the percentage of IFN-γ+ CD45RO+ population within CD3+CD8+ responder T cell populations when PBMCs are squeeze-loaded with the indicated amount of mRNAs encoding for CMV pp65 antigen, CD86 and/or mbIL-12.
Figure 15:
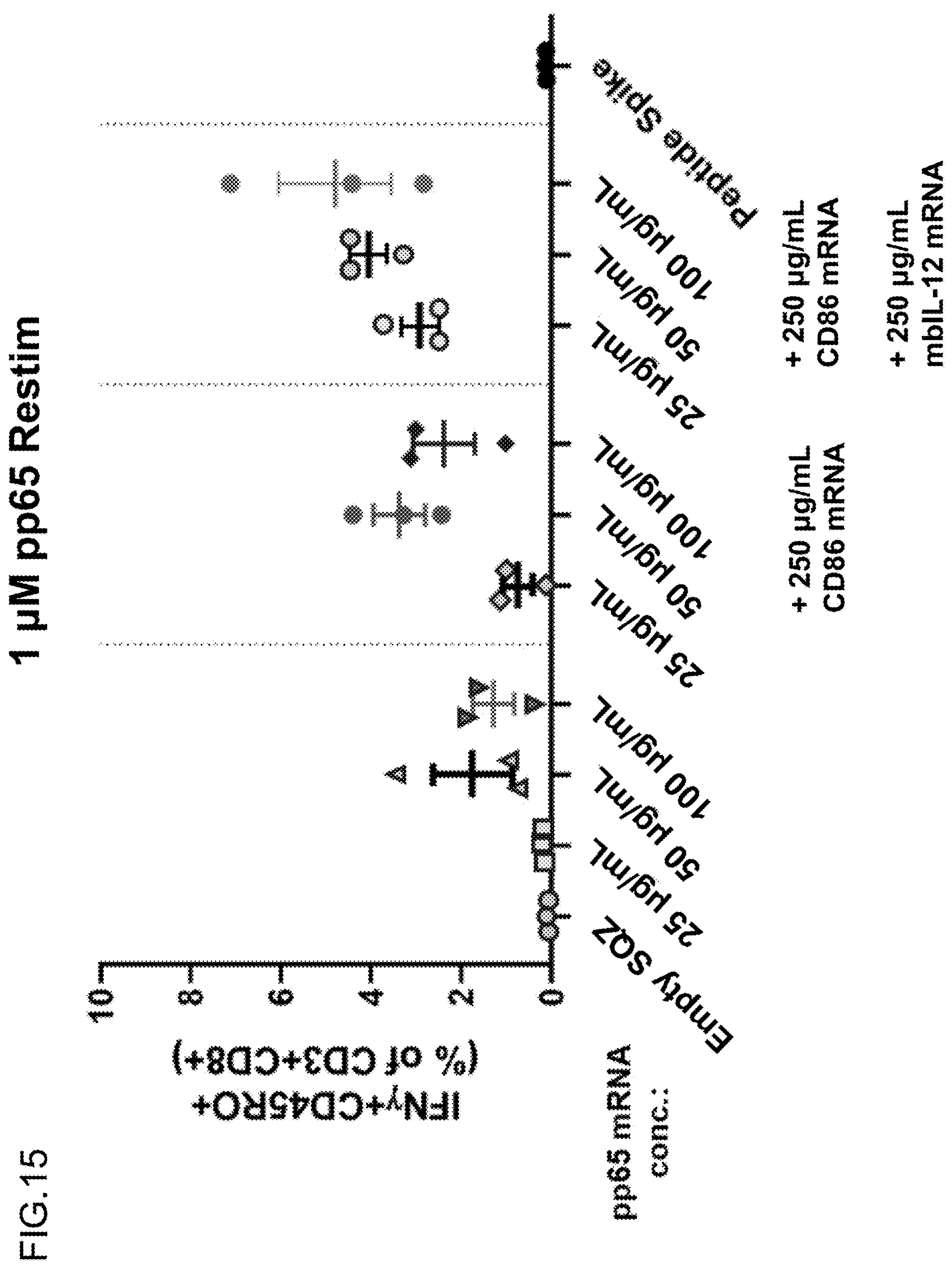
FIG. 15 is a graph showing the percentage of IFN-γ+ CD45RO+ population within CD3+CD8+ responder T cell populations when PBMCs are squeeze-loaded with the indicated amount of mRNAs encoding for CMV pp65 antigen, CD86 and/or mbIL-12, and subsequently further re-stimulated with 1 μM of pp65 antigen.
Figure 16B:
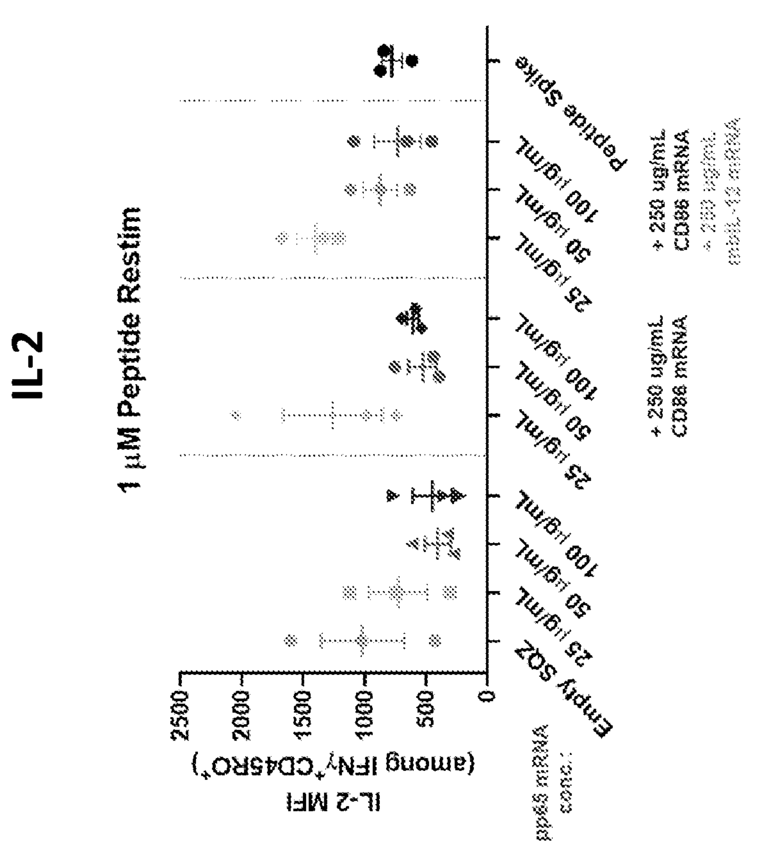
FIGS. 16A-E show the amount of expression for functionality marker IFN-γ, IL-2, TNF-α, Granzyme B, PD-1 respectively within activated responder T cell populations when PBMCs are squeeze-loaded with the indicated amount of mRNAs encoding for CMV pp65 antigen, CD86 and/or mbIL-12, and subsequently further re-stimulated with 1 μM of pp65 antigen.
Figure 16A:
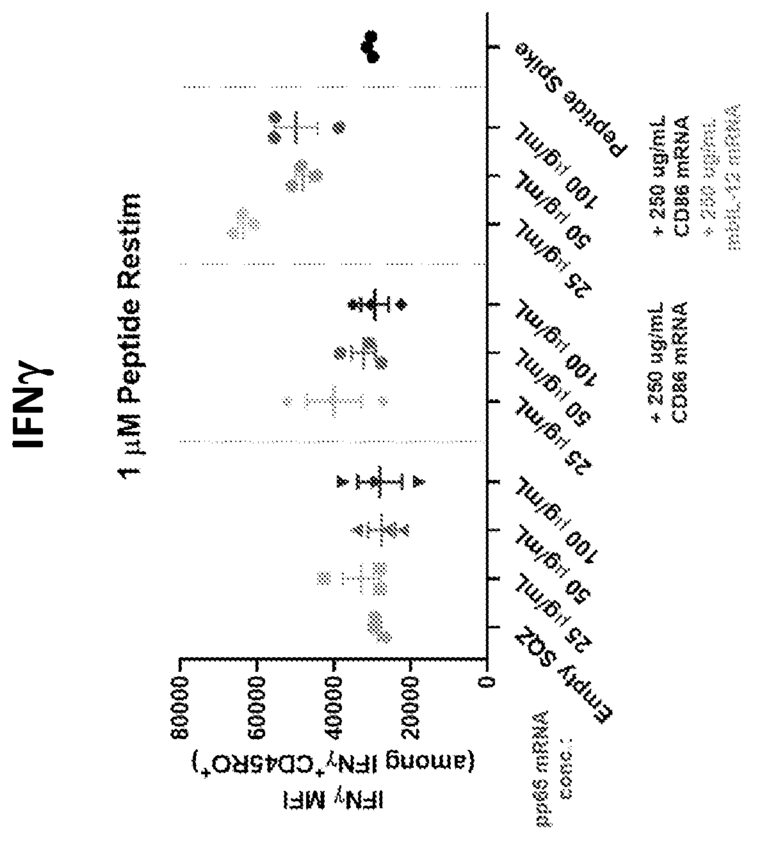
Figure 16C:
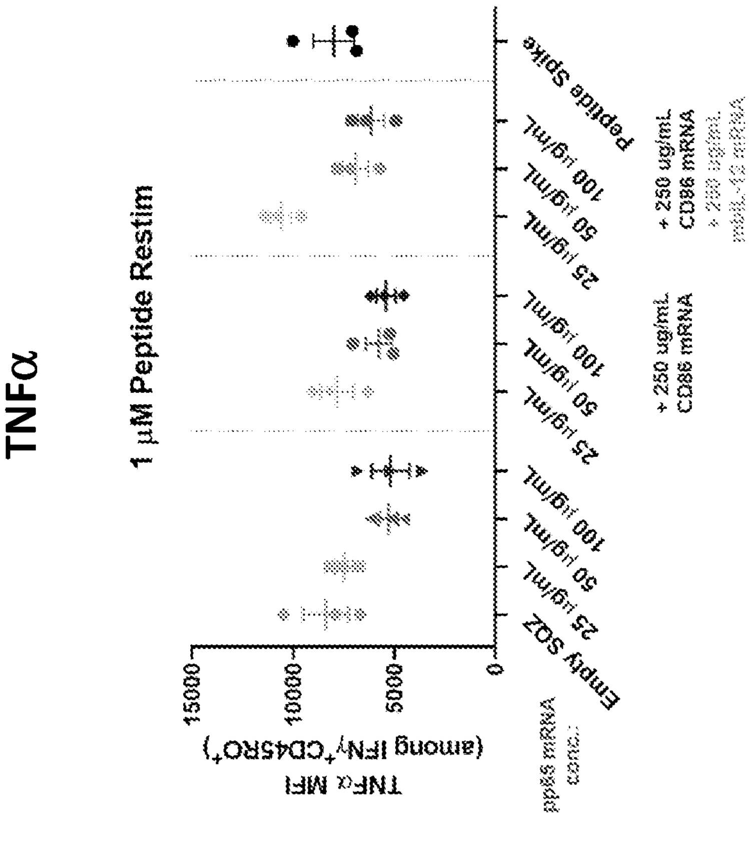
Figure 16D:
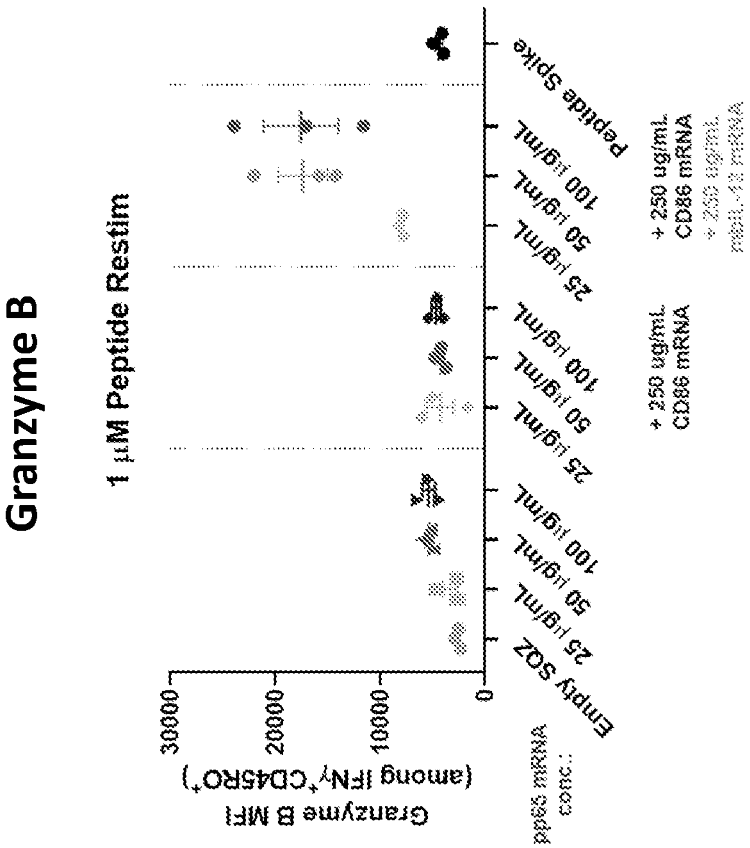
Figure 16E:
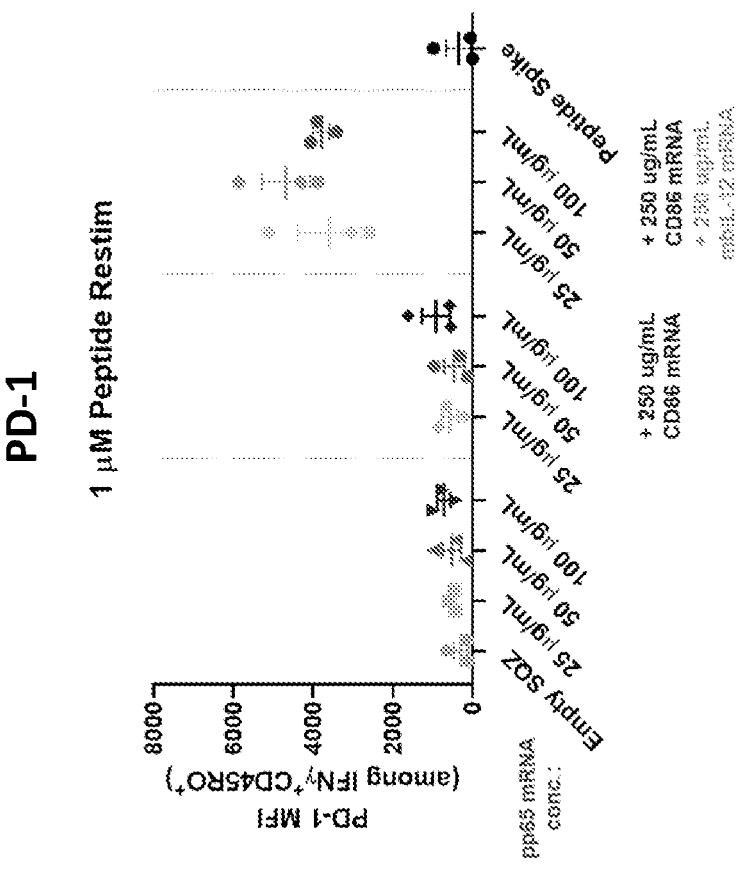

FIG. 14 shows the concentration effects of CMV pp65 mRNA for mRNA-loaded PBMCs in activating antigen-specific T cells without restimulation. FIG. 15 shows the concentration effects of CMV pp65 mRNA mRNA for mRNA-loaded PBMCs in activating antigen-specific T cells with 1 μM of antigen restimulation. As shown in FIG. 15, T cell activation was observed at all 50 ug/mL and 100 ug/mL of squeeze-loaded pp65 mRNA, as demonstrated by induction of IFN-γ+CD45RO+ populations within CD3+CD8+ responders. Both figures show a higher percentage of IFN-γ+CD45RO+CD3+ CD8+ cells when the CMV pp65 mRNA were squeezed with CD86 mRNA and mbIL-12 mRNA.

FIGS. 16A-E show that the antigen-specific CD8 T cells were polyfunctional as shown by IFNg, IL-2, TNFa, Granzyme B, PD-1 expression. The further introduction of mRNAs encoding signal 2/3 mRNAs in PBMCs further upregulated these functional markers as compared to antigen alone (i.e., squeeze-loading of pp65 mRNA alone into PBMCs).

Example 13

To measure the effects of CpG maturation on squeezed cells, human donor HLA-A*02+ PBMCs were squeeze-loaded with different mRNAs encoding effectors mediating Signal 1, Signal 2, and/or Signal 3 respectively. For each PBMC sample, half of the cells were matured with 1 μM of CpG 7909 for 4 hours. At the end of 4-hour maturation, excess CpG 7909 was washed and the cells were plated and incubated for 5 days at 37° C. On day 5, the activation of CD3+ CD8+ cells and activity was measured via ICS as well as tetramer analysis. The effect of various mRNA squeeze-loaded cells matured with CpG 7909 were compared to that of PBMCs squeeze-processed with empty payload and spiked with CMV pp65 peptide and also to that of PBMCs treated with PMA/Ionomycin.

Methods

Human PBMCs isolated from a CMV+ HLA-A*02+ leukopak were stained with CMVpp65 tetramer specific to NLVPMVATV (495-503 aa; SEQ ID NO:88) to determine that these PBMCs have pre-existing pp65-specific CD8 T cells. Subsequently the PBMCs were prepared at a density of $2\times10^7$ cells/mL and combined with mRNA encoding CMV pp65 (Signal 1), CD86 (Signal 2), and/or membrane-bound interleukin-12 (mbIL-12) (Signal 3). The cells were squeeze processed in the presence of the respective mRNAs at room temperature using a Cell Squeeze® system and chip through a constriction of 3.5 μm width, 10 μm length, and 70 μm depth at 60 psi in RPMI medium. PBMCs squeeze processed with empty payload (Empty squeeze) and further with 10 nM CMV pp65 peptide was used as a control. The following concentrations and mixtures of each mRNA were tested.

TABLE 2

| Sample | Signal 1 (CO pp65 mRNA) | Signal 2 (CO CD86 inRNA) | Signal 3 (CO mbIL-12 inRNA) |
|---|---|---|---|
| Empty SQZ | — | — | — |
| A | 10 μg/mL | — | — |
| B | 50 μg/mL | — | — |
| C | 10 μg/mL | 250 μg/mL | — |
| D | 50 μg/mL | 250 μg/mL | — |
| E | 10 μg/mL | — | 250 μg/mL |
| F | 50 μg/mL | — | 250 μg/mL |
| G | 10 μg/mL | 250 μg/mL | 250 μg/mL |

TABLE 2-continued

| Sample | Signal 1 (CO pp65 mRNA) | Signal 2 (CO CD86 inRNA) | Signal 3 (CO mbIL-12 inRNA) |
|---|---|---|---|
| H | 50 μg/mL | 250 μg/mL | 250 μg/mL |
| I | Empty SQZ cells + 10 nM pp65 CMV peptide spike | | |
| J | Empty SQZ cells + PMA/Ionomycin on Day 6 | | |

For example, for Sample G, a total volume of 500 μL of cells in a cell suspension was squeeze processed with mRNAs at the following concentrations: 10 ug/mL of CMV pp65 mRNA, 250 ug/mL of CD86 mRNA, and 250 ug/mL of membrane-bound interleukin-12 mRNA. For each sample, a subset of cells was matured with 1 μM of CpG 7909 for 4 hours, then washed and cultured.

The cells were further incubated another 5 days. At the final day of incubation, the resulting cells were re-stimulated with 1 μM CMV pp65 peptide, and their activation and activity was measured via ICS. TNF-α, IFN-γ, IL-2, PD-1, and Granzyme B were assessed in CD3+ CD8+ responder cells.

In addition to ICS evaluation, the cells were stained with CMVpp65 tetramer to determine the number of antigen-specific CD8 T cells after expansion on day 5.

Results

Figure 17A:
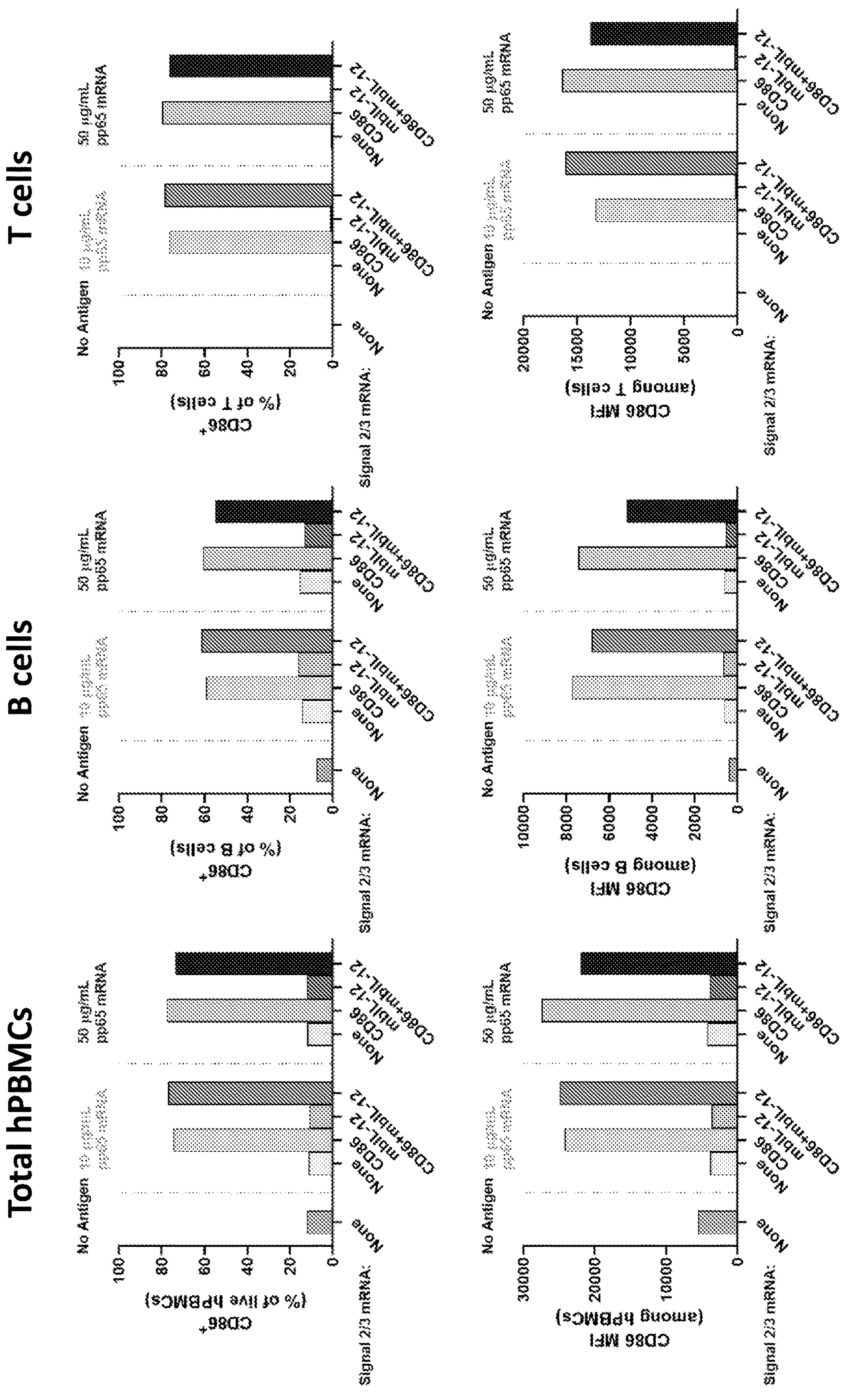
FIGS. 17A, B contain graphs showing CD-86 expression in PBMCs and constituent cell types within PBMCs that am squeeze-loaded with the indicated amount of mRNAs encoding for CMV pp65 antigen, CD86 and/or membrane-bound IL-12 (mbIL-12).
Figure 17B:
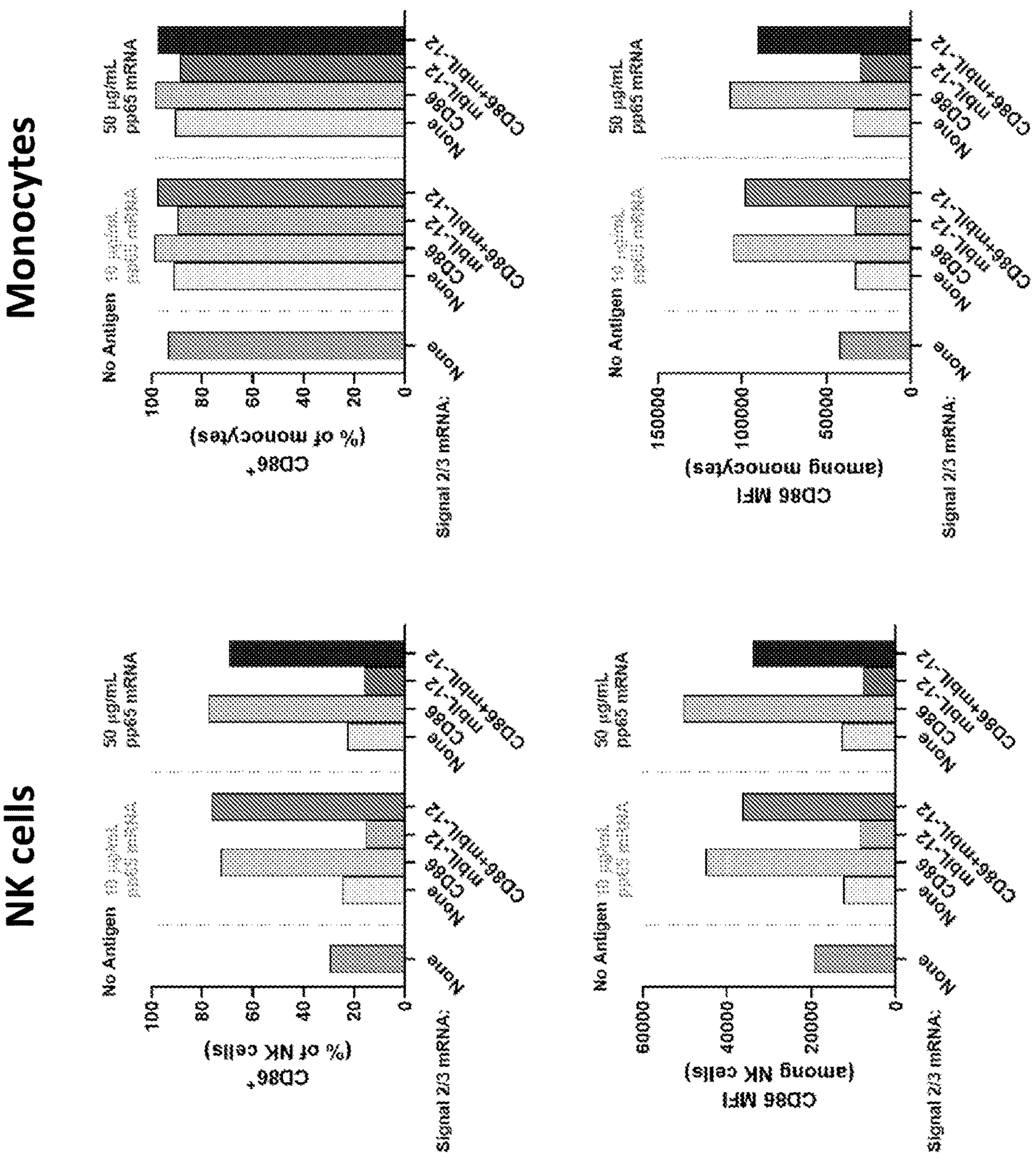
Figure 18A:
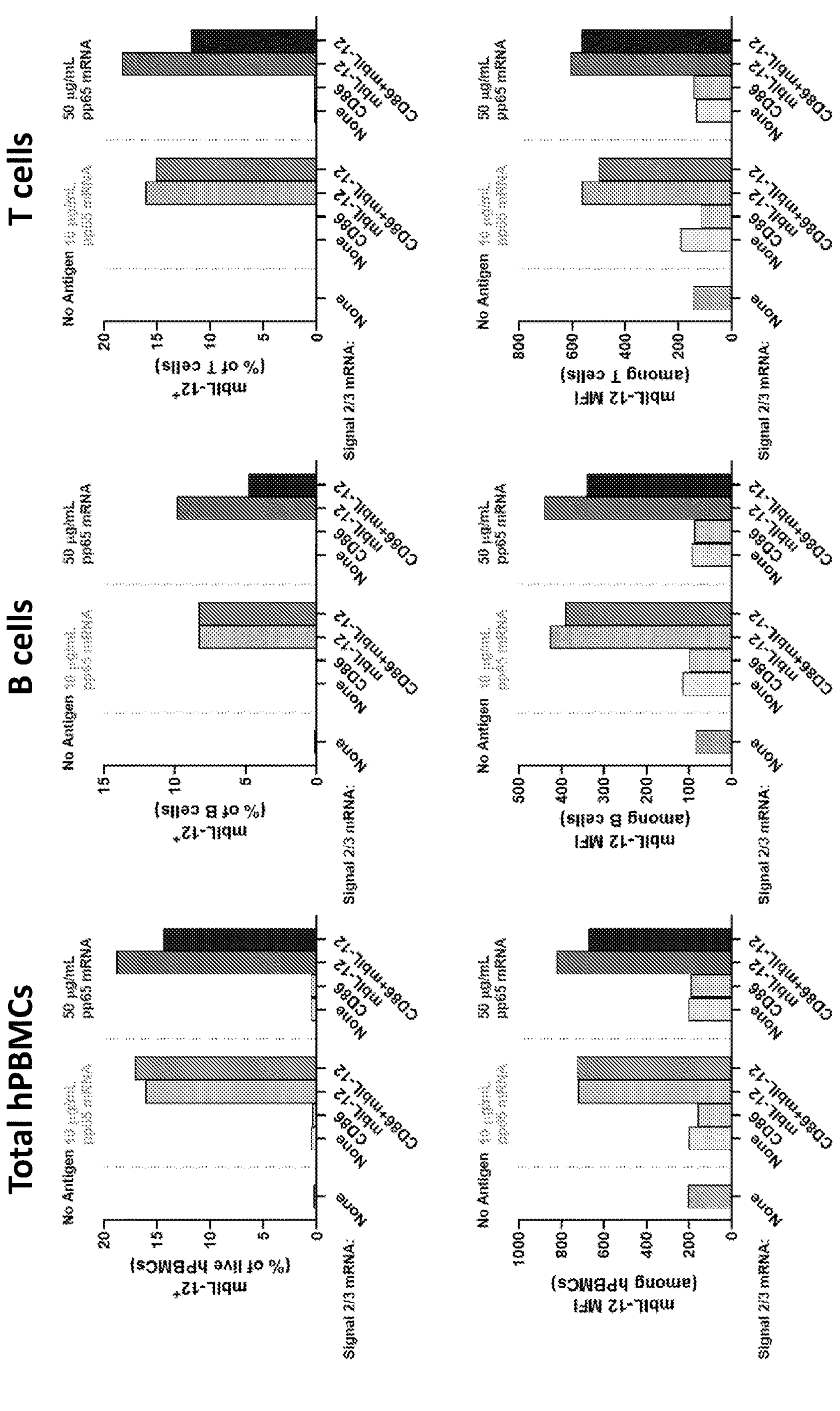
FIGS. 18A, B contain graphs showing membrane-bound IL-12 (mbIL-12) expression in PBMCs and constituent cell types within PBMCs that are squeeze-loaded with the indicated amount of mRNAs encoding for CMV pp65 antigen, CD86 and/or mbIL-12.
Figure 18B:
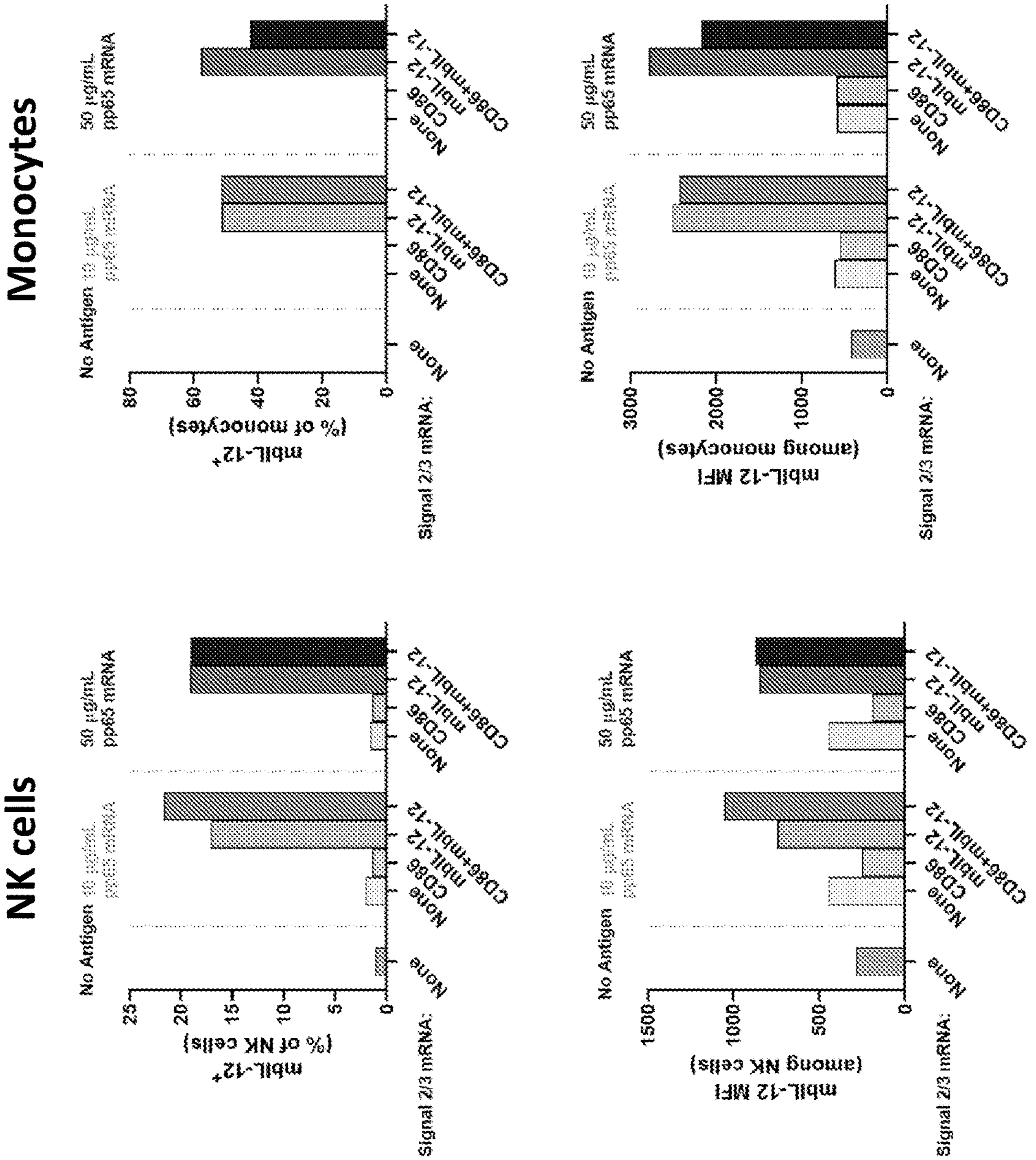

As shown by intracellular staining, there was successful translation of CD86 mRNA (FIGS. 17A, 17B) and mbIL-12 mRNA (FIGS. 18A, 18B) at 24 hours subsequent to squeeze-mediated delivery of mRNAs encoding CD86 or mbIL-12 respectively.

Figure 19:
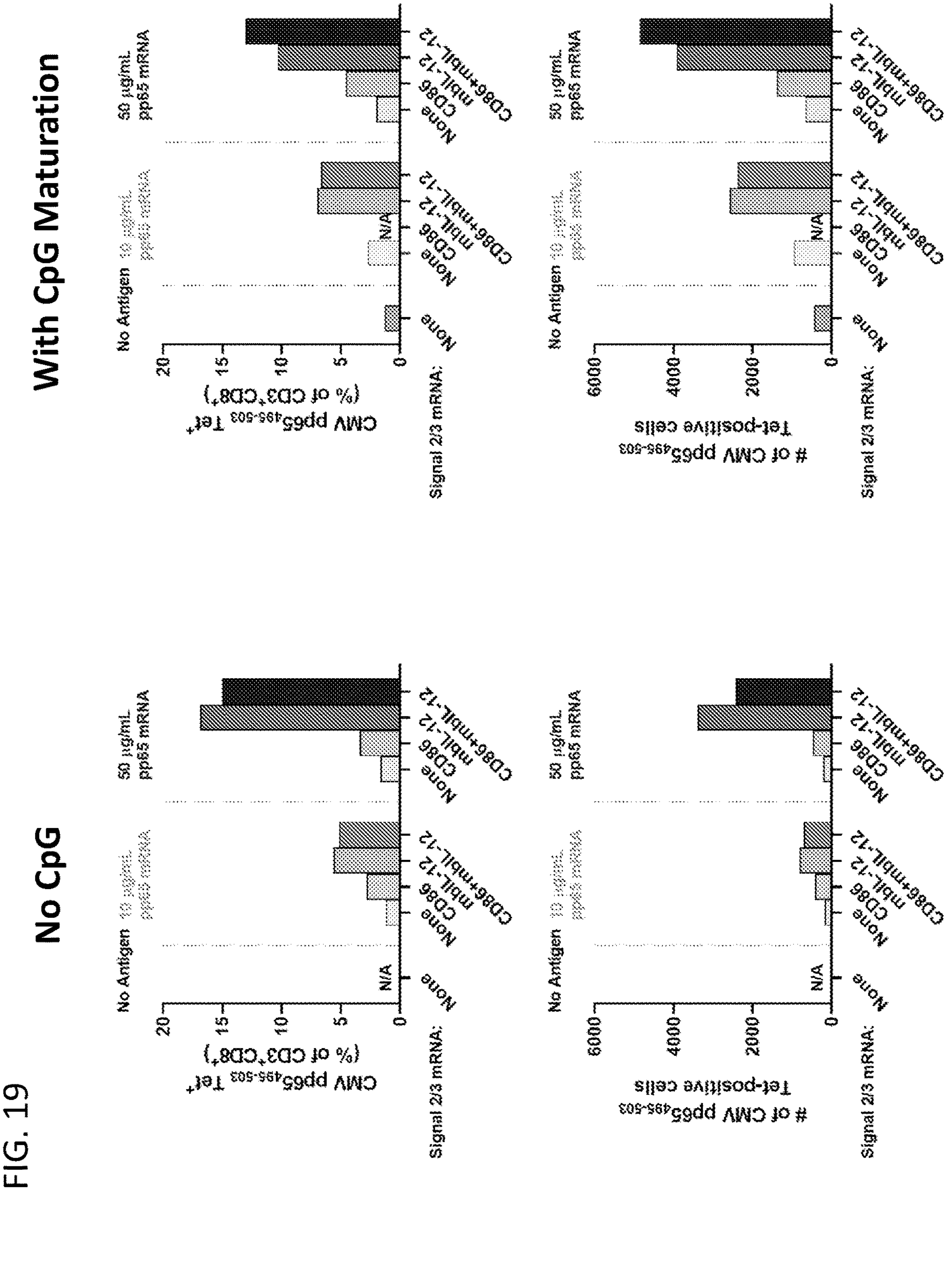
FIG. 19 contains graphs showing the amount of CMV pp65 tetramer-positive responder T cells, and the percentage of CMV pp65 tetramer-positive population within CD3+ CD8+ responder T cells when PBMCs are squeeze-loaded with the indicated amount of mRNAs encoding for CMV pp65 antigen, CD86 and/or mbIL-12, and further cultured with or without CpG adjuvant activation.

FIG. 19 show increased expansion in CMV pp65 tetramer-specific (TET-specific) CD3+CD8+ responder cells after squeeze-loading PBMCs with pp65 and CD86 and/or mbIL-12 mRNA under conditions with CpG maturation and without CpG maturation, as compared to squeeze-loading PBMCs with pp65 mRNA alone. This example demonstrates that while CpG maturation led to a slight decrease in the percentage of Tet+ cells (FIG. 19 upper panels), it resulted in higher Tet+ counts than without CpG maturation (FIG. 19 lower panels). Further, the co-delivery of CD86 and/or mbIL-12 mRNAs further augmented both the number and percentage of Tet-specific responder cells compared to squeezing CMV pp65 mRNA alone.

Figure 20:
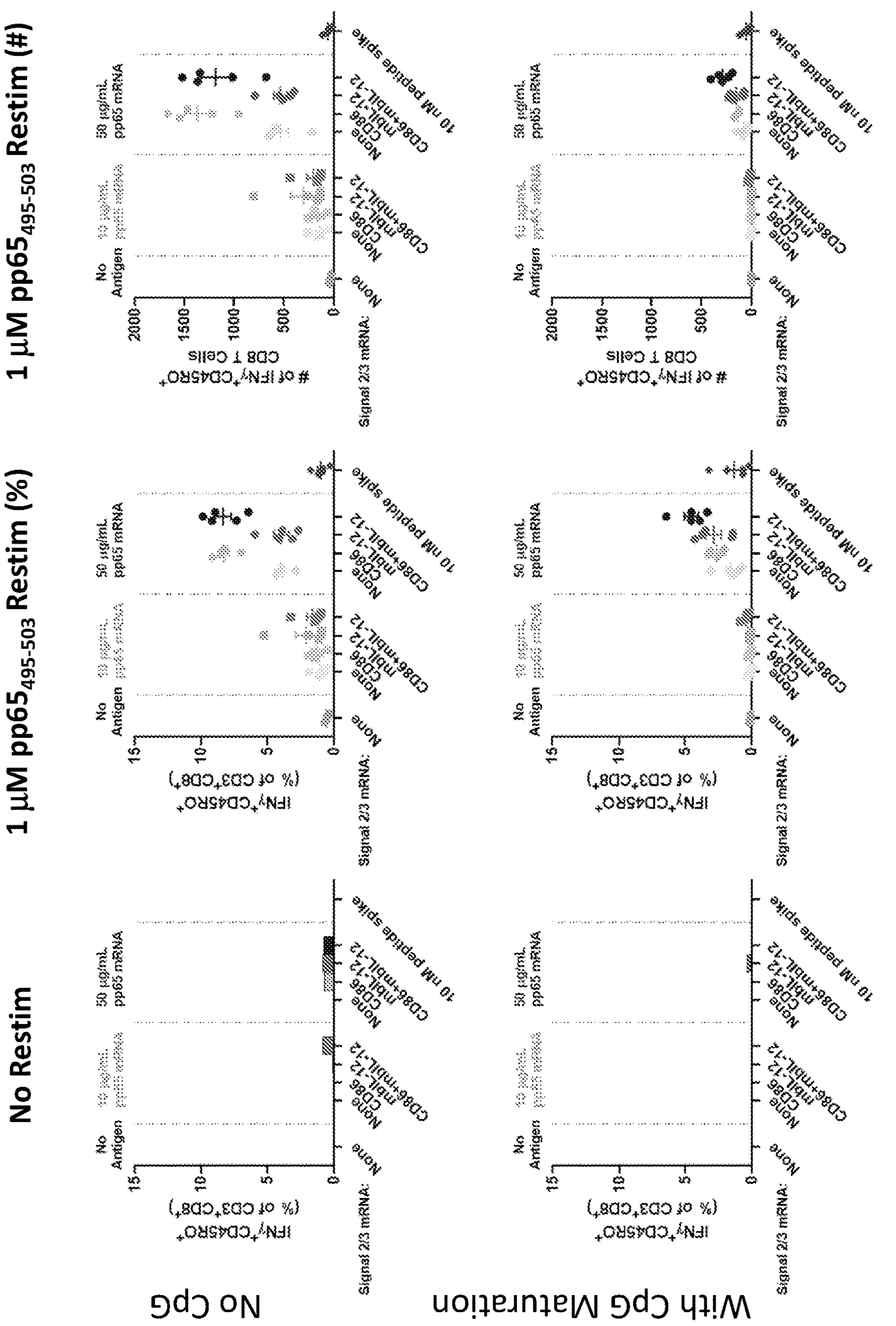
FIG. 20 contains graphs showing the amount of CMV pp65 tetramer-positive responder T cells, and the percentage of CMV pp65 tetramer-positive population within CD3+ CD8+ responder T cells when PBMCs are squeeze-loaded with the indicated amount of mRNAs encoding for CMV pp65 antigen, CD86 and/or mbIL-12, that are treated with or without re-stimulation by 1 μM of pp65 antigen, and further cultured with or without conditioning by CpG adjuvant.
Figure 21A:
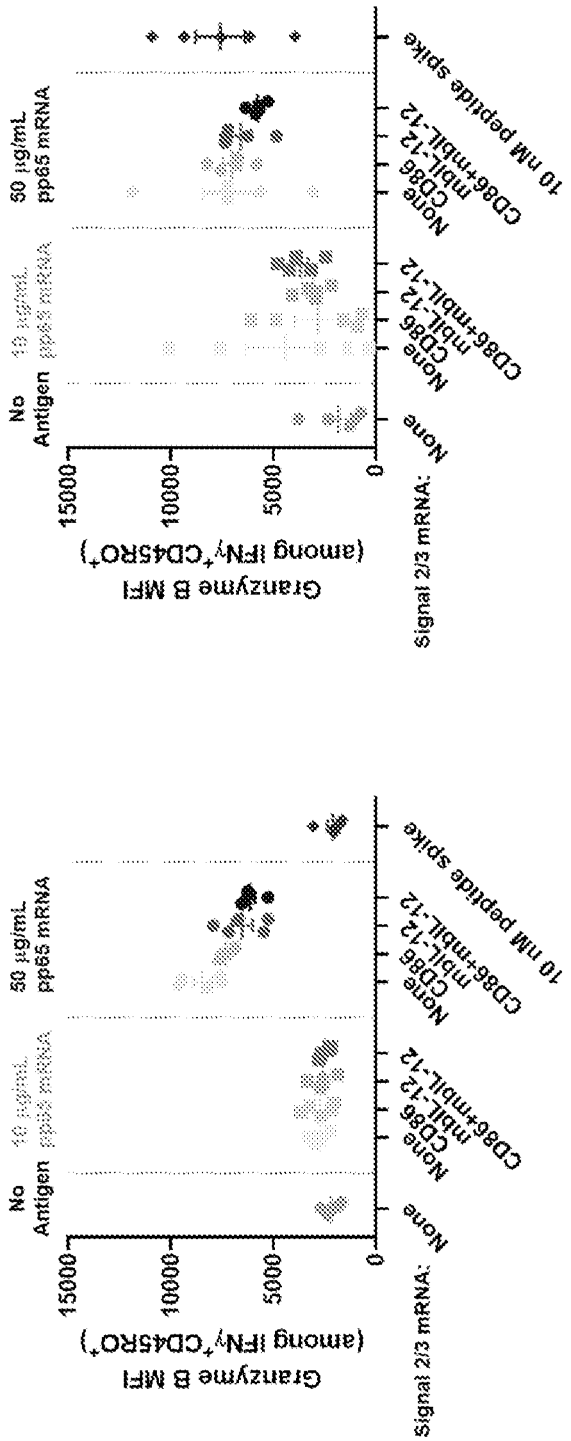
FIGS. 21 A, B, C, D, E contain graphs showing the amount of expression for functionality marker Granzyme B, IFN-γ, IL-2, TNF-α, PD-1 respectively within activated responder T cell populations when PBMCs are squeeze-loaded with the indicated amount of mRNAss encoding for CMV pp65 antigen, CD86 and/or mbIL-12.
Figure 21B:
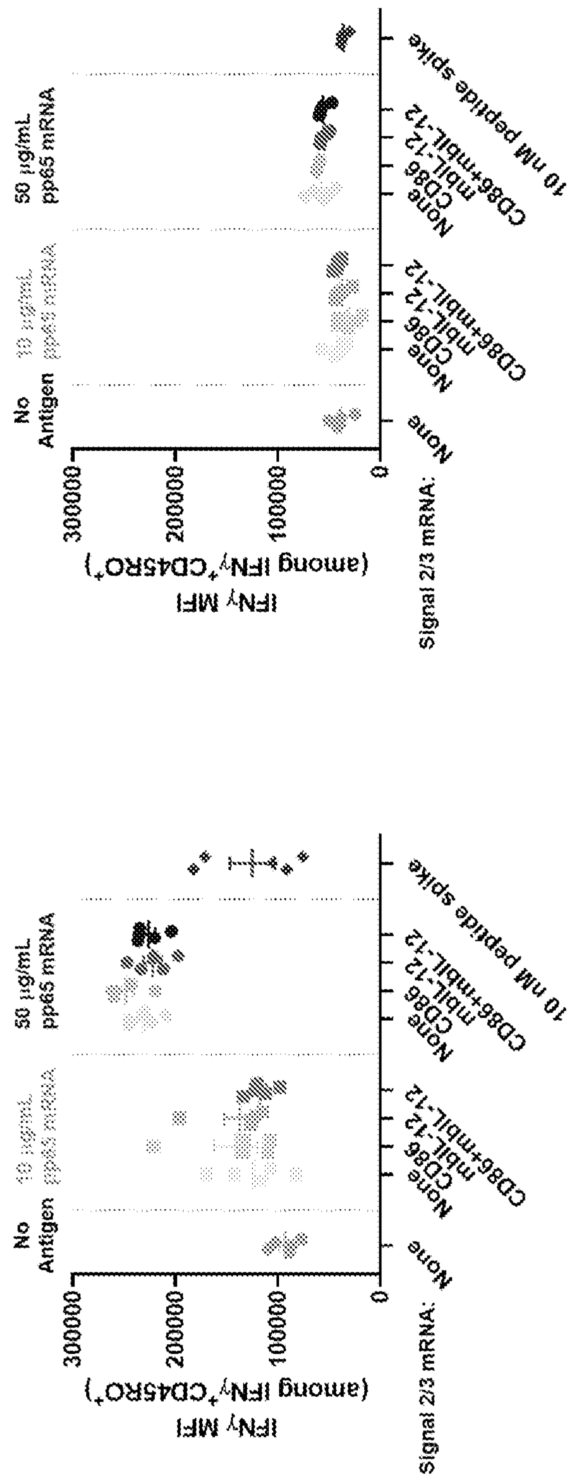
Figure 21C:
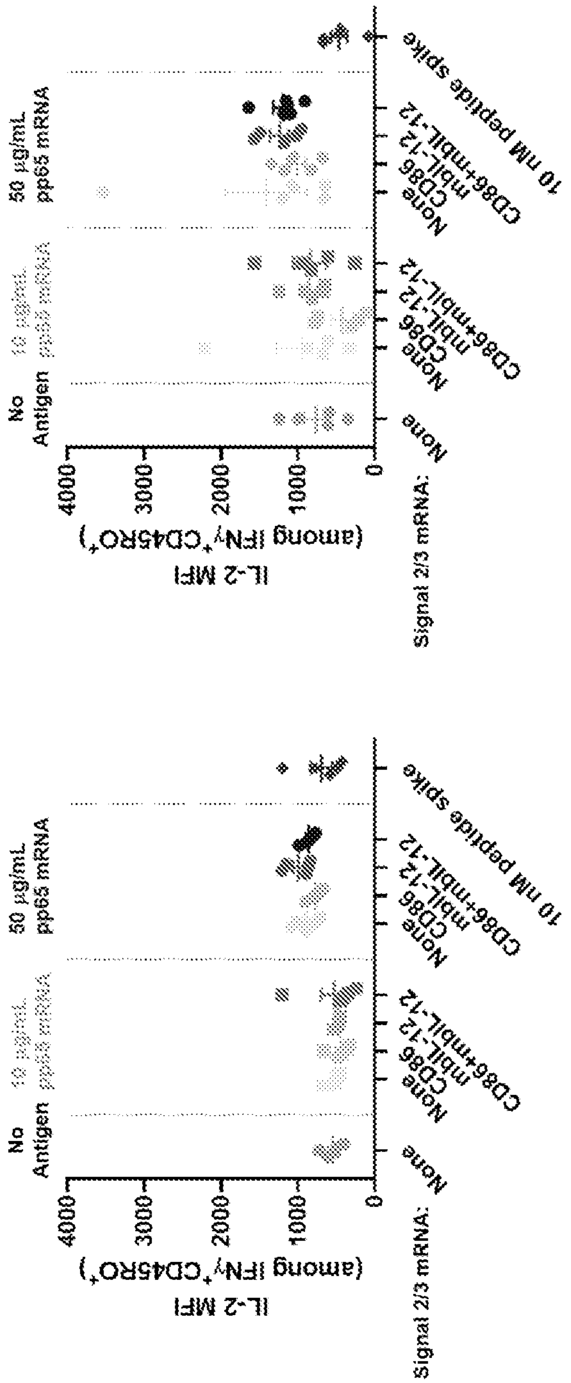
Figure 21D:
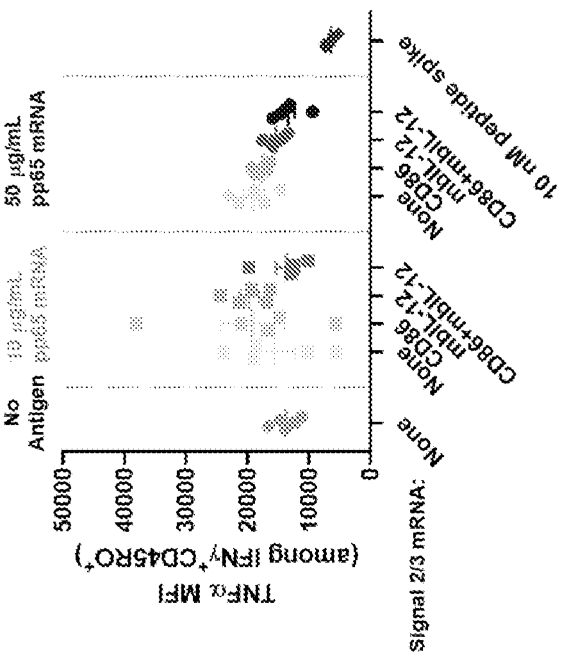
Figure 21D:
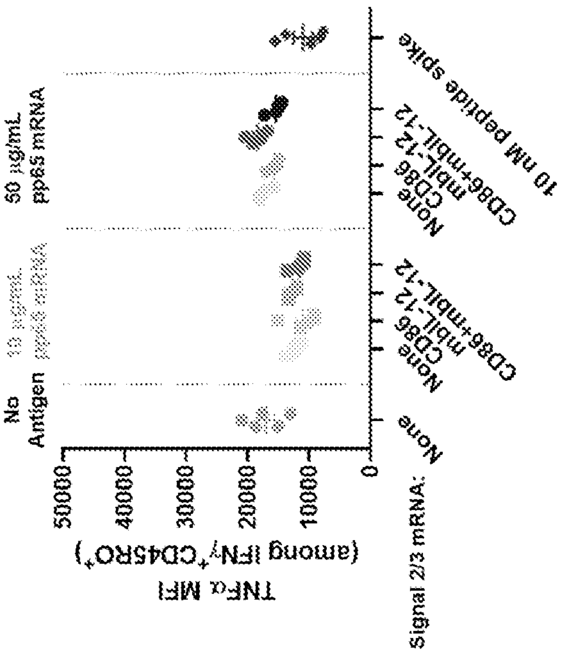
Figure 21E:
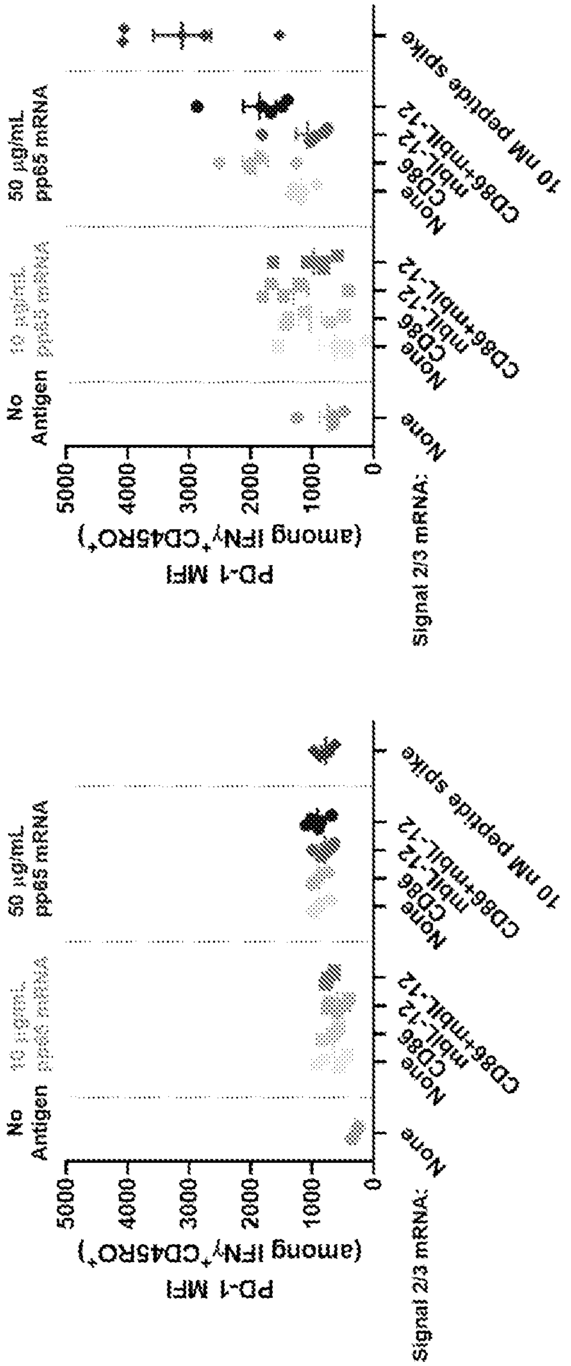

As shown in FIG. 20, under conditions with and without CpG maturation, there was increased activation of responder T cells when the mRNAs encoding mediators of Signal 1 mRNA was codelivered with mRNAs encoding mediators of Signal 2 and/or 3, as demonstrated by increased IFNγ+ CD45RO+ populations within CD3+CD8+ responders.

As shown in FIGS. 21 A-E, the functional markers of TNF-α, IFN-γ, IL-2, PD-1, and Granzyme B were upregulated in T cell responders when PBMCs were squeeze-loaded with pp65 mRNA as compared to PBMCs squeeze-processed without antigen. The results indicate the activated antigen-specific T cells were polyfunctional.

Example 14

To assess the co-squeezing (simultaneous squeeze-loading) of various mRNAs respectively encoding mediators for Signals 1, 2, or 3 in T cell activation, their ability to address multiple different HLA haplotypes, and the resulting enhanced T cell responses, human donor HLA-A*02+ PBMCs (HLA-A*02+, HLA-B*07+, HLA-B*35+) were squeeze-loaded with combinations of mRNAs respectively encoding mediators for Signals 1, 2, or 3 in T cell activation.

Methods

Human PBMCs isolated from a CMV+ HLA-A*02+ leukopak were stained with CMVpp65 tetramer specific to NLVPMVATV (495-503 aa; SEQ ID NO:88) to determine that these PBMCs have pre-existing pp65-specific CD8 T cells. Subsequently the PBMCs were prepared at a density of $4\times10^7$ cells/mL and combined with mRNA encoding CMV pp65 (Signal), CD86 (Signal 2), membrane-bound interleukin-2 (mbIL-2), and/or membrane-bound interleukin-12 (mbIL-12) (Signal 3). The cells were squeeze processed in the presence of mRNAs at room temperature using a Cell Squeeze® system and chip through a constriction of 3.5 μm width, 10 μm length, and 70 μm depth at 60 psi in RPMI medium. PBMCs squeezed processed with empty payloads and spiked with 10 nM CMV pp65 peptide, and PBMCs treated with 1×PMA/Ionomycin were used as controls. The following concentrations and mixtures of each mRNA were tested.

TABLE 3

| Sample | Signal 1 (CO pp65 mRNA) | Signal 2 (CO CD86 mRNA) | Signal 3 (CO mbIL-2 mRNA) | Signal 3 (CO mbIL-12 mRNA) |
|---|---|---|---|---|
| A | — | — | — | — |
| B | — | 250 μg/mL | 250 μg/mL | — |
| C | — | 250 μg/mL | — | 250 μg/mL |
| D | 50 μg/mL | — | — | — |
| E | 50 μg/mL | 250 μg/mL | 250 μg/mL | — |
| F | 50 μg/mL | 250 μg/mL | — | 250 μg/mL |
| G | Empty SQZ cells + 10 nM $pp65_{495-503}$ peptide spike | | | |
| H | Empty SQZ cells + PMA/Ionomycin on Day 5 | | | |

For example, for Sample F, a total volume of 500 ul of cells in a cell suspension was squeeze processed with mRNAs at the following concentrations of 50 μg/mL pp65 mRNA (Signal 1), 250 μg/mL of CD86, and/or 250 μg/mL of mbIL-12 mRNA. Cells in each sample were then matured with 1 μM CpG 7909 for 4 hours, after which, a portion of the cells were washed and then cryopreserved for 4 days. Upon thawing, they were left in culture for 5 days to evaluate ICS responses. Some cells were cultured immediately as fresh for 5 days to compare ICS responses. On day 5, these cells were restimulated under three different conditions: 1) with HLA-A*02-restricted pp65 minimal epitope (NLVPMVATV: SEQ ID NO:88), 2) with HLA-B*07-restricted pp65 minimal epitope (RPHERNGFTVL: SEQ ID NO:89), or (3) HLA-B*35-restricted pp65 minimal epitope (TPRVTGGGAM; SEQ ID NO:90). Antigen-specific responses will be measured via ICS by assessing TNF-α, IFN-γ expression in CD3+ CD8+ responder cells. In addition, mRNA expression was assessed at 24 hours post squeeze as well as 24 hours post thaw.

Results

Figure 22A:
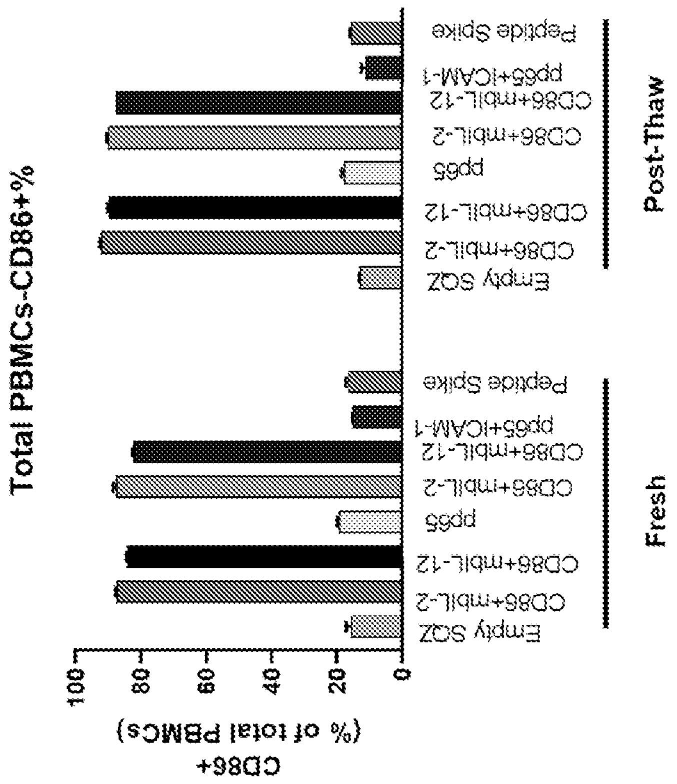
FIGS. 22A, B contain graphs showing the percentage of CD86-expressing cells and amount of CD86 expression, respectively, in PBMCs and constituent cell types within PBMCs that are squeeze-loaded with the indicated mRNAs encoding for CMV pp65 antigen, CD86, membrane-bound IL-2 (mbIL-2) and/or membrane-bound IL-12 (mbIL-12).
Figure 22A:
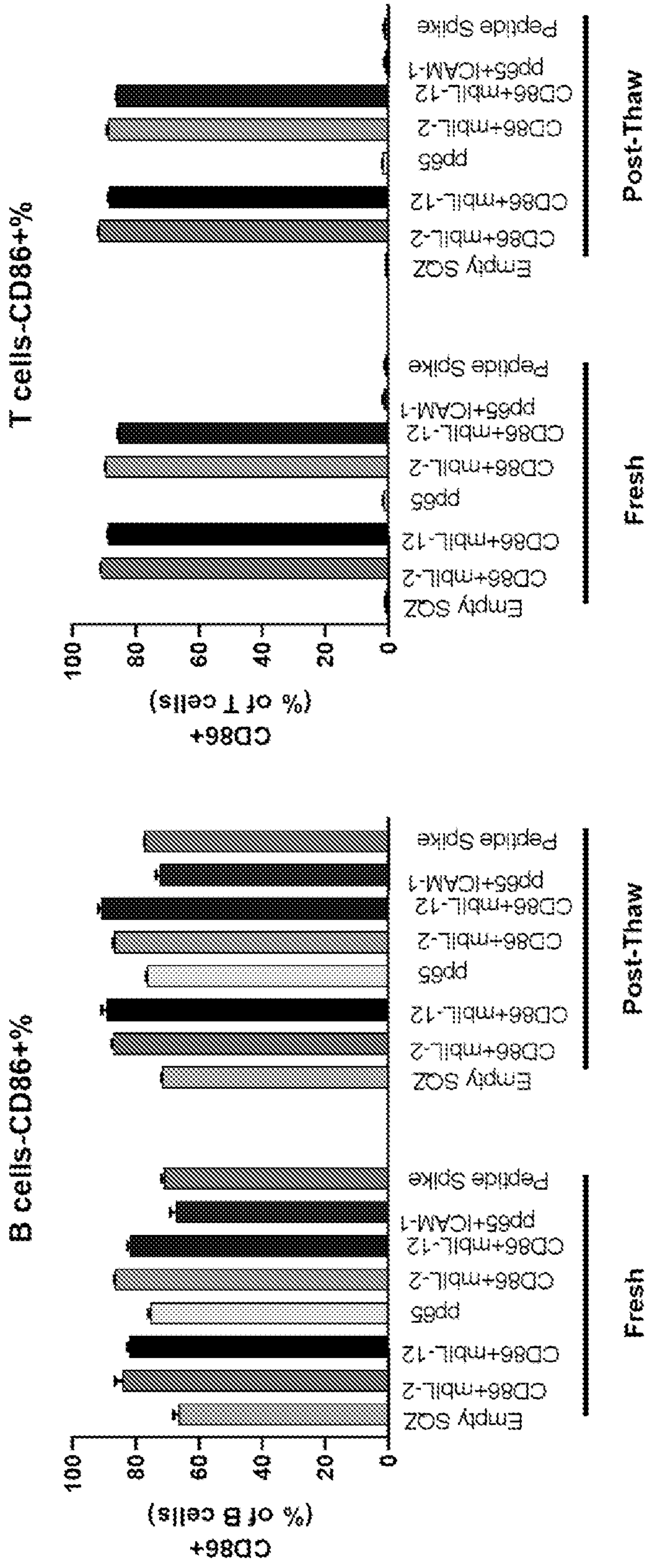
Figure 22A:
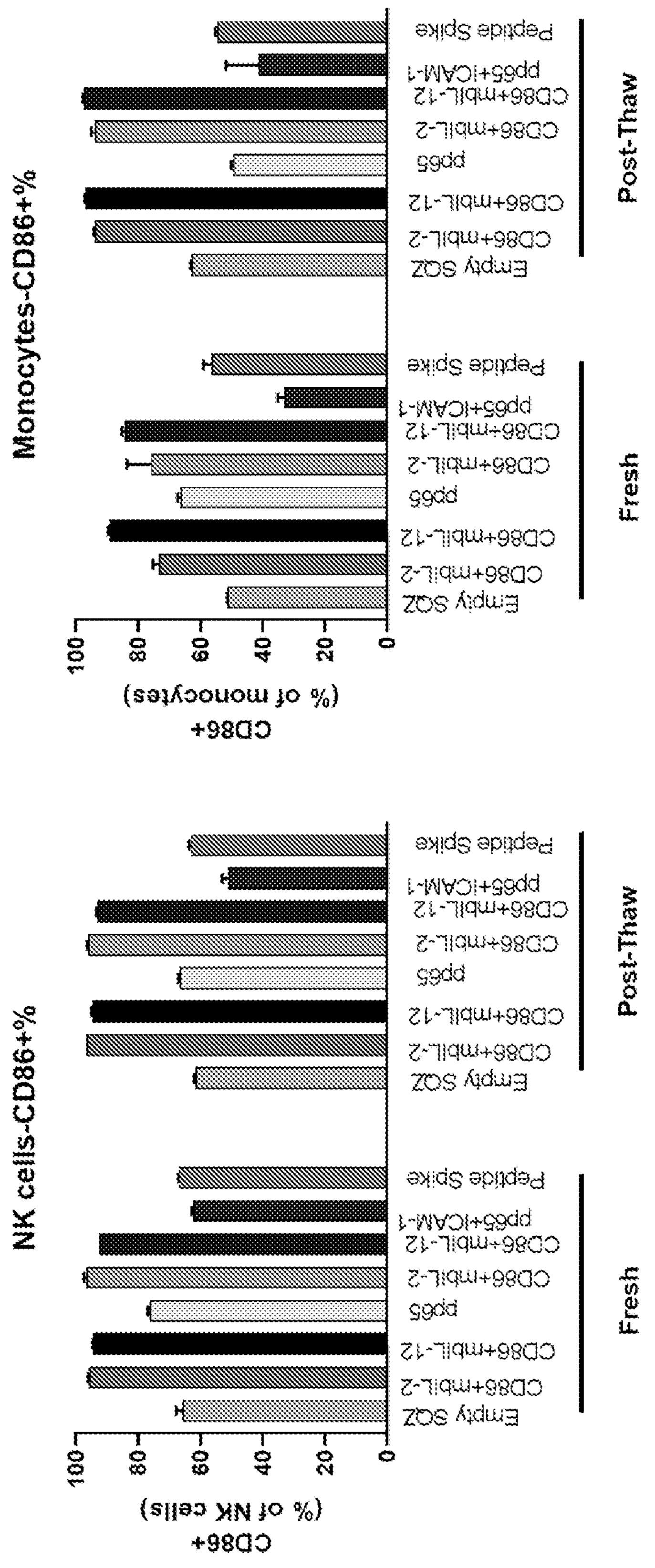
Figure 22B:
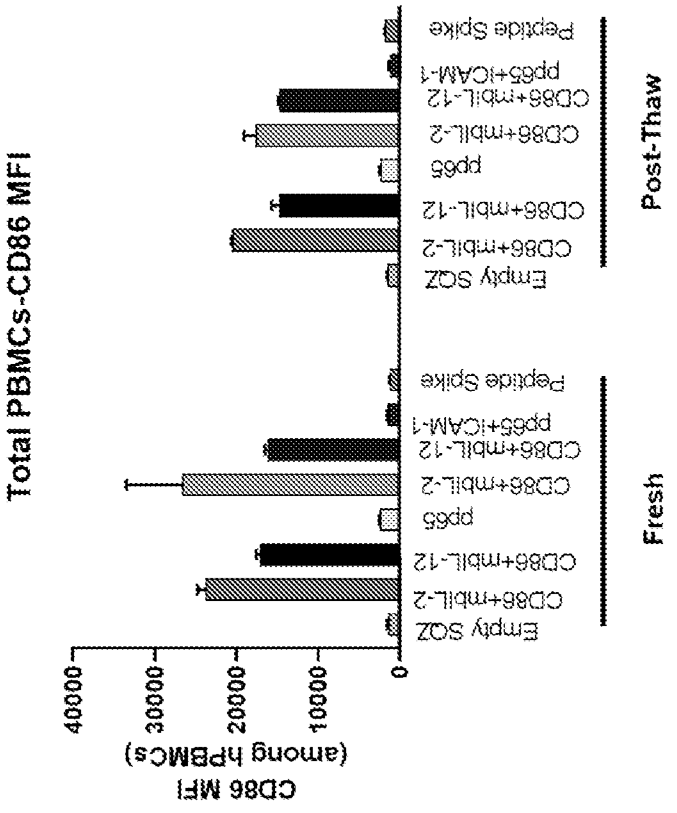
Figure 22B:
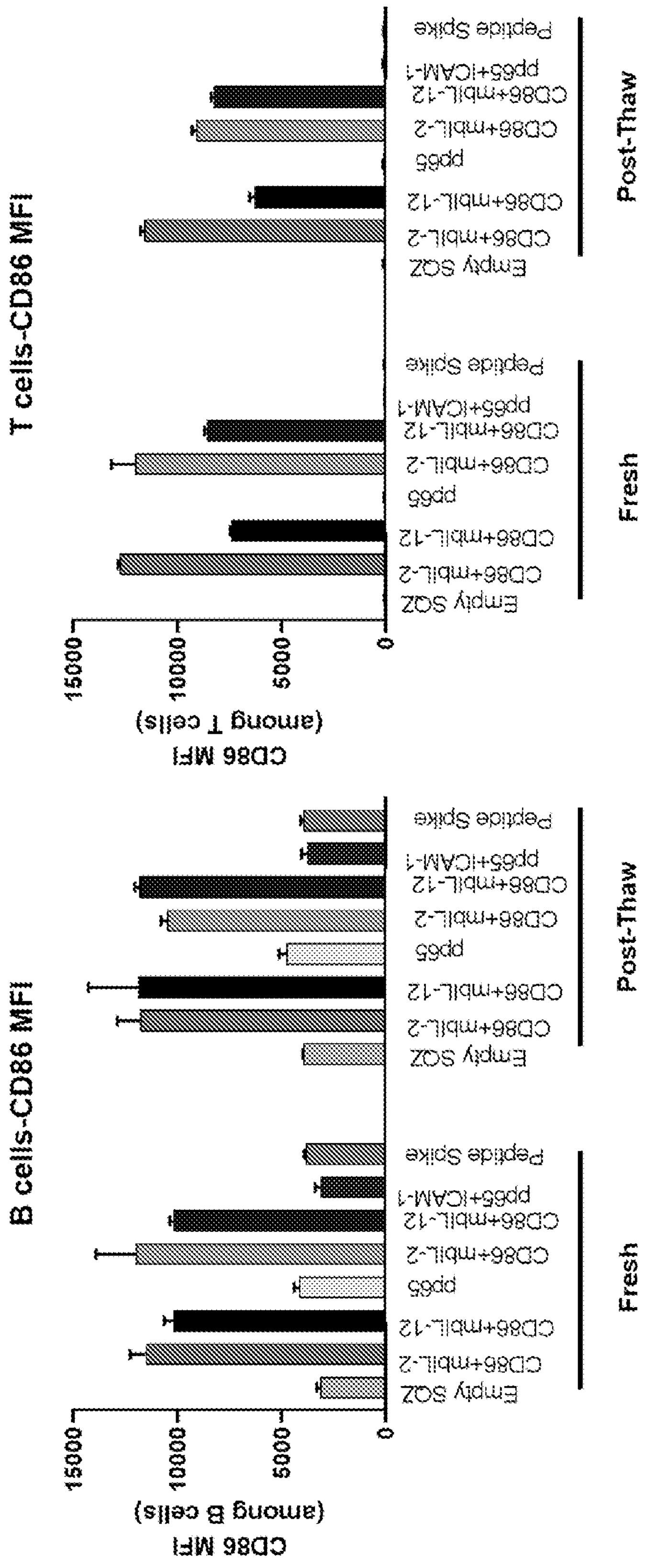
Figure 22B:
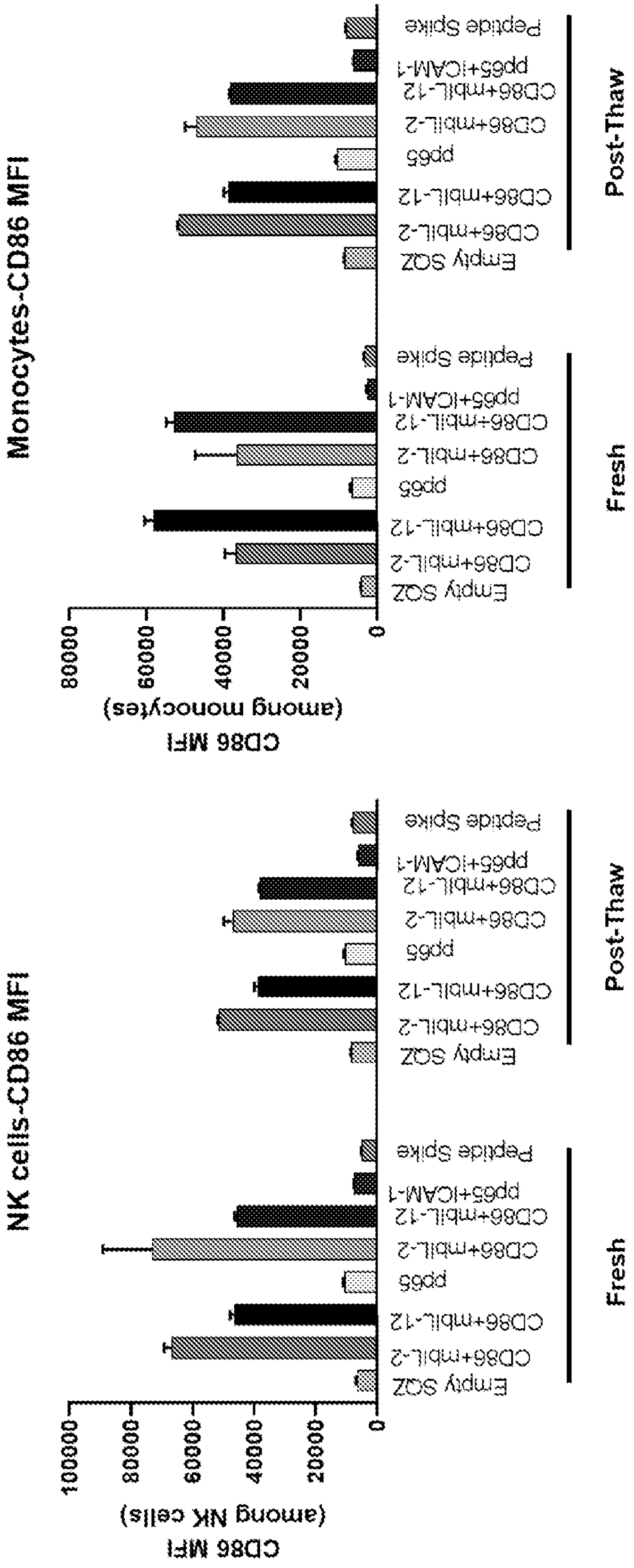
Figure 23A:
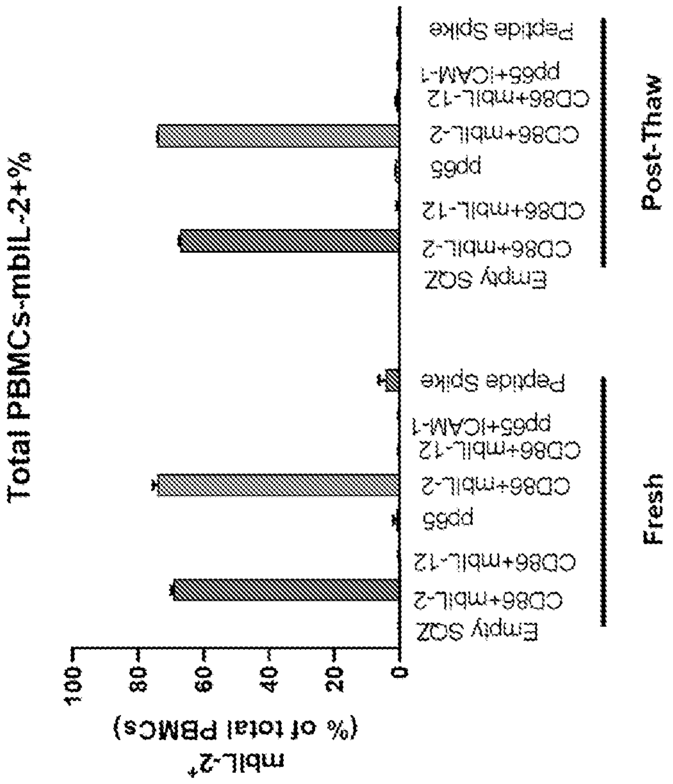
FIGS. 23A, B contain graphs showing the percentage of membrane-bound IL-2 (mbIL-2)-expressing cells and amount of mbIL-2 expression, respectively, in PBMCs and constituent cell types within PBMCs that are squeeze-loaded with the indicated mRNAs encoding for CMV pp65 antigen, CD86, membrane-bound IL-2 (mbIL-2) and/or membrane-bound IL-12 (mbIL-12).
Figure 23A:
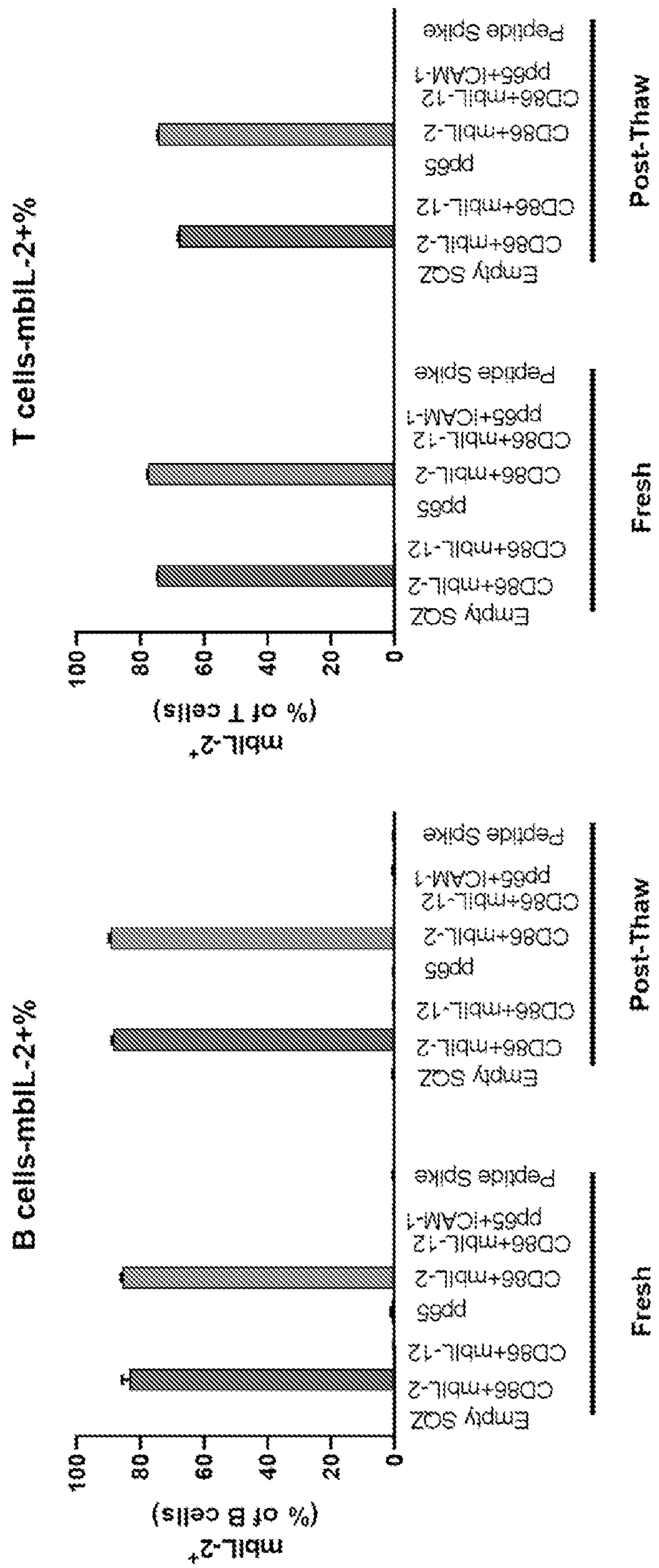
Figure 23A:
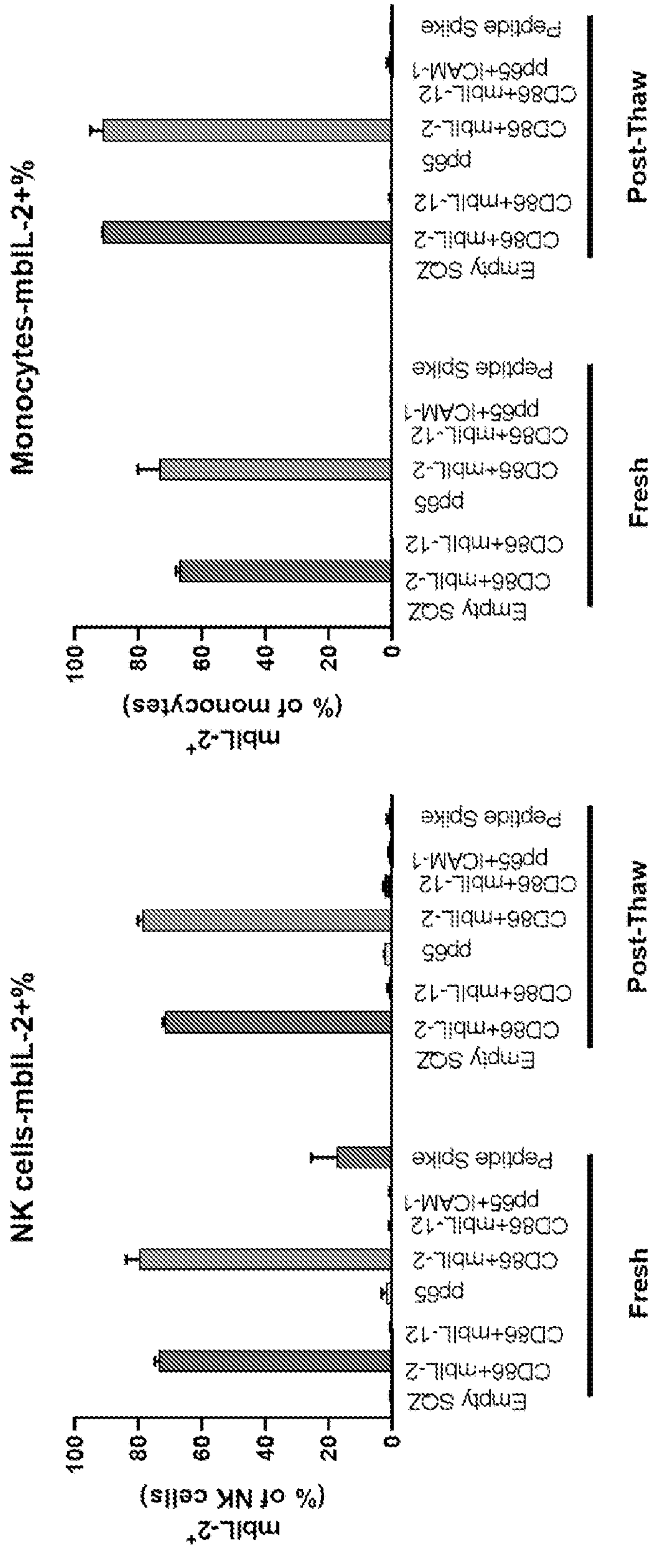
Figure 23B:
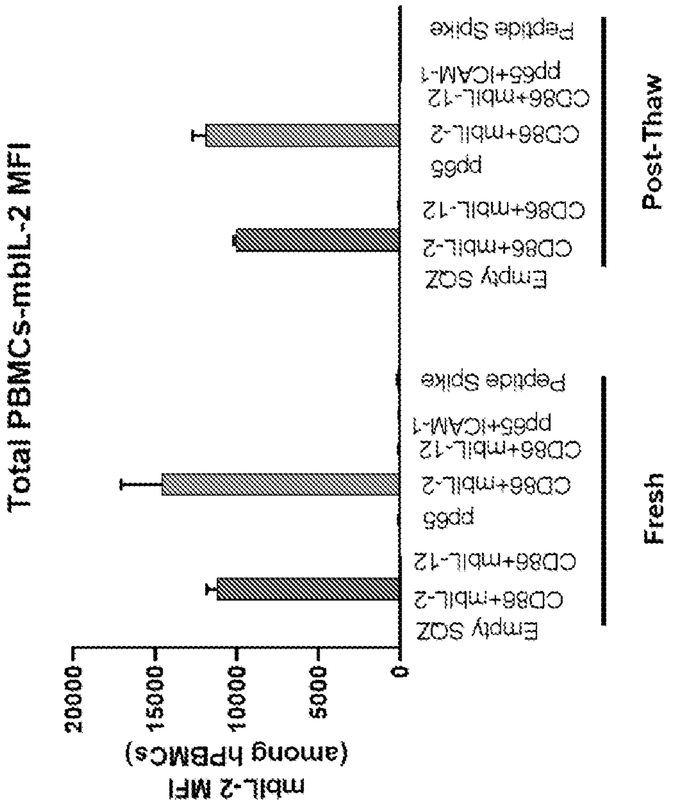
Figure 23B:
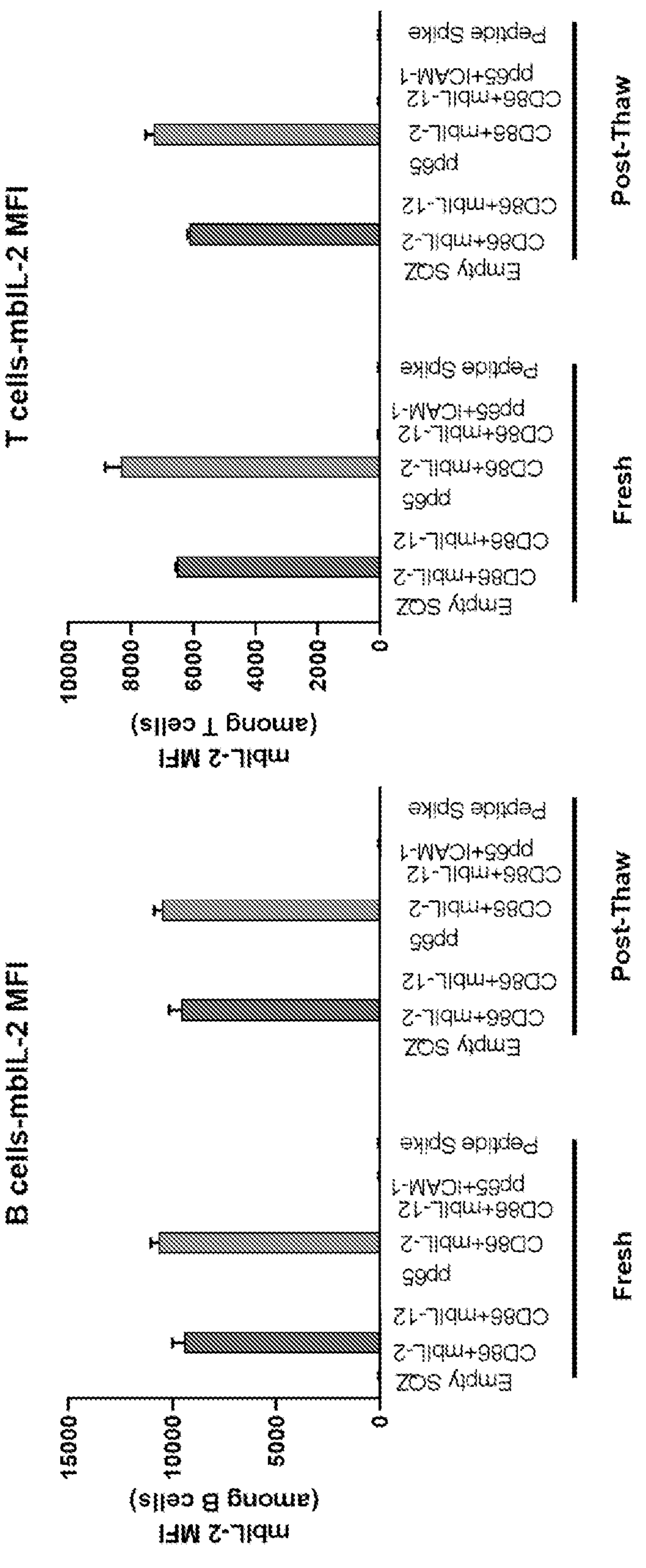
Figure 23B:
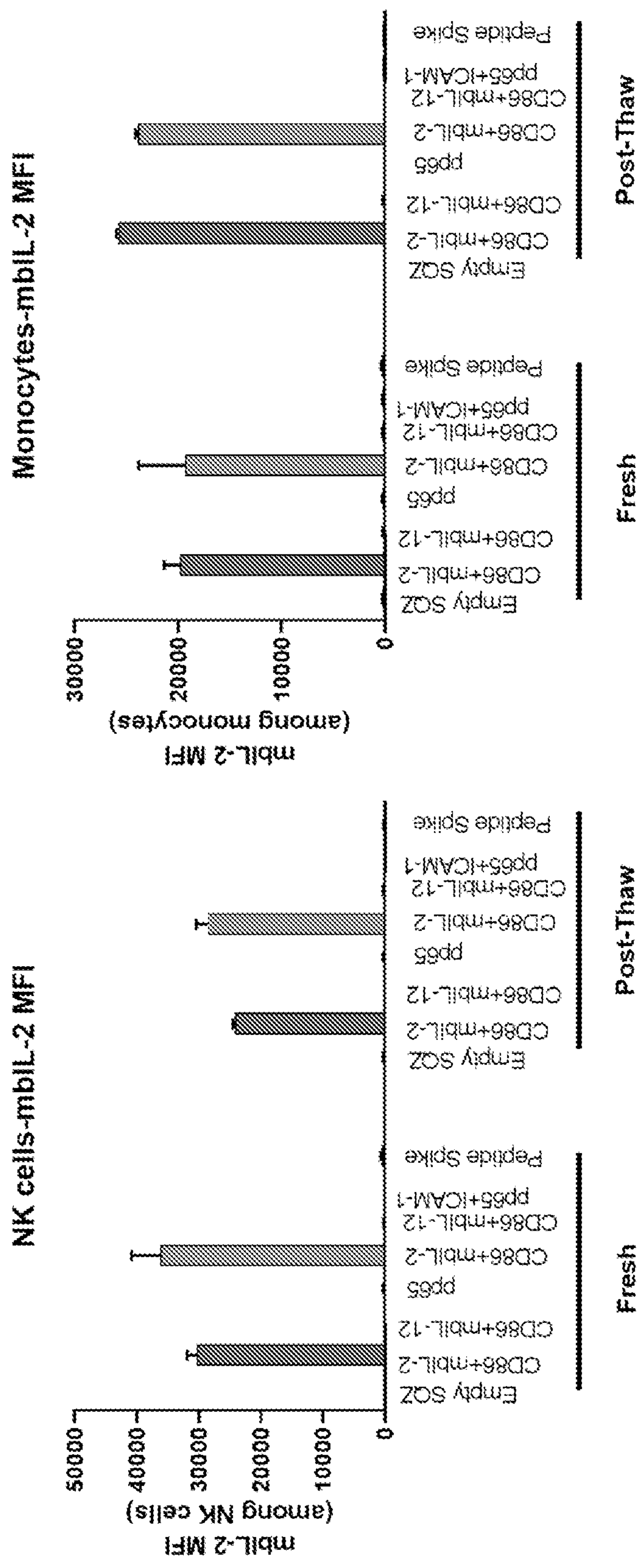
Figure 24A:
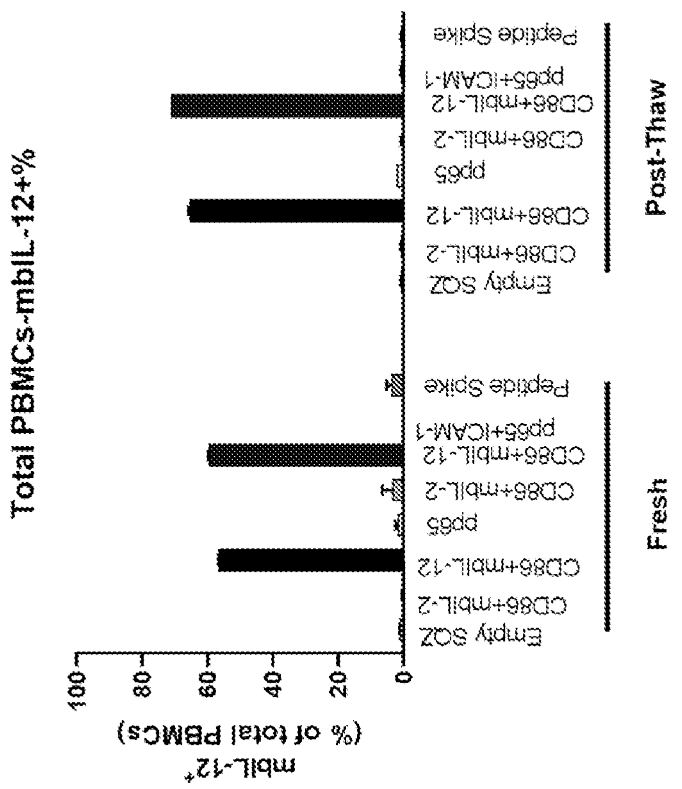
FIGS. 24A, B contain graphs showing the percentage of membrane-bound IL-12 (mbIL-12)-expressing cells and amount of mbIL-12 expression, respectively, in PBMCs and constituent cell types within PBMCs that are squeeze-loaded with the indicated mRNAs encoding for CMV pp65 antigen, CD86, membrane-bound IL-2 (mbIL-2) and/or membrane-bound IL-12 (mbIL-12).
Figure 24A:
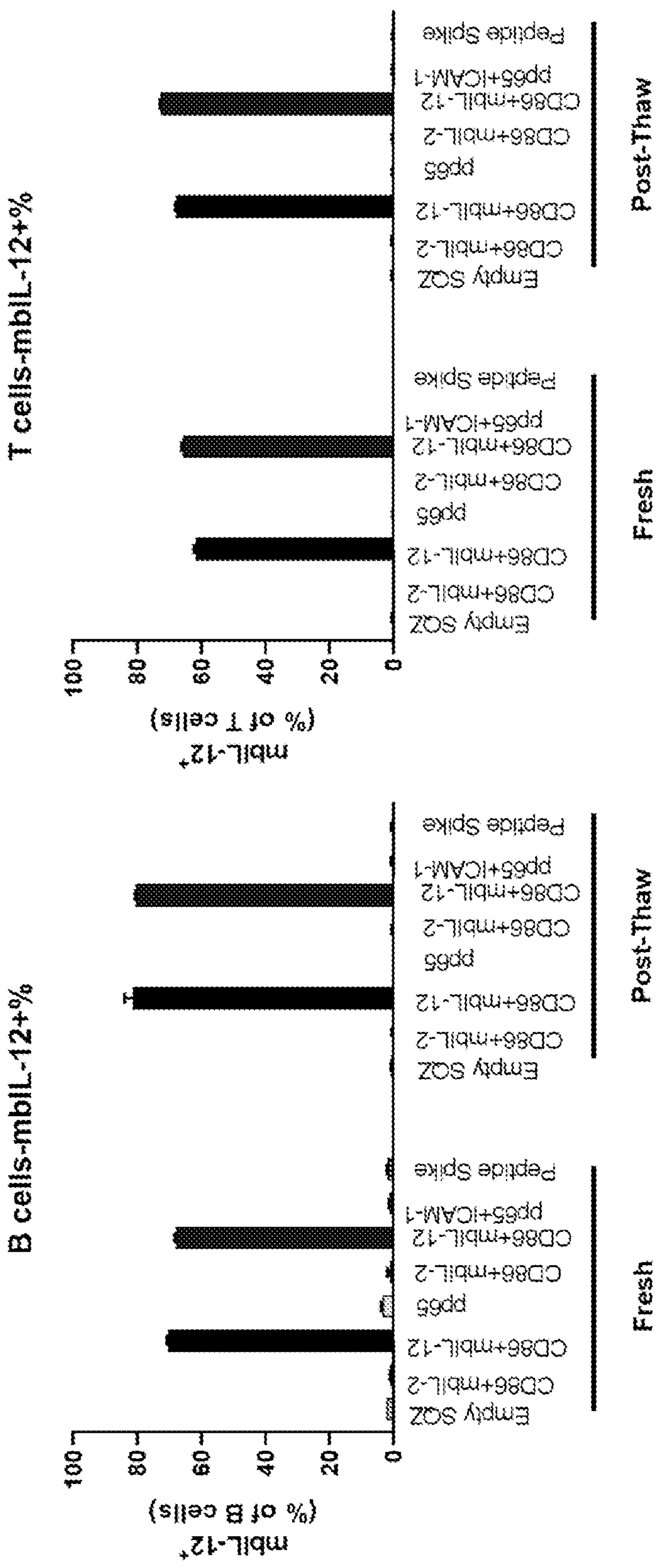
Figure 24A:
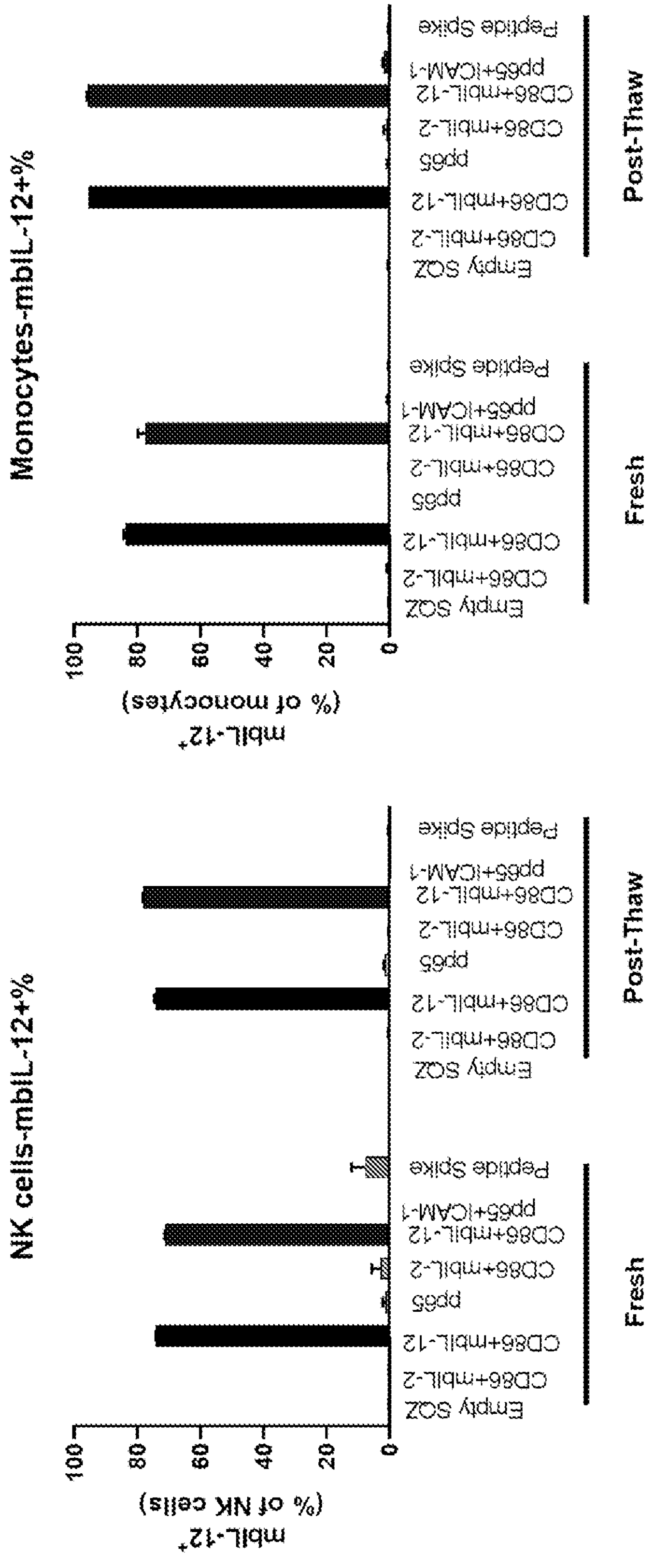
Figure 24B:
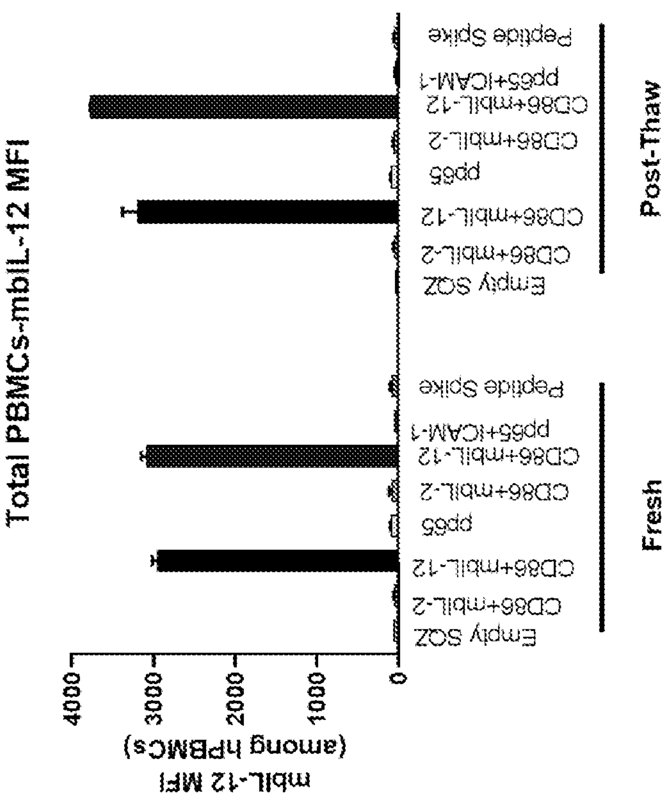
Figure 24B:
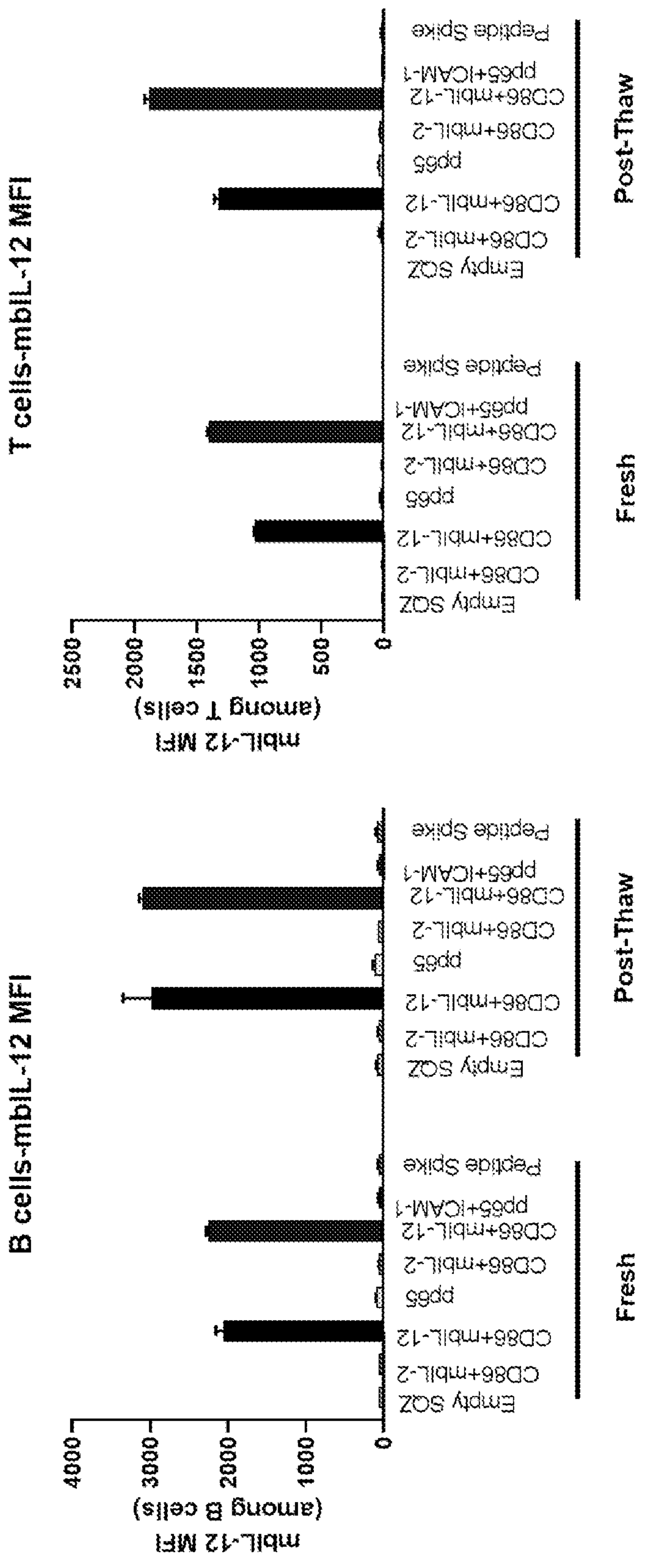
Figure 24B:
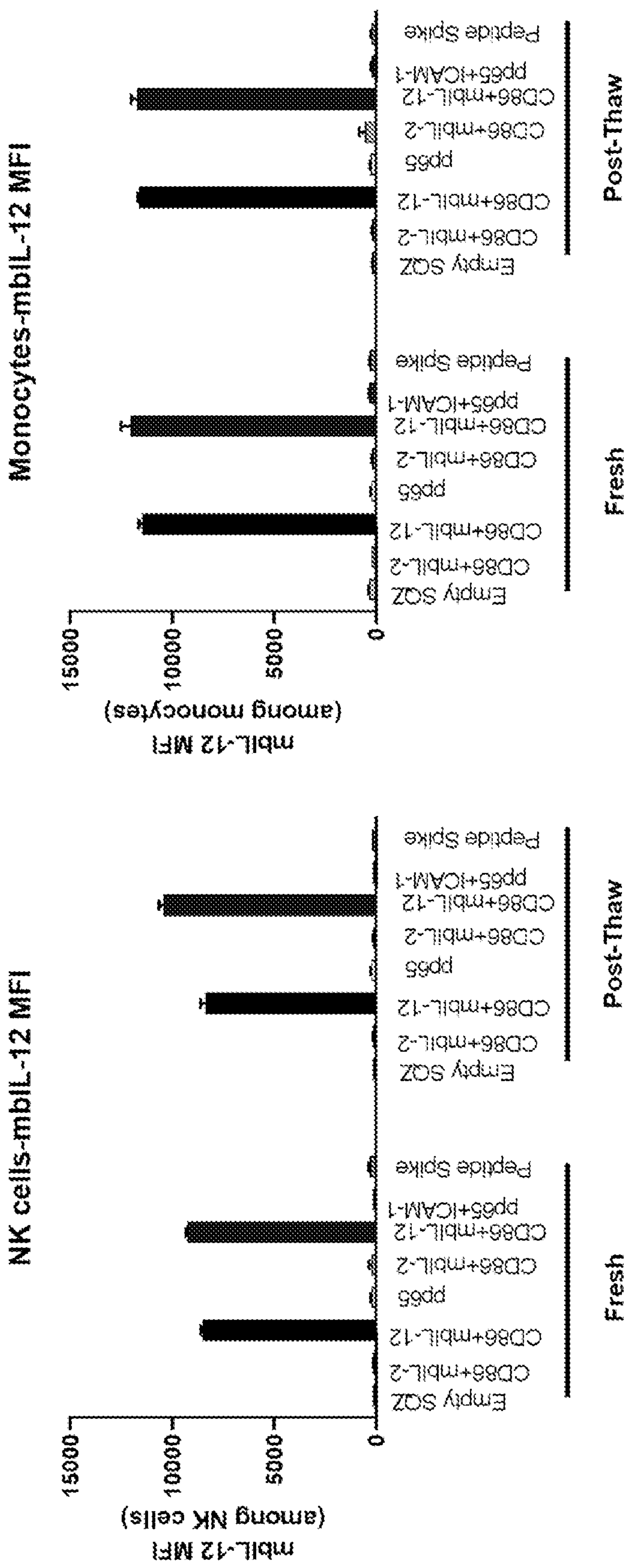

As shown by intracellular staining, there was successful translation of CD86 mRNA (FIGS. 22A, 22B), mb-IL2 (FIGS. 23A, 23B) and mbIL-12 mRNAs (FIGS. 24A, 24B) at 24 hours subsequent to squeeze-mediated delivery of the corresponding mRNAs.

Figure 25:
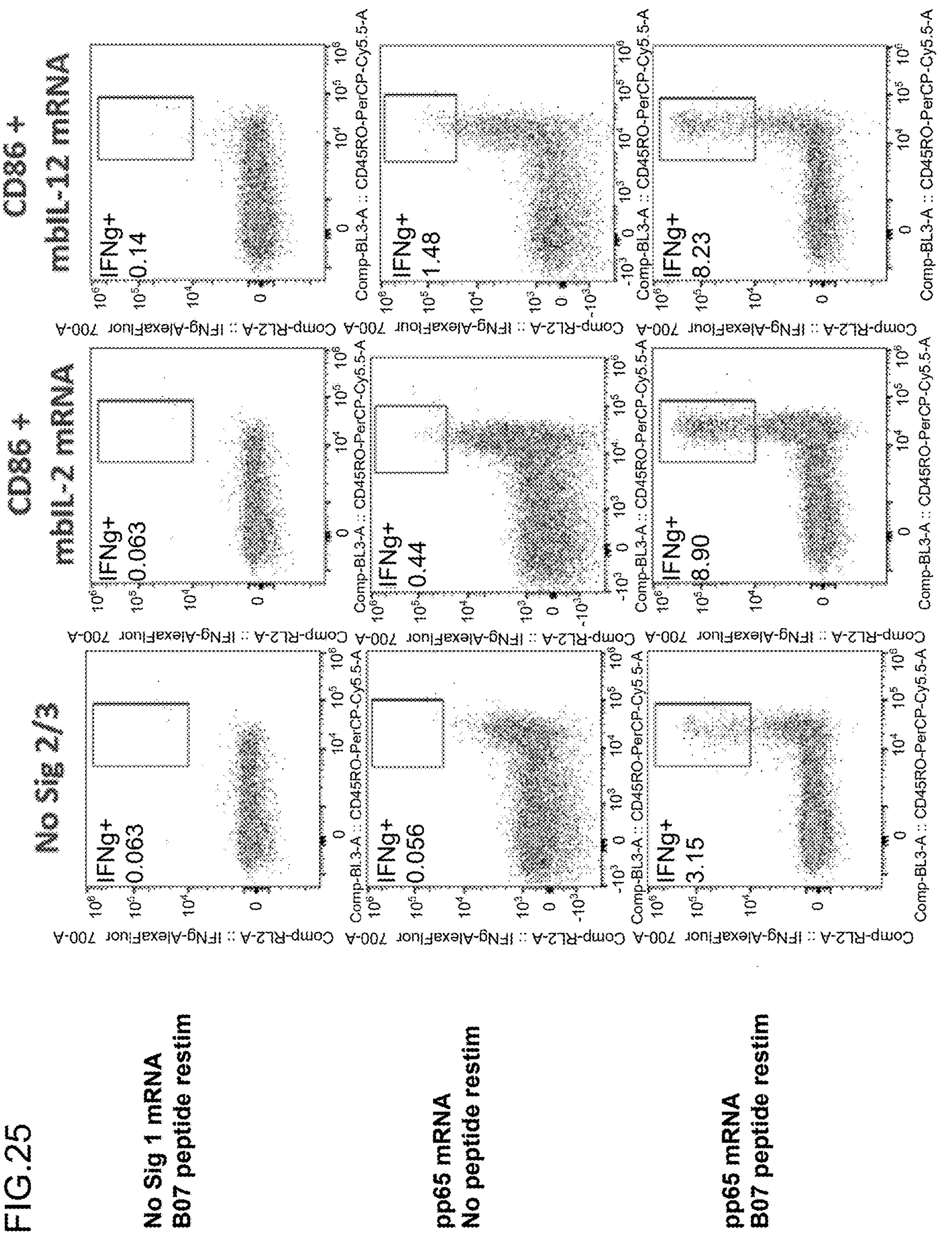
FIG. 25 contains graphs showing the amount of IFN-γ+ population within CD3+CD8+ responder T cells when PBMCs are squeeze-loaded with the indicated mRNAs encoding for CMV pp65 antigen, CD86, mbIL-2 and/or mbIL-12, with or without further re-stimulation with 1 μM of HLA-B*07-restricted pp65 antigen peptide (B07 peptide restim).
Figure 26:
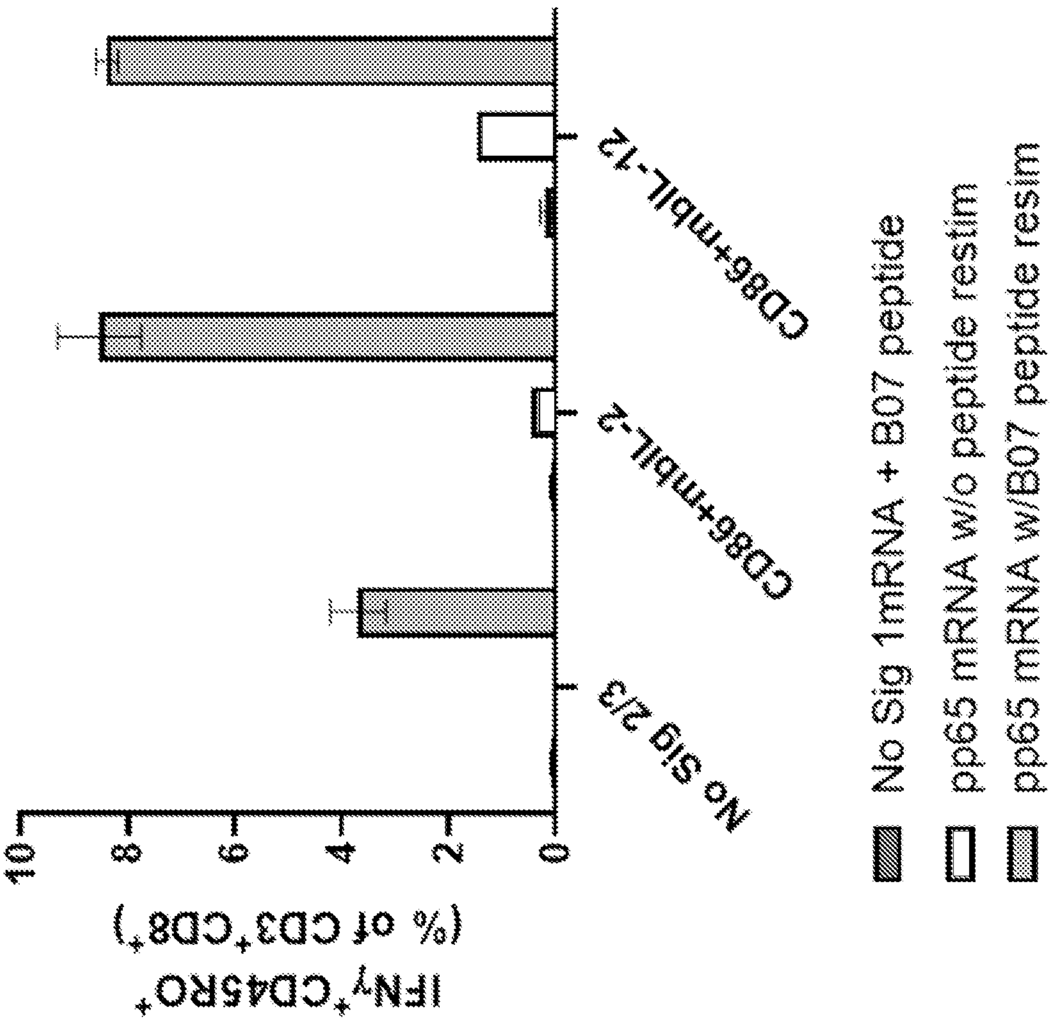
FIG. 26 is a graph showing the amount of IFN-γ+ CD45RO+ population within CD3+CD8+ responder T cells when PBMCs are squeeze-loaded with the indicated mRNAs encoding for CMV pp65 antigen, CD86, mbIL-2 and/or mbIL-12, with or without further re-stimulation with 1 μM of HLA-B*07-restricted pp65 antigen peptide (B07 peptide restim).
Figure 27A:
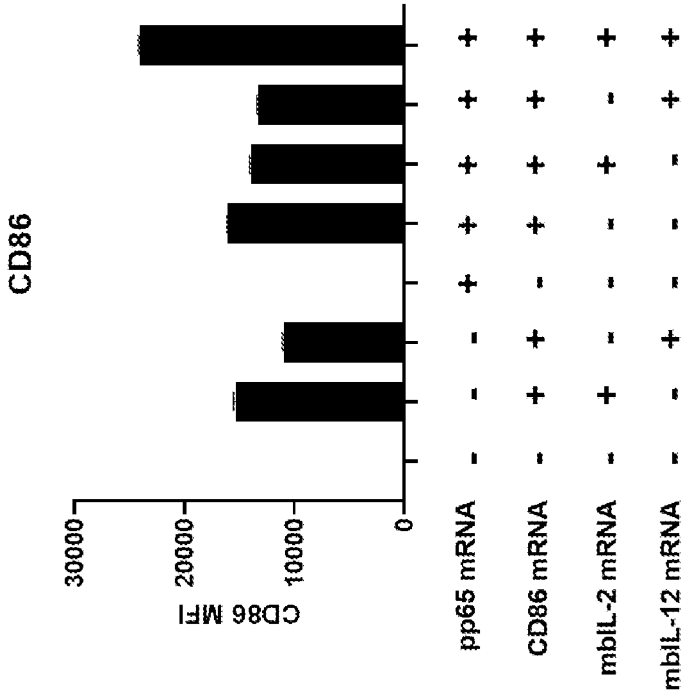
FIGS. 27A, B are graphs showing the amount of CD86 expression and percentage of CD86-expressing cells, respectively, in PBMCs that are squeeze-loaded with the indicated mRNAs encoding for CMV pp65 antigen, CD86, membrane-bound IL-2 (mbIL-2) and/or membrane-bound IL-12 (mbIL-12).
Figure 27B:
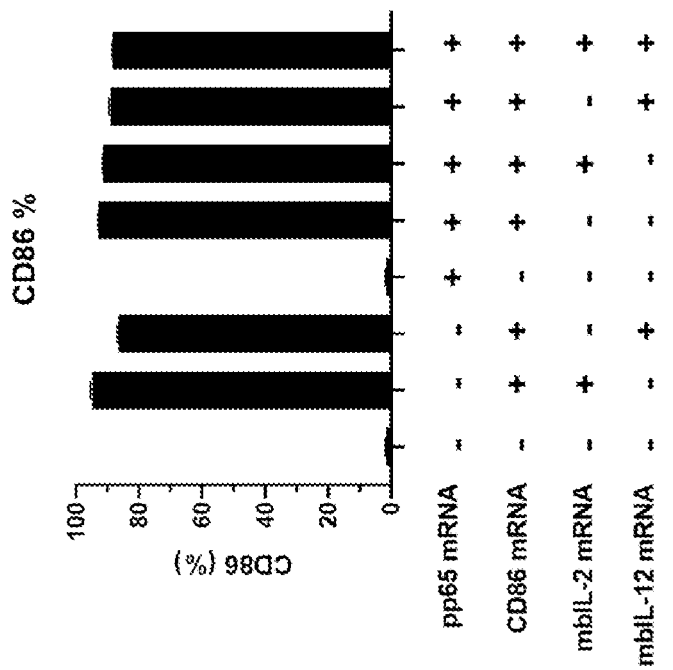
FIGS. 27C, D are graphs showing the amount of membrane-bound IL-2 (mbIL-2) expression and percentage of mbIL-2-expressing cells, respectively, in PBMCs that are squeeze-loaded with the indicated mRNAs encoding for CMV pp65 antigen, CD86, membrane-bound IL-2 (mbIL-2) and/or membrane-bound IL-12 (mbIL-12).
FIGS. 27E, F are graphs showing the amount of membrane-bound IL-2 (mbIL-2) expression and percentage of mbIL-2-expressing cells, respectively, in PBMCs that are squeeze-loaded with the indicated mRNAs encoding for CMV pp65 antigen, CD86, membrane-bound IL-2 (mbIL-2) and/or membrane-bound IL-12 (mbIL-12).
Figure 27D:
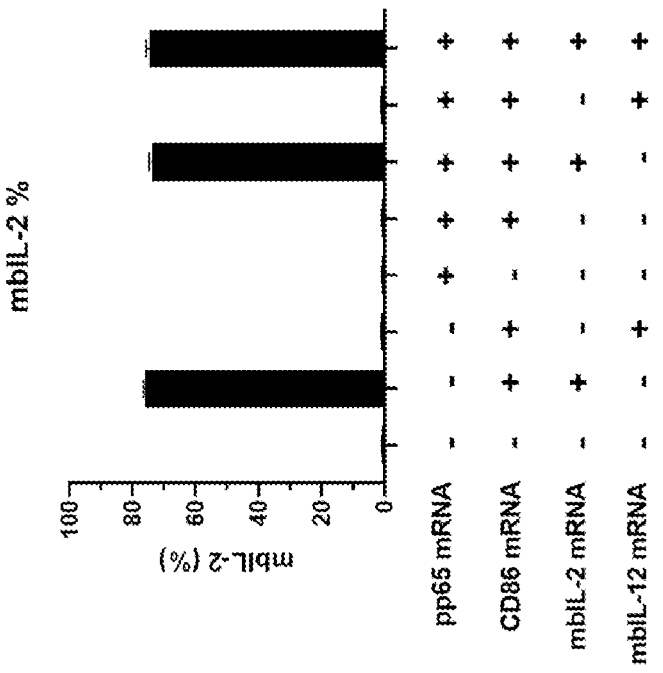
Figure 27C:
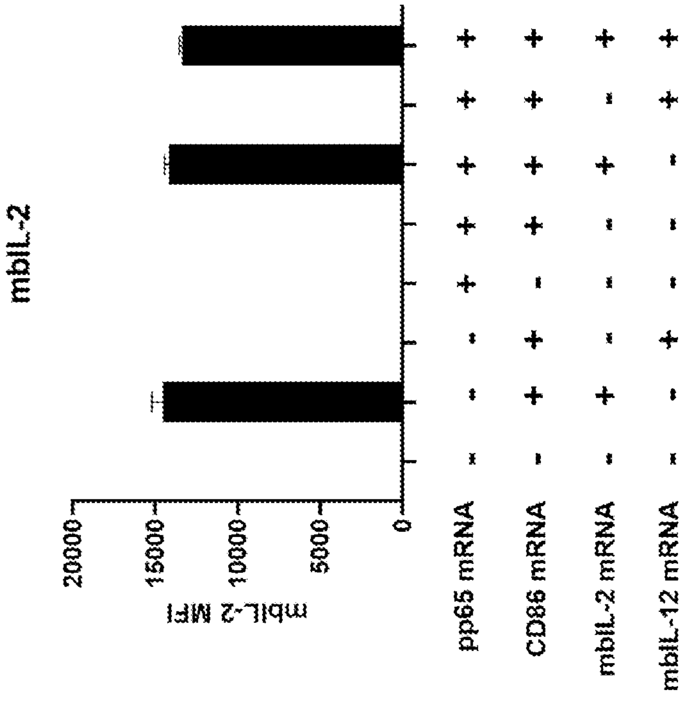
Figure 27F:
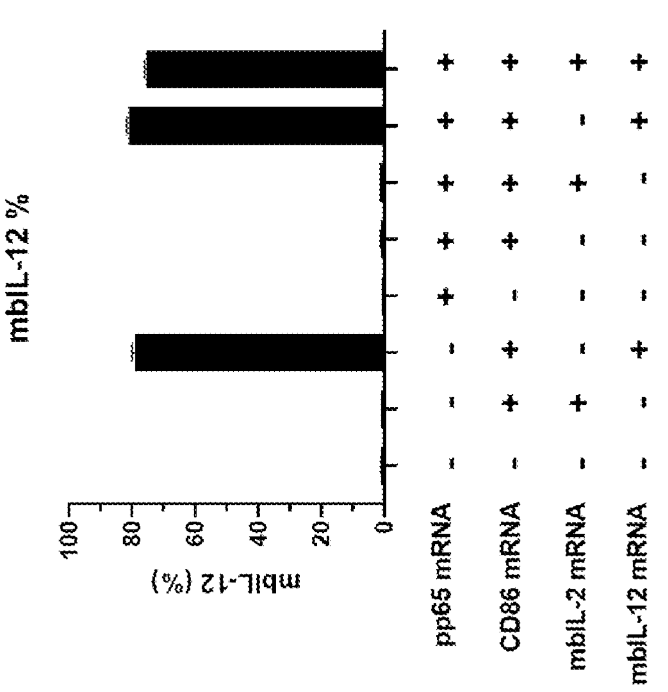
Figure 27E:
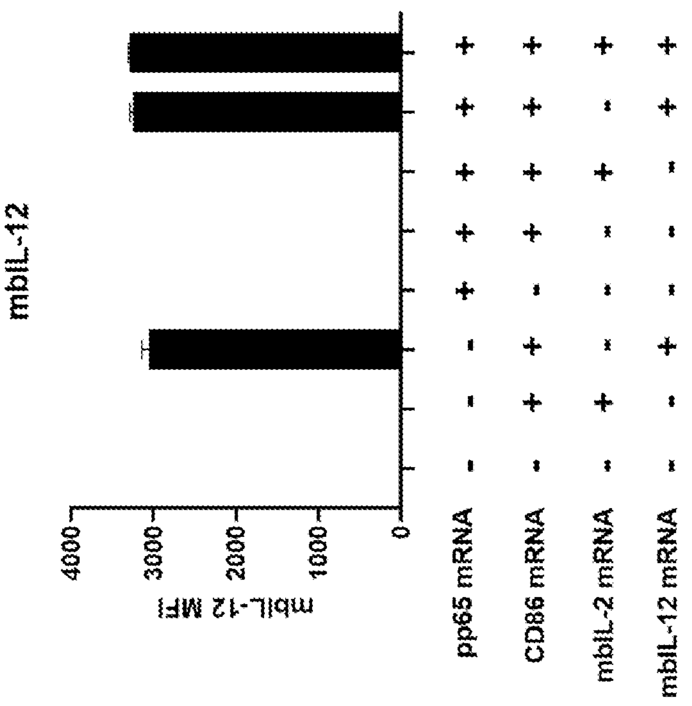

As shown in FIG. 25, there was an enhanced activation for antigen-specific T cell responders for PBMCs squeezed with CD86 and mbIL2 mRNA and also for PBMCs squeezed with CD86 and mbIL12 mRNA under conditions with restimulation of an HLA-B*07-restricted pp65 minimal epitope and without. In addition, there was a substantially enhanced T cell responder activation in instances of peptide restimulation with the HLA-B*07-restricted pp65 minimal epitope as shown in FIG. 26 as demonstrated by a significantly higher percentage of IFN-γ CD45RO+ population within CD3+ CD8+ responder cells in the group with peptide restimulation.

To show polyfunctionality of these antigen-specific CD8 T cells. TNFa production was also measured by intracellular staining. Upon restimulation, TNFa-producing CD8 T cells could be detected. Of note, the level of TNFa was increased when PBMCs were squeeze-loaded with CD86, mbIL-2, and/or mbIL-12 mRNAs.

Example 15

To assess the co-squeezing (simultaneous squeeze-loading) of various mRNA separately encoding effectors of MHC Signals 1, 2, or 3 in T cell activation, their ability to address multiple different HLA haplotypes, and the resulting enhanced responses, human donor HLA-A*02-+ PBMCs were squeeze-loaded with combinations of mRNAs respectively encoding mediators for Signals 1, 2, or 3 in T cell activation.

Methods

Human PBMCs isolated from a CMV+ HLA-A*02+ leukopak were stained with CMVpp65 tetramer specific to NLVPMVATV (495-503 aa; SEQ ID NO:88) to determine that these PBMCs have pre-existing pp65-specific CD8 T cells. Subsequently the PBMCs were prepared at a density of $5\times10^7$ cells/mL and combined with mRNA encoding CMV pp65 (Signal 1), CD86 (Signal 2), membrane-bound interleukin-2 (mbIL-2), and/or membrane-bound interleukin-12 (mbIL-12) (Signal 3). The cells were squeeze processed in the presence of the mRNA(s) at room temperature using a Cell Squeeze® system and chip through a constriction of 3.5 μm width, 10 μm length, and 70 μm depth at 60 psi in RPMI medium. Empty squeeze processed cells spiked with 10 nM CMV pp65 peptide and cells treated with 1×PMA/Ionomycin were used as a control. The following concentrations and mixtures of each mRNA were tested.

TABLE 4

| Sample | Signal 1 (CO pp65 mRNA) | Signal 2 (CO CD86 mRNA) | Signal 3 (CO mbIL-2 mRNA) | Signal 3 (CO mbIL-12 mRNA) |
|---|---|---|---|---|
| A | — | — | — | — |
| B | — | 250 μg/mL | 250 μg/mL | — |
| C | — | 250 μg/mL | — | 250 μg/mL |
| D | 50 μg/mL | — | — | — |
| E | 50 μg/mL | 250 μg/mL | — | — |
| F | 50 μg/mL | 250 μg/mL | 250 μg/mL | — |
| G | 50 μg/mL | 250 μg/mL | — | 250 μg/mL |
| H | 50 μg/mL | 250 μg/mL | 250 μg/mL | 250 μg/mL |
| I | Empty SQZ cells + 10 nM pp65 Peptide Pool Spike (5 different peptides) | | | |
| K | PMA/Ionomycin | | | |

For example, for Sample H, a total volume of 500 uL of cells in a cell suspension was squeeze processed with mRNAs at the following concentrations: 50 μg/mL pp65 mRNA (Signal 1), 250 μg/mL of CD86, 250 μg/mL of mbIL-2 mRNA, and/or 250 μg/mL of mbIL-12 mRNA. Cells in each sample were collected into RPMI+10% human serum and 1 μM CpG 7909 and incubated at 37 C for 4 hours. Following incubation, the cells were washed by centrifugation and resuspended in RPMI+10% fetal bovine serum and incubated at 37° C. for 5 days.

On day 1, aliquots of each sample were collected for analysis of mRNA expression by flow cytometry. The PBMC constituent cell composition is defined by staining for cell-specific markers (CD3, CD19, CD14, and CD56) and expression of each respective RNA is measured by staining for CD86, IL-2, and IL-12.

On day 5, 12 wells of each sample group of cells were plated and each sample group was restimulated with A 1-restricted pp65 epitope (YSEHPTFTSQY; SEQ ID NO:91), B7-restricted pp65 epitope (RPHERNGFTVL; SEQ ID NO:89), or B7-restricted pp65 epitope (TPRVTGGGAM; SEQ ID NO:90) respectively, in the presence of golgi stop and golgi plug for 5 hours.

The cells were then stained for expression of: IFN-γ, TNF-α, IL-2, Granzyme B, and PD-1 in CD3+ CD8+ responder cells.

The cells were analyzed by flowcytometry and epitope-specific cells were identified by IFNg production.

Results

CD86, mbIL-2, and mbIL-12 MFI expression were measured on Day 1, as shown in FIG. 27. These results indicate successful translation of all three mRNAs squeeze loaded into PBMCs.

Expression of CD86, mbIL-2, and mbIL-12 were also measured as a percentage of T cells within the PBMCs on Day 1. These results indicate that more than 75% of the total T cells successfully translated the mRNAs squeeze loaded inside the cells.

Figure 28:
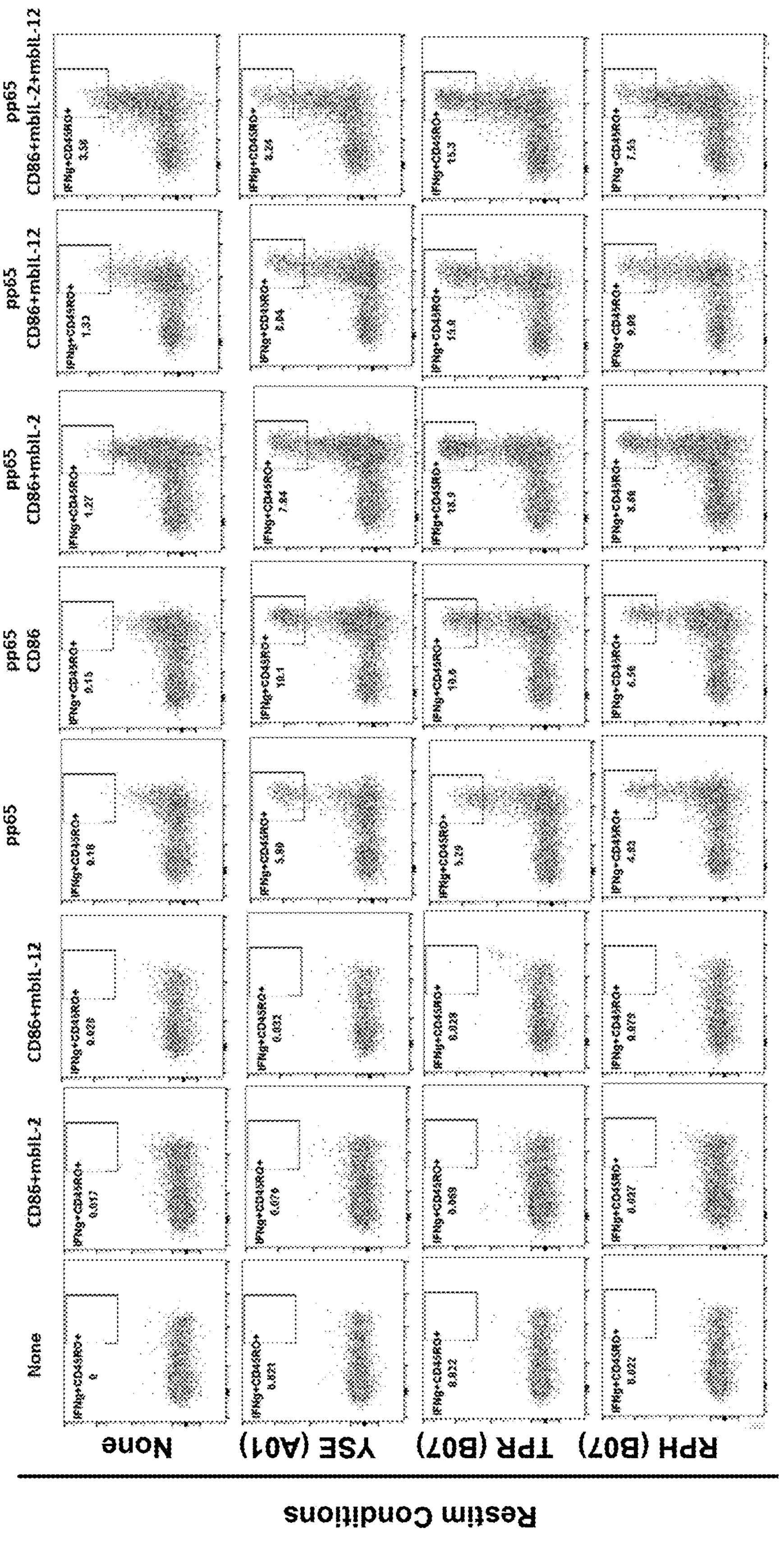
FIG. 28 contain graphs showing the amount of IFN-γ+ CD45RO+ population within CD3+CD8+ responder T cells when PBMCs are squeeze-loaded with the indicated mRNAs encoding for CMV pp65 antigen, CD86, mbIL-2 and/or mbIL-12, with or without further re-stimulation with 1 μM of pp65 antigen peptide specific to HLA-A*01 or HLA-B*07-restriction (YSE(A01), TPR(B07) or RPH (B07).

As shown in FIG. 28, there was an enhanced T cell activation when pp65-loaded PBMCs with the membrane bound cytokines and/or the costimulatory molecules co-delivered for several different haplotypes, as indicated by the enhanced T cell activation observed with the presence of each respective re-stimulation (YSE(A01), TPR(B07) or RPH(B07)) to expand the HLA-*A01, HLA-*B07 or HLA-*B07 responder T cells respectively.

Example 16

To determine if co-delivery of Signal 2 and Signal 3 mediators can enhance the ability to stimulate T cell responses by antigen presenting cells squeeze-loaded with Influenza M1 antigen, human donor HLA-A*02+ PBMCs were squeeze-loaded with different mRNAs encoding effectors mediating Signal 1. Signal 2, and/or Signal 3 respectively. The activation of CD3+ CD8+ cells and activity was measured via ICS and tetramer analysis. The effect of various mRNA squeeze-loaded cells restimulated with peptide were compared to that of control PBMCs incubated with M1 peptide (peptide spike control).

Methods

Human PBMCs isolated from an Influenza M1+HLA-A*02+ leukopak were stained with M1 tetramer to determine that these PBMCs have pre-existing M1-specific CD8 T cells. Subsequently the PBMCs were prepared at a density of $4\times10^7$ cells/mL and combined with mRNA encoding Influenza M1 (Signal 1), CD86 (Signal 2), and/or membrane-bound interleukin-12 (mbIL-12) (Signal 3). The cells were squeeze processed in presence of the respective mRNA(s) at room temperature using a Cell Squeeze® system and chip through a constriction of 3.5 μm width, 10 μm length, and 70 μm depth at 60 psi in RPMI medium. PBMCs squeeze-processed with empty payload and spiked with 100 nM Influenza M1 peptide was used as a control. The following concentrations and mixtures of each mRNA were tested.

TABLE 5

| Sample | Conditions | Signal 1 mRNA Conc. | Signal 2 mRNA Conc. | Signal 3 mRNA Conc. |
|---|---|---|---|---|
| A | Empty SQZ | — | — | — |
| B | M1 mRNA SQZ | 10 μg/mL | — | — |
| C | M1 + CD86 + mbIL-2 mRNA SQZ | | 250 μg/mL | 250 μg/mL |
| D | M1 + CD86 + mbIL-12 mRNA SQZ | | | |
| E | M1 mRNA SQZ | 50 μg/mL | — | — |
| F | M1 + CD86 + mbIL-2 mRNA SQZ | | 250 μg/mL | 250 μg/mL |
| G | M1 + CD86 + mbIL-12 mRNA SQZ | | | |
| H | M1 mRNA SQZ | 250 μg/mL | — | — |
| 1 | M1 + CD86 + mbIL-2 mRNA SQZ | | 250 μg/mL | 250 μg/mL |
| J | M1 + CD86 + mbIL-12 mRNA SQZ | | | |
| K | CD86 + mbIL-2 mRNA SQZ | — | 250 μg/mL | 250 μg/mL |
| L | CD86 + mbIL-12 mRNA SQZ | — | 250 μg/mL | 250 μg/mL |
| M | Empty SQZ (100 nM Peptide Spike) | — | — | — |

For example, for Sample G, a total volume of 200 ul of cells in a cell suspension was squeezed processed with mRNA(s) at the following concentrations of 50 ug/mL of Influenza M1 mRNA, 250 ug/mL of CD86 mRNA, and/or 250 ug/mL of mbIL-12 mRNA.

Following squeeze-processing, the squeeze-loaded PBMCs were transferred to RPMI+10% fetal bovine serum and incubated for 5 days at 37° C.

At the final day of incubation, the resulting cells were re-stimulated with 1 μM Influenza M1 peptide, and their activation and activity was measured via ICS. TNF-α, IFN-γ, IL-2, PD-1, and Granzyme B were assessed in CD3+ CD8+ responder cells. Additionally, cells were stained for Influenza M1 tetramer specific to GILGFVFTL peptide (58-66 aa; SEQ ID NO:92).

Results

As shown by intracellular staining, there was successful translation of CD86 mRNA, mbIL-2 mRNA, and mbIL-12 mRNA (FIG. 29) at 24 hours subsequent to squeeze-mediated delivery of the respective mRNAs.

FIG. 30 shows the concentration effects of squeeze-loading PBMCs with Influenza M1 mRNA on activation of antigen-specific T cells when coupled with 1 μM of antigen restimulation. As shown in FIG. 31, activation of antigen-specific T cells were observed for PBMCS squeeze-loaded with each of the three concentrations of Influenza M1. Both FIGS. 30 and 31 show a higher percentage of IFNγ+ CD45RO+ population within the CD3+CD8+ responder cells when the Influenza M1 mRNA was co-delivered with CD86 mRNA and mbIL-12 mRNA.

As shown in FIG. 32, the combination of squeezing with CD86 and mbIL-2 or mbIL-12 mRNA yielded a significant expansion of Influenza M1 CD8 T cells as measured by tetramer-positive CD8 T cells. Also, there was no antigen-independent expansion of these cells when mbIL-12 was present. On the other hand, mbIL-2 mRNA led to some antigen-independent expansion of these cells.

For the polyfunctionality markers, there was increased Granzyme B expression and upregulation of IFNg, IL-2, and TNFa cytokines suggesting higher polyfunctionality. They were further upregulated by the presence of signal 2 and 3 mRNAs in PBMCs compared to antigen alone (i.e., M1 mRNA alone) (data not shown).

Example 17

To determine if immune cells of a specific HLA haplotype squeeze-loaded with mRNA encoding for HPV16 E6 can induce an antigen-specific T cell response, human donor HLA-B*07+ PBMCs were squeeze-loaded with E6 mRNA. The ability of E6 mRNA-loaded PBMCS to stimulate HLA-B*07-restricted E6 specific T responder cells were measured using an IFN-γ ELISpot assay. The effect of PBMCs squeeze-loaded with E6 mRNA were compared to that of untreated and mock-squeeze-loaded (empty) controls.

Methods

To generate $E6_{15-24}$-specific T cells, HLA-B*07 transgenic mice were vaccinated twice 3 times (prime/boost/boost) at 2-week intervals with an emulsion of $E6_{15-24}$ peptide, hepatitis B virus core peptide (TPPAYRPPNAPIL; SEQ ID NO:93), and incomplete Freund's Adjuvant. One week after the final vaccination, mice were euthanized and the spleens and draining lymph nodes were extracted. Tissue extracts were dissociated into single cell suspensions. Cells were then cultured for 6 days at 37° C. in the presence of $E6_{15-24}$ peptide and IL-2. At the end of the 6 days, cells were cryopreserved until the day of co-culturing with PBMCs.

Human PBMCs from an HLA-B*07+ donor were prepared at a density of $5\times10^7$ cells/mL and combined with 0.5 mg/ml of E6 mRNA. PBMCs were squeeze processed in the presence of the E6 mRNA using a Cell Squeeze® system and chip through a constriction of 3.5 μm width, 10 μm length, and 70 μm depth at 60 psi in RPMI medium. Untreated PBMCs (No Contact) and PBMCs squeeze processed in the absence of E6 mRNA (Empty squeeze) were used as negative controls.

Following squeeze-processing, the squeeze-loaded PMBCs were transferred to RPMI+10% human serum with 1 μM CpG ODN 2006 and incubated for 4 hours at 37° C. The squeeze-loaded PBMCs were then washed twice with CTL medium+1% L-glutamine before being resuspended in CTL medium+1% L-glutamine.

$5\times10^4$ of either E6 mRNA squeeze-loaded PBMCs (E6 mRNA), untreated PBMCs (No Contact), mock-squeeze-loaded PBMCs (Empty squeeze), or No Contact PBMCs spiked with 1 mM $E6_{15-24}$ peptide (positive control) were placed in a co-culture with $5\times10^5$ $E6_{15-24}$ responder T cells (generated in HLA-B*07 transgenic mice) in a 96-well INF-γ ELISpot plate. The plate was incubated overnight at 37° C. and then developed according to the manufacturer's instructions.

Results

As shown in FIG. 34, HLA-B*07+ human PBMCs squeeze-loaded with E6 mRNA led to an increase in IFN-γ response in HLA-B*07 $E6_{15-24}$-specific T cells upon co-culture, as indicated by an increase in both IFN-γ Spot forming units (SFU) (FIG. 35) and IFN-γ mean spot size (FIG. 36) in ELISPOT assay. These IFN-γ responses in HLA-B*07 $E6_{15-24}$-specific T cells were significantly increased in E6 mRNA-loaded PBMCs as compared to the No Contact and Empty squeeze controls. These results demonstrate that HLA-B*07+ PBMCs squeeze-loaded with E6 mRNA can process and present the $E6_{15-24}$ epitope and induce HLA-B*07-restricted E6-specific T cells responses.

Example 18

To determine the length of time immune cells squeeze-loaded with E7 mRNA can elicit an antigen-specific T cell response, human donor HLA-A*02+ PBMCs were squeeze-loaded with E7 mRNA and incubated for various lengths of time before assessing the ability to stimulate E7-specific T cells by IFN-γ ELISA.

Methods

Human PBMCs from an HLA-A*02+ donor were prepared at a density of $5\times10^7$/mL, and squeeze-processed using a Cell Squeeze® system and chip through a constriction of 3.5 μm width, 10 μm length, and 70 μm depth at 60 psi with (i) 0.5 mg/ml of E7 mRNA, (ii) 0.5 mg/ml E6 mRNA, (iii) 0.5 mg/ml E7 mRNA and 0.25 mg/ml E6 mRNA, (iv) E7.6 synthetic long peptide (SLP) or (v) with no cargo (Empty squeeze) in RPMI 164) medium. Following squeeze-processing, the squeeze-loaded PMBCs were transferred to RPMI+10% human serum with 1 μM CpG ODN 2006 and incubated for 4 hours at 37° C. The squeeze-loaded PBMCs were subsequently washed twice in co-culture medium (X-VIVO 15+5% human serum), before resuspension in fresh co-culture medium. A portion of the cells were set aside for immediately co-culturing with $E7_{11-20}$ responder T cells (Cellero) and the remaining cells were cryopreserved.

$3\times10^5$ squeeze-loaded PBMCs were then placed in co-culture with $3\times10^4$ HLA-A*02+ $E7_{11-20}$ responder T cells (Cellero) in a 96-well plate. As a positive control, 0.1 μM of the $E7_{11-20}$ peptide was added directly to untreated PBMCs and responder cells in the 96-well plate. After incubating the co-culture for 18 hours at 37° C., co-culture supernatants were harvested. An IFNγ ELISA was conducted according to the manufacturer's protocol to determine the concentration of IFNγ in the culture supernatant for each sample.

Cryopreserved squeeze-loaded PBMCs were thawed and rested in culture for 8, 4, or 0 hours before addition of $E7_{11-20}$ responder T cells. After 8, 4, or 0 hours in culture, $3\times10^5$ squeeze-loaded PBMCs were co-cultured with $3\times10^4$ HLA-A*02+$E7_{11-20}$ responder T cells (Cellero) in a 96-well plate. After incubating the co-culture for 18 hours at 37° C., co-culture supernatants were harvested. An IFNγ ELISA was conducted according to the manufacturer's protocol to determine the concentration of IFNγ in the culture supernatant for each sample.

Results

As shown in FIGS. 38A and 39A, human PBMCs squeeze-loaded with E7 mRNA are capable of eliciting an immune response as measured by IFN-γ production from $E7_{11-20}$ responder T cells upon co-culture immediately after squeeze-loading of E7 mRNA. As shown in FIGS. 38B and 39B, human PBMCs squeeze-loaded with E7 mRNA are capable of eliciting an immune response for at least up to 8 hours post squeeze processing as measured by IFN-γ production from $E7_{11-20}$ responder T cells. These results demonstrate that HLA-A*02+ human PBMCs squeeze-loaded with E7 mRNA can elicit an E7-specific T cells response for at least 8 hours post squeeze processing.

Example 19

To determine if immune cells squeeze-loaded with E6 mRNA can elicit an E6-specific immune response, human donor HLA-A*02+ PBMCs were squeeze-loaded with E6 mRNA and the ability to stimulate $E6_{29-38}$ TCR Jurkat-Lucia NFAT reporter cells was assessed by luminescence.

Methods

E6 TCR Jurkat-Lucia NFAT reporter cells were generated by transducing $E6_{29-38}$ TCR expressing lentivirus into Jurkat-Lucia NFAT cells (InvivoGen) that have had their endogenous TCRα/β knocked-our. These cells have an integrated NFAT-inducible Lucia reporter which can be activated through engagement of the $E6_{29-38}$ TCR with MHC-I (HLA-A*02 restricted) bound with the cognate $E6_{29-38}$ epitope.

Human PBMCs from an HLA-A*02+ donor were prepared at a density of $4\times10^7$/mL, and squeeze-processed through a constriction of 3.5 μm width, 10 μm length, and 70 μm depth at 60 psi with (i) 500 μg/ml E6 mRNA and 500 μg/ml E7 mRNA, (ii) mRNAs encoding for CD86, membrane-bound IL-2 (mbIL-2) and membrane-bound IL-12 (mbIL-12), (iii) E6 and E7 mRNA, and mRNAs encoding for CD86, mbIL-2 and mbIL-12, (iv) E6 and E7 SLP or (v) with no cargo (empty squeeze) in RPMI 1640 medium at room temperature. Following squeeze-processing, the squeeze-loaded PMBCs were transferred to RPMI+10% human serum with 1 μM CpG ODN 2006 and incubated for 4 hours at 37° C. The squeeze-loaded PBMCs were subsequently washed twice in co-culture medium (X-VIVO 15+5% human serum), before resuspension in fresh co-culture medium.

$4\times10^5$ squeeze-loaded PBMCs were then placed in co-culture with $1\times10^5$$E6_{29-38}$ TCR Jurkat-Lucia NFAT cells in a 96-well plate. As a positive control, 1 μM of the $E6_{29-38}$ epitope was added directly to untreated PBMCs and $E6_{29-38}$ TCR Jurkat-Lucia NFAT cells in the 96-well plate. After incubating the co-culture for 16-18 hours at 37° C., the co-culture supernatants were harvested. A QUANTI-Luc Gold assay (InvivoGen) was conducted with the culture supernatant according to the manufacturer's protocol to measure Lucia luciferase via luminescence due to the activation of the NFAT-inducible Lucia reporter.

Results

As shown in FIGS. 40, 41A, and 41B, human PBMCs squeeze-loaded with E6 mRNA and co-cultured with $E6_{26-38}$ TCR Jurkat-Lucia NFAT reporter cells led to an increase in NFAT activation and luminescence compared to the empty squeeze control. The results demonstrate that HLA-A*02+ human PBMCs squeeze-loaded with E6 mRNA can elicit an $E6_{29-38}$ immune response.

Example 20

This study evaluated the expansion of $E7_{11-19}$ TCR- or $E6_{29-38}$ TCR-transduced CD8 T cells upon co-culture with autologous PBMCs that were squeeze-loaded with mRNAs encoding for HPV16 antigens and signal 2/3 mediators (SQZ-eAPC-HPV cells).

Methods

Human PBMCs were isolated from an HLA-A*02+ leukopak. $CD8^+$ T cells were isolated via negative selection on day 0. A medium of R10 (RPMI 1640+10% fetal bovine serum+100 U/mL penicillin+100 μg/mL streptomycin) supplemented with 100 IU/mL of IL-2 (R10+IL-2) was prepared. T cells were centrifuged at 500 rcf for 5 minutes at room temperature. The supernatant was aspirated, and cells were resuspend at a cell concentration of $2\times10^6$ cells/mL in R10+IL-2. Anti-CD3/CD28 Dynabeads were washed and resuspended at a bead concentration of $2\times10^6$ Dynabeads/mi in R10+IL-2. 3 mL of T cells and 3 mL of Dynabeads were combined in a flask, with the final cell and Dynabead concentration equaling $1\times10^6$ cells/ml, and placed in an incubator at 37° C., 5% $CO_2$ for 2 days.

On day 2, the $CD8^+$ T cells were transduced with either an $E7_{11-19}$ TCR- or an $E6_{29-38}$ TCR-expressing lentivirus. 40 mL T cell medium was prepared comprising X-VIVO 15+5% human serum+300 IU/ml IL-2. $CD8^+$ T cells were harvested and resuspended at $1\times10^6$ cells/mL in T cell medium. In a 24-well plate, 500 μL of $CD8^+$ T cells was combined with 50 μL of LentiBOOST and either 84.7 μL of E7 TCR lentivirus ($1\times10^7$ TU) or 49.5 μL, of E6 TCR lentivirus ($1\times10^7$ TU). T cells medium was added to each of the transductions to bring the volume to 1 mL total. The cells were spinoculated by centrifuge for 2 hours at 2,000 ref at 32° C. The plate placed in an incubator at 37° C., 5% $CO_2$ overnight. A second lentiviral transduction following the same protocol as the first lentiviral transduction was performed on day 3.

On day 4, the lentivirus was removed and T cells were cultured at $1\times10^6$ cells/mL for 4 days in R10+300 IU/mL IL-2. On day 7·$E7_{11-19}$ pentamer and $E6_{29-38}$ tetramer staining were performed to determine the percentage of cells expressing the E6 or E7 TCR (FIG. 42A). Fresh R 10 media was also added to bring the cell concentration back to $1\times10^6$ cells/mL The E7- or E6-TCR transduced T cells were then co-cultured at a concentration of 0.1% pent/tet+ T cells with autologous PBMCs that had been squeezed with mRNAs encoding E6 and E7, and/or Sig 2 mRNA(CD86 mRNA)/Sig 3 mRNA (mbIL-2, and mbIL-12 mRNA), for a total of 6 days.

On day 8, PBMCs from the same donor were thawed and four groups of squeeze-loaded autologous PBMCs were prepared according to the schedule below. Specifically, the PBMCs were squeezed processed at room temperature using a microfluidic constriction (10 μm depth, 3.5 μm width, and 70 μm length) at 60 psi in RPMI medium.

TABLE 6

| Group | Squeeze Condition | Squeeze Volume |
|---|---|---|
| A | Empty Squeeze | 300 μL |
| B | 500 μg/mL E6 mRNA and 500 μg/mL E7 mRNA | 300 μL |
| C | 250 μg/mL CD86 mRNA, 250 μg/mL mbIL-2 mRNA, and 250 μg/mL mbIL-12 mRNA | 300 μL |
| D | 500 μg/mL E6 mRNA, 500 μg/mL E7 mRNA, 250 μg/mL CD86 mRNA, 250 μg/mL mbIL-2 mRNA, and 250 μg/mL mbIL-12 mRNA | 300 μL |

The E7- or E6-TCR transduced T cells were then co-cultured at a cell concentration of with the autologous PBMCs that had been squeeze processed with E6 and E7 mRNA, and/or signal 2 mediator mRNA (CD86 mRNA)/signal 3 mediator mRNA (mbIL-2 and mbIL-12 mRNA). Co-cultures were plated in a 96-well plate with $2\times10^5$ total cells; wherein $5\times10^4$ of the cells were squeeze processed PBMCs and the remaining $1.5\times10^5$ cells were a combination of 0.1% E6 or E7 TCR expressing T cells and unprocessed autologous PBMCs. The co-culture was incubated at 37° C., 5% $CO_2$ for 6 days.

On day 14 (6 days after initiating the co-culture), $E7_{11-19}$ pentamer staining and $E6_{29-38}$ tetramer staining were performed, as well as an Intracellular Cytokine Staining (ICS). For the ICS, cells were first restimulated with either the $E7_{11-19}$ or $E6_{29-38}$ minimal epitope for 6 hours in the presence of GolgiPlug and GolgiStop. Cells were then stained for expression of IFNγ, TFNα, IL-2.

Results

As shown in FIGS. 42D to 42I, for both co-culture setups (E7 TCR T cells or E6 TCR T cells), the highest percentages of IFNγ-, TNF-α-, or IL-2-producing T cells were observed in the co-culture with PBMCs squeeze-loaded with E6, E7, CD86, mbIL-2, and mbIL-12 mRNA (E6+E7+signal 2/3 mRNA), as compared to co-culture with PBMCs squeeze-loaded with E6+E7 mRNA only or with signal 2/3 mRNA only. As shown in FIGS. 42B and 42C, E7 pentamer and E6 tetramer staining also corroborated the ICS results, wherein the highest proliferation of E6 tetramer+ or E7 pentamer+ T cells was observed in the co-culture with PBMCs squeeze-loaded with E6+E7+signal 2/3 mRNA, as compared to the co-culture with PBMCs squeeze-loaded with E6+E7 mRNA only or with signal 2/3 mRNA only.

These results indicated that PBMCs squeeze-loaded with mRNAs encoding for the HPV16 E6 and E7 antigens and signal 2/3 mediators stimulated stronger T cell activation and proliferation as compared to PBMCs squeeze-loaded with either the mRNAs encoding for the antigen or the mRNAs encoding the signal 2/3 mediators alone.

Example 21

This study evaluated the activation and expansion of pp65-specific human $CD8^+$ T cells in NSG-$(K^bD^b)^{null}$ $(IA)^{null}$ mice (NSG MHC-I/II DKO mice) after an immunization with human PBMCs that were squeeze-loaded with mRNAs encoding for CMV antigens and signal 2/3 mediators (SQZ-eAPC-CMV cells).

Methods

Cryopreserved human PBMCs, isolated from an HLA-A*02+ leukopak were thawed for use in this study. On day 0, 8 vials of HLA-A*02+ CMV+ cryopreserved PBMCs were thawed in a water bath. The vials containing the cells were centrifuged at 200 rcf for 10 minutes at room temperature. The supernatant was aspirated and the cells were resuspended at a cell concentration of ~$1\times10^7$ cells/mL in R10 (RPMI 1640+10% fetal bovine serum+100 U/mL penicillin+100 μg/mL streptomycin). The cells were rested for 1 hour at 37° C., after which, the cells were centrifuged at 500 rcf for 5 minutes at room temperature. The supernatant was aspirated and the cells were resuspended in 25 mL of PBS. The cells were centrifuged at 500 rcf for 5 minutes at room temperature. The supernatant was aspirated and the cells were resuspended in PBS at a final cell concentration of $1\times10^8$ cells/mL.

Two groups of squeeze-loaded PBMCs were prepared according to below:

The PBMCs were squeeze processed at room temperature using a microfluidic constriction (10 μm depth, 35 μm width, and 70 μm length) at 60 psi in RPMI medium. Specifically, PBMCs were either (1) squeeze processed with 500 μg/mL of mRNA encoding pp65 (pp65 only), or (2) squeeze loaded with 500 μg/mL of mRNA encoding pp65, and 250 ug/mL of each of: mRNA encoding signal 2 mediator (CD86), mRNA encoding signal 3 mediator (mbIL-2), and mRNA encoding another signal 3 mediator (mbIL-12) (eAPC-CMV, or eAPC-pp65).

The two groups of squeeze-processed cells were each split into two administration subgroups according to the schedule below. Group A, a fifth group, represented the control group comprising unprocessed (no contact) cells.

TABLE 7

| Group | Sample | Concentration |
|---|---|---|
| A | No contact | 130 μL of no contact cells + 520 μL of PBS (Day 0: 1 × $10^7$ cells/100 μL injection); (Day 7: 5 × $10^6$ cells/100 μL injection) |
| B | eAPC-CMV | 130 μL of eAPC cells + 520 μL of PBS (1 × $10^6$ cells/100 μL injection) |
| C | eAPC-CMV | 650 μL of eAPC cells 5 × $10^6$ cells/100 μL injection |

TABLE 7-continued

| Group | Sample | Concentration |
|---|---|---|
| D | pp65 only | 130 μL of pp65 cells + 520 μL of PBS<br>1 × $10^6$ cells/100 μL injection |
| E | pp65 only | 650 μL of pp65 cells<br>5 × $10^6$ cells/100 μL injection |

As shown in Table 8, for priming (day 0), five mice per group in all groups were given retro-orbital (R.O.) injections of the indicated amount of unprocessed PBMCs (no contact PBMCs) in the morning of day 0, and five mice per group were given respective R.O. injections for the indicated amount of squeeze-processed PBMCs for groups B-E in the afternoon of day 0.

On day 7, PBMCs were thawed and squeeze-processed according to a similar procedure described above and two groups of processed PBMCs (eAPC-CMV, pp65 only) were prepared for boost administration, with concentrations according to Table 7 above.

As shown in Table 8, for boosting (day 7), the 5 mice per group were given R.O. injections of the indicated amount of unprocessed PBMCs (no contact PBMCs) for group A, or the indicated amount of processed PBMCs for groups B-E.

TABLE 8

| Group | hPBMC engraftment (day 0) | Prime Conditions (day 0) | Boost Conditions (day 7) | # of NSG dKO mice | Injection Vol |
|---|---|---|---|---|---|
| A | 10M No Contact PBMCs | — | 5M No Contact PBMCs | 5 | 100 μL/ mouse |
| B | 9M No Contact PBMCs | 1M eAPC-pp65 PBMCs | 1M eAPC-pp65 PBMCs | 5 | |
| C | 5M No Contact PBMCs | 5M eAPC-pp65 PBMCs | 1M eAPC-pp65 PBMCs | 5 | |
| D | 9M No Contact PBMCs | 1M pp65 mRNA PBMCs | 1M pp65 mRNA PBMCs | 5 | |
| E | 5M No Contact PBMCs | 5M pp65 mRNA PBMCs | 5M pp65 mRNA PBMCs | 5 | |

On day 12, blood was collected from the mice by Submandibular Blood Collection (SMB) bleed into a sterile EDTA vacutainer. A 2× surface stain was performed with HLA-A*02 pp65 tetramer (NLVPMVATV; SEQ ID NO:88) in FACS buffer in the following ratios:

1:25 dilution of mouse FcR block

1:100 dilution of antibodies

1:20 dilution of HLA-A*02 pp65 tetramer (NLVPMVATV; SEQ ID NO:88)

Specifically, 100 μL of whole blood and 100 μL of 2× surface stain were added into a 14 ml FACs tube, and incubated in the dark for 30 minutes at room temperature. 2 mL of 1×BD™ FACS lysis solution (1:10 dilution with di$H_2O$) was added to each tube. The tubes were then gently vortexed and incubated in the dark for 10 minutes at room temperature. The cells were subsequently centrifuged at 400 rcf for 5 minutes at room temperature. The supernatant was aspirated and the cells were resuspended in 0.2 mL of FACS buffer. The cells were centrifuged again at 500 rcf for 4 minutes at room temperature. The supernatant was decanted and resuspended in 0.2 mL of FACS buffer. The pp65 tetramer stain was performed with reagents as described above.

On day 14, mice were sacrificed, with blood was collected by terminal bleeding, and spleens harvested. With the collected samples, pp65 tetramer staining was performed, as was Intracellular Cytokine Staining (ICS). The spleens were collected in tubes with 1 mL of R 10 media. Individual spleens were placed over a 40 um cell strainer on a 50 mL conical tube. The spleens were pressed through the strainer using the plunger from a syringe. The resultant material was washed through the strainers with cold FACS isolation buffer. Each tube was then filled with FACS isolation buffer up to 15 mL. The cells were centrifuged at 500 rcf for 5 minutes at room temperature. The supernatant was aspirated and the cells were resuspended in 0.5 mL of R10 media.

Prior to staining, the pp65 tetramer was centrifuged at 14000 rcf for 5 minutes at 4° C. 100 μL of cells at a concentration of $2\times10^7$ cells/mL were transferred to a 96-well V-bottom plate. The plate was centrifuged at 500 rcf for 4 minutes at room temperature. The supernatant was decanted and the cells were washed with 200 μL of PBS. The supernatant was decanted and the cells were resuspended using a Live/Dead Fixable Near IR Dead Cell Stain Kit with 50 μL of Live/Dead Near IR diluted in PBS (1:1000). The cells were incubated in the dark for 10 minutes at room temperature. A mixture of pp65 tetramer and FcR block mix was prepared with a 1:25 dilution of each in FACs buffer. Similarly, a mixture of FcR block only was prepared with a dilution in 1:25 in FACS buffer and used for a fluorescence minus one (FMO) control. Cells were incubated in the dark for 30 minutes. Antibody surface staining mixtures were prepared at 1:75 dilution ratio for each of the antibodies listed below in FACS buffer:

Anti-mouse CD45

Anti-human CD45

Anti-human CD3

Anti-human CD8

Anti-human CD45RO

50 μL of the surface stain mixture was added to the cell suspensions and were incubated for 15 minutes in the dark in room temperature. Then, 50 μL of FACS buffer were added to each well. The cells were centrifuged at 500 rcf for 4 minutes at room temperature. The supernatant was decanted and the cells were washed with 200 μl of FACS buffer. The cells were centrifuged at 500 rcf for 4 minutes at room temperature. The supernatant was decanted and the cells were resuspended in 2 (0 μL of FACS buffer. 150 μL of sample was run on the Attune N×T Flow Cytometer at 100 μL/min.

For the ICS, cells were either (1) not restimulated; (2) restimulated with the pp65 minimal epitope; or (3) restimulated with 1 M of PMA/Ionomycin for 6 hours in a 37° C., 5% $CO_2$ incubator in the presence of GolgiPlug™ and GolgiStop™. After a total of 6 hours of restimulation, the cells were transferred to a 96-well V-bottom plate. The cells were centrifuged at 500 rcf for 4 minutes at room temperature. The supernatant was decanted and the cells were resuspended with 200 μL of PBS. The cells were centrifuged at 500 rcf for 4 minutes at room temperature. Live/Dead Near IR diluted in PBS (1:1000) was prepared in PBS. Golgiplug™ (1:500) and Golgistop™ (1:750) were added. The supernatant was decanted and the cells were resuspended in 50 μL of Live/Dead Near IR diluted in PBS (1:1000) and Golgiplug™ and Golgistop™ mixture. The cells were incubated in the dark at room temperature for 10 minutes.

Antibody surface staining mixtures were prepared at 1:100 dilution ratio for each of the antibodies listed below with human FcR block (1:50 dilution) and Golgiplug™ (1:500) and Golgistop™ (1:750):

Anti-mouse CD45
Anti-human CD45
Anti-human CD3
Anti-human CD8
Anti-human CD45RO

50 μL of the surface antibody stain was added in addition to the Live/Dead Near IR diluted in PBS (1:1000) stain. The cells were incubated in the dark at room temperature for 15 minutes. 100 μL of FACS buffer was added and the cells were centrifuged at 500 rcf for 4 minutes at room temperature. The cells were washed with 200 μL of FACS buffer and centrifuged at 500 rcf for 4 minutes at room temperature. The supernatant was decanted and the cells were resuspended in 100 μL of BD CytoFix/CytoPerm™ Fixation and Permeabilization Solution. The cells were incubated in the dark for 20 minutes at 4 C. After incubation, 100 μL of 1× Perm/Wash buffer was added. The cells were centrifuged at 500 rcf for 4 minutes at room temperature. The supernatant was decanted and the cells were resuspended in 200 μL of 1× Perm/Wash buffer. The cells were centrifuged at 500 rcf for 4 minutes at room temperature. The supernatant was decanted and the cells were resuspended in 200 μl of 1×BD™ Perm/Wash buffer. The plate was incubated overnight at 4 C.

The cells were then stained the next day for expression of IFNγ, TFNα, IL-2. The cells were centrifuged at 500 crf for 4 minutes at room temperature. Antibody surface staining mixtures were prepared at 1:100 dilution ratio for anti-IFNγ, anti-TFNα, or anti-IL-2 in 1× Perm/Wash buffer. The cells were resuspended in 50 μL of the antibody staining mix. The cells were incubated in the dark at 4 C for 30 minutes. After incubation, 150 μL of 1× Perm/Wash buffer was added and the cells were centrifuged again for 500 rcf for 4 minutes at room temperature. The cells were resuspended in 200 μL of FACS buffer. 150 μL of sample was run on the Attune N×T Flow Cytometer at a flow rate of 100 μL/min.

Results

Figure 43E:
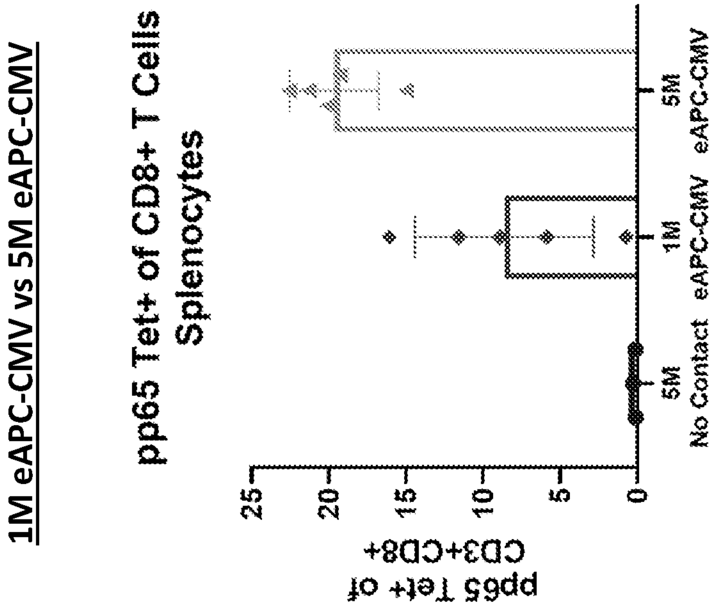
Figure 43F:
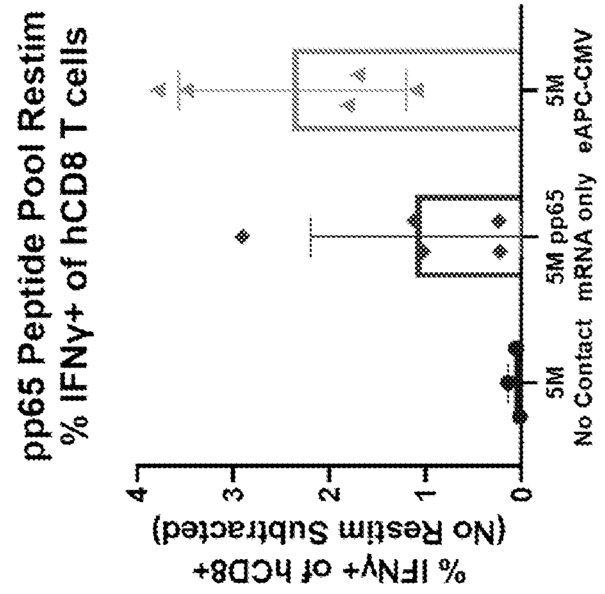
Figure 43G:
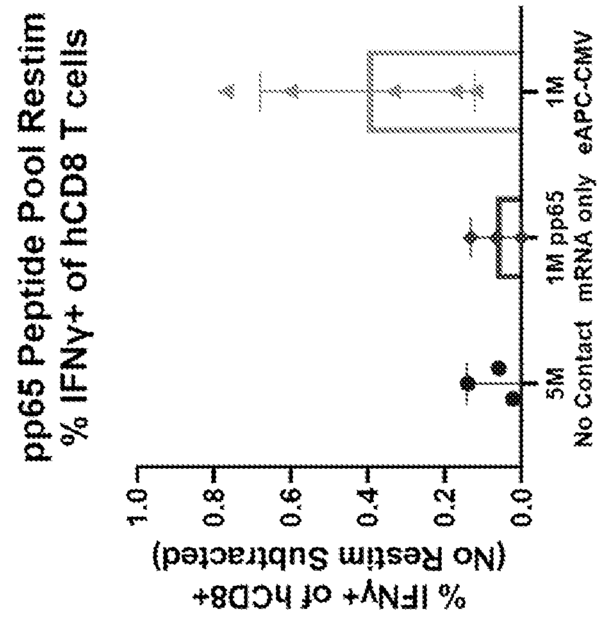
Figure 43H:
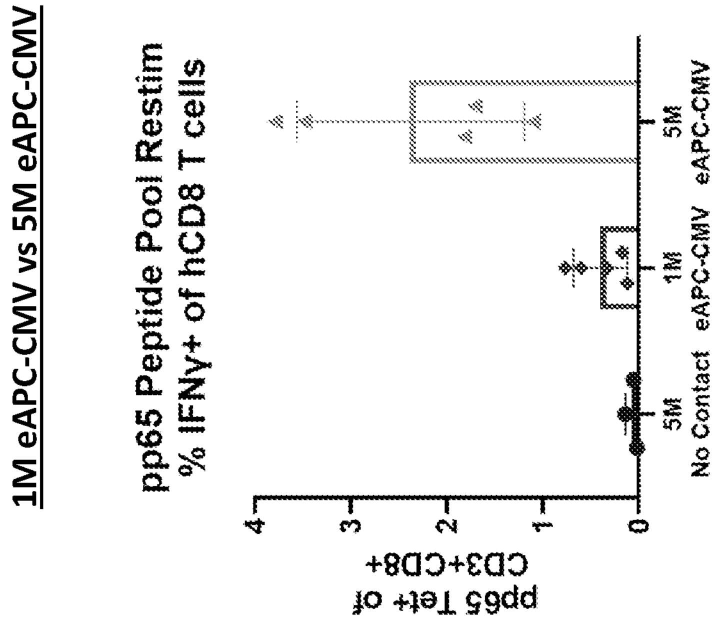
Figure 43I:
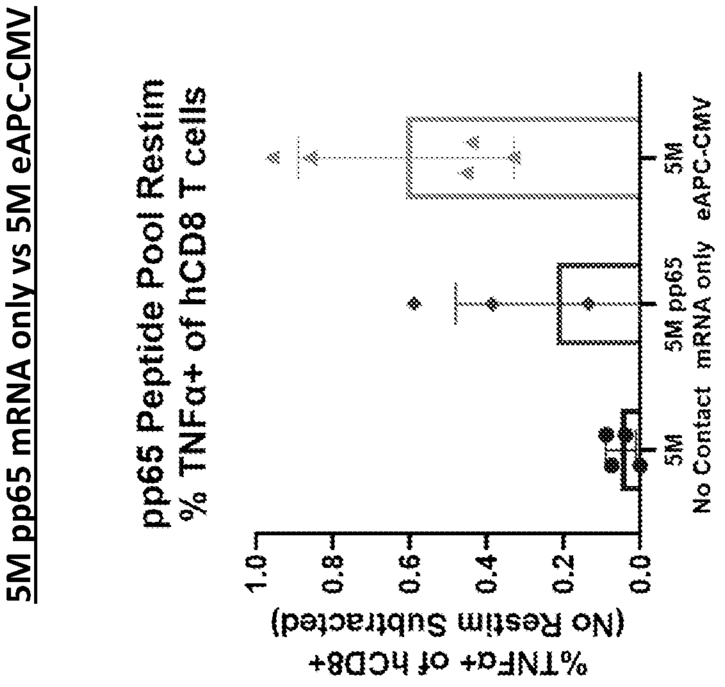
Figure 43J:
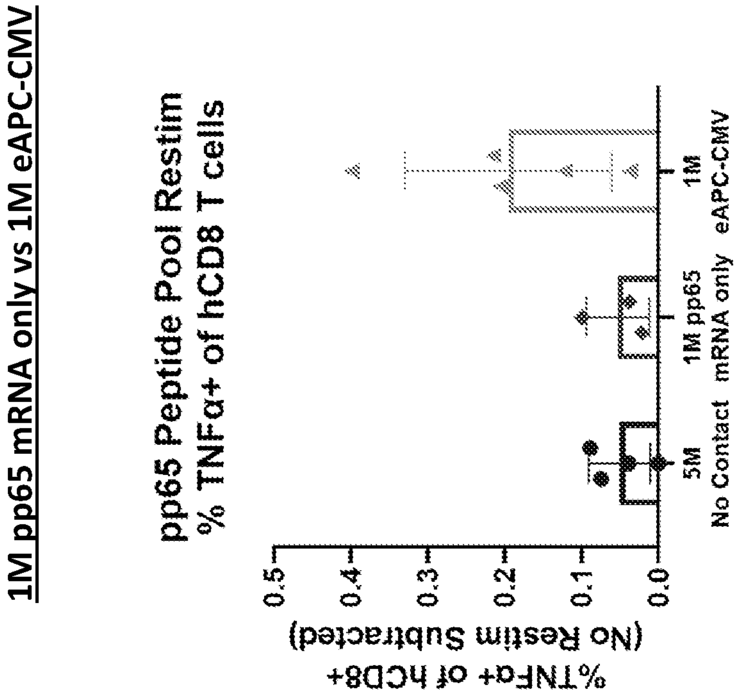
Figure 43K:
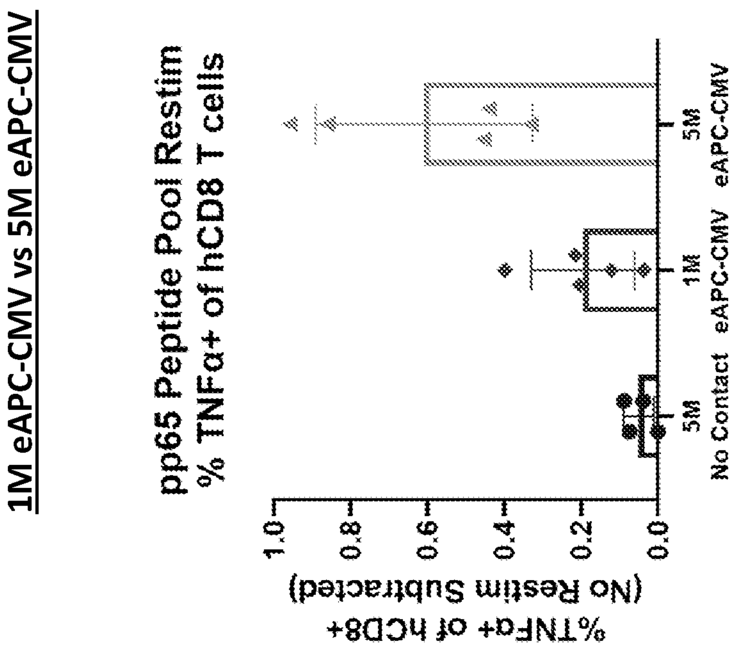

As shown in FIGS. 43A, B, C, D, E, there was a significant increase in the pp65 antigen-specific T cells in the mice immunized with eAPC-CMV cells (PBMCs squeeze-loaded with mRNAs encoding pp65 and sig2/sig3 mediators) compared to the mice that were immunized with unprocessed PBMCs (no contact), As shown in FIG. 43E, there was a dose-dependent increase in the percentage of pp65 tetramer+ T cells when comparing NSG MHC-I/II DKO mice immunized with $1\times10^6$ vs $5\times10^6$ eAPC-CMV cells. A similar dose dependence is observed when measuring the percentage of TNF-α and IFNγ-producing T cells after restimulation with a pool of pp65 minimal epitopes (FIGS. 43H and K). In addition, mice immunized with $5\times10^6$ eAPC-CMV cells trended towards having a higher percentage of pp65 tetramer+ cells (FIGS. 43A, C. D), as well as higher percentage of TNF-producing and IFNγ-producing T cells (FIGS. 43F, G, I, J) compared to mice immunized with $5\times10^6$ pp65 mRNA only cells (PBMCs squeeze-loaded with mRNA encoding pp65 only). Overall, this data demonstrates that human PBMCs squeezed with mRNAs encoding for pp65, CD86, mbIL-2, and mbIL-12 can stimulate and expand antigen-specific T cells in an in vivo humanized mouse model.

Sequence Listing

| SEQ ID NO | Sequence | Description |
|---|---|---|
| 1 | TIHDIILECV | HPV16-E6(29-38), human epitope |
| 2 | EVYDFAFRDL | HPV16-E6(48-57), murine epitope |
| 3 | YMLDLQPETT | HPV16-E7(11-20), human epitope |
| 4 | RAHYNIVTF | HPV16-E7(49-57), murine epitope |
| 5 | LPQL<u>S</u>TELQT | HPV16-E6(19-28) N-terminal polypeptide, human |
| 6 | QLCTELQT | HPV16-E6(21-28) N-terminal polypeptide, human |
| 7 | KQQLLRR | HPV16-E6(41-47) N-terminal polypeptide, native murine |
| 8 | VYSKQQLLRR | HPV16-E6(38-47) N-terminal polypeptide, classic murine |
| 9 | MHGDTPTLHE | HPV16-E7(1-10) N-terminal polypeptide, human |

-continued

Sequence Listing

| SEQ ID NO | Sequence | Description |
|---|---|---|
| 10 | GQAEPD | HPV16-E7(43-48) N-terminal polypeptide, murine |
| 11 | Y**S**KQQLLRREVYDFAF | HPV16-E6(39-54) C-terminal polypeptide, human |
| 12 | YCKQQLL | HPV16-E6(39-45) C-terminal polypeptide, human |
| 13 | CIVYRDGN | HPV16-E6(58-65) C-terminal polypeptide, native murine |
| 14 | SIVYRDGNPYAVSDK | HPV16-E6(58-72) C-terminal polypeptide, classic murine |
| 15 | DLYCYEQLNDSSEEE | HPV16-E7(21-35) C-terminal polypeptide, human |
| 16 | CCKCDSTLRLCVQSTHVDIR | HPV16-E7(58-77 C-terminal polypeptide, native murine |
| 17 | SSKSDSTLRLSVQSTHVDIR | HPV16-E7(58-77) C-terminal polypeptide, classic murine |
| 18 | LPQLSTELQTTIHDIILECVYSKQQLLRREVYDFAF | HPV16-E6(19-54) SLP, human |
| 19 | QLCTELQTTIHDIILECVYCKQQLL | HPV16-E6(21-45) SLP, human |
| 20 | KQQLLRREVYDFAFRDLCIVYRDGN | HPV16-E6(41-65) SLP, native murine |
| 21 | VYSKQQLLRREVYDFAFRDLSIVYRDGNPYAVSDK | HPV16-E6(38-72) SLP, classic murine |
| 22 | MHGDTPTLHEYMLDLQPETTDLYCYEQLNDSSEEE | HPV16-E7(1-35) SLP, human |
| 23 | QLCTELQTYMLDLQPETTYCKQQLL | HPV16-E7.6 SLP, human |
| 24 | GQAEPDRAHYNIVTFCCKCDSTLRLCVQSTHVDIR | HPV16-E7(43-77) SLP, native murine |
| 25 | GQAEPDRAHYNIVTFSSKSDSTLRLSVQSTHVDIR | HPV16-E7(43-77) SLP, classic murine |
| 26 | ggGGTCAACGTTGAgggggg<br>Bases shown in capital letters are phosphodiester, and those in lower case are phosphorothioate | ODN 1585 (Class A, mouse-specific) |
| 27 | ggGGGACGA:TCGTCgggggg<br>Bases shown in capital letters are phosphodiester, and those in lower case are phosphorothioate | ODN 2216 (Class A, human-selective) |

-continued

Sequence Listing

| SEQ ID NO | Sequence | Description |
|---|---|---|
| 28 | gggGACGAC:GTCGTGgggggg Bases shown in capital letters are phosphodiester, and those in lower case are phosphorothioate | ODN 2336 (Class A, human preferred) |
| 29 | tccatgacgttcctgatgct Bases shown in capital letters are phosphodiester, and those in lower case are phosphorothioate | ODN 1668 (Class B, mouse specific) |
| 30 | tccatgacgttcctgacgtt Bases are phosphorothioate | ODN 1826 (Class B, mouse specific) |
| 31 | tcgtcgttttgtcgttttgtcgtt Bases are phosphorothioate | ODN 2006 (Class B, human selective) |
| 32 | tcg tcg ttg tcg ttt tgt cgt t Bases are phosphorothioate | ODN 2007 (Class B, bovine/porcine) |
| 33 | tcg acg ttc gtc gtt cgt cgt tc Bases are phosphorothioate | ODN BW006 (Class B, human & mouse) |
| 34 | tcg cga cgt tcg ccc gac gtt cgg ta Bases are phosphorothioate | ODN D-SL01 (Class B, multispecies) |
| 35 | tcgtcgttttcggcgc:gcgccg Bases are phosphorothioate | ODN 2395 (Class C, human/mouse) |
| 36 | tcgtcgtcgttc:gaacgacgttgat Bases are phosphorothioate | ODN M362 (Class C, human/mouse) |
| 37 | tcg cga acg ttc gcc gcg ttc gaa cgc gg Bases are phosphorothioate | ODN D-SL03 (Class C, multispecies) |
| 38 | MHGDTPTLHEYMLDLQPETTDLYCYEQLNDSSEEE | E7 |
| 39 | LYCYEQLNDSSEEEDEIDGPAGQAEPDRAHYNIVT | E7 |
| 40 | GQAEPDRAHYNIVTFCCKCDSTLRLCVQSTHVDIR | E7 |
| 41 | TLRLCVQSTHVDIRTLEDLLMGTLGIVCPICSQKP | E7 |
| 42 | MHQKRTAMFQDPQERPRKLPQLCTELQTTIHD | E6 |
| 43 | LPQLCTELQTTIHDIILECVYCKQQLLRREVY | E6 |
| 44 | KQQLLRREVYDFAFRDLCIVYRDGN | E6 |
| 45 | RDLCIVYRDGNPYAVCDKCLKFYSKI | E6 |
| 46 | DKCLKFYSKISEYRHYCYSLYGTTL | E6 |
| 47 | HYCYSLYGTTLEQQYNKPLCDLLIR | E6 |
| 48 | YGTTLEQQYNKPLCDLLIRCINCQKPLCPEEK | E6 |
| 49 | RCINCQKPLCPEEKQRHLDKKQRFHNIRGRWT | E6 |
| 50 | DKKQRFHNIRGRWTGRCMSCCRSSRTRRETQL | E6 |
| 51 | MHQKRTAMFQDPQERPRKLPQLCTELQTTIHDIILECVYCKQQLL RREVYDFAFRDLCIV YRDGNPYAVCDKCLKFYSKISEYRHYCYSLYGTTLEQQYNKPLC DLLIRCINCOKPLCPE EKQRHLDKKQRFHNIRGRWTGRCMSCCRSSRTRRETQL | E6 protein (full-length) |
| 52 | MHGDTPTLHEYMLDLQPETTDLYCYEQLNDSSEEEDEIDGPAGQ AEPDRAHYNIVTFCCKCDSTLRLCVQSTHVDIRTLEDLLMGTLGI VCPICSQKP | E7 protein (full-length) |

-continued

Sequence Listing

| SEQ ID NO | Sequence | Description |
|---|---|---|
| 53 | MRTALGDIGNMHGDTPTLHEYMLDLQPETTDLYCYEQLNDSSEE EDEIDGPAGQAEPDRAHYNIVTFCCKCDSTLRLCVQSTHVDIRT LEDLLMGTLGIVCPICSQKP | E7 Protein with D-box destruction motif (D-box E7) |
| 54 | MRVTAPRTLILLLSGALALTETWAGSMHGDTPTLHEYMLDLQPE TTDLYCYEQLNDSSEEEDEIDGPAGQAEPDRAHYNIVTFCCKCDS TLRLCVQSTHVDIRTLEDLLMGTLGIVCPICSQKPIVGIVAGLAV LAVVVIGAVVATVMCRRKSSGGKGGSYSQAASSDSAQGSDVSLTA | E7 Protein with sec/MITD domains (sec/MITD E7) |
| 55 | MHGDAPALHEYMLDLQPETTDLYCYEQLNDSSEEEDEIDGPAGQ AEPDRAHYNIVTFCCKCDSTLRLCVQSTHVDIRTLEDLLMGTLGI VCPICSQKP | E7 Protein with putative NLS mutant (NLS E7) |
| 56 | MHGDTPTLHEYMLDLQPETTDLYCYEQLNDSSEEEDEIDGPAGQ AEPDRAHYNIVTFCCKCDSTLRLCVQSTHVDIRTLEDLLMGTLG IVCPICSQKPKEKEKNKLKRKKLENKDKKDEERNKIREE | E7 protein with C-terminal KEKE motif (C-ter KEKE E7) |
| 57 | MQLCTELQTYMLDLQPETTYCKQQLL | E7.6 SLP |
| 58 | MQLCTELQTYMLDLQPETTYCKQQLLGGGGSQLCTELQTYMLDL QPETTYCKQQLLGGGGSQLCTELQTYMLDLQPETTYCKQQLLGG GGSQLCTELQTYMLDLQPETTYCKQQLLGGGGSQLCTELQTYML DLQPETTYCKQQLLGGGGSQLCTELQTYMLDLQPETTYCKQQLL | E7.6 SLP with 6 repeats |
| 59 | ATGCACCAAAAGAGAACTGCAATGTTTCAGGACCCACAGGAG CGACCCAGAAAGTTACCACAGTTATGCACAGAGCTGCAAACA ACTATACATGATATAATATTAGAATGTGTGTACTGCAAGCAAC AGTTACTGCGACGTGAGGTATATGACTTTGCTTTTCGGGATTT ATGCATAGTATATAGAGATGGGAATCCATATGCTGTATGTGAT AAATGTTTAAAGTTTTATTCTAAAATTAGTGAGTATAGACATT ATTGTTATAGTTTGTATGGAACAACATTA GAACAGCAATACAACAAACCGTTGTGTGATTTGTTAATTAGGT GTATTAACTGTCAA AAGCCACTGTGTCCTGAAGAAAAGCAAAGACATCTGGACAAA AAGCAAAGATTCCATAATATAAGGGGTCGGTGGACCGGTCGAT GTATGTCTTGTTGCAGATCATCAAGAACACGTAGAGAAACCCA GCTGTAA | E6 native mRNA |
| 60 | ATGCACCAGAAACGGACCGCCATGTTCCAGGATCCTCAAGAGA GGCCCAGAAAGCTGCCTCAGCTGTGTACCGAGCTGCAGACCAC CATCCACGACATCATCCTGGAATGCGTGTACTGCAAGCAGCAG CTCCTGCGGAGAGAGGTGTACGATTTCGCCTTCCGGGACCTGT GCATCGTGTACAGAGATGGCAACCCCTACGCCGTGTGCGACAA GTGCCTGAAGTTCTACAGCAAGATCAGCGAGTACCGGCACTAC TGCTACAGCCTGTACGGCACCACACTGGAACAGCAGTACAACA AGCCCCTGTGCGACCTGCTGATCCGGTGCATCAACTGCCAGAA ACCTCTGTGCCCCGAGGAAAAGCAGCGGCACCTGGACAAGAA GCAGCGGTTCCACAACATCAGAGGCCGGTGGACCGGCAGATG CATGAGCTGTTGTCGGAGCAGCAGAACCAGACGGGAAACCCA GCTGTGA | Codon-optimized E6 mRNA |
| 61 | ATGCATGGAGATACACCTACATTGCATGAATATATGTTAGATT TGCAACCAGAGACAACTGATCTCTACTGTTATGAGCAATTAAA TGACAGCTCAGAGGAGGAGGATGAAATAGATGGTCCAGCTGG ACAAGCAGAACCGGACAGAGCCCATTACAATATTGTAACCTTT TGTTGCAAGTGTGACTCTACGCTTCGGTTGTGCGTACAAAGCA CACACGTAGACATTCGTACTTTGGAAGACCTGTTAATGGGCAC ACTAGGAATTGTGTGCCCCATCTGTTCTCAGAAACCATAA | Native E7 mRNA |
| 62 | ATGAGAACAGCTCTTGGGGACATTGGTAACCATGGAGATACAC CTACATTGCATGAATATATGTTAGATTTGCAACCAGAGACAAC TGATCTCTACTGTTATGAGCAATTAAATGACAGCTCAGAGGAG GAGGATGAAATAGATGGTCCAGCTGGACAAGCAGAACCGGAC AGAGCCCATTACAATATTGTAACCTTTTGTTGCAAGTGTGACTC TACGCTTCGGTTGTGCGTACAAAGCACACACGTAGACATTCGT ACTTTGGAAGACCTGTTAATGGGCACACTAGGAATTGTGTGCC CCATCTGTTCTCAGAAACCATAA | D-box E7 mRNA |
| 63 | ATGCACGGCGACACCCCTACCCTGCACGAGTACATGCTGGACC TGCAGCCTGAGACAACCGACCTGTACTGCTACGAGCAGCTGAA CGACAGCAGCGAGGAAGAGGACGAGATCGACGGCCCTGCCGG CCAGGCCGAGCCTGATAGAGCCCACTACAACATCGTGACCTTC TGCTGCAAGTGCGACAGCACCCTGAGACTGTGCGTGCAGAGCA | Codon-optimized E7 mRNA v1 (CO v1) |

-continued

Sequence Listing

| SEQ ID NO | Sequence | Description |
|---|---|---|
| | CACACGTGGACATCAGAACCCTGGAAGATCTGCTGATGGGCAC<br>CTTGGGCATCGTGTGCCCCATCTGCAGCCAGAAGCCTTG | |
| 64 | ATGCACGGCGATACCCCTACACTGCACGAGTACATGCTGGACC<br>TGCAGCCTGAGACAACCGACCTGTACTGCTACGAGCAGCTGAA<br>CGACAGCAGCGAGGAAGAGGACGAGATTGACGGACCTGCCGG<br>ACAGGCCGAACCTGATAGAGCCCACTACAATATCGTGACCTTC<br>TGCTGCAAGTGCGACAGCACCCTGAGACTGTGTGTGCAGAGCA<br>CCCACGTGGACATCAGAACCCTGGAAGATCTGCTGATGGGCAC<br>CCTGGGCATCGTGTGCCCTATCTGTAGCCAGAAGCCTTGA | Codon-optimized E7 mRNA v2 (CO v2) |
| 65 | ATGAGAGTGACAGCCCCTCGGACACTGATCCTGCTGCTTTCTG<br>GTGCCCTGGCTCTGACAGAAACATGGGCCGGATCTATGCACGG<br>CGATACCCCTACACTGCACGAGTACATGCTGGACCTGCAGCCT<br>GAGACAACCGACCTGTACTGCTACGAGCAGCTGAACGACAGC<br>AGCGAGGAAGAGGACGAGATTGACGGACCTGCCGGACAGGCC<br>GAACCTGATAGAGCCCACTACAATATCGTGACCTTCTGCTGCA<br>AGTGCGACAGCACCCTGAGACTGTGTGTGCAGAGCACCCACGT<br>GGACATCAGAACCCTGGAAGATCTGCTGATGGGCACCCTGGGC<br>ATCGTGTGCCCTATCTGTAGCCAGAAGCCTATCGTGGGAATCG<br>TGGCCGGACTGGCTGTGCTGGCAGTGGTGGTTATTGGAGCCGT<br>GGTGGCCACAGTGATGTGCAGAAGAAAGAGCAGCGGCGGCAA<br>AGGCGGCAGCTATTCTCAGGCCGCCTCTAGCGATTCTGCCCA<br>GGGAAGTGATGTGTCCCTGACAGCTTGA | E7 codon opt v2 with sec/MITD domains mRNA (sec/MITD E7 CO) |
| 66 | ATGAGAACAGCTCTCGGCGACATCGGCAACATGCACGGCGAT<br>ACCCCTACACTGCACGAGTACATGCTGGACCTGCAGCCTGAGA<br>CAACCGACCTGTACTGCTACGAGCAGCTGAACGACAGCAGCG<br>AGGAAGAGGACGAGATTGACGGACCTGCCGGACAGGCCGAAC<br>CTGATAGAGCCCACTACAATATCGTGACCTTCTGCTGCAAGTG<br>CGACAGCACCCTGAGACTGTGTGTGCAGAGCACCCACGTGGAC<br>ATCAGAACCCTGGAAGATCTGCTGATGGGCACCCTGGGCATCG<br>TGTGCCCTATCTGTAGCCAGAAGCCTTGA | E7 codon opt. v2 with D-box motif mRNA (D-box E7 CO) |
| 67 | ATGCACGGCGATACCCCTACACTGCACGAGTACATGCTGGACC<br>TGCAGCCTGAGACAACCGACCTGTACTGCTACGAGCAGCTGAA<br>CGACAGCAGCGAGGAAGAGGACGAGATTGACGGACCTGCCGG<br>ACAGGCCGAACCTGATAGAGCCCACTACAATATCGTGACCTTC<br>TGCTGCAAGTGCGACAGCACCCTGAGACTGTGTGTGCAGAGCA<br>CCCACGTGGACATCAGAACCCTGGAAGATCTGCTGATGGGCAC<br>CCTGGGCATCGTGTGCCCTATCTGTAGCCAGAAGCCTAAAGAG<br>AAAGAGAAGAACAAGCTGAAGCGGAAGAAGCTCGAGAACAA<br>GGACAAGAAGGACGAGGAACGGAACAAGATCCGGGAAGAGT<br>GA | E7 codon opt. v2 with C-terminal KEKE mRNA v2 (C-ter KEKE E7 CO) |
| 68 | ATGCAGCTGTGTACCGAGCTGCAGACCTACATGCTGGACCTGC<br>AGCCTGAGACAACCTACTGCAAGCAGCAACTGCTTTGA | E7.6 SLP mRNA |
| 69 | ATGCAGCTGTGTACCGAGCTGCAGACCTACATGCTGGACCTGC<br>AGCCTGAGACAACCTACTGCAAGCAGCAACTGCTTGGCGGCGG<br>AGGCTCTCAGCTCTGTACTGAACTCCAGACATATATGCTCGAT<br>CTCCAGCCAGAAACCACGTACTGTAAACAGCAGCTCCTCGGAG<br>GCGGCGGATCTCAACTGTGCACCGAACTGCAAACTTATATGTT<br>GGATCTGCAACCCGAAACCACATATTGCAAGCAACAGTTGCTC<br>GGTGGCGGTGGCAGTCAGTTGTGCACAGAACTTCAGACTTACA<br>TGCTTGATCTTCAGCCCGAAACGACCTATTGCAAACAGCAGCT<br>TCTTGGCGGAGGCGGCAGCCAGTTGTGTACTGAGCTTCAAACT<br>TATATGCTTGACCTCCAACCAGAGACTACTTACTGCAAACAAC<br>AACTCCTCGGCGGTGGTGGAAGCCAGCTCTGCACGGAATTGCA<br>GACCTATATGCTCGACTTGCAACCGGAAACGACGTACTGCAAA<br>CAACAGCTGCTGTGA | E7.6 SLP Repeatx6 mRNA |
| 70 | ATGCACGGCGATGCCCCTGCCCTGCACGAGTACATGCTGGACC<br>TGCAGCCTGAGACAACCGACCTGTACTGCTACGAGCAGCTGAA<br>CGACAGCAGCGAGGAAGAGGACGAGATTGACGGACCTGCCGG<br>ACAGGCCGAACCTGATAGAGCCCACTACAATATCGTGACCTTC<br>TGCTGCAAGTGCGACAGCACCCTGAGACTGTGTGTGCAGAGCA<br>CCCACGTGGACATCAGAACCCTGGAAGATCTGCTGATGGGCAC<br>CCTGGGCATCGTGTGCCCTATCTGTAGCCAGAAGCCTTGA | E7 Codon Opt. v2 with NLS mutated (NLS E7 CO) |
| 71 | ATGATGGTGGACGGCGACAACAGCCACGTGGAAATGAAGCTG<br>GCCGTGGACGAGGAAGAGAACGCCGACAACAACACCAAGGCC<br>AACGTGACCAAGCCTAAGAGATGCAGCGGCAGCATCTGCTAC | TFRC_G4S_IFN-a2a mRNA |

-continued

Sequence Listing

| SEQ ID NO | Sequence | Description |
|---|---|---|
| | GGCACAATCGCCGTGATCGTGTTCTTCCTGATCGGCTTTATGAT<br>CGGCTACCTGGGCTACTGCAAGAGCAGTGATGGACCTGGCGAA<br>ACAGGCGGAGGCGGAGGATCTGGTGGCGGAGGAAGCGGTGGC<br>GGCGGATCTTGTGATCTGCCTCAGACACACAGCCTGGGCAGCA<br>GACGAACACTGATGCTGCTGGCCCAGATGCGGAAGATCAGCCT<br>GTTCAGCTGCCTGAAGGACCGGCACGATTTCGGCTTCCCTCAA<br>GAGGAATTCGGCAACCAGTTCCAGAAGGCCGAGACAATCCCT<br>GTGCTGCACGAGATGATCCAGCAGATCTTCAACCTGTTCTCCA<br>CCAAGGACAGCAGCGCCGCCTGGGATGAGACACTGCTGGACA<br>AGTTCTACACCGAGCTGTACCAGCAGCTGAATGACCTGGAAGC<br>CTGCGTGATCCAAGGCGTGGGAGTGACAGAGACACCCCTGATG<br>AAGGAAGATAGCATCCTGGCCGTGCGCAAGTACTTCCAGCGGA<br>TCACCCTGTACCTGAAAGAGAAGAAGTACAGCCCCTGCGCCTG<br>GGAAGTCGTGCGGGCCGAAATCATGAGAAGCTTCAGCCTGAG<br>CACCAACCTGCAAGAGAGCCTGCGGAGCAAAGAGTGA | |
| 72 | ATGATGGTGGACGGCGACAACAGCCACGTGGAAATGAAGCTG<br>GCCGTGGACGAGGAAGAGAACGCCGACAACAACACCAAGGCC<br>AACGTGACCAAGCCTAAGAGATGCAGCGGCAGCATCTGCTAC<br>GGCACAATCGCCGTGATCGTGTTCTTCCTGATCGGCTTTATGAT<br>CGGCTACCTGGGCTACTGCAAGAGCAGTGATGGACCTGGCGAA<br>ACAGGCGGAGGCGGAGGATCTGGTGGCGGAGGAAGTGGCGGC<br>GGAGGTTCTATTTGGGAGCTGAAGAAAGACGTGTACGTGGTGG<br>AACTGGACTGGTATCCCGATGCTCCTGGCGAGATGGTGGTGCT<br>GACCTGCGATACCCCTGAAGAGGACGGCATCACCTGGACACTG<br>GATCAGTCTAGCGAGGTGCTCGGCAGCGGCAAGACCCTGACCA<br>TCCAAGTGAAAGAGTTTGGCGACGCCGGCCAGTACACCTGTCA<br>CAAAGGCGGAGAAGTGCTGAGCCACAGCCTGCTGCTGCTCCAC<br>AAGAAAGAGGATGGCATTTGGAGCACCGACATCCTGAAGGAC<br>CAGAAAGAGCCCAAGAACAAGACCTTCCTGAGATGCGAGGCC<br>AAGAACTACAGCGGCCGGTTCACATGTTGGTGGCTGACCACCA<br>TCAGCACCGACCTGACCTTCAGCGTGAAGTCCAGCAGAGGCAG<br>CAGTGATCCTCAGGGCGTTACATGTGGCGCCGCTACACTGTCT<br>GCCGAAAGAGTGCGGGGCGATAACAAAGAATACGAGTACAGC<br>GTGGAATGCCAAGAGGACAGCGCCTGTCCAGCCGCCGAAGAG<br>TCTCTGCCTATCGAAGTGATGGTCGACGCCGTGCACAAGCTGA<br>AGTACGAGAACTACACCAGCAGCTTTTTCATCCGGGACATCAT<br>CAAGCCCGATCCTCCAAAGAACCTGCAGCTGAAGCCTCTGAAG<br>AACAGCAGACAGGTGGAAGTGTCCTGGGAGTACCCCGACACC<br>TGGTCTACACCCCACAGCTACTTCAGCCTGACCTTTTGCGTGCA<br>AGTGCAGGGCAAGTCCAAGCGCGAGAAAAAGGACCGGGTGTT<br>CACCGACAAGACCAGCGCCACCGTGATCTGCAGAAAGAACGC<br>CAGCATCAGCGTCAGAGCCCAGGACCGGTACTACAGCAGCTCT<br>TGGAGCGAATGGGCCAGCGTGCCATGTAGCGGAGGTGGTGGT<br>AGCGGAGGCGGCGGAAGCGGCGGTGGTGGATCAGGTGGTGGT<br>GGCTCTAGAAACCTGCCAGTGGCTACCCCTGATCCTGGCATGT<br>TCCCTTGTCTGCACCACAGCCAGAACCTGCTGAGAGCCGTGTC<br>CAACATGCTGCAGAAGGCCAGACAGACCCTGGAATTCTACCCC<br>TGCACCAGCGAGGAAATCGACCACGAGGACATCACCAAGGAT<br>AAGACCAGCACCGTGGAAGCCTGCCTGCCTCTGGAACTGACCA<br>AGAACGAGAGCTGCCTGAACAGCCGGGAAACCTCCTTCATCAC<br>CAACGGCTCTTGCCTGGCCAGCAGAAAGACAAGCTTCATGATG<br>GCCCTGTGCCTGAGCAGCATCTACGAGGACCTGAAGATGTACC<br>AGGTGGAATTCAAGACCATGAACGCCAAGCTGCTGATGGACCC<br>CAAGCGGCAGATCTTCCTGGACCAGAACATGCTGGCTGTGATC<br>GACGAGCTGATGCAGGCCCTGAACTTCAACAGCGAGACAGTG<br>CCCCAGAAGTCTAGCCTGGAAGAACCCGACTTCTACAAGACCA<br>AGATCAAGCTGTGCATCCTGCTGCACGCCTTCCGGATCAGAGC<br>CGTGACCATCGACAGAGTGATGAGCTACCTGAACGCCTCCTGA | TFRC_G4S_IL-12 mRNA |
| 73 | $(G_4S)_3$ | $G_4S$ Linker |
| 74 | $(EAAAK)_3$ | EAAAK linker |
| 75 | $(G_4S)_n$ | $G_4S$ Linker |
| 76 | (EAAAK)n | EAAAK linker |
| 77 | MMVDGDNSHVEMKLAVDEEENADNNTKANVTKPKRCSGSICYG<br>TIAVIVFFLIGFMIGYLGYCKSSDGPGETGGGGGSGGGGSGGGGS<br>APTSSSTKKTQLQLEHLLLDLQMILNGINNYKNPKLTRMLTFKFY<br>MPKKATELKHLQCLEEELKPLEEVLNLAQSKNFHLRPRDLISNIN<br>VIVLELKGSETTFMCEYADETATIVEFLNRWITFCQSIISTL | TFRC_G4S_IL-2 |

-continued

Sequence Listing

| SEQ ID NO | Sequence | Description |
|---|---|---|
| 78 | MLKKRGNHSTGLCLLVMFFMVLVALVGLGLGMFQLFHLQKETG GGGGSGGGGSGGGGS APTSSSTKKTQLQLEHLLLDLQMILNGINNYKNPKLTRMLTFKFY MPKKATELKHLQCLEEELKPLEEVLNLAQSKNFHLRPRDLISNINV IVLELKGSETTFMCEYADETATIVEFLNRWITFCQSIISTLT | FasL_G4S_IL-2 |
| 79 | MMVDGDNSHVEMKLAVDEEENADNNTKANVTKPKRCSGSICYG TIAVIVFFLIGFMIGYLGYCKSSDGPGETGGGGGSGGGGSGGGGS IWELKKDVYVVELDWYPDAPGEMVVLTCDTPEEDGITWTLDQSS EVLGSGKTLTIQVKEFGDAGQYTCHKGGEVLSHSLLLLHKKEDGI WSTDILKDQKEPKNKTFLRCEAKNYSGRFTCWWLTTISTDLTFSV KSSRGSSDPQGVTCGAATLSAERVRGDNKEYEYSVECQEDSACP AAEESLPIEVMVDAVHKLKYENYTSSFFIRDIIKPDPPKNLQLKPL KNSRQVEVSWEYPDTWSTPHSYFSLTFCVQVQGKSKREKKDRVF TDKTSATVICRKNASISVRAQDRYYSSSWSEWASVPCSGGGGSGG GGSGGGGSGGGGSRNLPVATPDPGMFPCLHHSQNLLRAVSNMLQ KARQTLEFYPCTSEEIDHEDITKDKTSTVEACLPLELTKNESCLNS RETSFITNGSCLASRKTSFMMALCLSSIYEDLKMYQVEFKTMNAK LLMDPKRQIFLDQNMLAVIDELMQALNFNSETVPQKSSLEEPDFY KTKIKLCILLHAFRIRAVTIDRVMSYLNAS | TFRC_G4S_IL-12 |
| 80 | MMVDGDNSHVEMKLAVDEEENADNNTKANVTKPKRCSGSICYG TIAVIVFFLIGFMIGYLGYCKSSDGPGETGGGGGSGGGGSGGGGS CDLPQTHSLGSRRTLMLLAQMRKISLFSCLKDRHDFGFPQEEFGN QFQKAETIPVLHEMIQQIFNLFSTKDSSAAWDETLLDKFYTELYQQ LNDLEACVIQGVGVTETPLMKEDSILAVRKYFQRITLYLKEKKYS PCAWEVVRAEIMRSFSLSTNLQESLRSKE | TFRC_G4S_IFN-a2a |
| 81 | MMVDGDNSHVEMKLAVDEEENADNNTKANVTKPKRCSGSICYG TIAVIVFFLIGFMIGYLGYCKSSDGPGETG | TFRC domain |
| 82 | MLKKRGNHSTGLCLLVMFFMVLVALVGLGLGMFQLFHLQKETG | FasL domain |
| 83 | ATGAGCCTGCTGACCGAAGTGGAAACCTATGTGCTGAGCATTG TGCCGAGCGGCCCGCTGAAAGCGGAAATTGCGCAGCGCCTGG AAGATGTGTTTGCGGGCAAAAACACCGATCTGGAAGTGCTGAT GGAATGGCTGAAAACCCGCCCGATTCTGAGCCCGCTGACCAAA GGCATTCTGGGCTTTGTGTTTACCCTGACCGTGCCGAGCGAAC GCGGCCTGCAGCGCCGCCGCTTTGTGCAGAACGCGCTGAACGG CAACGGCGATCCGAACAACATGGATAAAGCGGTGAAACTGTA TCGCAAACTGAAACGCGAAATTACCTTTCATGGCGCGAAAGAA ATTGCGCTGAGCTATAGCGCGGGCGCGCTGGCGAGCTGCATGG GCCTGATTTATAACCGCATGGGCGCGGTGACCACCGAAGTGGC GTTTGGCCTGGTGTGCGCGACCTGCGAACAGATTGCGGATAGC CAGCATCGCAGCCATCGCCAGATGGTGACCACCACCAACCCGC TGATTCGCCATGAAAACCGCATGGTGCTGGCGAGCACCACCGC GAAAGCGATGGAACAGATGGCGGGCAGCAGCGAACAGGCGGC GGAAGCGATGGATATTGCGAGCCAGGCGCGCCAGATGGTGCA GGCGATGCGCACCATTGGCACCCATCCGAGCAGCAGCGCGGG CCTGAAAGATGATCTGCTGGAAAACCTGCAGGCGTATCAGAAA CGCATGGGCGTGCAGATGCAGCGCTTTAAA | Influenza M1 mRNA (Native sequence) |
| 84 | ATGTCTCTGCTGACCGAGGTCGAGACATACGTGCTGAGCATCG TGCCTAGCGGCCCTCTGAAGGCCGAGATCGCCCAGAGACTGGA AGATGTGTTCGCCGGCAAGAACACCGACCTGGAAGTGCTGATG GAATGGCTGAAAACCAGACCTATCCTGAGCCCCCTGACAAAGG GCATCCTGGGCTTCGTGTTCACCCTGACCGTGCCAAGCGAGAG AGGCCTGCAGCGCAGAAGGTTCGTGCAGAACGCCCTCAACGG CAATGGCGACCCCAACAACATGGATAAGGCTGTGAAGCTGTAT AGAAAGCTGAAAAGAGAGATCACATTTCACGGCGCTAAAGAG ATTGCCCTCTCCTACAGCGCCGGAGCCCTGGCTTCTTGTATGGG ACTGATCTACAACAGAATGGGAGCCGTGACCACCGAGGTGGC CTTCGGCCTGGTGTGCGCCACATGCGAGCAAATCGCAGATAGC CAGCACAGAAGCCATCGGCAGATGGTCACCACAACAAACCCT CTGATCCGGCACGAGAACCGGATGGTGCTGGCCAGCACCACCG CCAAGGCCATGGAACAGATGGCCGGCAGCTCTGAGCAGGCCG CTGAAGCCATGGACATCGCCAGCCAGGCTAGACAGATGGTTCA GGCCATGAGAACCATCGGCACCCACCCTTCTAGCTCCGCCGGA CTGAAGGACGACCTGCTGGAAAATCTGCAAGCCTACCAGAAG CGGATGGGCGTGCAGATGCAGCGGTTTAAGTAG | Influenza M1 mRNA (Codon-optimized) |

-continued

Sequence Listing

| SEQ ID NO | Sequence | Description |
|---|---|---|
| 85 | ATGGAAAGCAGAGGCAGACGGTGCCCCGAGATGATCTCTGTG<br>CTGGGCCCTATCTCTGGCCACGTGCTGAAGGCCGTGTTCAGCA<br>GAGGCGATACACCTGTGCTGCCCCACGAGACAAGACTGCTGCA<br>GACAGGCATCCATGTGCGGGTGTCACAGCCTAGCCTGATCCTG<br>GTGTCTCAGTACACCCCTGACAGCACCCCTTGTCACAGAGGCG<br>ACAATCAGCTGCAGGTCCAGCACACCTACTTCACCGGCAGCGA<br>GGTGGAAAACGTGTCCGTGAACGTGCACAATCCCACCGGCAG<br>ATCCATCTGTCCCAGCCAAGAGCCTATGAGCATCTACGTGTAC<br>GCCCTGCCTCTGAAGATGCTGAACATCCCCAGCATCAATGTGC<br>ATCACTACCCCTCTGCCGCCGAGCGGAAACACAGACATCTGCC<br>TGTGGCCGATGCCGTGATTCACGCCTCTGGCAAACAGATGTGG<br>CAGGCCAGACTGACAGTGTCCGGACTGGCTTGGACCAGACAGC<br>AGAACCAGTGGAAAGAACCCGACGTGTACTACACCAGCGCCTT<br>CGTGTTCCCCACCAAGGATGTGGCCCTGAGACACGTTGTGTGC<br>GCCCACGAACTCGTGTGCAGCATGGAAAACACCCGGGCCACC<br>AAGATGCAAGTGATCGGCGACCAGTACGTGAAGGTGTACCTG<br>GAAAGCTTCTGCGAGGATGTGCCCAGCGGCAAGCTGTTCATGC<br>ACGTGACACTGGGCTCCGACGTGGAAGAGGACCTGACCATGA<br>CCAGAAATCCCCAGCCTTTCATGCGGCCTCACGAGAGAAATGG<br>CTTCACCGTGCTGTGCCCCAAGAACATGATCATCAAGCCCGGC<br>AAGATCAGCCACATCATGCTGGACGTGGCCTTCACCAGCCACG<br>AGCACTTTGGACTGCTGTGTCCTAAGAGCATCCCCGGCCTGAG<br>CATCAGCGGCAACCTGCTGATGAATGGCCAGCAGATCTTCCTG<br>GAAGTGCAGGCCATCCGGGAAACCGTGGAACTGAGACAGTAC<br>GACCCTGTGGCTGCCCTGTTCTTCTTCGACATCGACCTGCTGCT<br>CCAGAGAGGCCCTCAGTACTCTGAGCACCCCACCTTTACCAGC<br>CAGTACCGGATCCAGGGAAAGCTGGAATACCGGCACACCTGG<br>GATAGACACGATGAAGGTGCTGCCCAGGGCGACGATGATGTG<br>TGGACAAGCGGCAGCGATAGCGACGAGGAACTGGTCACCACC<br>GAGAGAAAGACCCCTAGAGTTACAGGCGGAGGCGCTATGGCT<br>GGCGCCTCTACATCTGCCGGACGGAAGAGAAAGAGCGCCTCTT<br>CTGCCACCGCCTGTACAAGCGGCGTGATGACAAGAGGCAGGCT<br>GAAAGCCGAGAGCACAGTGGCCCCTGAAGAGGACACAGACGA<br>GGACAGCGACAACGAGATTCACAACCCCGCCGTGTTTACCTGG<br>CCTCCTTGGCAGGCTGGAATCCTGGCCAGAAACCTGGTGCCTA<br>TGGTGGCCACAGTGCAGGGCCAGAACCTGAAGTACCAAGAGT<br>TCTTCTGGGACGCCAACGACATCTACCGGATCTTCGCCGAACT<br>GGAAGGCGTGTGGCAACCAGCCGCTCAGCCTAAGAGAAGAAG<br>GCACAGACAAGACGCTCTGCCCGGACCTTGTATCGCCAGCACT<br>CCCAAGAAGCACAGAGGCTGA | CMV pp65 mRNA (Codon-optimized) |

What is claimed is:

1. A composition comprising nucleated cells, wherein the nucleated cells comprise a protein or fragment thereof or a mRNA encoding the protein or fragment thereof, and wherein the protein or fragment thereof stimulates an immune response in an individual in need thereof in an HLA agnostic manner when the nucleated cells are administered to the individual, wherein the protein or fragment thereof comprises two or more antigens that comprise a plurality of immunogenic epitopes, wherein the nucleated cells further comprise one or more agents that mediate a signal for T cell activation, wherein the one or more agents comprise one or more co-stimulatory molecules and one or more cytokines, and wherein the nucleated cells comprising the protein or fragment thereof and further comprising the one or more agents induce an antigen-specific T cell activation at a level that is higher by about 10% or more compared to a corresponding nucleated cell not comprising an agent that mediates a signal for T cell activation.

2. The composition of claim 1, wherein the protein or fragment thereof comprises one or more immunoproteasome-targeting motifs, wherein the nucleated cells comprising the protein or fragment thereof comprising one or more immunoproteasome-targeting motifs lead to increased IFNγ secretion by antigen-specific responder T cells compared to nucleated cells comprising the protein or fragment thereof and not comprising the one or more immunoproteasome-targeting motifs.

3. The composition of claim 2, wherein the one or more immunoproteasome-targeting motifs is (a) at the N-terminus and/or the C-terminus of the fusion protein, and/or (b) a destruction box (D-box) domain, a KEKE domain, and/or a sec/MITD domain.

4. The composition of claim 1, wherein the at least one epitope is flanked on the N-terminus and/or the C-terminus by one or more heterologous peptide sequences.

5. The composition of claim 4, wherein the one or more heterologous peptide sequences are derived from an immunogenic synthetic long peptide (SLP).

6. The composition of claim 1, wherein the protein is a human papillomavirus (HPV) protein and/or a hepatitis B virus (HBV) protein.

7. The composition of claim 6, wherein (a) the HPV protein is an HPV E6 or HPV E7 protein, and/or (b) the HBV protein is a core protein, a small surface antigen, a medium surface antigen, a large surface antigen, an e antigen, an X antigen, or a polymerase protein.

8. The composition of claim 1, wherein the nucleated cells: (a) are autologous or allogeneic to the individual, (b) comprise immune cells, (c) comprise a plurality of peripheral blood mononuclear cells (PBMCs), (d) comprise one or more of T cells, B cells, NK cells, monocytes, dendritic cells, and/or NK-T cells, and/or (e) have been conditioned with an adjuvant to form conditioned nucleated cells.

9. The composition of claim 1, wherein the nucleated cells have been modified to comprise a chimeric membrane-bound cytokine.

10. A method of stimulating an immune response in an individual in need thereof, the method comprising administering an effective amount of the composition of claim 1 to the individual, wherein after the administration an immune response is stimulated in the individual in an HLA agnostic manner.

11. A method of treating a cancer, an infectious disease, or a viral-associated disease in an individual in need thereof, the method comprising administering an effective amount of the composition of claim 1 to the individual.

12. A method of stimulating an immune response in an individual in need thereof, the method comprising administering an effective amount of the composition of claim 1 to the individual, wherein after the administration an immune response is stimulated in the individual in an HLA agonistic manner.

13. A method of treating a cancer, an infectious disease, or a viral-associated disease in an individual in need thereof, the method comprising administering an effective amount of the composition of claim 1 to the individual.

14. A composition comprising nucleated cells, wherein the nucleated cells comprise a protein or fragment thereof or a mRNA encoding the protein or fragment thereof, wherein the protein or fragment thereof stimulates an immune response in an individual in need thereof in an HLA agnostic manner when the nucleated cells are administered to the individual, wherein the protein or fragment thereof comprises two or more antigens that comprise a plurality of immunogenic epitopes, wherein the protein or fragment thereof is comprised in a fusion protein with one or more immunoproteasome-targeting motifs, and wherein the nucleated cells comprising the fusion protein lead to increased IFNγ secretion by antigen-specific responder T cells compared to nucleated cells comprising the protein or fragment thereof and not comprising the one or more immunoproteasome-targeting motifs.

15. The composition of claim 14, wherein the one or more immunoproteasome-targeting motifs is (a) at the N-terminus and/or the C-terminus of the fusion protein, and/or (b) a destruction box (D-box) domain, a KEKE domain, and/or a sec/MITD domain.

* * * * *